US007728017B2

(12) United States Patent
Lauffer et al.

(10) Patent No.: US 7,728,017 B2
(45) Date of Patent: Jun. 1, 2010

(54) INHIBITORS OF C-MET AND USES THEREOF

(75) Inventors: David J. Lauffer, Stow, MA (US); Alexander Aronov, Watertown, MA (US); Pan Li, Lexington, MA (US); David D. Deininger, Waltham, MA (US); Kira McGinty, Medford, MA (US); Dean Stamos, Carlsbad, CA (US); Jon H. Come, Cambridge, MA (US); Michelle Stewart, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 601 days.

(21) Appl. No.: 11/606,524

(22) Filed: Nov. 30, 2006

(65) Prior Publication Data

US 2007/0191369 A1 Aug. 16, 2007

Related U.S. Application Data

(60) Provisional application No. 60/740,737, filed on Nov. 30, 2005, provisional application No. 60/740,741, filed on Nov. 30, 2005, provisional application No. 60/740,859, filed on Nov. 30, 2005.

(51) Int. Cl.
*C07D 513/04* (2006.01)
*A61K 31/433* (2006.01)
(52) U.S. Cl. ...................... 514/363; 548/126
(58) Field of Classification Search ................. 548/126; 514/363
See application file for complete search history.

(56) References Cited

FOREIGN PATENT DOCUMENTS

| WO | 02/12236 | 2/2002 |
| WO | 2005/010005 | 2/2005 |
| WO | 2007/075567 | 7/2007 |

OTHER PUBLICATIONS

Deshmukh et al. Indian Journal of Chemistry (1984), 23B (8), 793-5.*

Kelarev, V. I. et al., Synthesis of 1,2,4,-triazolo [3,4-B]-1,3,4-thiadiazole derivatives with the fragments of sterically-hindered phenol Izvestiya Vysshikh Uchebnykh Zavedenii, Khimiya i Khimicheskaya Teckhnologiya, 2003, vol. 46(7), Abstract & Compound CAS Nos. 773072-92-7, 773072-93-8, 773072-94-9, 773072-98-3, 773073-06-6, 773073-07-7; Database CA Chemical Abstracts Service, Columbus, Ohio, US, retrieved from STN Database accession No. 2004:400043; CODEN: IVUKAR; ISSN: 0579-2991; XP002434078.

Wermuth C G: "Molecular Variations Based on Isosteric Replacements" Practice of Medicinal Chemistry, 1996, pp. 203-237, Academic Press, USA; XP002190259.

Udupi, R. H. et al., "Synthesis and Biological evaluation of 3-substituted-4-[6'-methoxynapth-2' -yl] propionamido-5-mercapto-1,2,4-triazoles" Indian Journal of Heterocyclic Chemistry, 2002, vol. 12(1), Abstract & Compound CAS No. 497085-79-7P; Database CA Chemical Abstracts Service, Columbus, Ohio, US, retrieved from STN Database accession No. 2002:775245; CODEN: IJCHEI; ISSN: 0971-1627; XP002434079.

Liu, Su-Yan et al., "Synthesis of 6-nitrobenzimidazole derivatives" Gaodeng Xuexiao huaxue xuebao, 2000, vol. 21 (9) Abstract & Compound CAS Nos. 326587-38-6, 326587-39-7, 326587-40-0, 326587-41-1, 326587-42-2, 326587-43-3, 326587-44-4, 326587-45-5, Database CA Chemical Abstract Service, Columbus, Ohio, US, retrieved from STN Database accession No. 2000:830662 CODEN: Kthpdm; ISSN: 0251-0790; XP00243080.

Udupi, R. H. et al., "Synthesis and biological evaluation of 3-substituted 4-[2'-(4"-isobutylphenyl) propionamido]-5-mercapto-1,2,4-triazoles and their derivatives" Journal of the Indian Chemical Society, 2000, vol. 77(6), Abstract & Compound CAS No. 297179-65-8; Database CA Chemical Abstract Service, Columbus, Ohio, US, retrieved from STN Database accession No. 2000:494154; CODEN: JICSAH; ISSN: 0019-4522; XP002434081.

Christensen J G et al., "c-Met as a target for human cancer and characterization of inhibitors for therapeutic intervention" Cancer Letters, 2005, vol. 225, pp. 1-26; New York, NY, US; ISSN: 0304-3835; XP004939070.

Basu N. K. et al., "s-Triazolopyridazines: synthesis as potential therapeutic agents" Journal Chemical Society, 1963, pp. 5660-5664; XP009088851.

* cited by examiner

*Primary Examiner*—Kahsay T Habte
(74) *Attorney, Agent, or Firm*—Daniel A. Pearson

(57) ABSTRACT

The present invention provides compounds useful as inhibitors of c-Met tyrosine kinase. The invention also provides pharmaceutically acceptable compositions comprising the compounds of the invention and methods of using the compositions in the treatment of various proliferative disorders.

6 Claims, 5 Drawing Sheets

INHIBITORS OF C-MET AND USES THEREOF

CROSS REFERENCE TO RELATED APPLICATIONS

This present application claims the benefit, under 35 U.S.C. §119, to U.S. Provisional Application No. 60/740,737 filed Nov. 30, 2005, U.S. Provisional Application No. 60/740,741 filed Nov. 30, 2005, and U.S. Provisional Application No. 60/740,859 filed Nov. 30, 2005, the entire disclosures of which are incorporated herein by reference.

TECHNICAL FIELD OF THE INVENTION

The present invention relates to compounds useful as inhibitors of c-Met. The invention also provides pharmaceutically acceptable compositions comprising the compounds of the invention and methods of using the compositions in the treatment of various disorders.

BACKGROUND OF THE INVENTION

Hepatocyte growth factor (HGF), also known as scatter factor, is a multi-functional growth factor that enhances transformation and tumor development by inducing mitogenesis and cell motility. Further, HGF promotes metastasis by stimulating cell motility and invasion through various signaling pathways. In order to produce cellular effects, HGF must bind to its receptor, c-Met, a receptor tyrosine kinase. c-Met, a widely expressed heterodimeric protein comprising of a 50 kilodalton (kDa) α-subunit and a 145 kDa β-subunit (Maggiora et al., *J. Cell Physiol.*, 173:183-186, 1997), is overexpressed in a significant percentage of human cancers and is amplified during the transition between primary tumors and metastasis. The various cancers in which c-Met overexpression is implicated include, but are not limited to, gastric adenocarcinoma, renal cancer, small cell lung carcinoma, colorectal cancer, prostate cancer, brain cancer, liver cancer, pancreatic cancer, and breast cancer. c-Met is also implicated in atherosclerosis and lung fibrosis. Accordingly, there is a great need to develop compounds useful as inhibitors of c-Met protein kinase receptor.

SUMMARY OF THE INVENTION

It has been found that compounds of this invention, and pharmaceutically acceptable compositions thereof, are effective as inhibitors of c-Met. Accordingly, the invention features compounds having the formula:

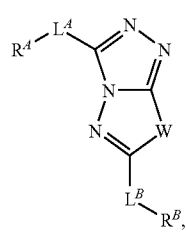

(I)

or a pharmaceutically acceptable salt or prodrug thereof, where each of $L^A$, $L^B$, $R^A$, $R^B$, and W is as defined herein.

The invention also provides pharmaceutical compositions that include a compound of formula I and a pharmaceutically acceptable carrier, adjuvant, or vehicle. In addition, the invention provides methods of treating or lessening the severity of a proliferative disease, condition, or disorder in a patient that includes the step of administering to the patient a therapeutically effective dose of a compound of formula I, or a pharmaceutical composition thereof.

DETAILED DESCRIPTION OF THE INVENTION

Definitions and General Terminology

Figure 1:
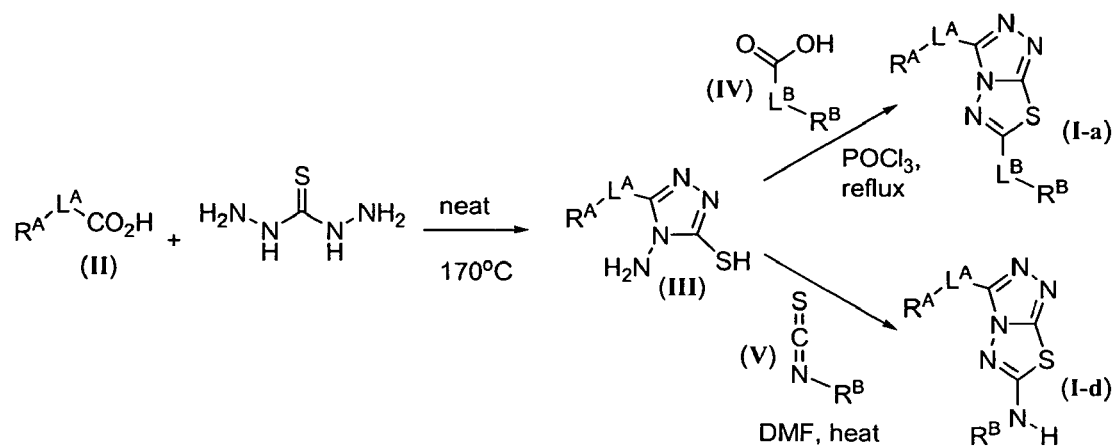
FIG. 1 shows a general scheme for the preparation of triazolothiadiazoles of the invention (compounds of formulae I-a and I-d).

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by J^X. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl. The terms "alkyl" and the prefix "alk-," as used herein, are inclusive of both straight chain and branched saturated carbon chain. The term "alkylene," as used herein, represents a saturated divalent hydrocarbon group derived from a straight or branched chain saturated hydrocarbon by the removal of two hydrogen atoms, and is exemplified by methylene, ethylene, isopropylene and the like. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds. The term "alkylidene," as used herein, represents a divalent straight chain alkyl linking group.

The term "cycloaliphatic" (or "carbocycle") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle," "heterocyclyl," "heterocycloaliphatic," or "heterocyclic" as used herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring." Examples of aryl rings would include phenyl, naphthyl, and anthracene.

The term "heteroaryl," used alone or as part of a larger moiety as in "heteroaralkyl," or "heteroarylalkoxy," refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl, and the like) or heteroaryl (including heteroaralkyl, heteroarylalkoxy, and the like) group may contain one or more substituents. Suitable substituents on the unsaturated carbon atom of an aryl or heteroaryl group include: halogen; —R°; —OR°; —SR°; 1,2-methylenedioxy; 1,2-ethylenedioxy; phenyl (Ph), optionally substituted with R°; —O(Ph), optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°C(O)OR°; —NR°NR°C(O)R°; —NR°NR°C(O)N(R°)$_2$; —NR°NR°C(O)OR°; —C(O)C(O)R°; —C(O)CH$_2$C(O)R°; —C(O)OR°; —C(O)R°; —C(S)R°; —C(O)N(R°)$_2$; —C(S)N(R°)$_2$; —B(OR°)$_2$; —OC(O)N(R°)$_2$; —OC(O)R°; —C(O)N(OR°)R°; —C(NOR°)R°; —S(O)$_2$R°; —S(O)$_3$R°; —S(O)$_2$N(R°)$_2$; —S(O)R°; —NR—S(O)$_2$N(R°)$_2$; —NR—S(O)$_2$R°; —N(OR°)R°; —C(=NH)—N(RO)$_2$; —(CH$_2$)$_{0-2}$NHC(O)R°; -L-R°; -L-N(R°)$_2$; -L -SR°; -L-OR°; -L-(C$_{3-10}$ cycloaliphatic), -L-(C$_{6-10}$ aryl), -L-(5-10 membered heteroaryl), -L -(5-10 membered heterocyclyl), oxo, C$_{1-4}$ haloalkoxy, C$_{1-4}$haloalkyl, -L-NO$_2$, -L-CN, -L-OH, -L-CF$_3$; or two substituents, on the same carbon or on different carbons, together with the carbon or intervening carbons to which they are bound, form a 5-7 membered saturated, unsaturated, or partially saturated ring, wherein L is a C$_{1-6}$ alkylene group in which up to three methylene units are replaced by —NH—, —NR°—, —O—, —S—, —C(O)O—, —OC(O)—, —C(O)CO—, —C(O)—, —C(O)NH—, —C(O)NR°—, —C(=N—CN), —NHCO—, —NR°CO—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NH—, —NHC(O)NR°—, —NR°C(O)NR°, —OC(O)NH—, —OC(O)NR°—, —NHS(O)$_2$NH—, —NR°S(O)$_2$NH—, —NHS(O)$_2$NRO—, —NR°S(O)$_2$NR°—, —S(O)—, or —S(O)$_2$—, and wherein each occurrence of R° is independently selected from hydrogen, optionally substituted C$_{1-6}$ aliphatic, an unsubstituted 5 to 6 membered heteroaryl or heterocyclic ring, phenyl, or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3- to 8-membered cycloalkyl ring, wherein said heteroaryl or heterocyclyl ring has 1 to 3 heteroatoms independently selected from nitrogen, oxygen, or sulfur. Optional substituents on the aliphatic group of R° are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —O(haloC$_{1-4}$ aliphatic), or haloC$_{1-4}$ aliphatic, wherein each of the foregoing C$_{1-4}$ aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHC(O)O(alkyl), =NNHS(O)$_2$(alkyl), or =NR*, where each R* is independently selected from hydrogen or an optionally substituted C$_{1-8}$ aliphatic. Optional substituents on the aliphatic group of R* are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —C(O)NH$_2$, —C(O)NH(C$_{1-4}$ aliphatic), —C(O)N(C$_{1-4}$ aliphatic)$_2$, —O(halo-C$_{1-4}$ aliphatic), and halo(C$_{1-4}$ aliphatic), where each of the foregoing C$_{1-4}$ aliphatic groups of R* is unsubstituted; or two R* on the same nitrogen are taken together with the nitrogen to form a 5-8 membered heterocyclyl or heteroaryl ring having 1-3 heteroatoms independently selected from nitrogen, oxygen, and sulfur.

In some embodiments, optional substituents on the nitrogen of a non-aromatic heterocyclic ring include —R⁺, —N(R⁺)$_2$, —C(O)R⁺, —C(O)OR⁺, —C(O)C(O)R⁺, —C(O)CH$_2$C(O)R⁺, —S(O)$_2$R⁺, —S(O)$_2$N(R⁺)$_2$, —C(=S)N(R⁺)$_2$, —C(=NH)—N(R⁺)$_2$, or —NR⁺S(O)$_2$R⁺; wherein R⁺ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R⁺, on the same substituent or different substituents, taken together with the atom(s) to which each R⁺ group is bound, form a 5-8-membered heterocyclyl, aryl, or heteroaryl ring or a 3-8 membered cycloalkyl ring, wherein said heteroaryl or heterocyclyl ring has 1-3 heteroatoms independently selected from nitrogen, oxygen, or sulfur. START Optional substituents on the aliphatic group or the phenyl ring of R⁺ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —O(halo(C$_{1-4}$ aliphatic)), or halo(C$_{1-4}$ aliphatic), wherein each of the foregoing C$_{1-4}$ aliphatic groups of R⁺ is unsubstituted.

As detailed above, in some embodiments, two independent occurrences of R°(or R⁺, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

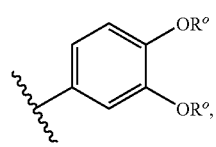

these two occurrences of R° are taken together with the oxygen atoms to which they are bound to form a fused 6-membered oxygen containing ring:

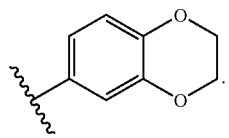

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

In some embodiments, a methylene unit of the alkyl or aliphatic chain is optionally replaced with another atom or group. Examples of such atoms or groups would include, but are not limited to, —NR°—, —O—, —S—, —C(O)O—, —OC(O)—, —C(O)CO—, —C(O)—, —C(O)NR°—, —C(=N—CN), —NR°CO—, —NR—C(O)O—, —S(O)$_2$NR°—, —NR°S(O)$_2$—, —NR°C(O)NR°—, —OC(O)NR°—, —NR°S(O)$_2$NR°—, —S(O)—, or —S(O)$_2$—, wherein R° is defined herein. Unless otherwise specified, the optional replacements form a chemically stable compound. Optional atom or group replacements can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement occurs at the terminal end, the replacement atom is bound to an H on the terminal end. For example, if one methylene unit of —CH$_2$CH$_2$CH$_3$ was optionally replaced with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below) represents substitution of the substituent at any substitutable position in any of the rings within the multiple ring system. For example, Figure a represents possible substitution in any of the positions shown in Figure b.

Figure b

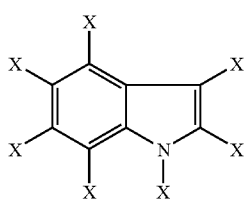

This also applies to multiple ring systems fused to optional ring systems (which would be represented by dotted lines). For example, in Figure c, X is an optional substituent both for ring A and ring B.

Figure c

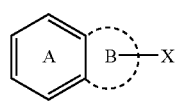

If, however, two rings in a multiple ring system each have different substituents drawn from the center of each ring, then, unless otherwise specified, each substituent only represents substitution on the ring to which it is attached. For example, in Figure d, Y is an optionally substituent for ring A only, and X is an optional substituent for ring B only.

Figure d

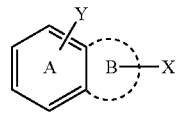

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalamnne and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound that is transformed in vivo into a compound of formula I, I-a, I-b, or I-c, or a compound listed in Tables 1, 2, or 3. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic (C$_1$-C$_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphorylation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Description of Compounds of the Invention

The present invention features compounds having the formula:

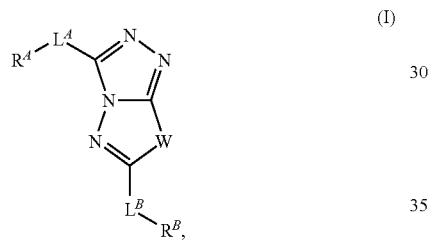

or a pharmaceutically acceptable salt or prodrug thereof, wherein

W is —S—, —C($R^C$)=C($R^C$)—, or —C($R^{++}$)$_2$S—;

$L^A$ is a $C_{1-2}$ alkylene, optionally substituted with 1-4 $R^{LA}$, wherein one or both carbons of said alkylene are optionally replaced with —O—, —N($R^{++}$)—, —S—, —S(O)—, or —S(O)$_2$—; and each $R^{LA}$ is, independently, selected from —O$R^{++}$, —O(halo($C_{1-4}$ aliphatic)), —S$R^{++}$, or $C_{1-4}$ aliphatic, each of which is optionally substituted with up to three substituents independently selected from halogen, —OH, —O$R^{++}$, —S$R^{++}$, —NO$_2$, —CN, —N($R^{++}$)$_2$; or two $R^{LA}$ together on the same carbon atom are =O, =S, =NN($R^{++}$)$_2$, =NNHC(O)($R^{++}$), =NNHC(O)O$R^{++}$, =NNHS(O)$_2$($R^{++}$), or =N($R^{++}$); or two $R^{LA}$ together on the same carbon atom form a $C_{3-5}$ cycloalkyl, an ethylenedioxy, or an ethylenedithio;

$R^A$ is selected from:

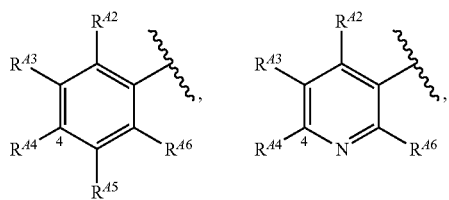

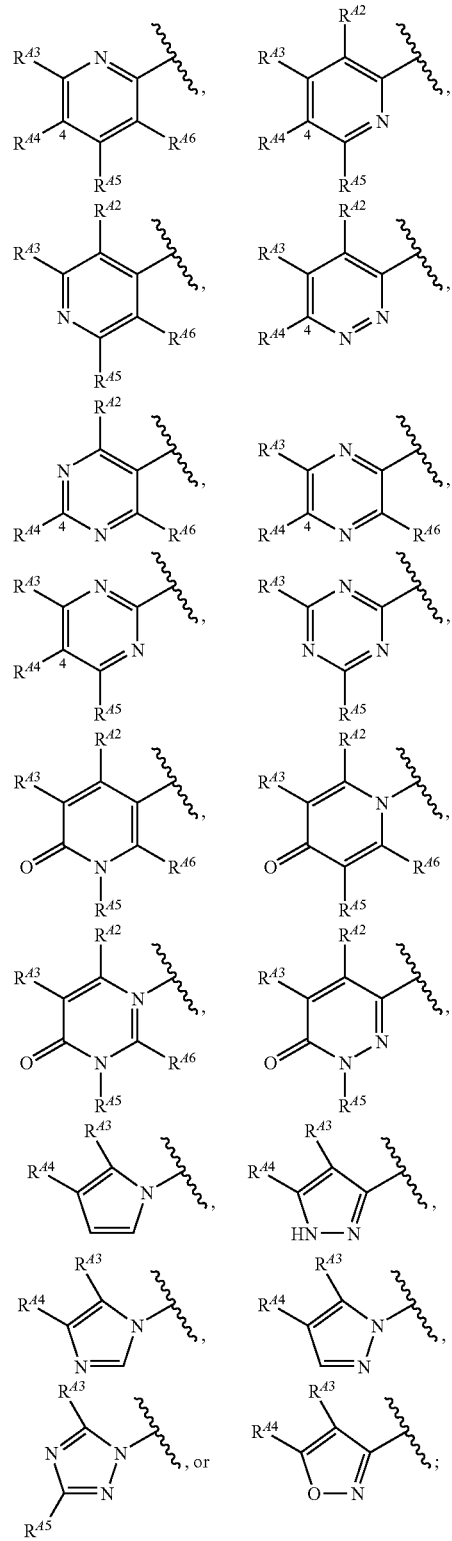

each of $R^{A2}$ and $R^{A6}$ is, independently, selected from hydrogen, halogen, —CN, —C(O)O$R^{++}$, —C(O)$R^{++}$, —C(O)N($R^{++}$)$_2$, —C(S)N($R^{++}$)$_2$, —C(NH)N($R^{++}$)$_2$, —O$R^{++}$, —O(halo($C_{1-4}$ aliphatic)), —OC(O)N($R^{++}$)$_2$, —S$R^{++}$, —NO$_2$, —N($R^{++}$)$_2$, —N($R^{++}$)C(O)($R^{++}$), —N($R^{++}$)C(O)

N(R$^{++}$)$_2$, —N(R$^{++}$)C(O)OR$^{++}$, —N(R$^{++}$)N(R$^{++}$)C(O)R$^{++}$, —N(R$^{++}$)N(R$^{++}$)C(O)N(R +)$_2$, —N(R$^{++}$)N(R$^{++}$)C(O)OR, —N(R$^{++}$)S(O)$_2$N(R$^{++}$)$_2$, —N(R$^{++}$)S(O)$_2$R$^{++}$, —S(O)$_2$R$^{++}$, —S(O)$_2$N(R$^{++}$)$_2$, —S(O)R$^{++}$, and C$_{1-4}$ aliphatic optionally substituted with substituents independently selected from halogen, —OR$^{++}$, —SR$^{++}$, —NO$_2$, —CN, —N(R$^{++}$)$_2$, or —N(R)C(O)(R$^{++}$);

R$^{43}$ is R$^{Ar}$; or R$^{43}$, R$^{44}$ and the carbons to which they are bonded form a 6 membered aryl ring optionally substituted with up to 4 independent occurrences of R$^{Ar}$, or a 5-6 membered heterocyclyl or heteroaryl ring containing at least one O, N, or S, wherein said heterocyclyl or heteroaryl ring is optionally substituted with up to 3 independent occurrences of R$^{Ar}$;

R$^{44}$ is —OH, —B(OR*)$_2$, —SR*, —N(R*)$_2$, —N(R*)C(O)R*, —N(R*)C(O)N(R*)$_2$, —N(R*)C(O)OR*, —N(R*)N(R*)C(O)R*, —N(R*)N(R*)C(O)N(R*)$_2$, —N(R*)N(R*)C(O)OR*, —N(R*)S(O)$_2$N(R*)$_2$, —N(R*)S(O)$_2$R*, —C(O)OR*, —C(O)N(R*)$_2$;

R$^{45}$ is hydrogen or R$^{Ar}$;

L$^B$ is a covalent bond between R$^B$ and the carbon to which L$^B$ is bonded or is a saturated or unsaturated C$_{1-4}$ alkylene chain optionally substituted with up to 5 groups, independently selected from halogen, C$_{1-4}$ aliphatic, halo(C$_{1-4}$ aliphatic), —OR$^{++}$, —O(halo(C$_{1-4}$ aliphatic)), —NO$_2$, —CN, —C(O)OR$^{++}$, —C(O)N(R$^{++}$)$_2$, or —N(R$^{++}$)$_2$, wherein up to two saturated carbons of said alkylene chain are optionally replaced by —C(O)—, —C(O)N(R$^{++}$)—, —C(O)N(R$^{++}$)N(R$^{++}$)—, —C(O)O—, —N(R$^{++}$)—, —N(R$^{++}$)C(O)—, —N(R$^{++}$)C(O)O—, —N(R$^{++}$)S(O)$_2$—, —N(R$^{++}$)C(O)N(R$^{++}$)—, —N(R$^{++}$)N(R$^{++}$)—, —O—, —OC(O)—, —OC(O)N(R$^{++}$)—, —S—, —S(O)—, —S(O)$_2$—, or —S(O)$_2$N(R$^{++}$)—;

R$^B$ is halogen, NH$_2$, or a C$_{1-8}$ aliphatic group, optionally substituted with R; a 6-10 membered aryl ring; a 3-7 membered carbocyclic ring, a 5-10 membered heteroaryl ring having 1-4 heteroatoms independently selected from nitrogen, oxygen, and sulfur; or a 3-10 membered heterocyclyl ring having 1-4 heteroatoms independently selected from nitrogen, oxygen, and sulfur; wherein each of said aryl, heteroaryl, or heterocyclyl rings is optionally substituted with up to five independent occurrences of R$^{Ar}$;

each R$^C$ is, independently, —CN, —NO$_2$, R$^{++}$, or —O(C$_{1-4}$ aliphatic);

R is halogen, —R$^o$, —OR$^o$, —SR$^o$, —OC(O)(C$_{1-8}$ aliphatic), Ph optionally substituted with R$^o$, —O(Ph) optionally substituted with R$^o$, —CH$_2$(Ph) optionally substituted with R$^o$, —CH$_2$CH$_2$(Ph) optionally substituted with R$^o$, —NO$_2$, —CN, —N(R$^o$)$_2$, —NR$^o$C(O)R$^o$, —NR$^o$C(O)N(R$^o$)$_2$, —NR$^o$C(O)OR$^o$, —NR$^o$NR$^o$C(O)R$^o$, —NR$^o$NR$^o$C(O)N(R$^o$)$_2$, —NR$^o$NR$^o$C(O)OR$^o$, —C(O)C(O)R$^o$, —C(O)CH$_2$C(O)R$^o$, —C(O)OR$^o$, —C(O)R$^o$, —C(O)N(R$^o$)$_2$, —OC(O)N(R$^o$)$_2$, —S(O)$_2$R$^o$, —S(O)$_2$N(R$^o$)$_2$, —S(O)R$^o$, —NR$^o$S(O)$_2$N(R$^o$)$_2$, —NR—S(O)$_2$R$^o$, —C(=S)N(R$^o$)$_2$, —C(=NH)—N(R$^o$)$_2$, or —(CH$_2$)$_y$NHC(O)R$^o$, wherein y is 1 to 4; or two R together on the same carbon atom are =O, =S, =NNHR*, =NN(R*)$_2$, =NNHC(O)R*, =NNHC(O)O(C$_{1-8}$ aliphatic), =NNHS(O)$_2$(C$_{1-8}$ aliphatic), or =NR*;

each R$^{Ar}$ is, independently, selected from halogen, —R$^o$, —OR$^o$, —SR$^o$, —OC(O)(C$_{1-8}$ aliphatic), Ph optionally substituted with up to five independent occurrences of —R$^o$, —CH$_2$ (Ph) optionally substituted with up to five independent occurrences of —R$^o$, —(CH$_2$)$_y$(Ph) optionally substituted with up to five independent occurrences of —R$^o$, —NO$_2$, —CN, —N(R$^o$)$_2$, —NR$^o$C(O)R$^o$, —NR$^o$C(O)N(R$^o$)$_2$, —NR$^o$C(O)OR$^o$, —NR$^o$NR$^o$C(O)R$^o$, —NR—NR$^o$C(O)N(R$^o$)$_2$, —NR$^o$NR$^o$C(O)OR$^o$, —C(O)CH$_2$C(O)R$^o$, —C(O)OR$^o$, —C(O)R$^o$, —C(O)N(R$^o$)$_2$, —OC(O)N(R$^o$)$_2$, —S(O)$_2$R$^o$, —S(O)$_2$N(R$^o$)$_2$, —S(O)R$^o$, —NR$^o$S(O)$_2$N(R$^o$)$_2$, —NR$^o$S(O)$_2$R$^o$, —C(S)N(R$^o$)$_2$, —C(NH)N(R$^o$)$_2$, and —(CH$_2$)$_y$NHC(O)R$^o$, wherein y is 1 to 4; or two adjacent R$^{Ar}$ groups taken together are 1,2-methylenedioxy or 1,2-ethylenedioxy;

each R$^{++}$ is independently, hydrogen or C$_{1-4}$ aliphatic;

each R* is, independently, hydrogen or C$_{1-8}$ aliphatic optionally substituted with up to five independent occurrences of —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —C(O)NH$_2$, —C(O)NH(C$_{1-4}$ aliphatic), —C(O)N(C$_{1-4}$ aliphatic)$_2$, —O(halo(C$_{1-4}$ aliphatic)), or halo(C$_{1-4}$ aliphatic); or two R* on the same nitrogen are taken together with the nitrogen to form a 5-8 membered heterocyclyl or heteroaryl ring having 1-3 heteroatoms independently selected from nitrogen, oxygen, and sulfur;

each R$^o$ is, independently, hydrogen, optionally substituted C$_{1-6}$ aliphatic, an unsubstituted 5-6 membered heteroaryl or heterocyclic ring, -Ph, or —O(Ph), wherein each substituent of said optionally substituted aliphatic of R$^o$ is, independently, —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —C(O)NH$_2$, —C(O)NH(C$_{1-4}$ aliphatic), —C(O)N(C$_{1-4}$ aliphatic)$_2$, —O(halo(C$_{1-4}$ aliphatic)), or halo(C$_{1-4}$ aliphatic); or two R$^o$ on the same nitrogen are taken together with the nitrogen to form a 5-8 membered heterocyclyl or heteroaryl ring having 1-3 heteroatoms independently selected from nitrogen, oxygen, and sulfur; and with the proviso that when L$^A$R$^A$ is —S—CH$_2$-pyridyl, then L$^B$R$^B$ is not —S—CH$_2$-pyridyl.

In one aspect, the compound of formula I is a triazolothiadiazole having the formula:

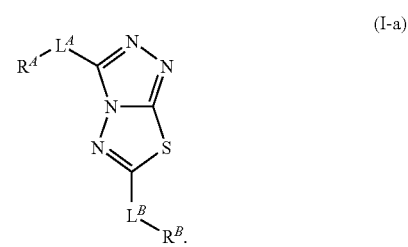

(I-a)

In another aspect, the compound of formula I is a triazolopyridazine having the formula:

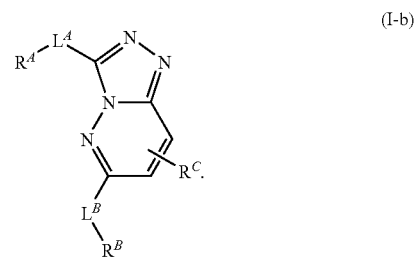

(I-b)

In one embodiment, R$^C$ is hydrogen.

In yet another aspect, the compound of formula I is a triazolothiadiazine having the formula:

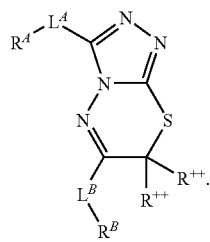

(I-c)

In one embodiment, R⁺⁺ is hydrogen.

In another embodiment, for any compound of formula I, I-a, I-b, or I-c, $L^A$ is selected from: a $C_{1-2}$ alkylene, optionally substituted with 1-4 $R^{LA}$, wherein one or both carbons of said alkylene are optionally replaced with —O—, —S—, —S(O)—, or —S(O)$_2$—; and each $R^{LA}$ is, independently, selected from —OR⁺⁺, —O(halo($C_{1-4}$ aliphatic)), —SR⁺⁺, and $C_{1-4}$ aliphatic, each of which optionally substituted with up to three substituents independently selected from halogen, —OH, —OR⁺⁺, —SR⁺⁺, —NO$_2$, —CN, —N(R⁺⁺)$_2$; or two $R^{LA}$ together on the same carbon atom are =O, =S, =NN(R⁺⁺)$_2$, =NNHC(O)(R⁺⁺), =NNHC(O)OR⁺⁺, =NNHS(O)$_2$(R⁺⁺), or =N(R⁺⁺); or two $R^{LA}$ together on the same carbon atom form a $C_{3-5}$ cycloalkyl, an ethylenedioxy, or an ethylenedithio. Examples include the following linkers:

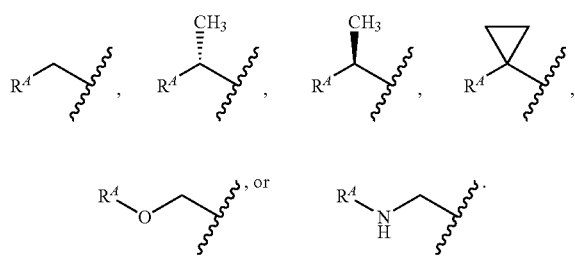

In one embodiment for a any compound of formula I, I-a, I-b, or I-c, $R^A$ is selected from:

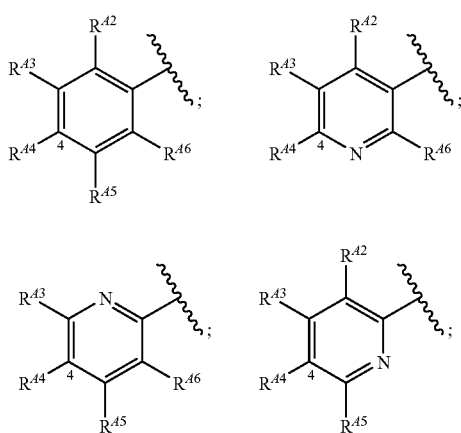

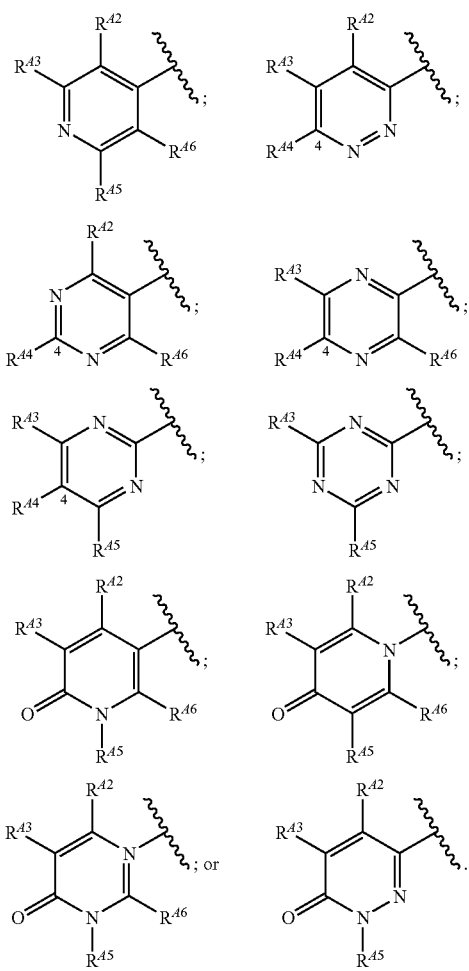

In another embodiment for a any compound of formula I, I-a, I-b, or I-c, $R^A$ is selected from:

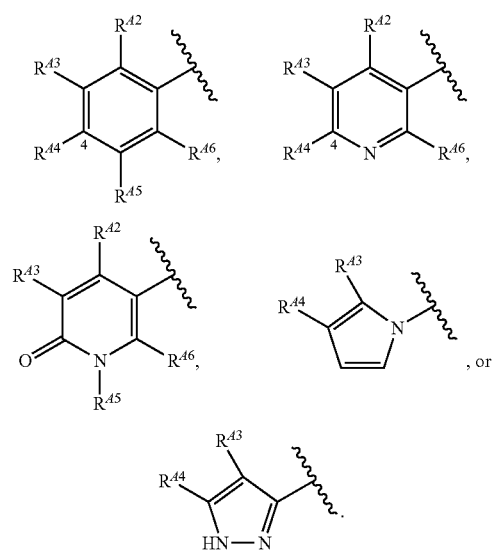

For those compounds of formula I, I-a, I-b, or I-c where $R^A$ comprises a bicyclic system, $R^{A3}$, $R^{A4}$ and the carbons to which they are bonded optionally form a heterocyclyl or heteroaryl ring selected from:

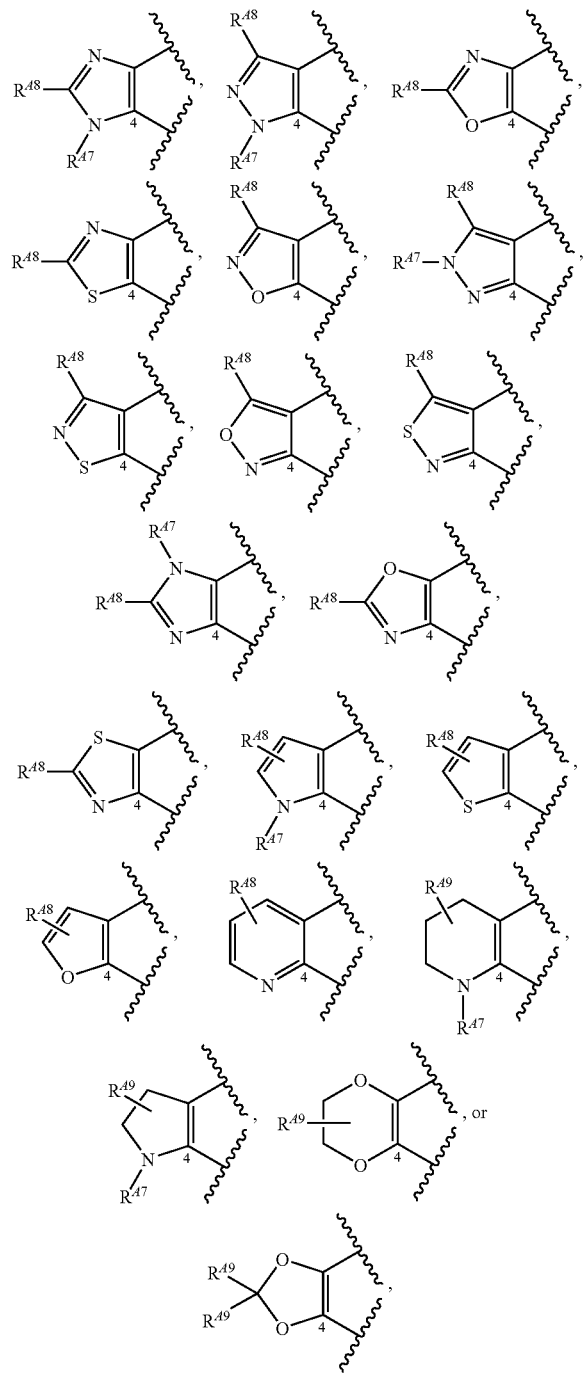

wherein the 4-position of the ring defined by $R^A$ is as indicated and, each $R^{A7}$ is, independently, hydrogen, —R°, —N(R°)$_2$, —NR°C(O)R°, —NR°C(O)N(R°)$_2$, —NR°CO$_2$R°, —C(O)CH$_2$C(O)R°, —CO$_2$R°, —C(O)C(O)R°, —C(O)R°, —C(O)N(R°)$_2$, —S(O)$_2$R°, —C(=S)N(R°)$_2$, —C(=NH)—N(R°)$_2$, or —(CH$_2$)$_j$NHC(O)R°;

each $R^{A8}$ is, independently, hydrogen, halogen, —CN, —CO$_2$R$^{++}$, —C(O)R$^{++}$, —C(O)N(R)$_2$, —C(S)N(R$^{++}$)$_2$, —C(NH)N(R$^{++}$)$_2$, —OR$^{++}$, —O(halo(C$_{1-4}$ aliphatic)), —OC(O)N(R$^{++}$)$_2$, —SR$^{++}$, —NO$_2$, —N(R$^{++}$)$_2$, —N(R$^{++}$)C(O)(R$^{++}$), —N(R$^{++}$)C(O)N(R$^{++}$)$_2$, —N(R$^{++}$)CO$_2$R$^{++}$, —N(R$^{++}$)N(R$^{++}$)C(O)R$^{++}$, —N(R$^{++}$)N(R$^{++}$)C(O)N(R$^{++}$)$_2$, —N(R$^{++}$)N(R$^{++}$)CO$_2$R$^{++}$, —N(R$^{++}$)SO$_2$N(R$^{++}$)$_2$, —N(R$^{++}$)SO$_2$R$^{++}$, —S(O)$_2$R$^{++}$, —SO$_2$N(R$^{++}$)$_2$, —S(O)R$^{++}$, or a C$_{1-4}$ aliphatic group optionally substituted with substituents independently selected from halogen, —OR$^{++}$, —SR$^{++}$, —NO$_2$, —CN, —N(R$^{++}$)$_2$, or —N(R$^{++}$)C(O)(R$^{++}$); and each $R^{A9}$ is, individually, hydrogen, F, Cl, C$_{1-4}$ aliphatic, or halo(C$_{1-4}$ aliphatic).

In one example, $R^A$ is

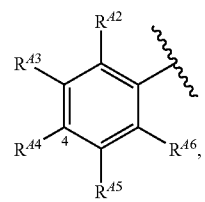

and $R^{A4}$ is OH.

In another example, $R^A$ is selected from:

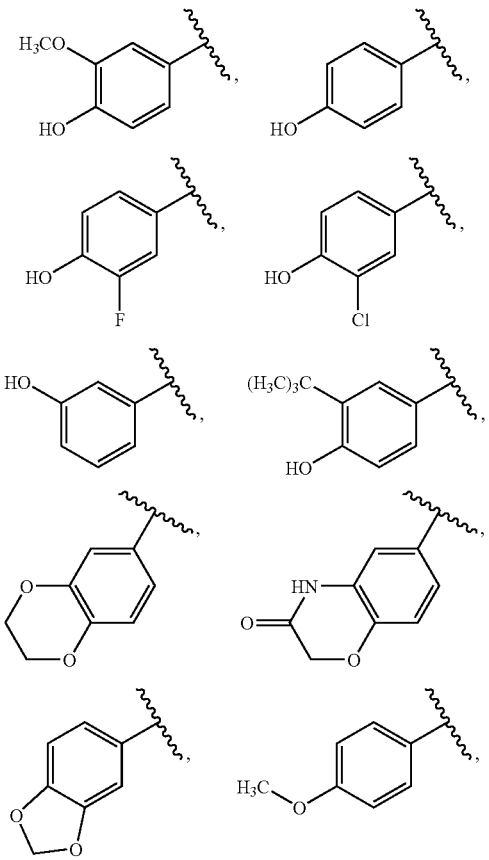

-continued
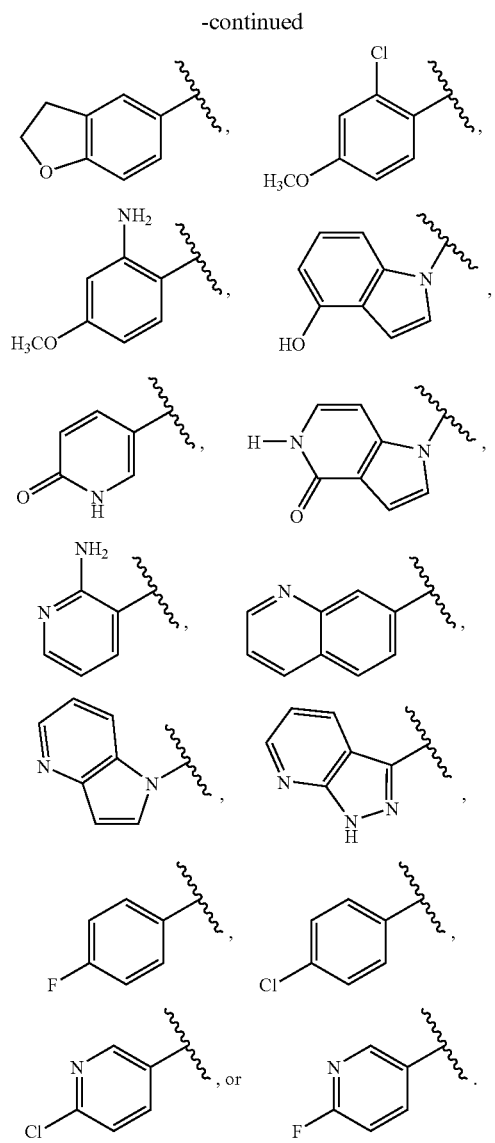
In another embodiment for any compound of formula I, I-a, I-b, or I-c, $L^B$ is a covalent bond, —CH$_2$—, or —N(R*)—.
In yet another embodiment for any compound of formula I, I-a, I-b, or I-c, $R^B$ is selected from the group consisting of:
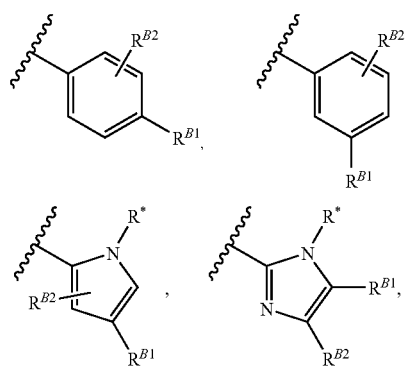
-continued
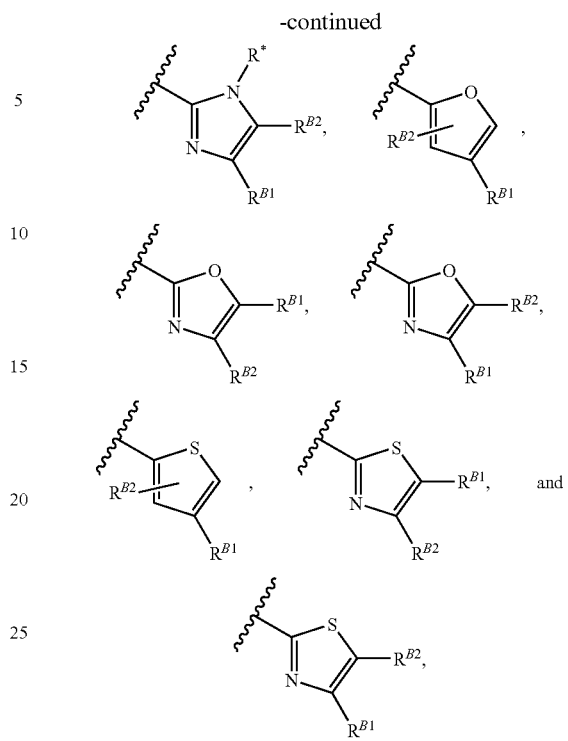
wherein each of $R^{B1}$ and $R^{B2}$ is, independently, hydrogen or $R^{Ar}$.
Examples of $L^B R^B$ groups include the following:
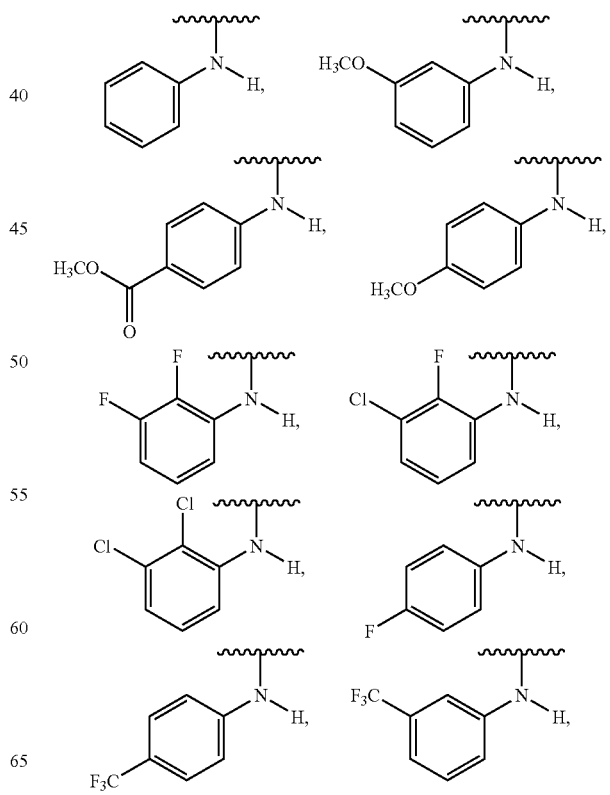

-continued
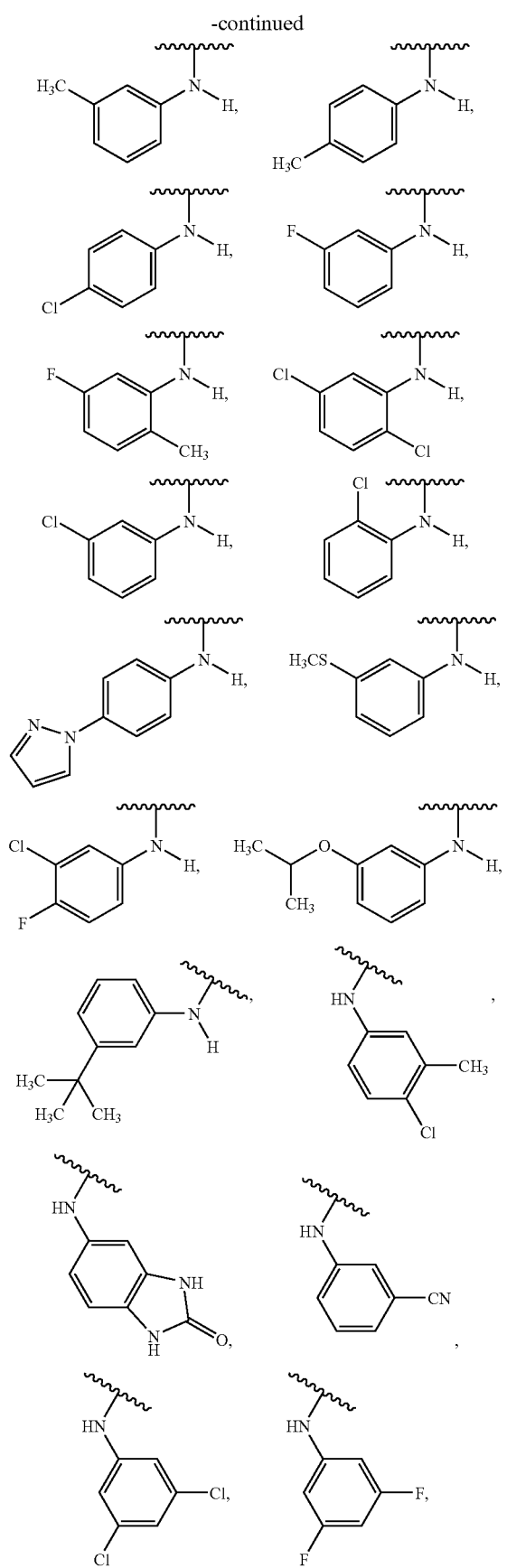
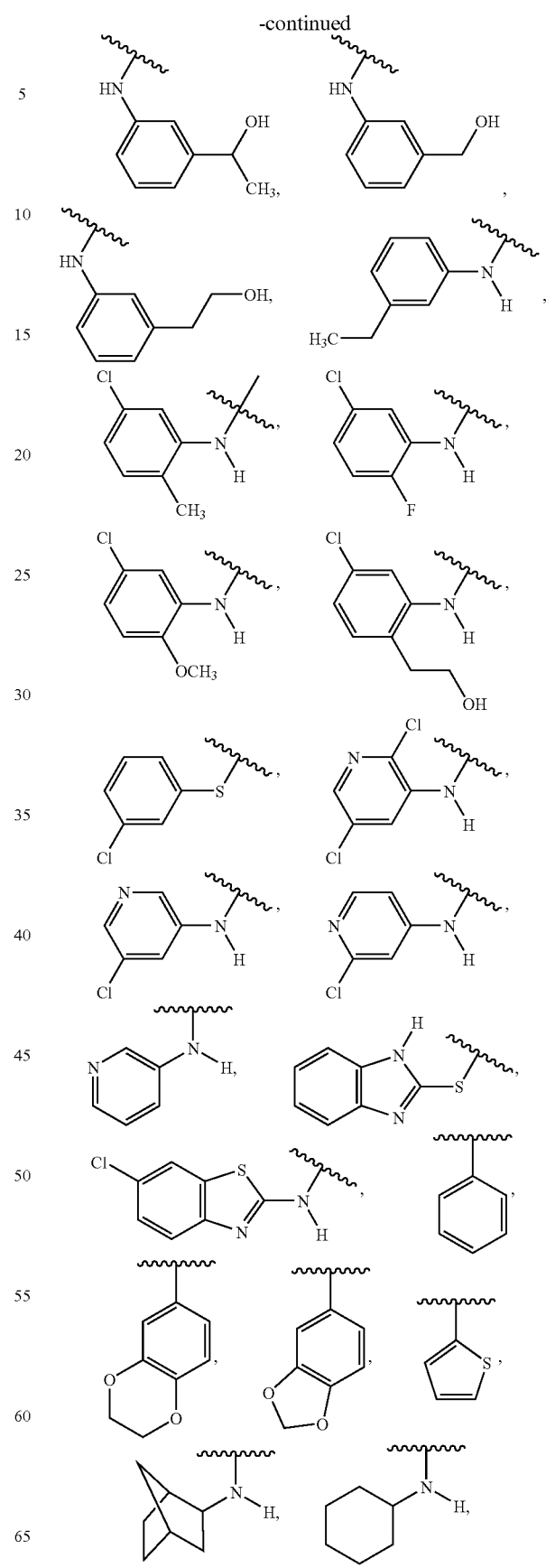

-continued
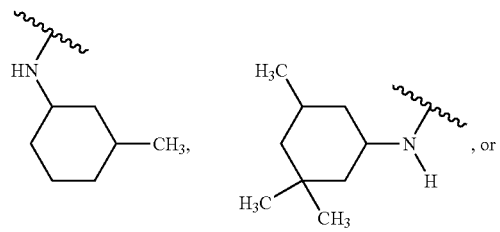
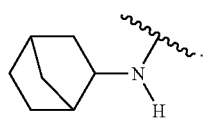
In another aspect, the invention features a compound selected from the group of compounds listed in Tables 1, 2, or 3.
TABLE 1
Compounds of formula Ia
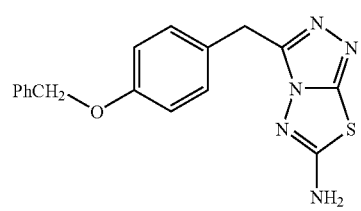
1
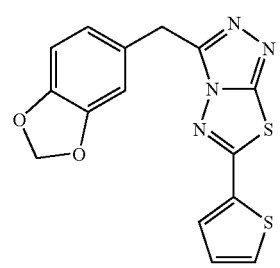
2
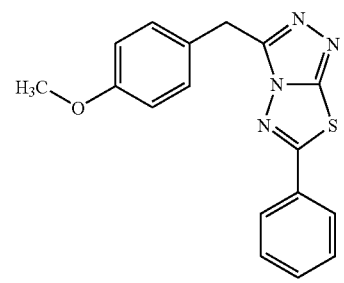
3
TABLE 1-continued
Compounds of formula Ia
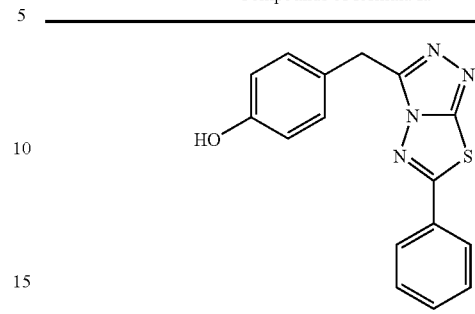
4
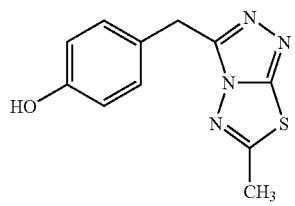
5
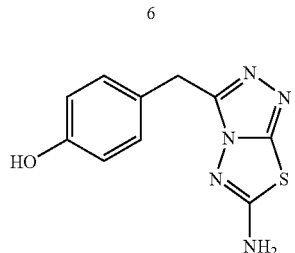
6
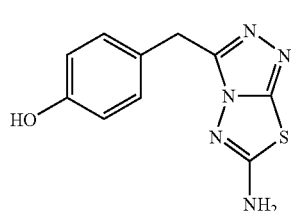
7
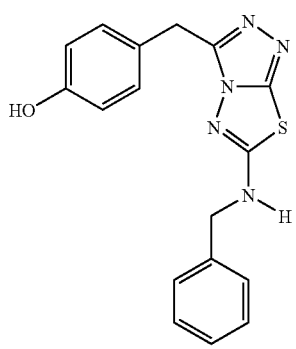
8

TABLE 1-continued

Compounds of formula Ia

TABLE 1-continued
Compounds of formula Ia
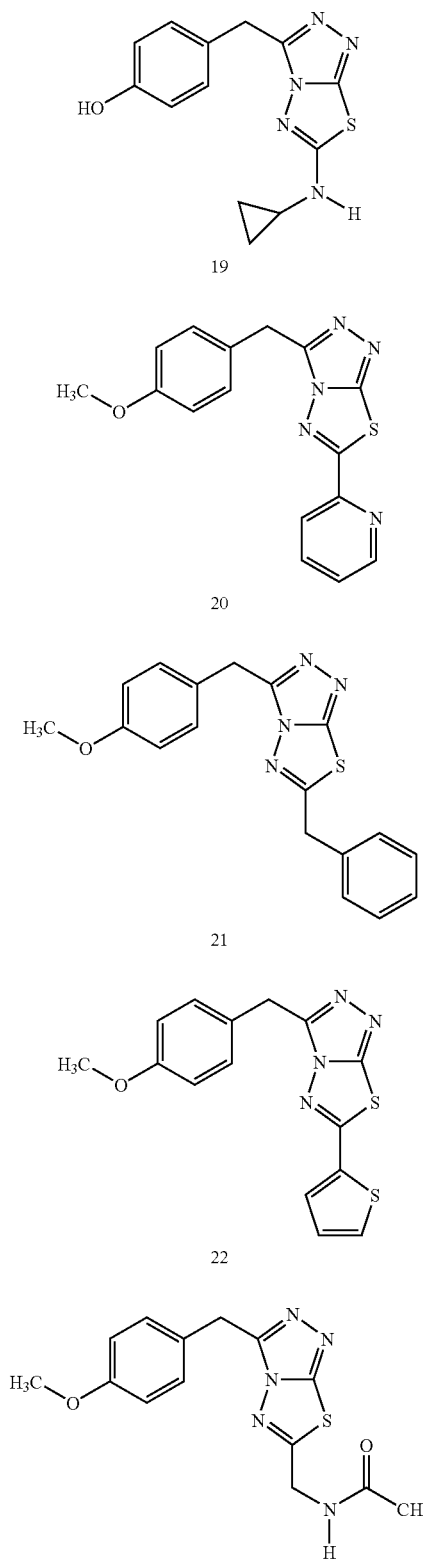
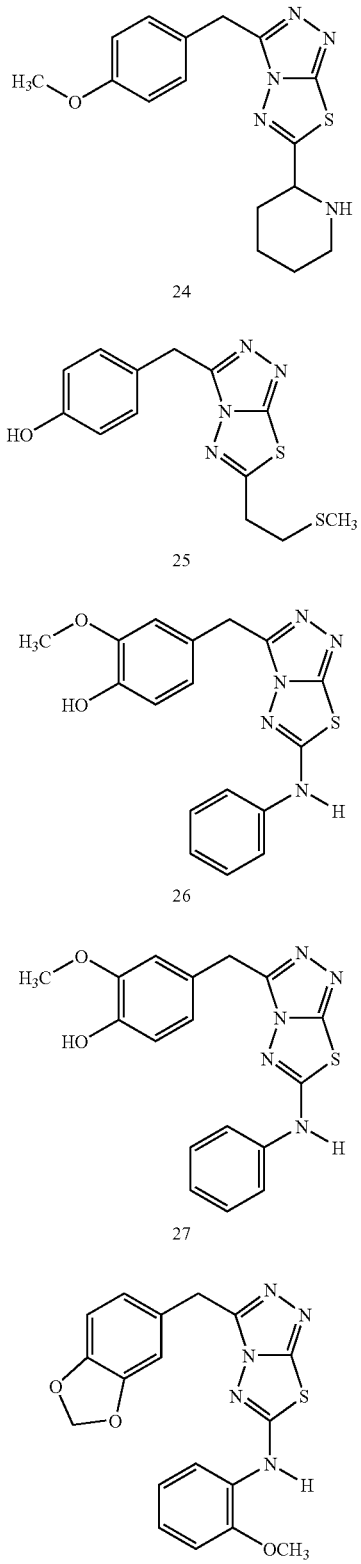

TABLE 1-continued
Compounds of formula Ia
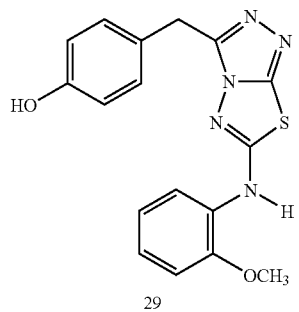
29
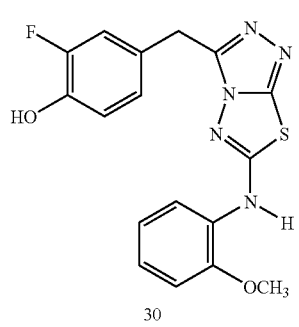
30
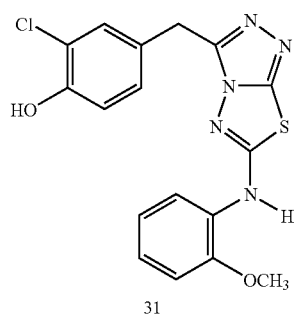
31
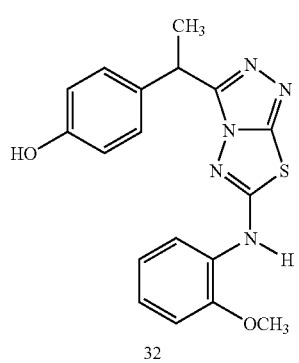
32
TABLE 1-continued
Compounds of formula Ia
33
34
35
36
37

TABLE 1-continued

Compounds of formula Ia

TABLE 1-continued
Compounds of formula Ia
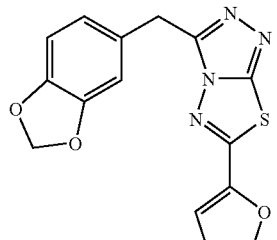
48
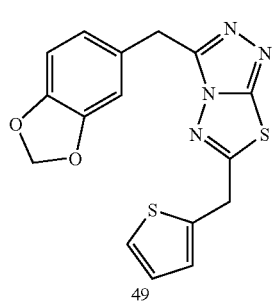
49
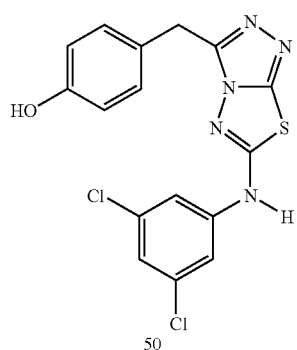
50
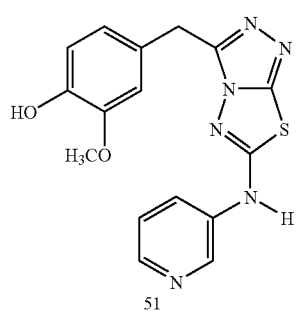
51
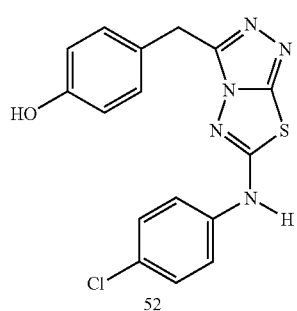
52
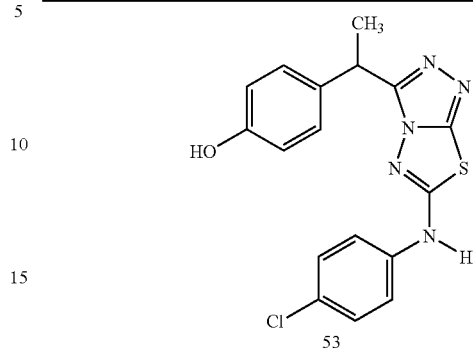
53
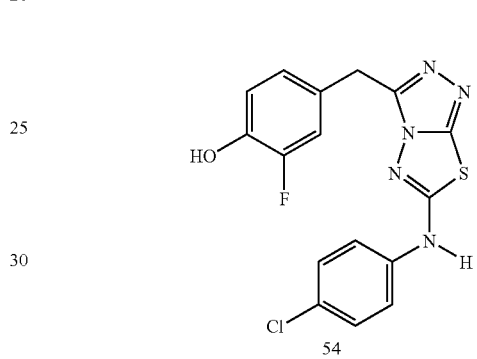
54
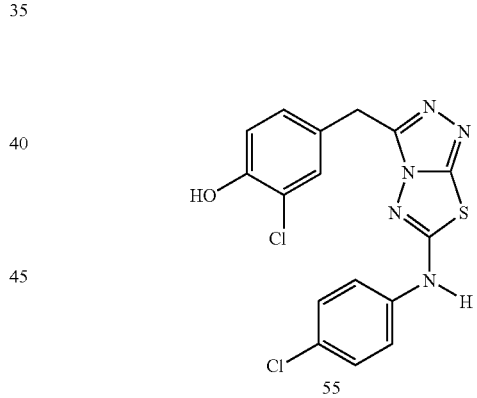
55
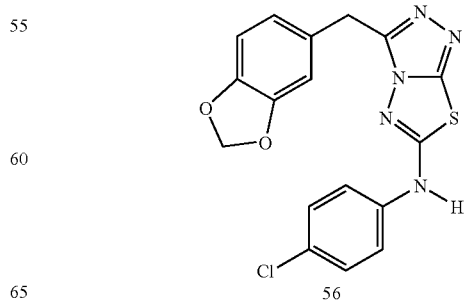
56

TABLE 1-continued
Compounds of formula Ia
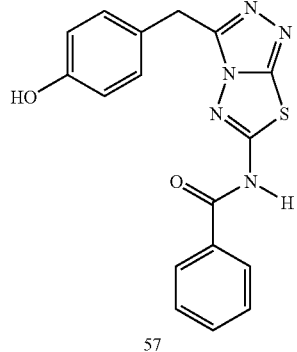
57
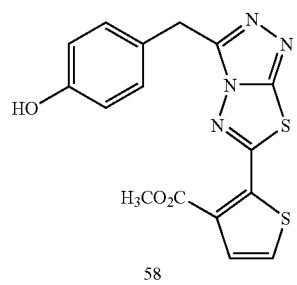
58
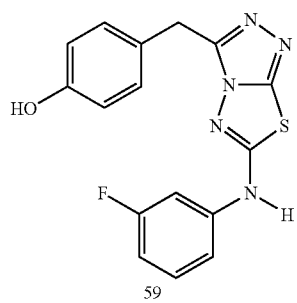
59
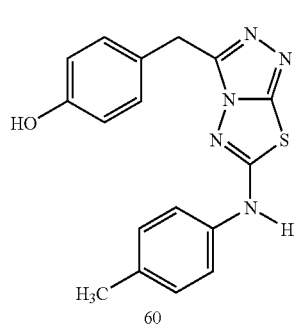
60
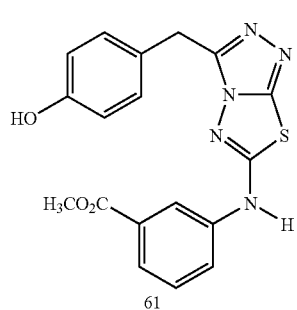
61
TABLE 1-continued
Compounds of formula Ia
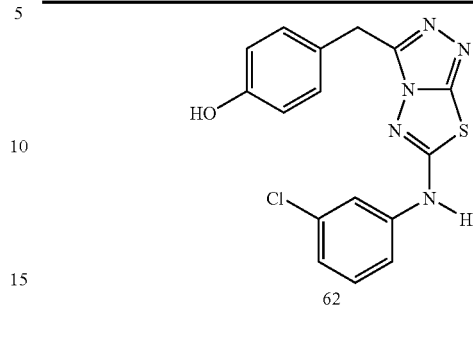
62
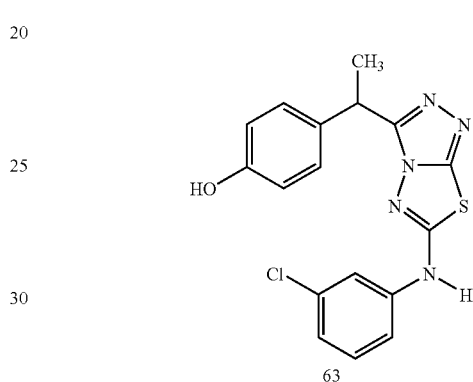
63
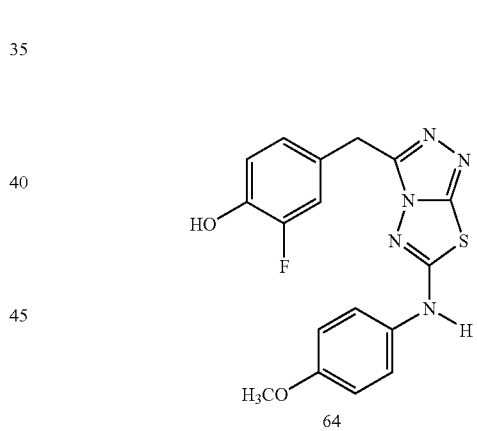
64
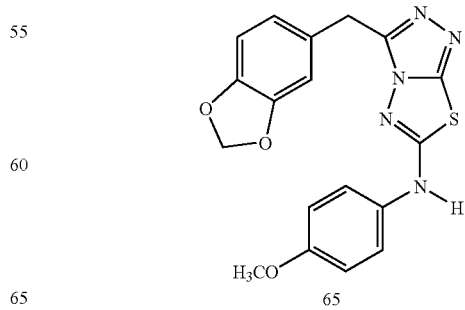
65

TABLE 1-continued
Compounds of formula Ia
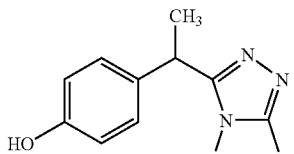
66
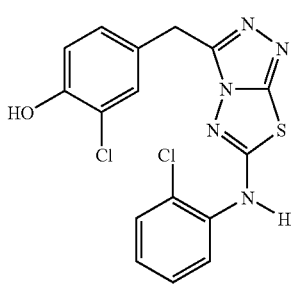
67
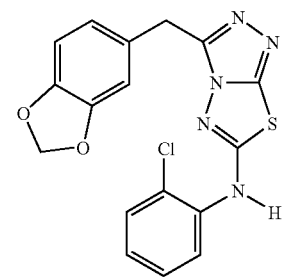
68
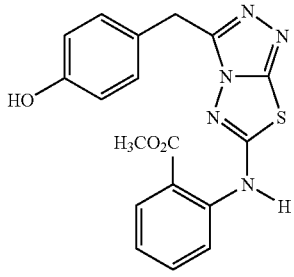
69
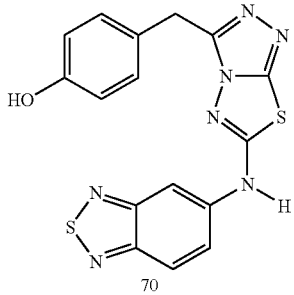
70
TABLE 1-continued
Compounds of formula Ia
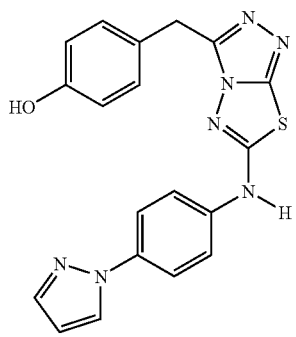
71
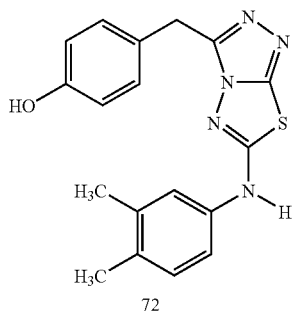
72
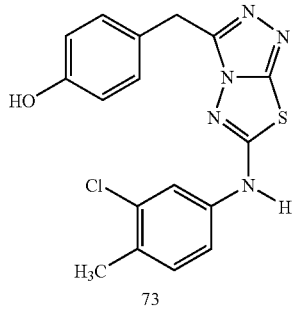
73
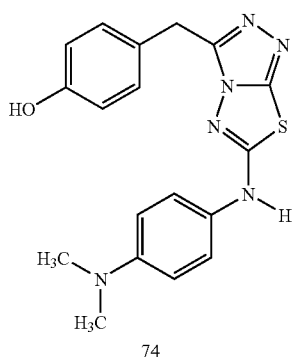
74

TABLE 1-continued
Compounds of formula Ia
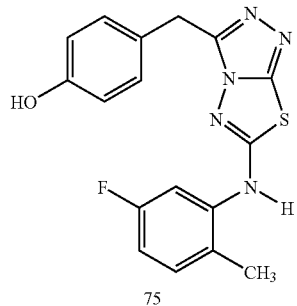
75
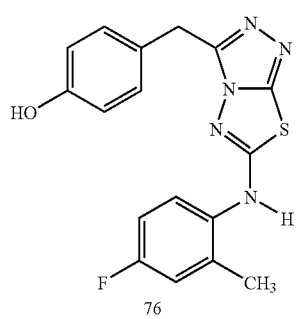
76
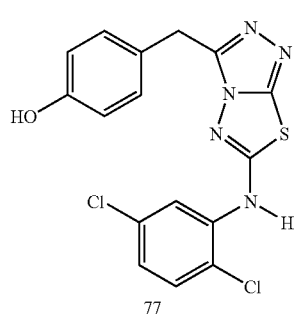
77
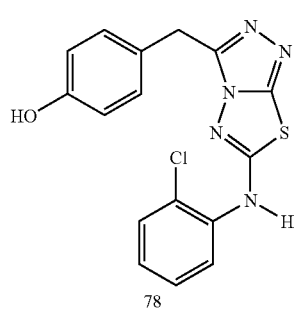
78
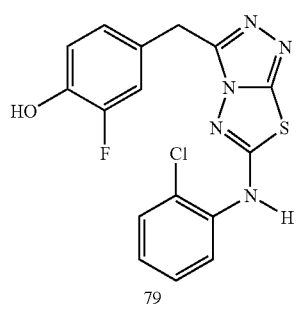
79
TABLE 1-continued
Compounds of formula Ia
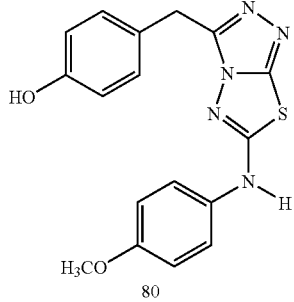
80
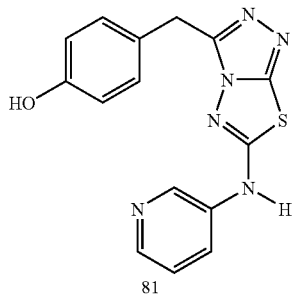
81
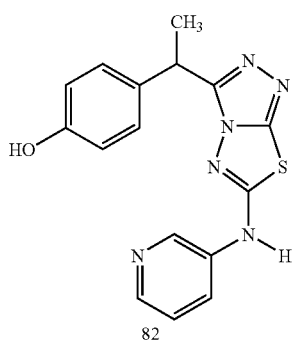
82
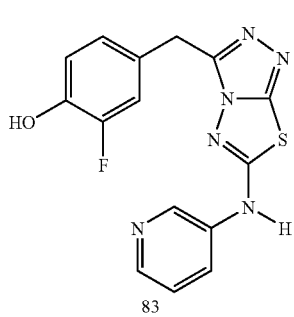
83
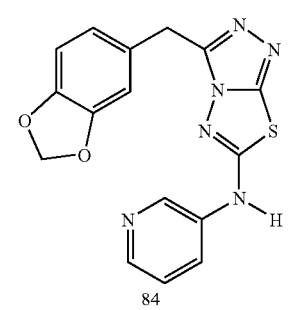
84

TABLE 1-continued
Compounds of formula Ia
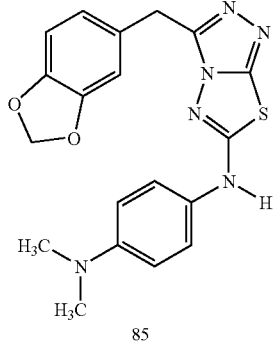
85
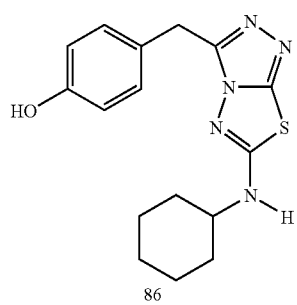
86
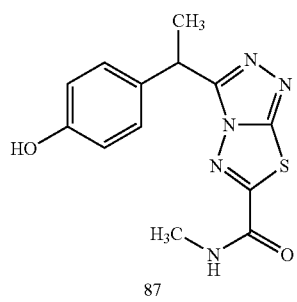
87
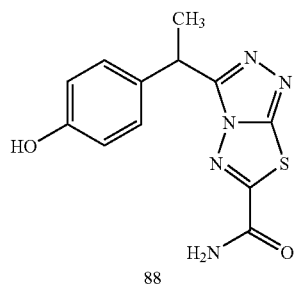
88
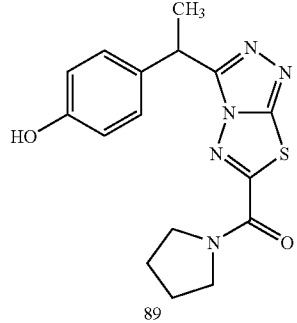
89
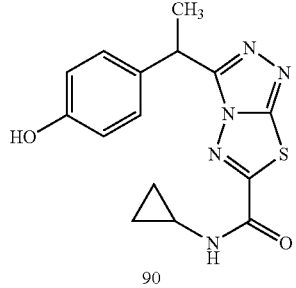
90
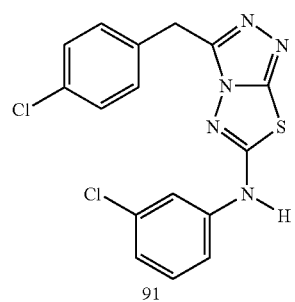
91
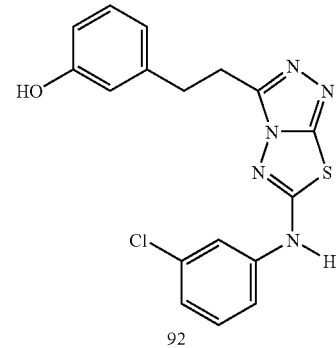
92
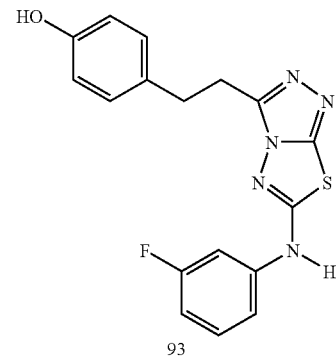
93

TABLE 1-continued
Compounds of formula Ia
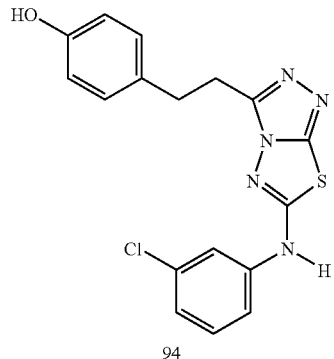
94
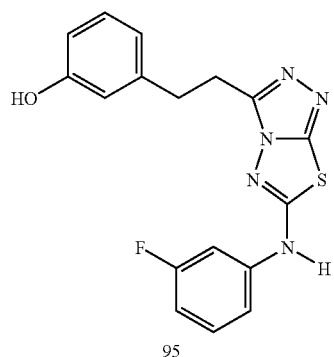
95
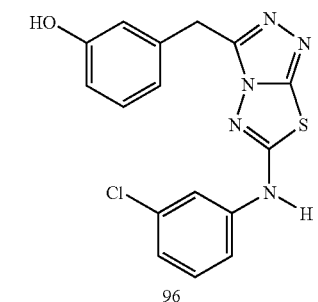
96
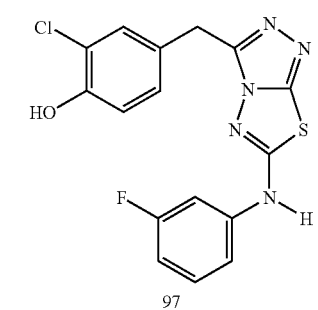
97
TABLE 1-continued
Compounds of formula Ia
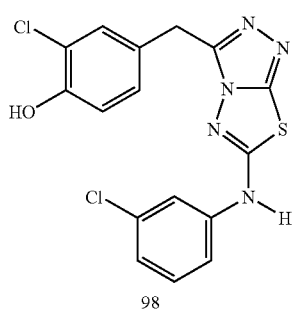
98
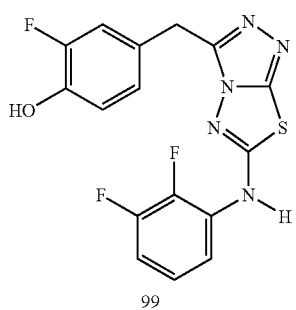
99
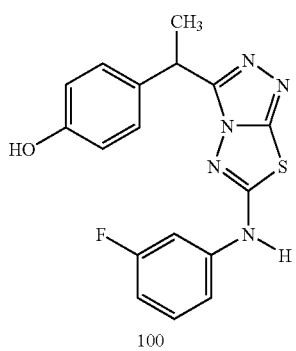
100
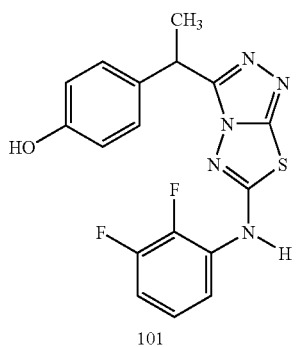
101

TABLE 1-continued
Compounds of formula Ia
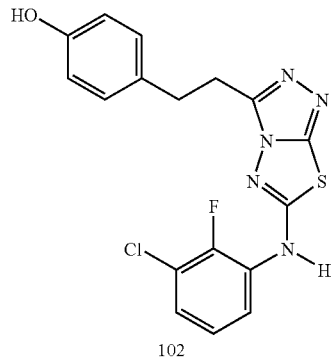
102
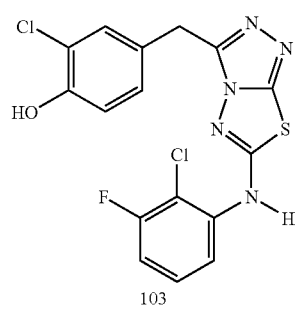
103
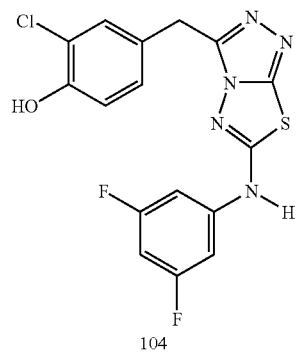
104
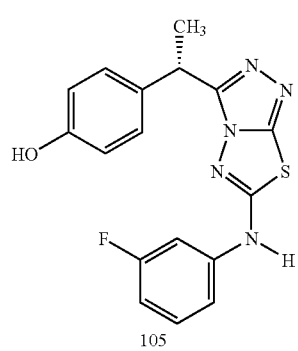
105
TABLE 1-continued
Compounds of formula Ia
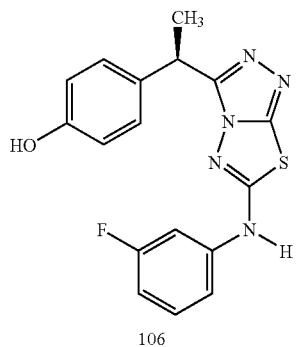
106
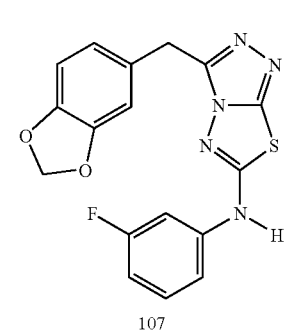
107
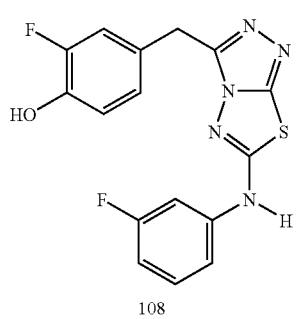
108
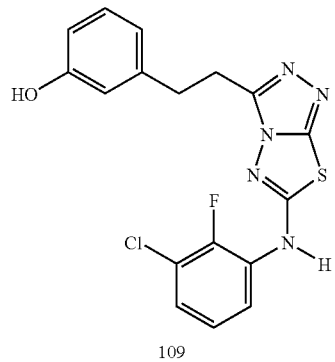
109

TABLE 1-continued
Compounds of formula Ia
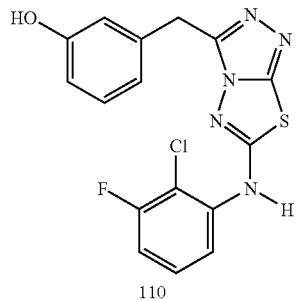
110
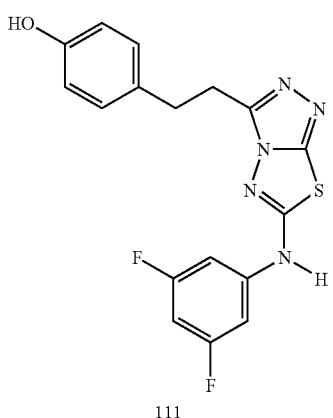
111
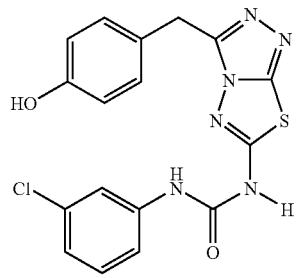
112
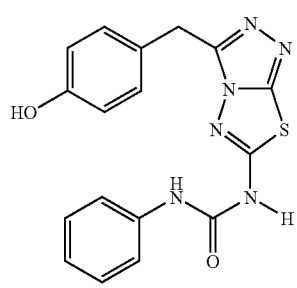
113
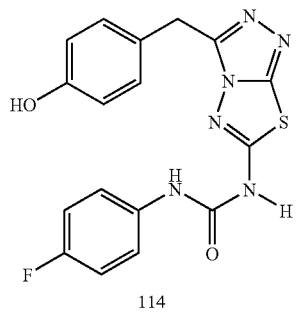
114
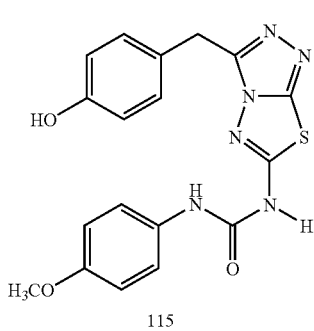
115
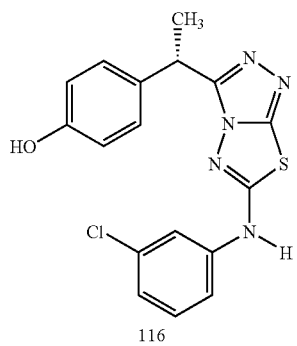
116
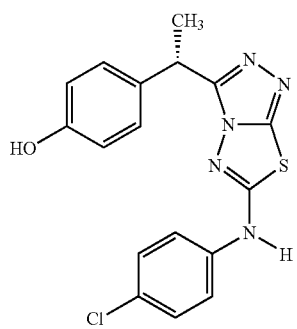
117

TABLE 1-continued
Compounds of formula Ia
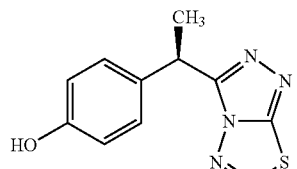
118
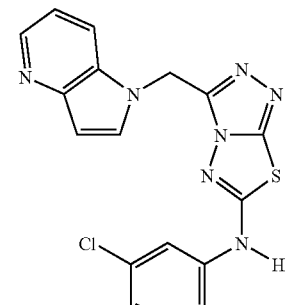
119
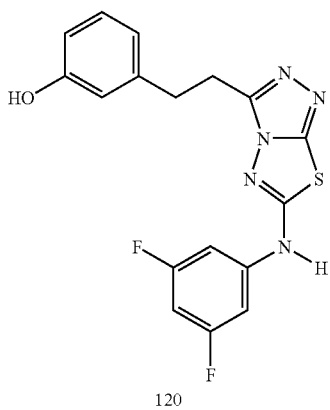
120
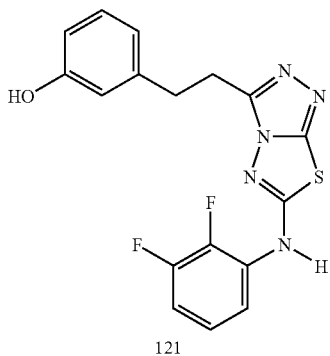
121
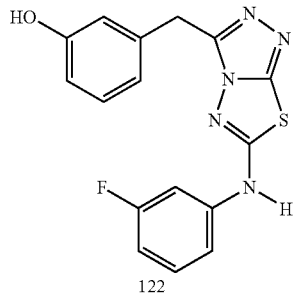
122
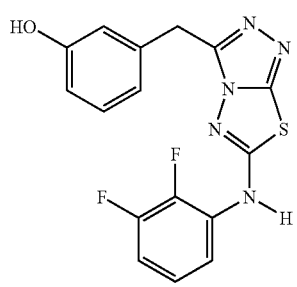
123
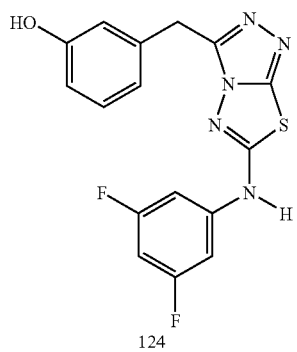
124
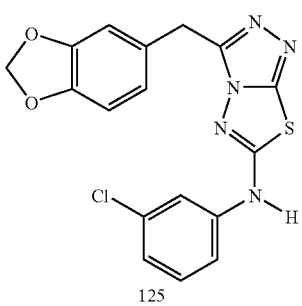
125
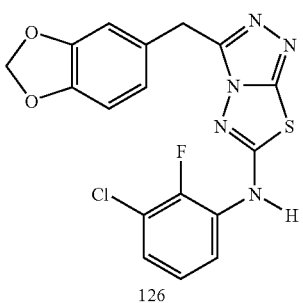
126

TABLE 1-continued
Compounds of formula Ia
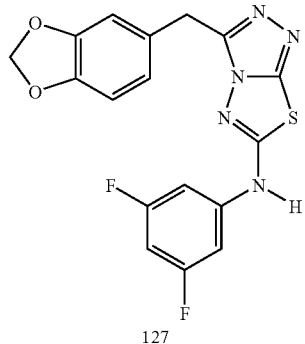
127
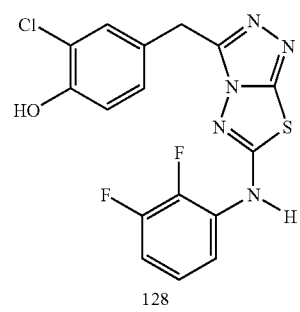
128
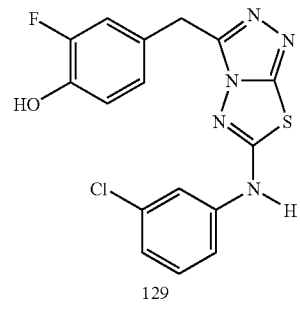
129
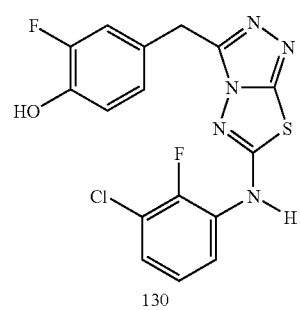
130
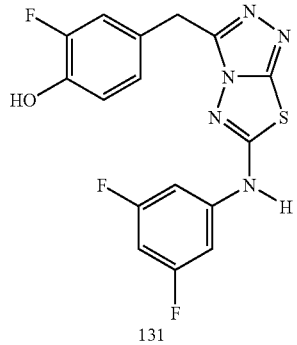
131
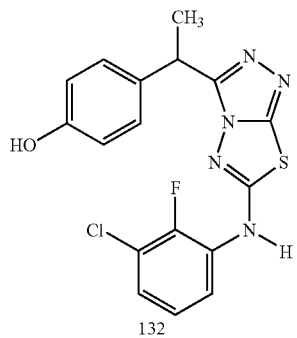
132
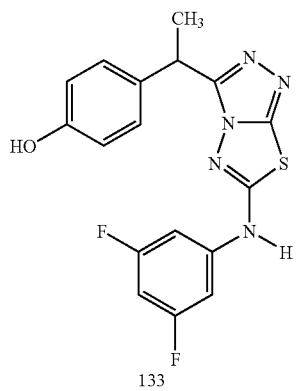
133
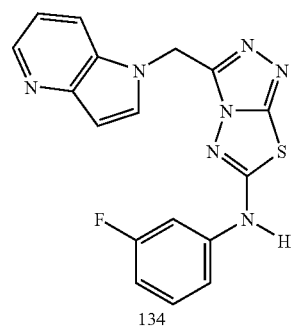
134

TABLE 1-continued
Compounds of formula Ia
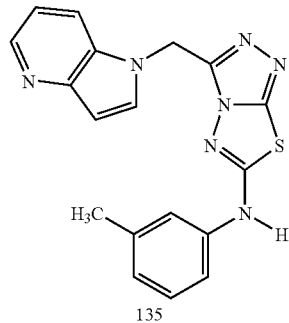
135
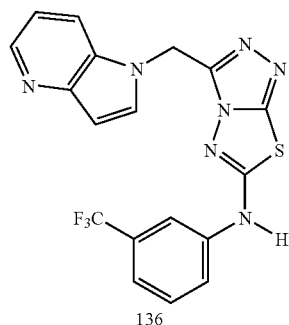
136
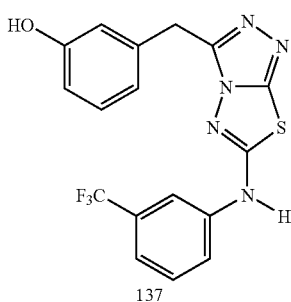
137
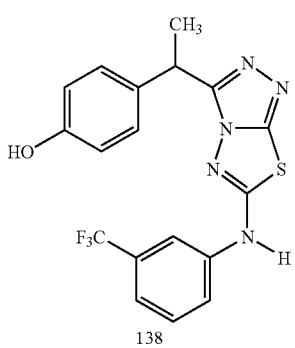
138
TABLE 1-continued
Compounds of formula Ia
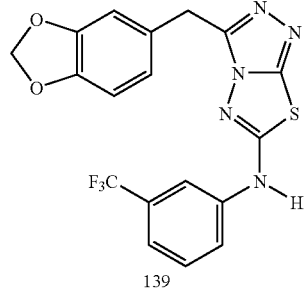
139
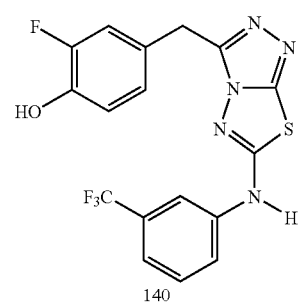
140
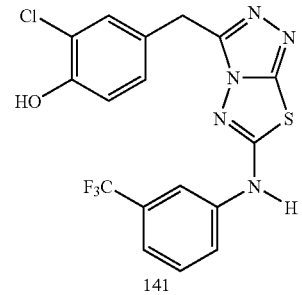
141
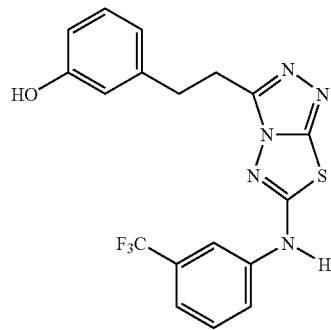
142
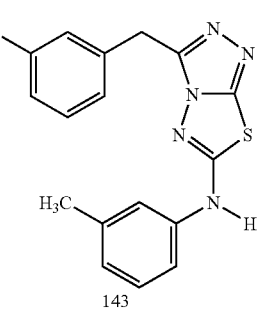
143

TABLE 1-continued
Compounds of formula Ia
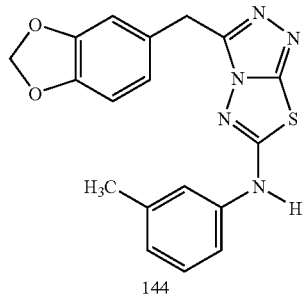
144
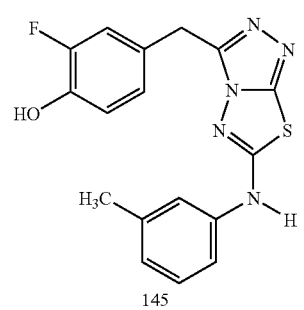
145
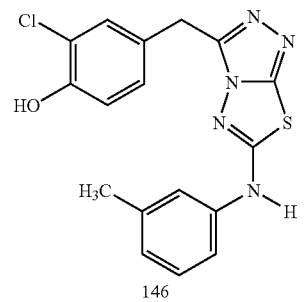
146
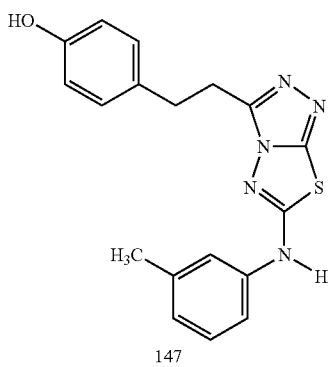
147
TABLE 1-continued
Compounds of formula Ia
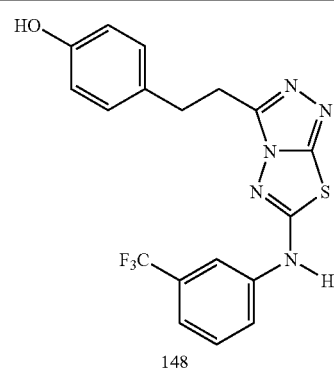
148
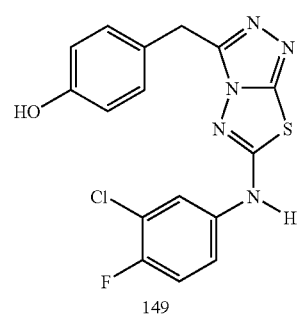
149
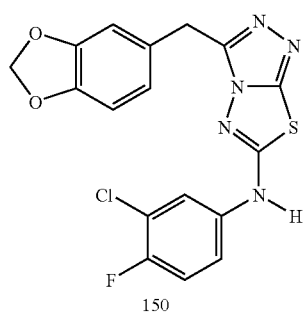
150
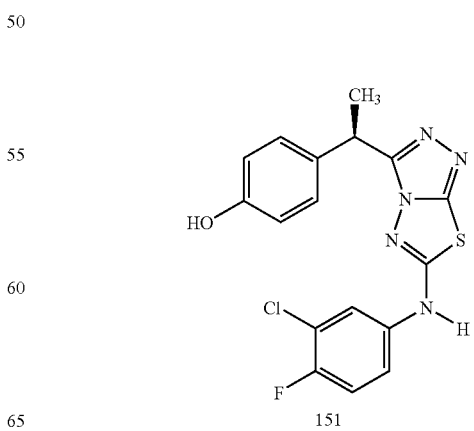
151

TABLE 1-continued
Compounds of formula Ia
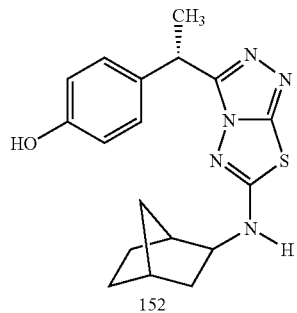
152
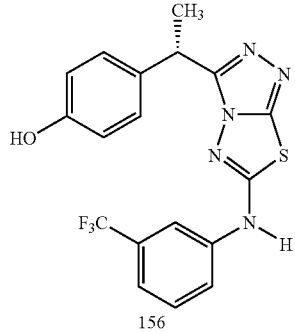
156
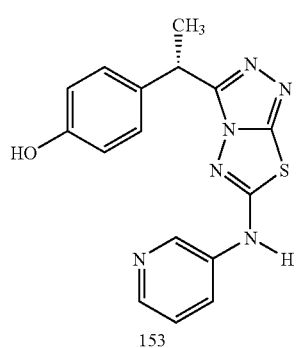
153
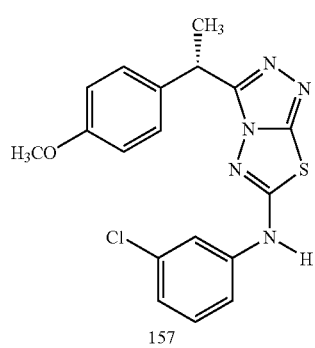
157
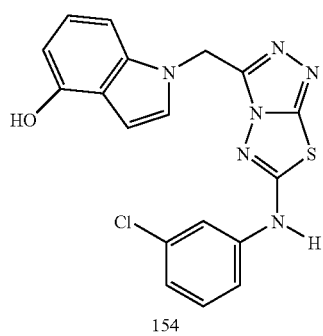
154
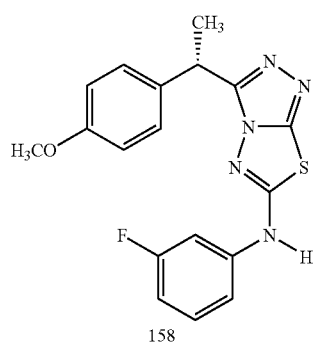
158
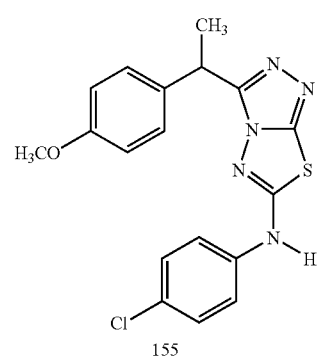
155
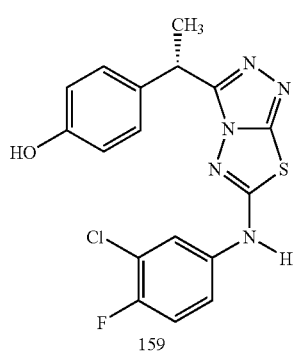
159

TABLE 1-continued
Compounds of formula Ia
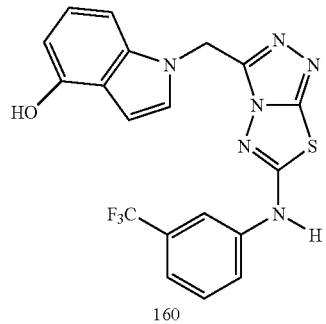
160
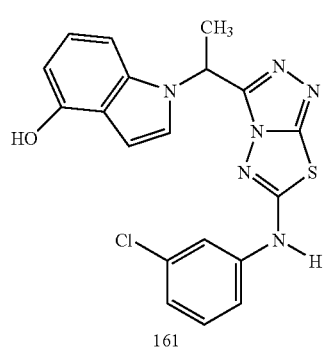
161
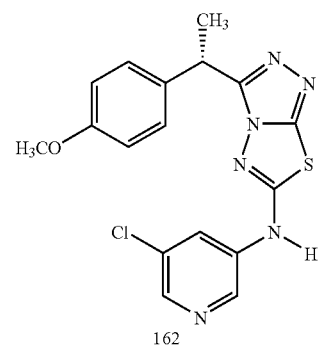
162
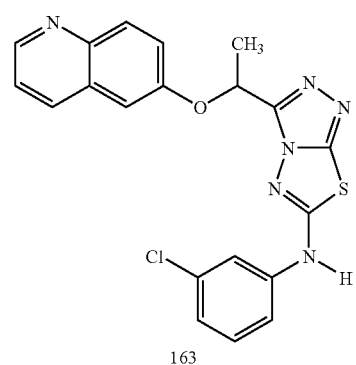
163
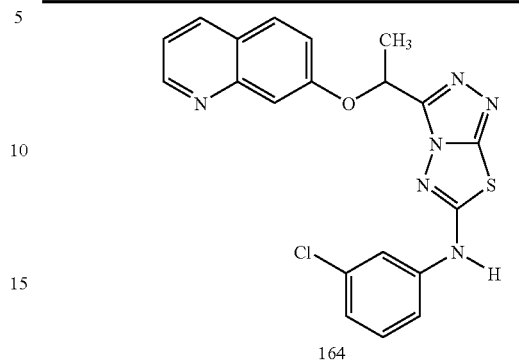
164
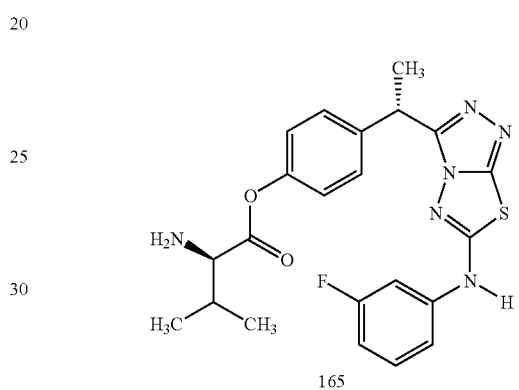
165
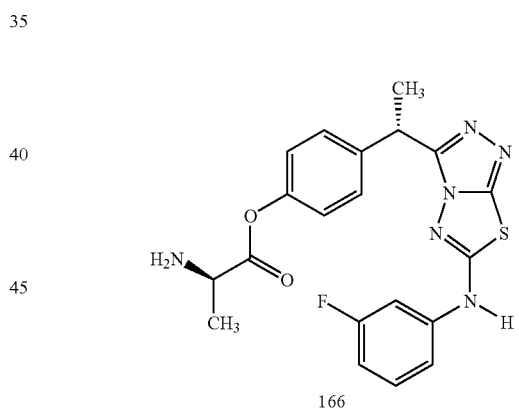
166
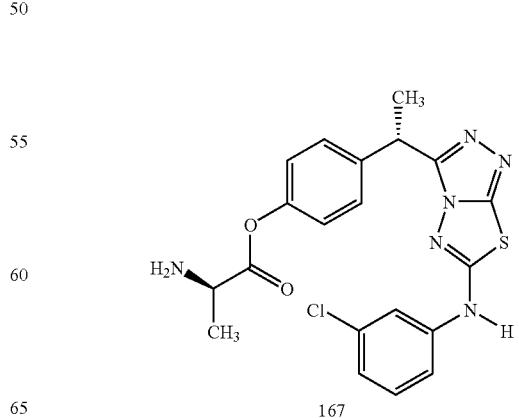
167

TABLE 1-continued
Compounds of formula Ia
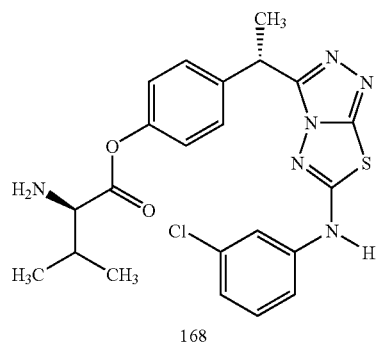
168
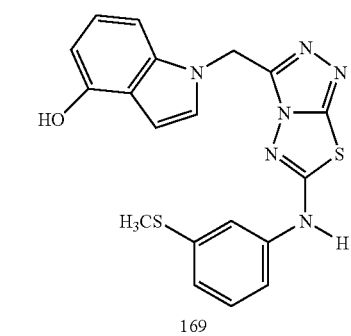
169
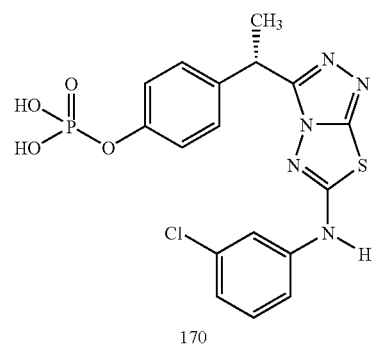
170
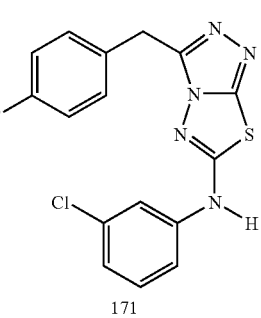
171
TABLE 1-continued
Compounds of formula Ia
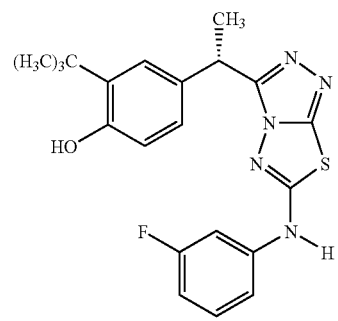
172
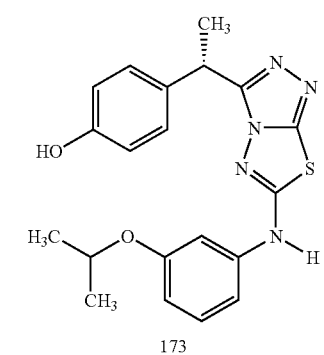
173
TABLE 2
Compounds of formula I-b
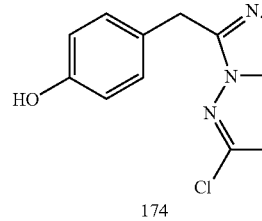
174
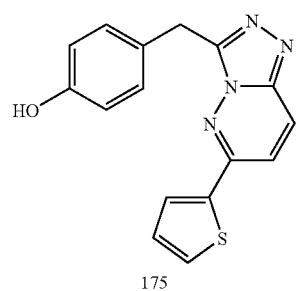
175

TABLE 2-continued
Compounds of formula I-b
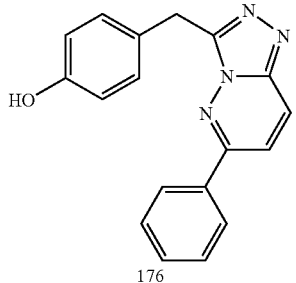
176
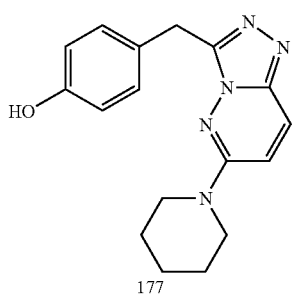
177
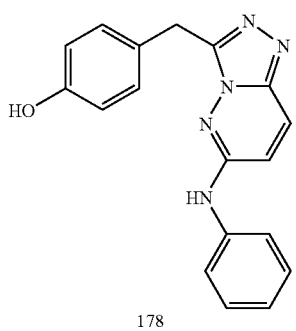
178
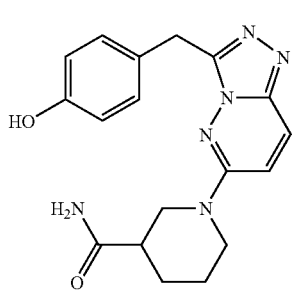
179
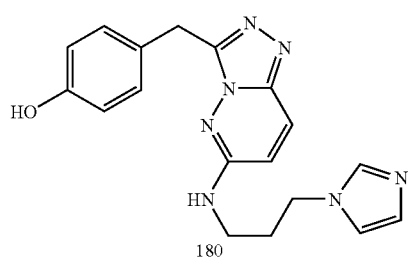
180
TABLE 2-continued
Compounds of formula I-b
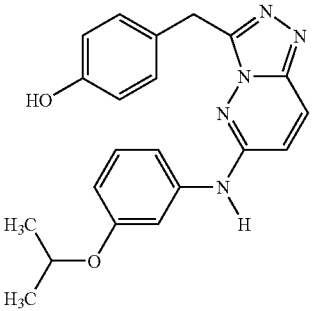
181
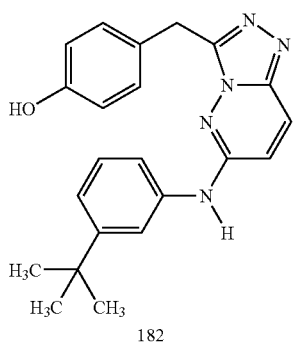
182
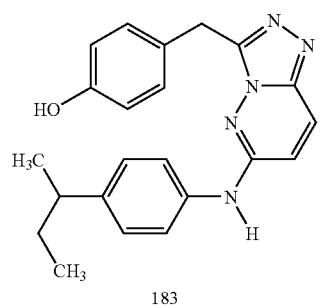
183
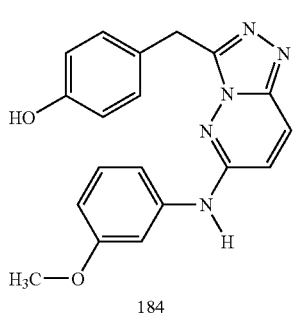
184

TABLE 2-continued
Compounds of formula I-b
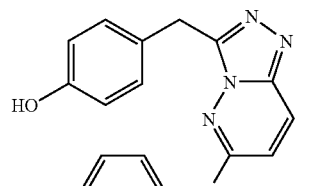
185
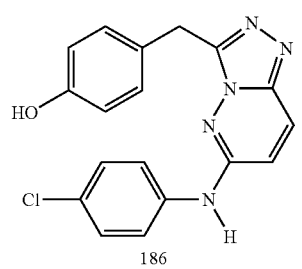
186
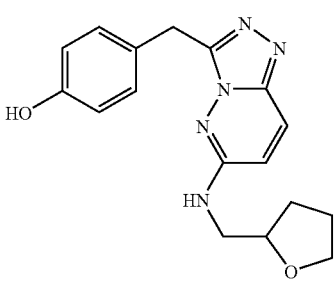
187
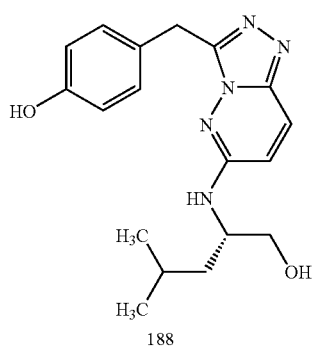
188
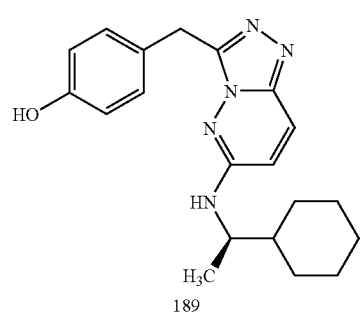
189
TABLE 2-continued
Compounds of formula I-b
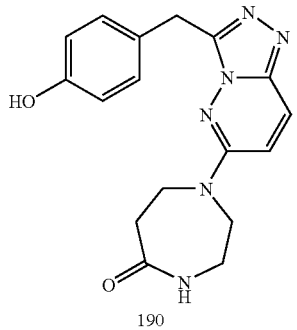
190
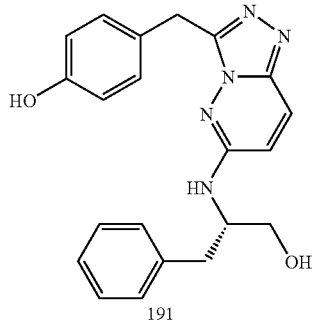
191
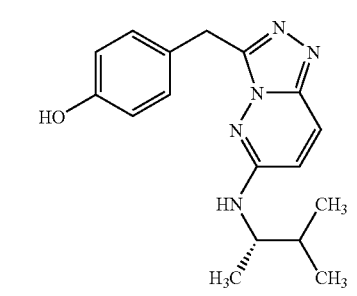
192
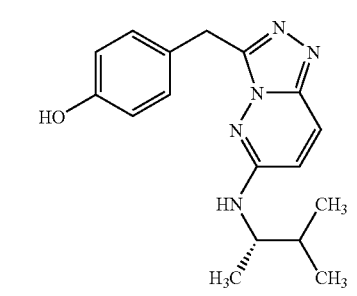
193

TABLE 2-continued
Compounds of formula I-b
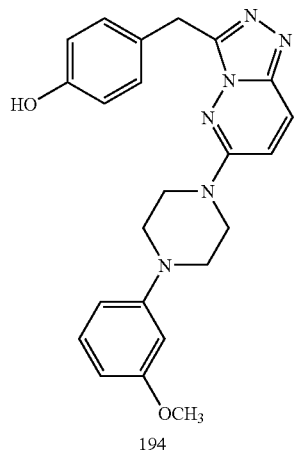
194
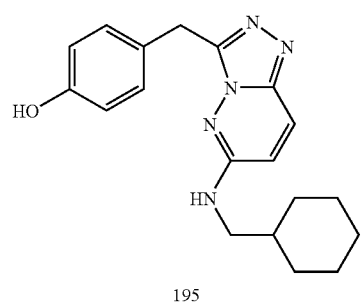
195
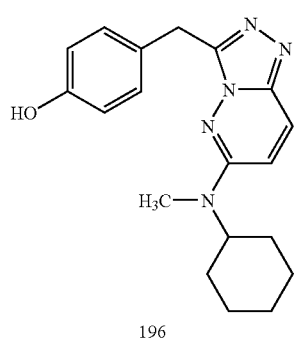
196
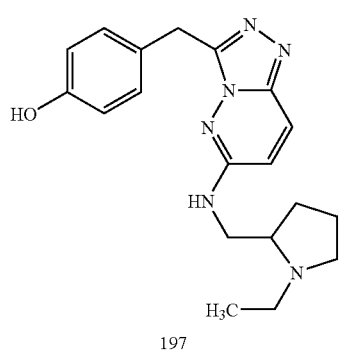
197
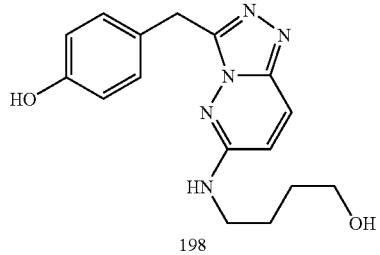
198
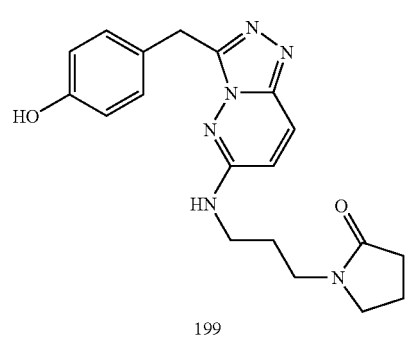
199
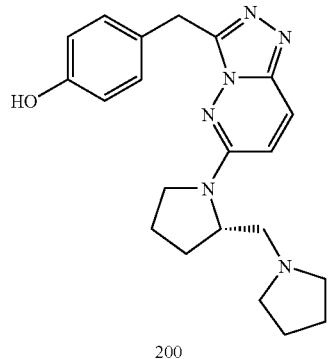
200
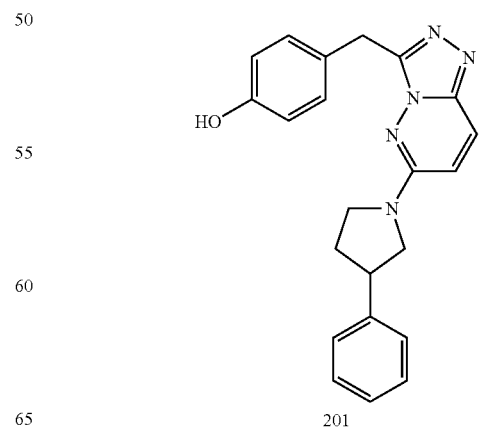
201

TABLE 2-continued
Compounds of formula I-b
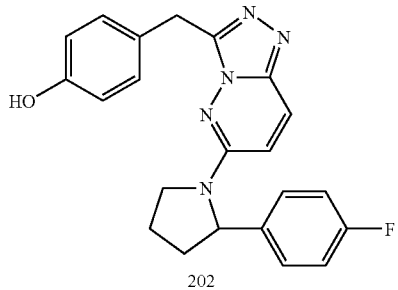
202
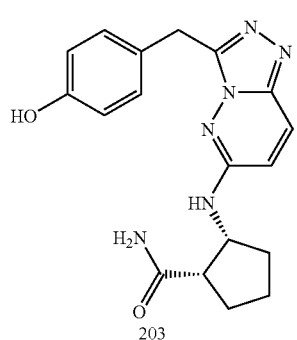
203
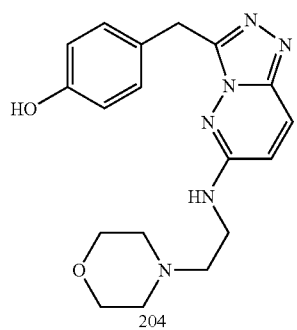
204
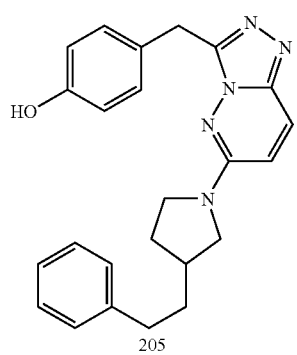
205
TABLE 2-continued
Compounds of formula I-b
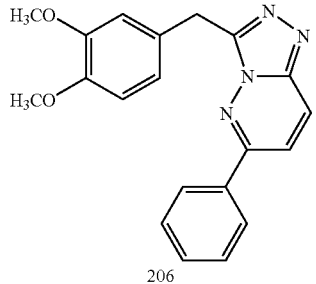
206
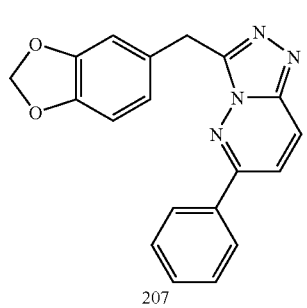
207
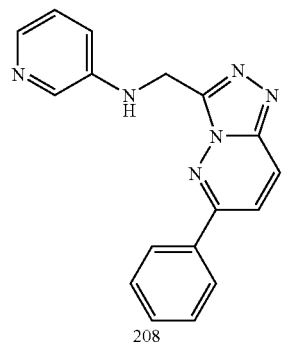
208
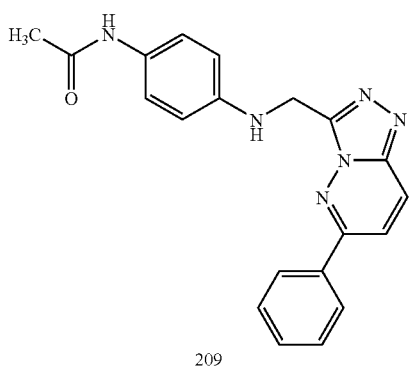
209

TABLE 2-continued
Compounds of formula I-b
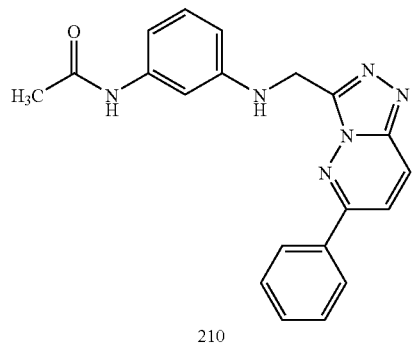
210
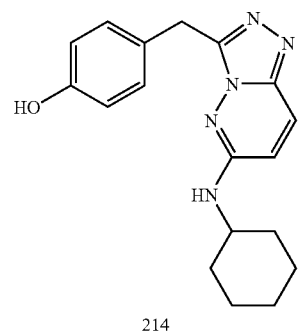
214
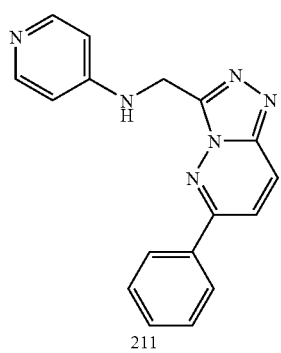
211
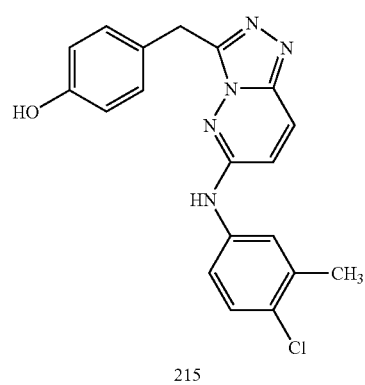
215
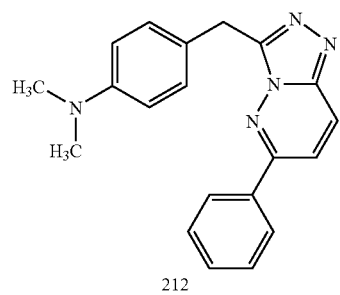
212
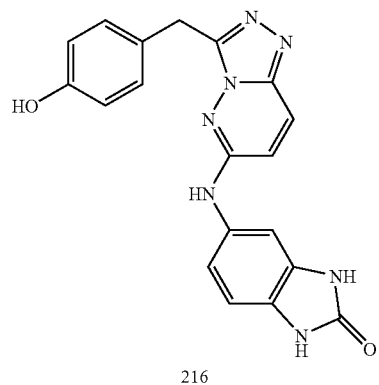
216
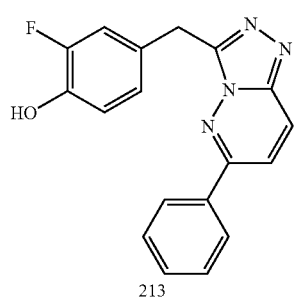
213
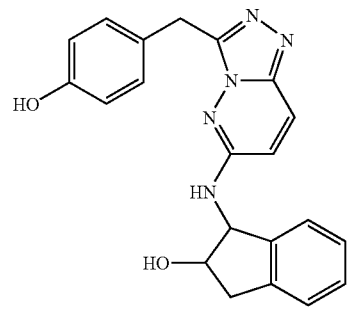
217

TABLE 2-continued
Compounds of formula I-b
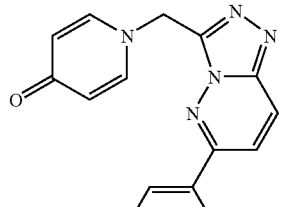
218
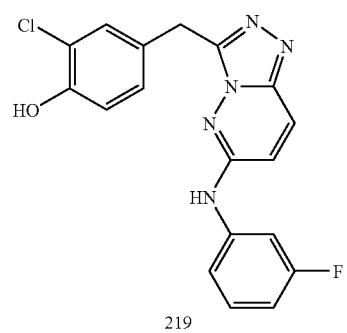
219
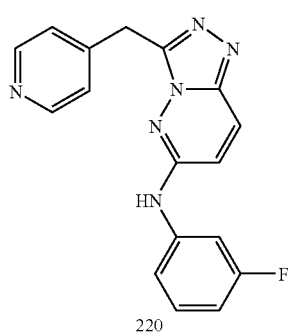
220
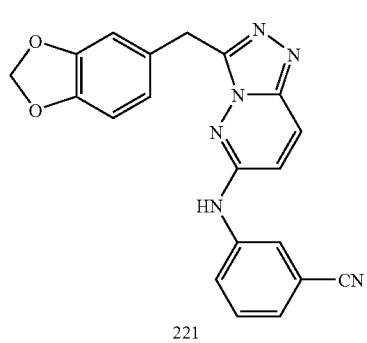
221
TABLE 2-continued
Compounds of formula I-b
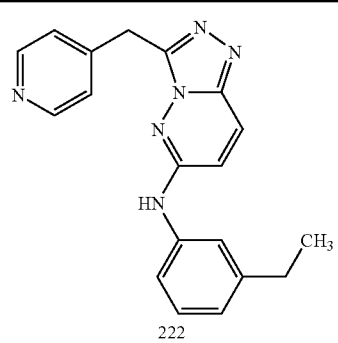
222
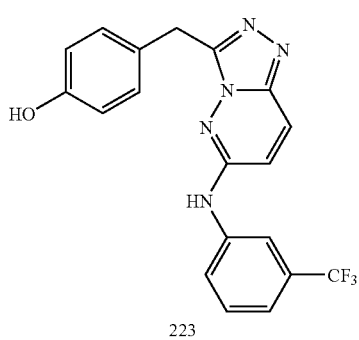
223
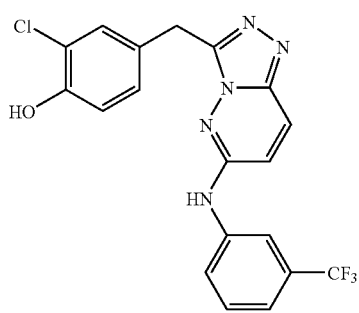
224
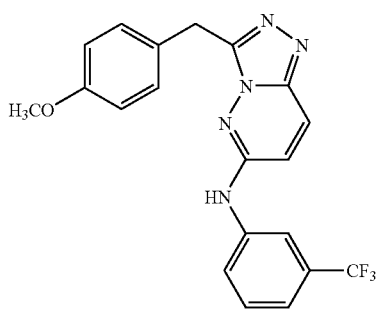
225

TABLE 2-continued
Compounds of formula I-b
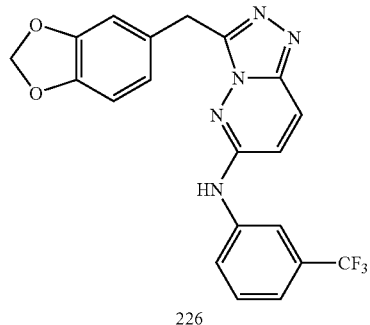
226
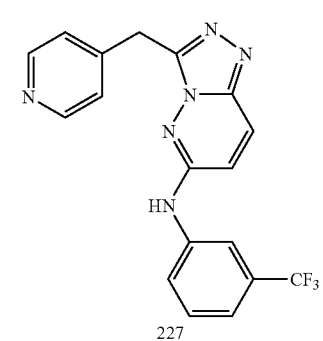
227
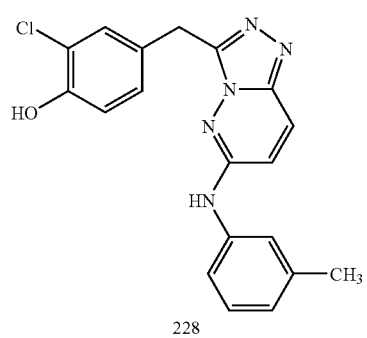
228
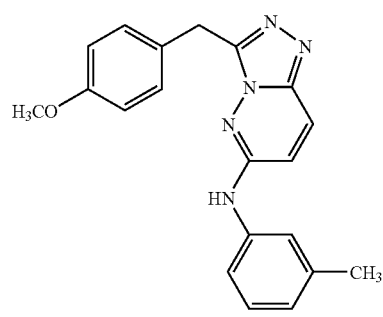
229
TABLE 2-continued
Compounds of formula I-b
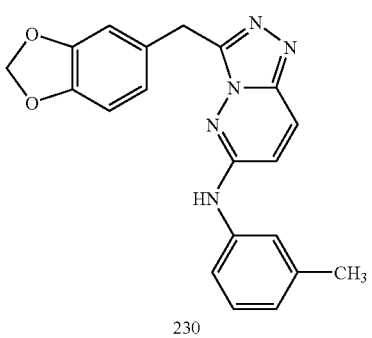
230
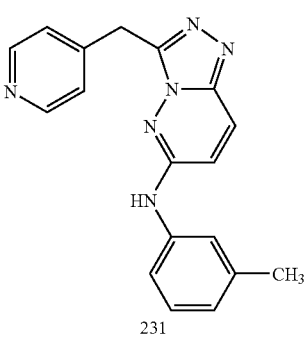
231
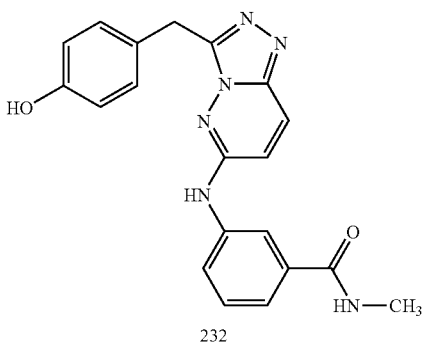
232
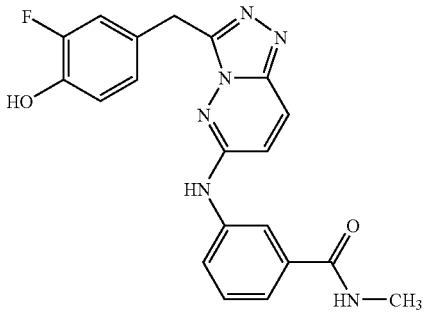
233

TABLE 2-continued
Compounds of formula I-b
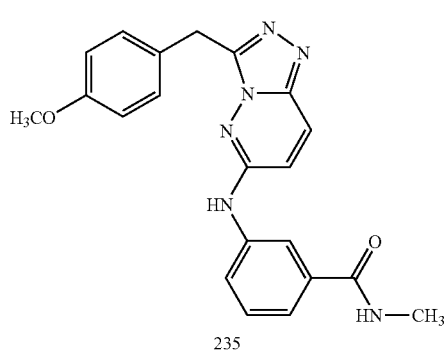
234
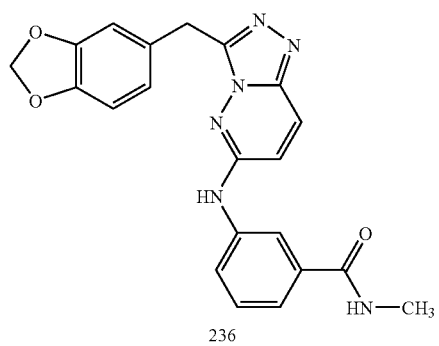
235
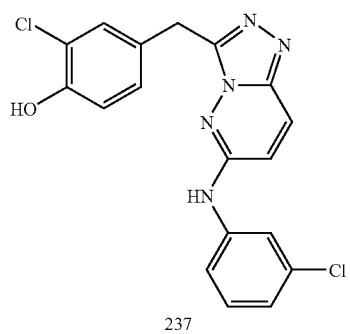
236
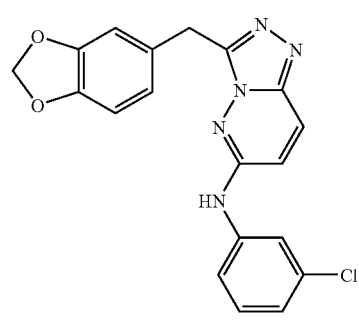
237
TABLE 2-continued
Compounds of formula I-b
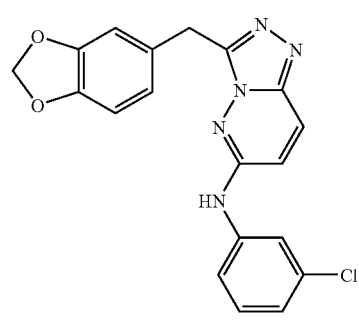
238
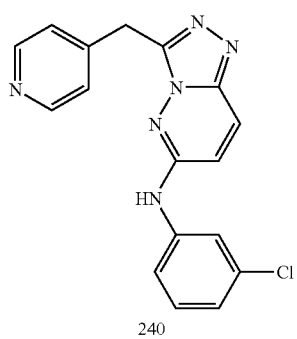
239
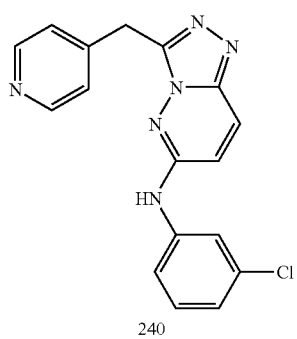
240
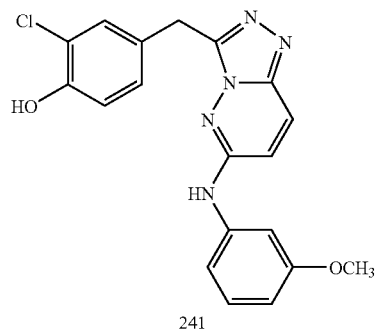
241

TABLE 2-continued
Compounds of formula I-b
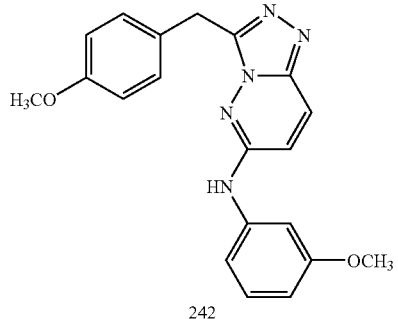
242
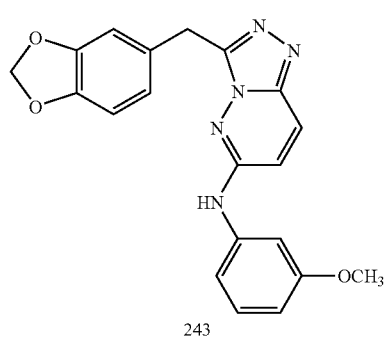
243
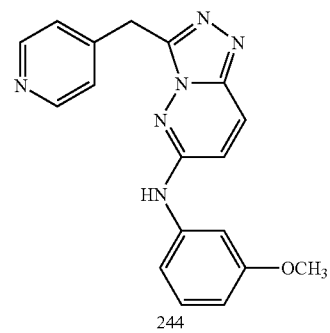
244
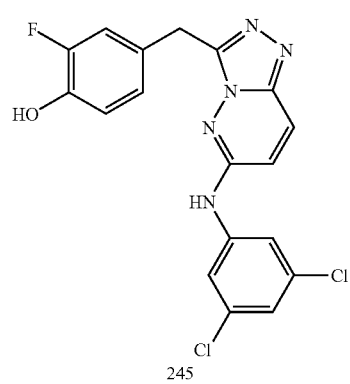
245
TABLE 2-continued
Compounds of formula I-b
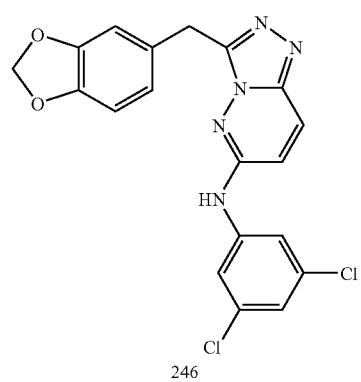
246
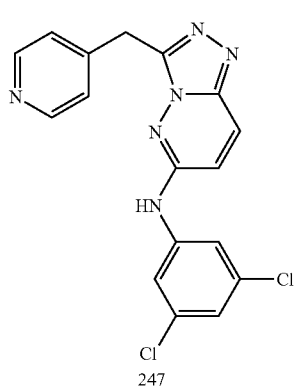
247
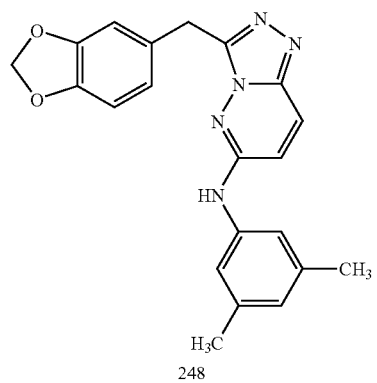
248
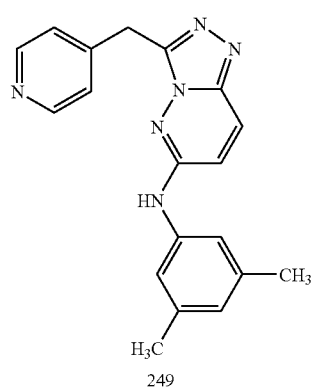
249

TABLE 2-continued
Compounds of formula I-b
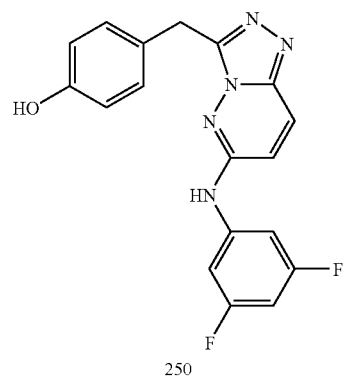
250
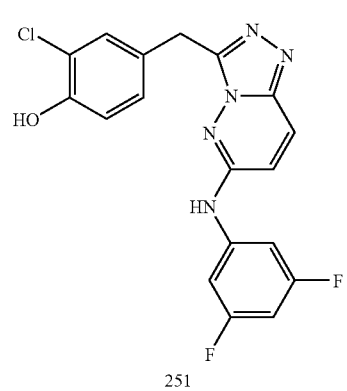
251
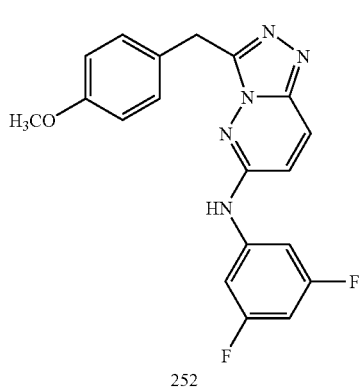
252
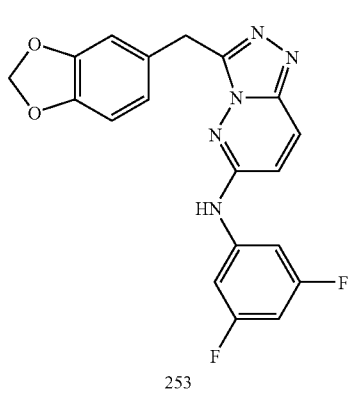
253
TABLE 2-continued
Compounds of formula I-b
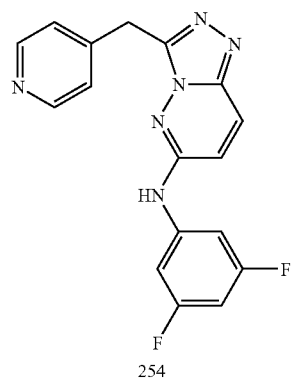
254
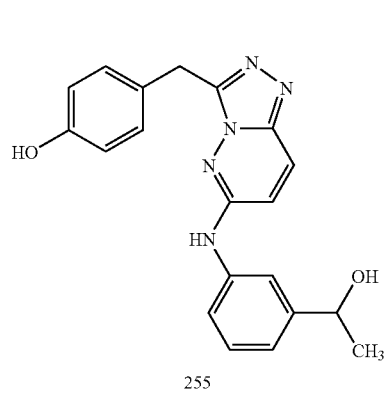
255
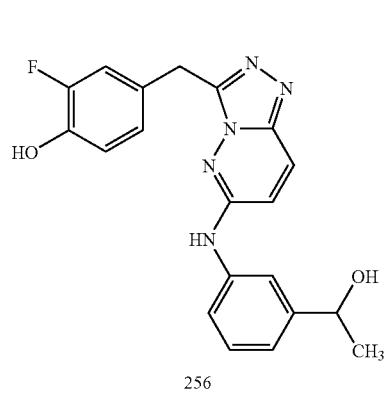
256
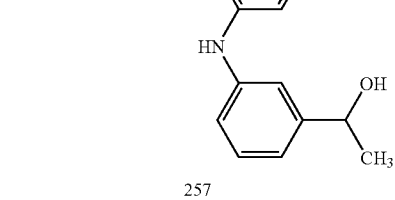
257

TABLE 2-continued
Compounds of formula I-b
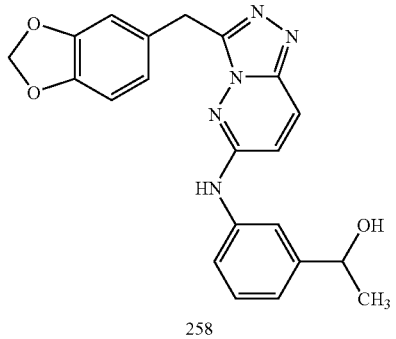
258
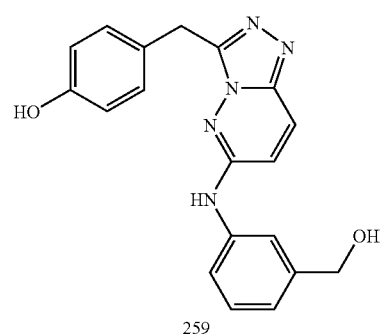
259
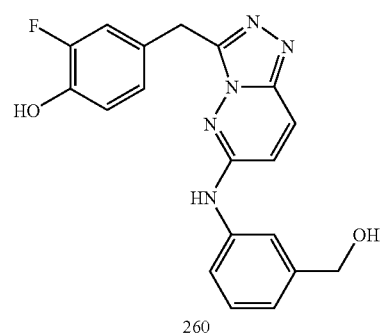
260
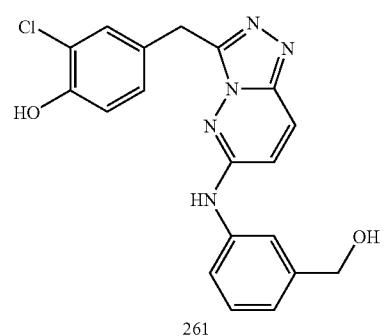
261
TABLE 2-continued
Compounds of formula I-b
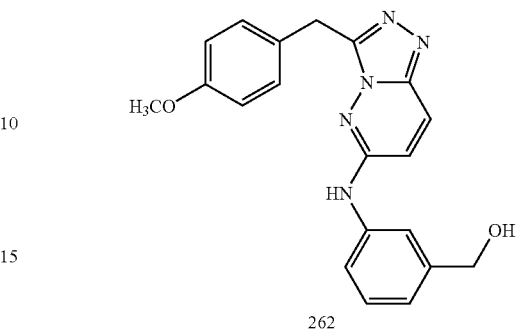
262
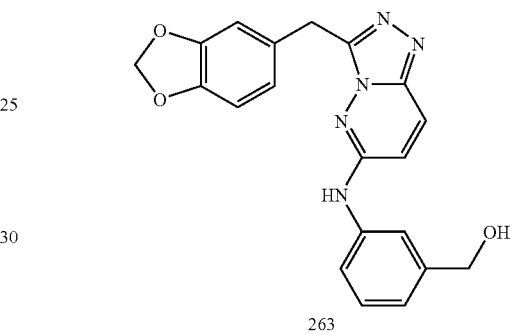
263
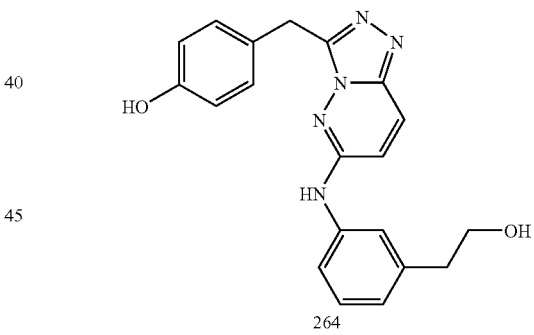
264
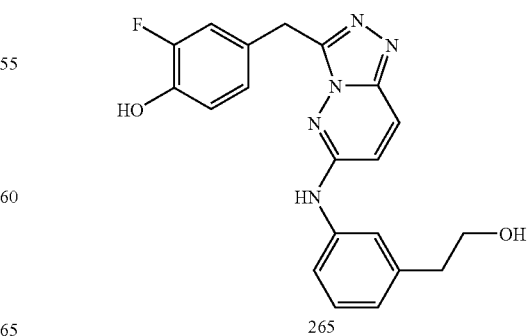
265

TABLE 2-continued

Compounds of formula I-b 266, 267, 268, 269, 270, 271, 272, 273, 274

TABLE 2-continued
Compounds of formula I-b
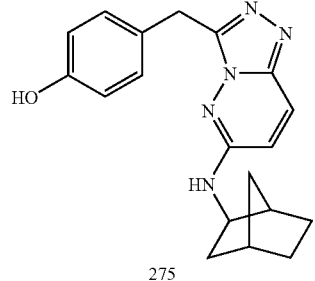
275
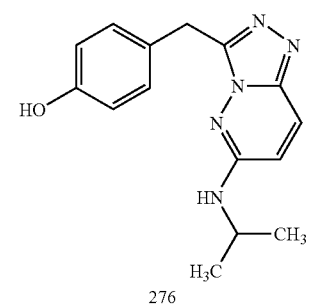
276
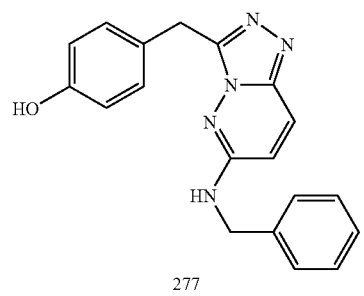
277
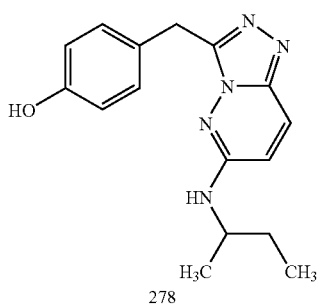
278
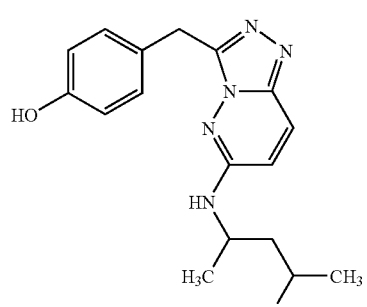
279
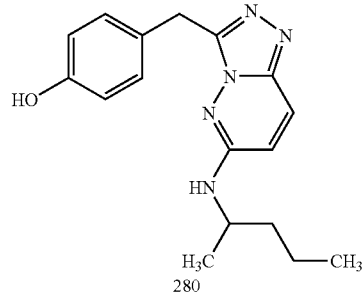
280
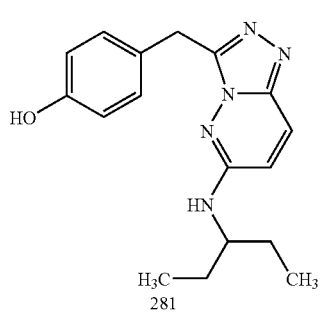
281
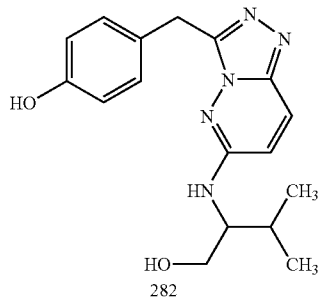
282
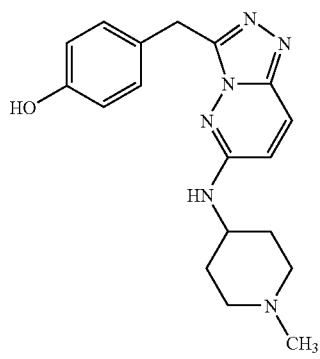
283

TABLE 2-continued
Compounds of formula I-b
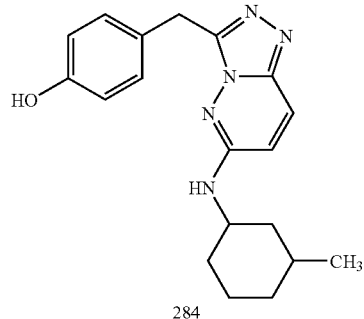
284
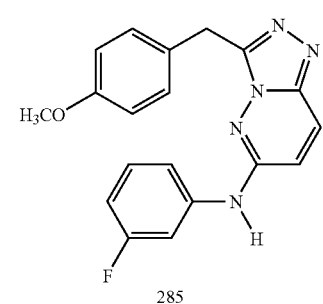
285
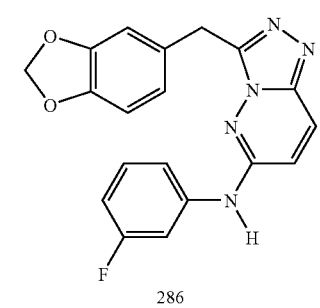
286
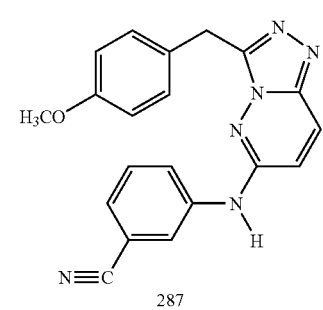
287
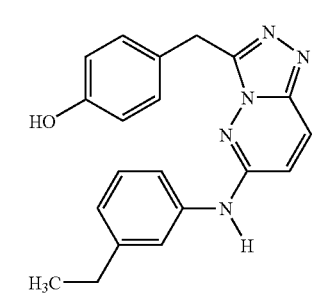
288
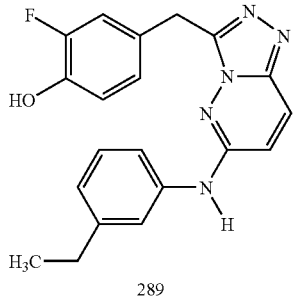
289
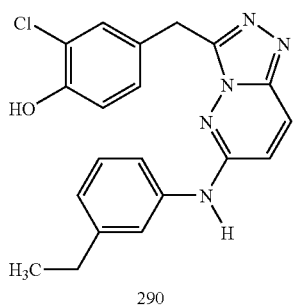
290
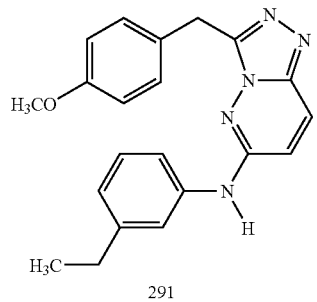
291
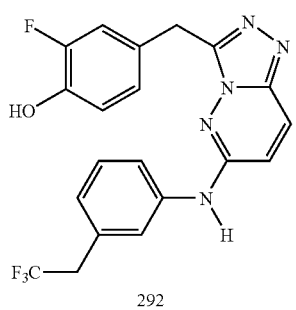
292
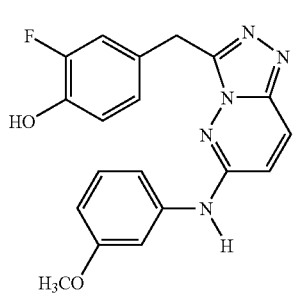
293

TABLE 2-continued
Compounds of formula I-b
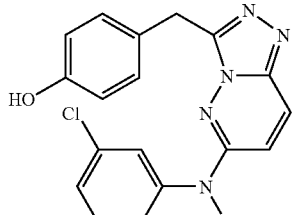
294
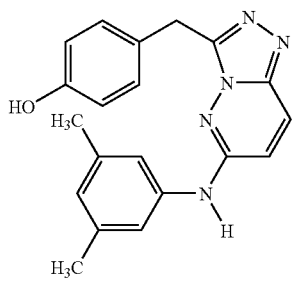
295
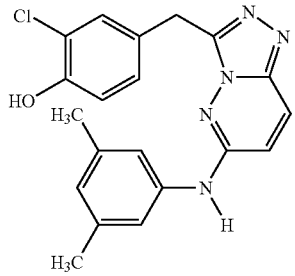
296
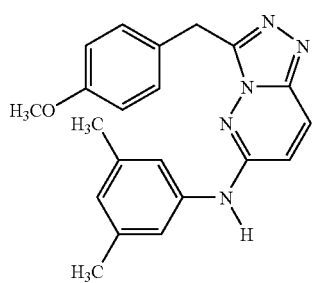
297
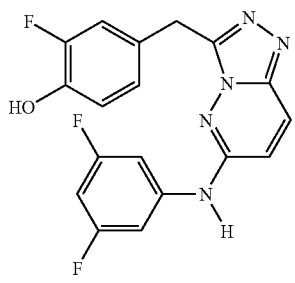
298
TABLE 2-continued
Compounds of formula I-b
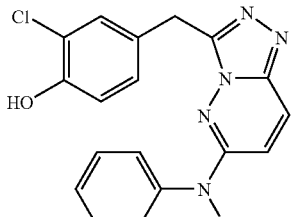
299
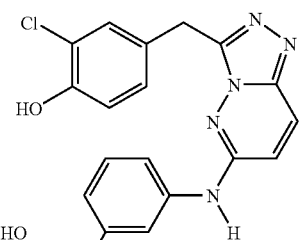
300
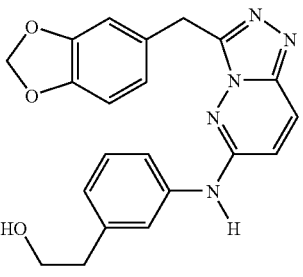
301
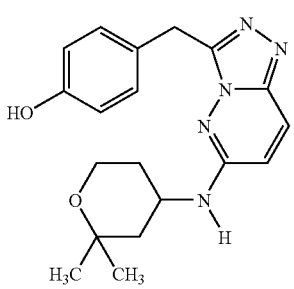
302
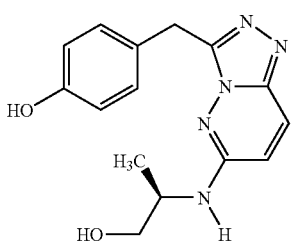
303

TABLE 2-continued
Compounds of formula I-b
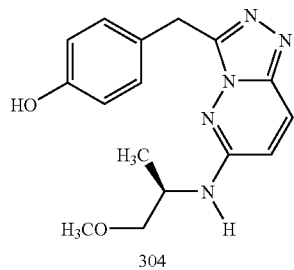
304
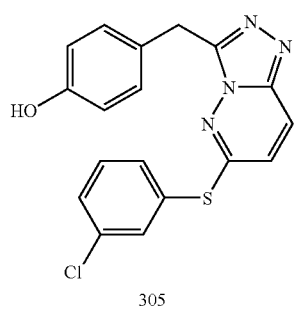
305
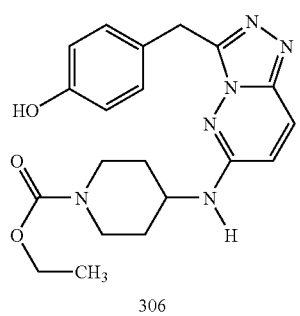
306
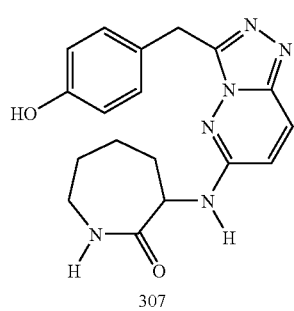
307
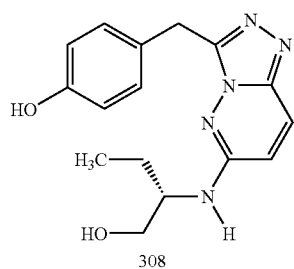
308
TABLE 2-continued
Compounds of formula I-b
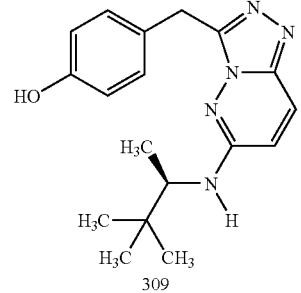
309
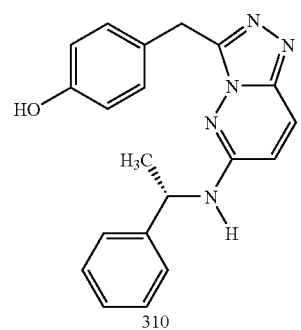
310
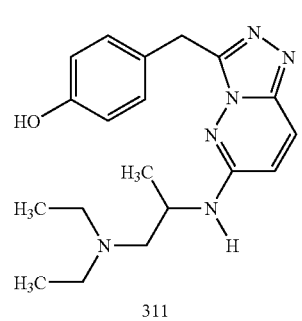
311
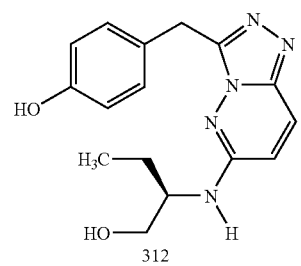
312
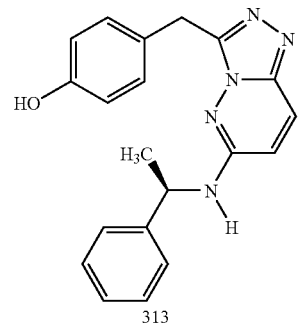
313

TABLE 2-continued
Compounds of formula I-b
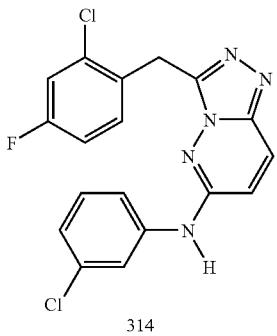
314
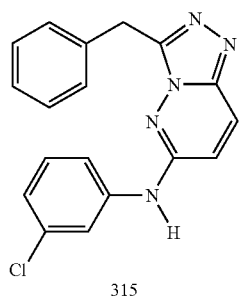
315
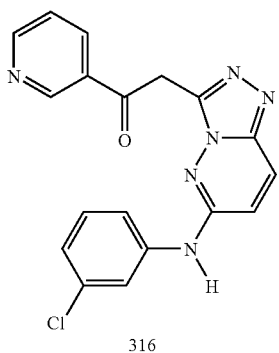
316
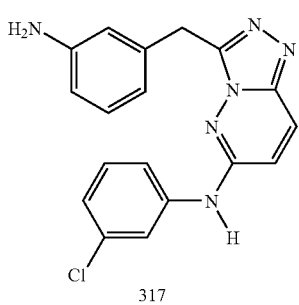
317
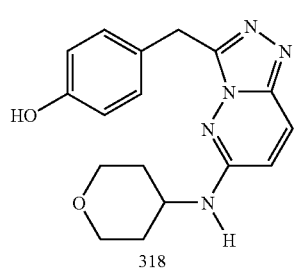
318
TABLE 2-continued
Compounds of formula I-b
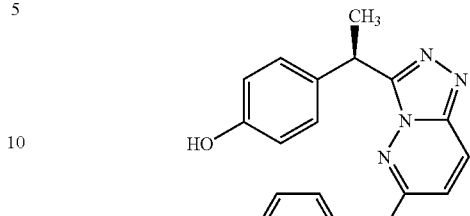
319
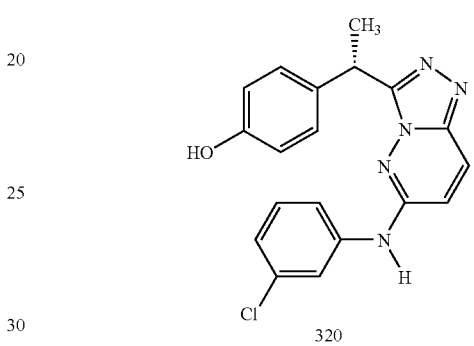
320
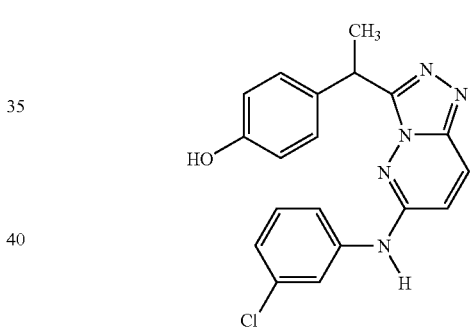
321
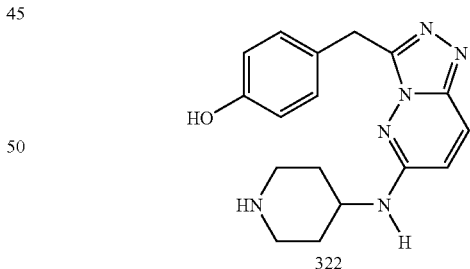
322
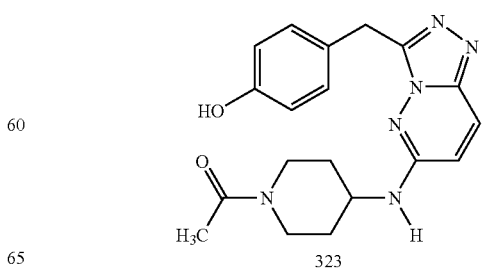
323

TABLE 2-continued
Compounds of formula I-b
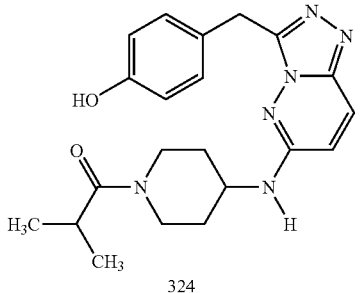
324
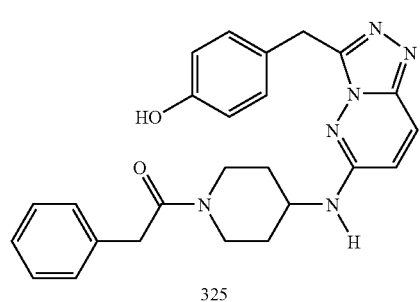
325
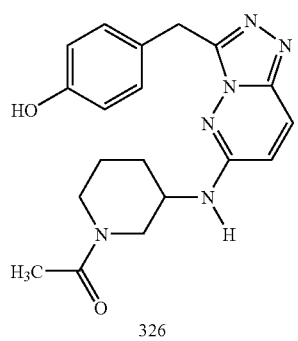
326
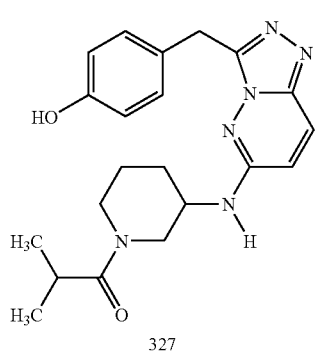
327
TABLE 2-continued
Compounds of formula I-b
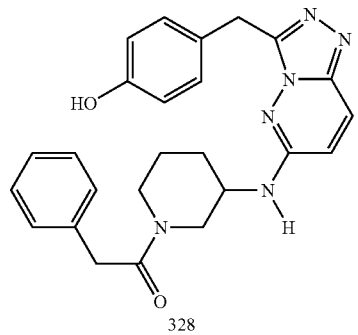
328
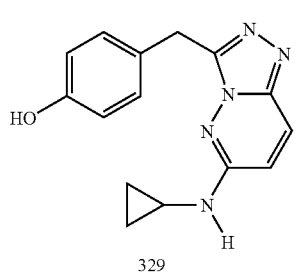
329
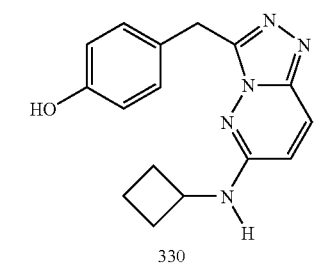
330
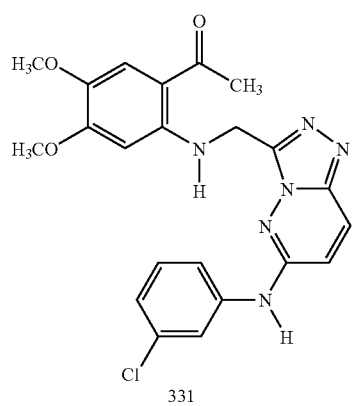
331

TABLE 2-continued
Compounds of formula I-b
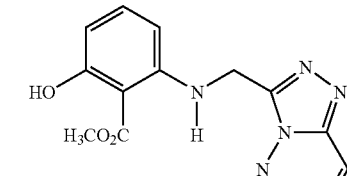
332
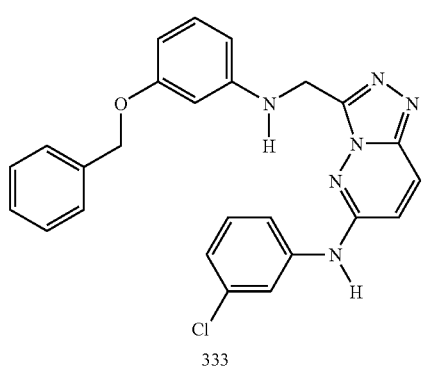
333
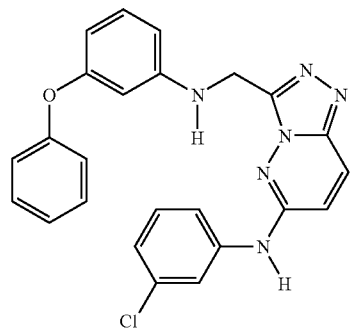
334
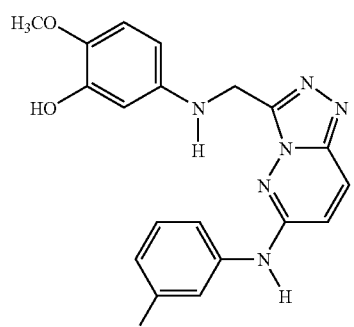
335
TABLE 2-continued
Compounds of formula I-b
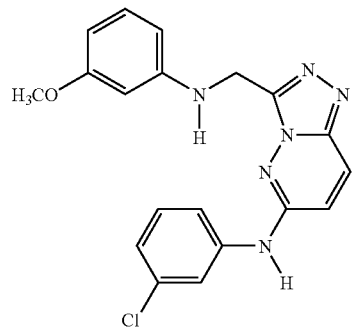
336
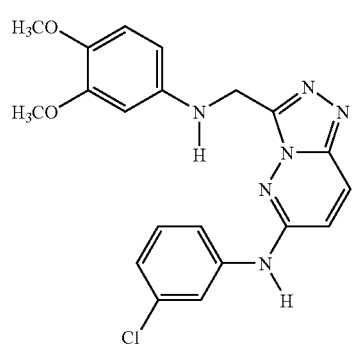
337
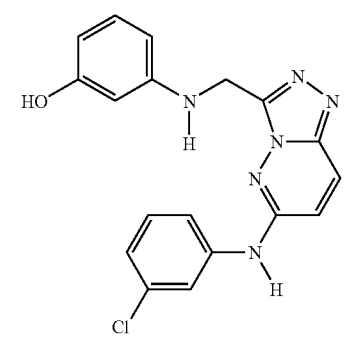
338
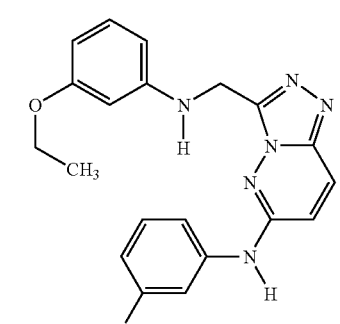
339

TABLE 2-continued
Compounds of formula I-b
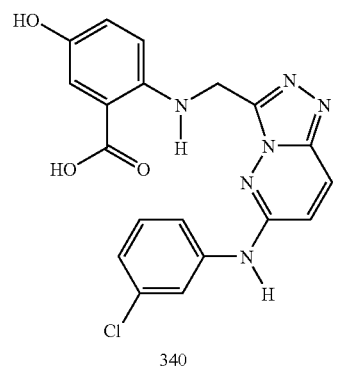
340
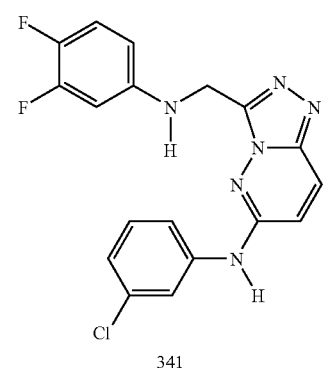
341
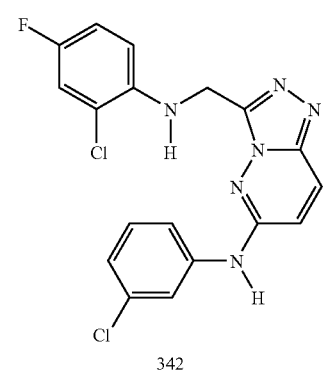
342
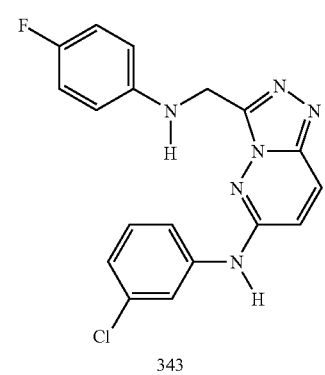
343
TABLE 2-continued
Compounds of formula I-b
344
345
346
347

TABLE 2-continued
Compounds of formula I-b
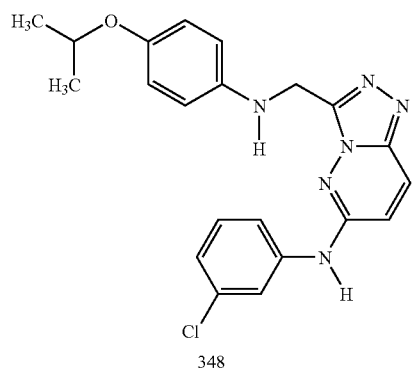
348
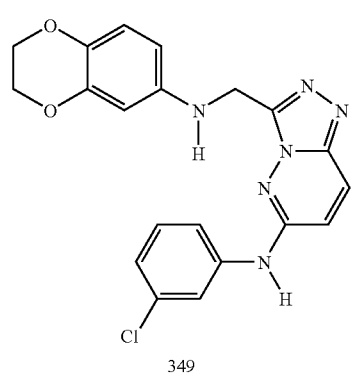
349
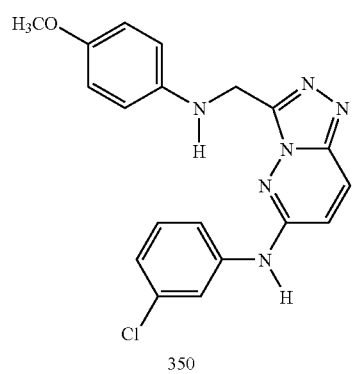
350
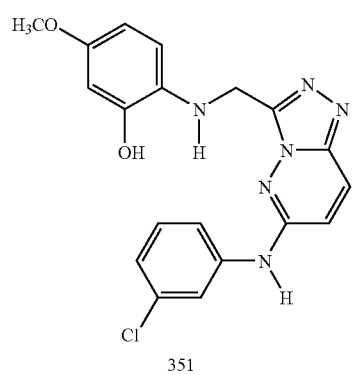
351
TABLE 2-continued
Compounds of formula I-b
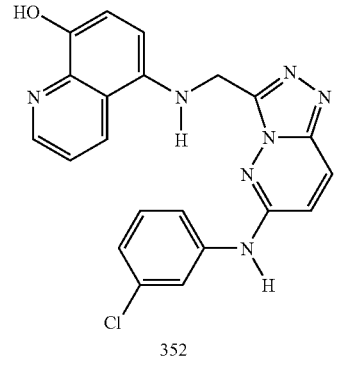
352
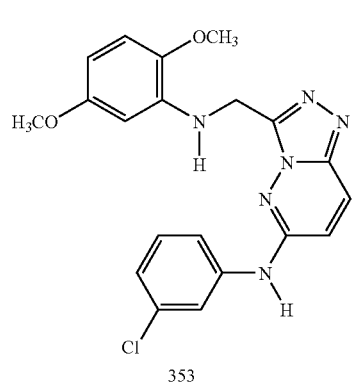
353
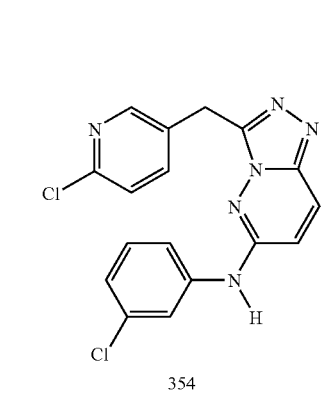
354
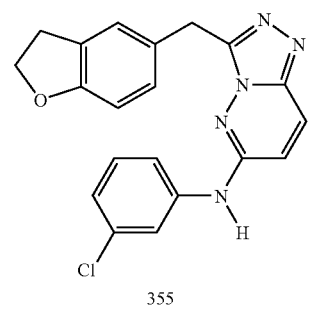
355

TABLE 2-continued
Compounds of formula I-b
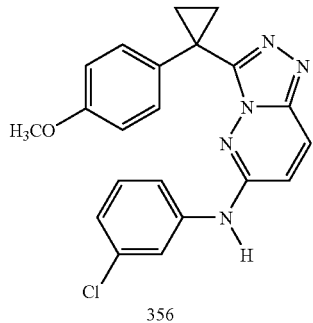
356
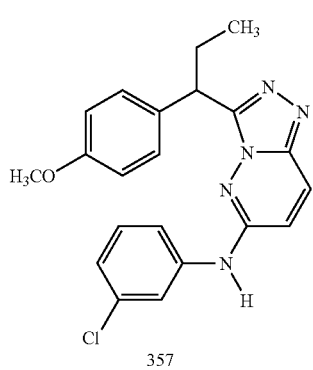
357
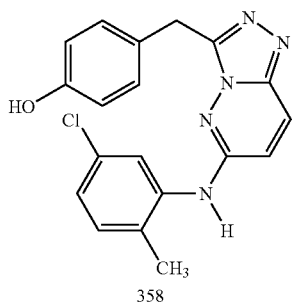
358
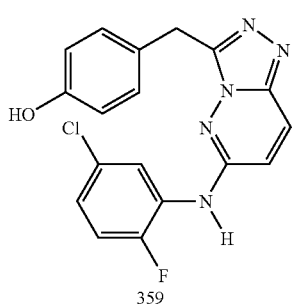
359
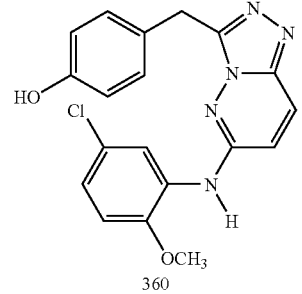
360
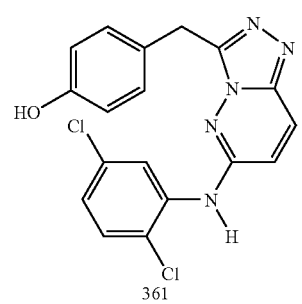
361
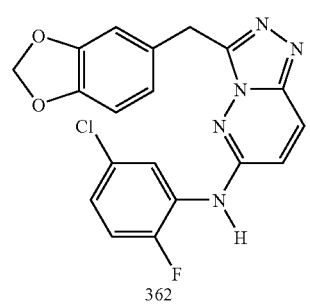
362
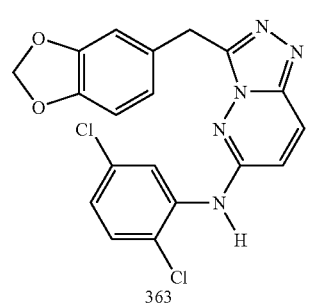
363
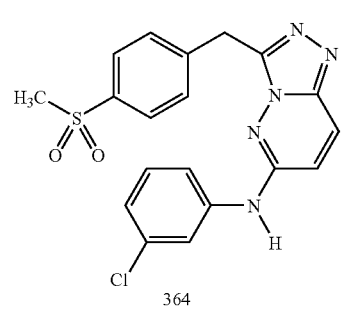
364

TABLE 2-continued
Compounds of formula I-b
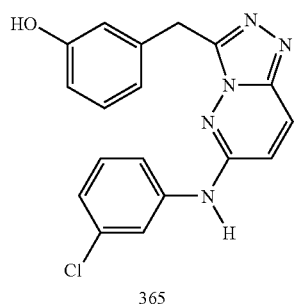
365
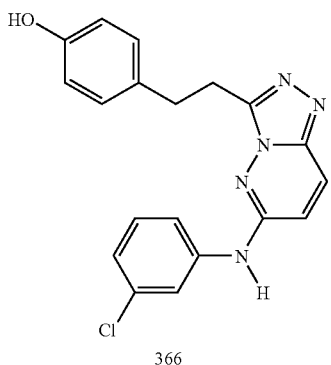
366
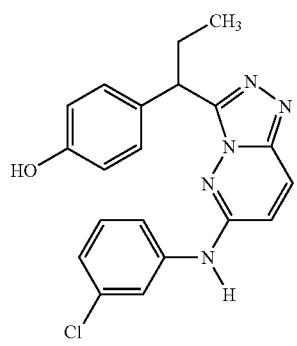
367
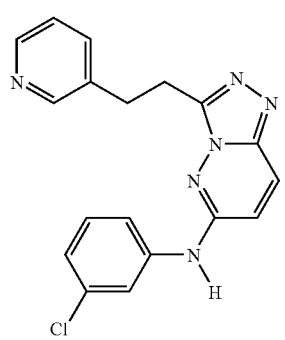
368
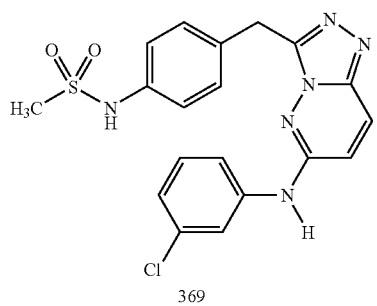
369
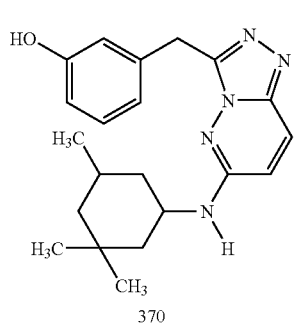
370
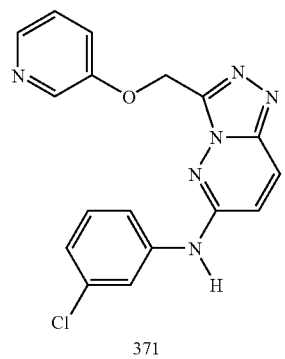
371
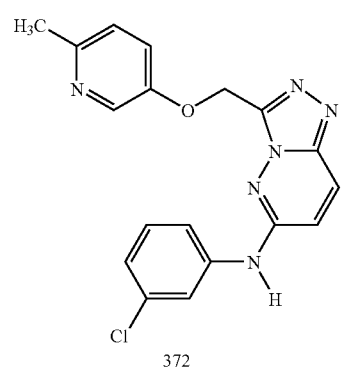
372

TABLE 2-continued
Compounds of formula I-b
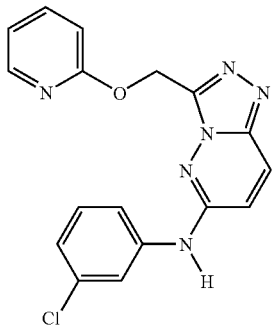
373
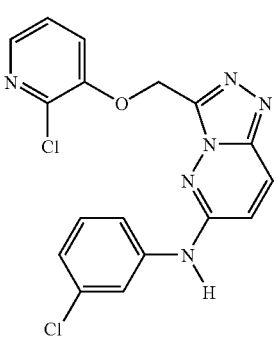
374
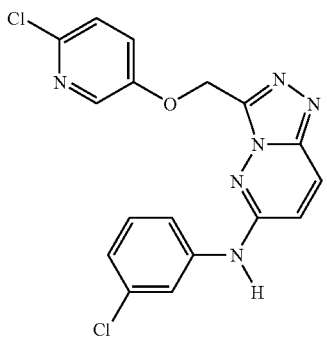
375
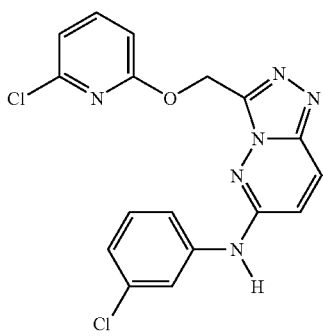
376
TABLE 2-continued
Compounds of formula I-b
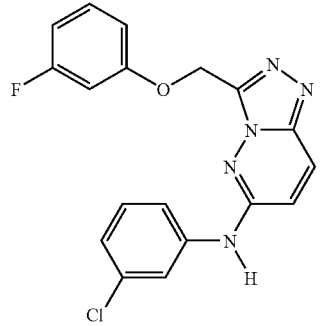
377
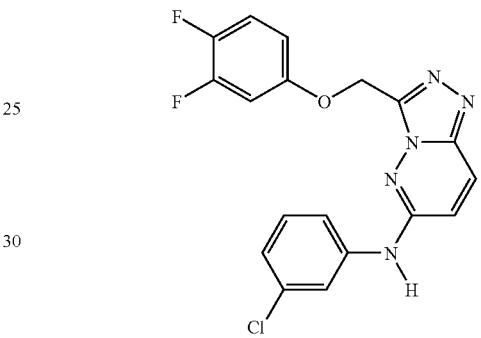
378
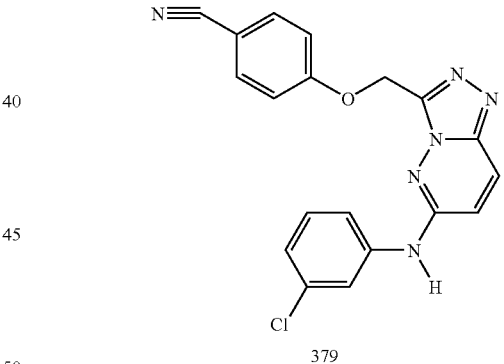
379
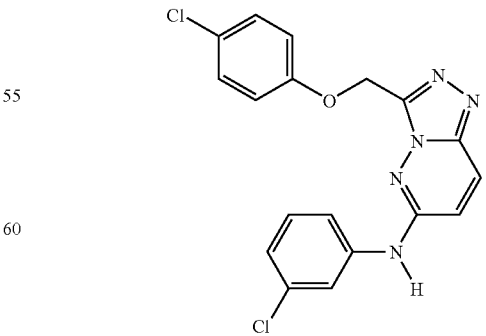
380

TABLE 2-continued
Compounds of formula I-b
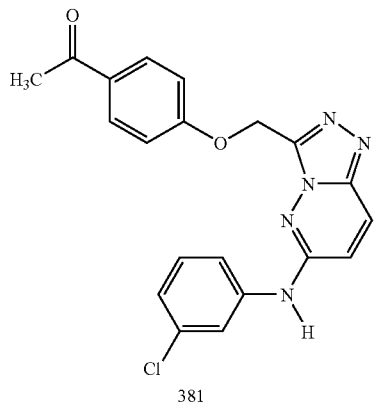
381
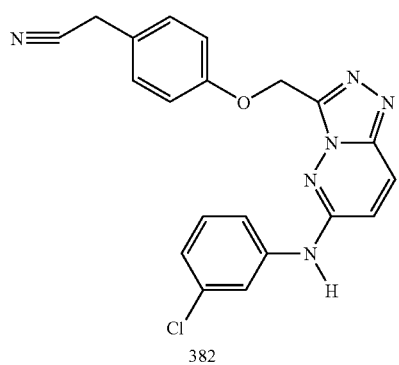
382
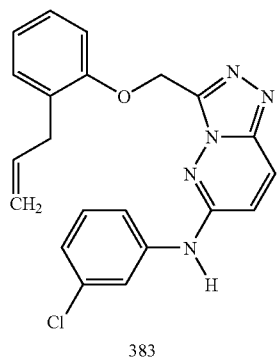
383
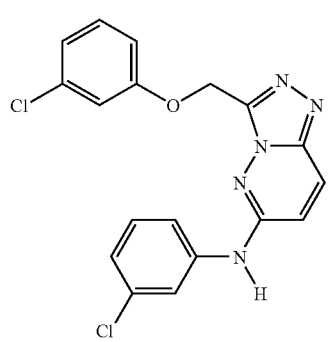
384
TABLE 2-continued
Compounds of formula I-b
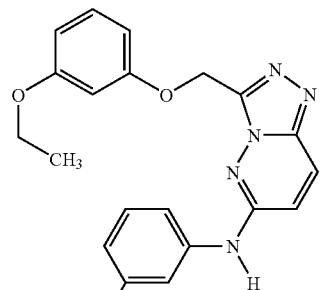
385
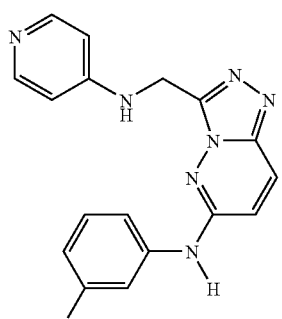
386
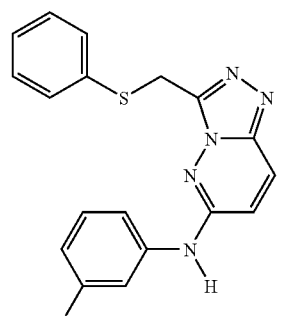
387
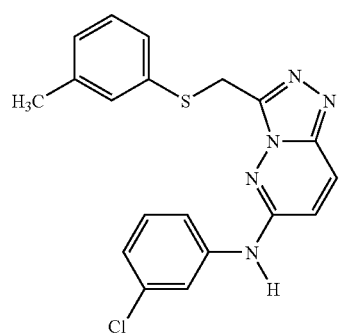
388

TABLE 2-continued
Compounds of formula I-b
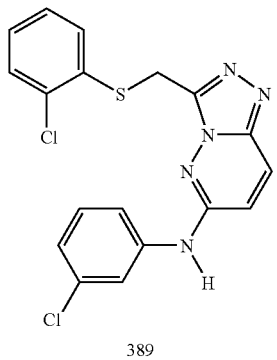
389
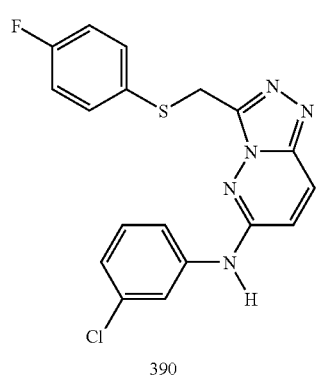
390
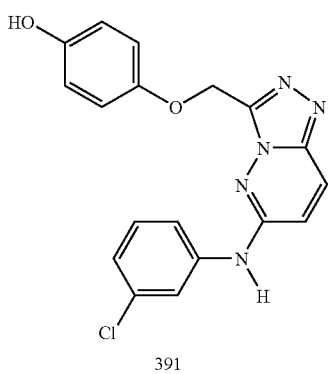
391
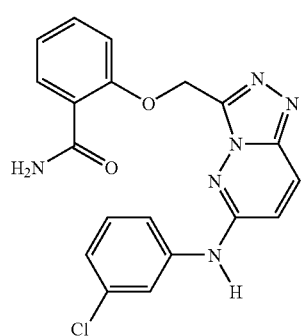
392
TABLE 2-continued
Compounds of formula I-b
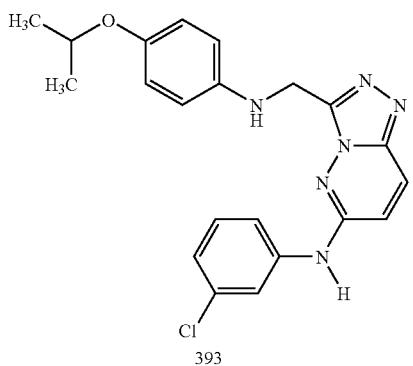
393
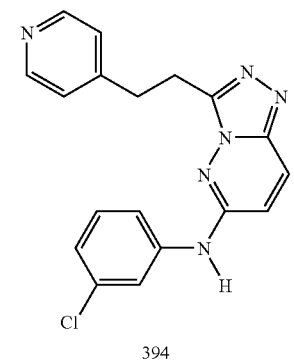
394
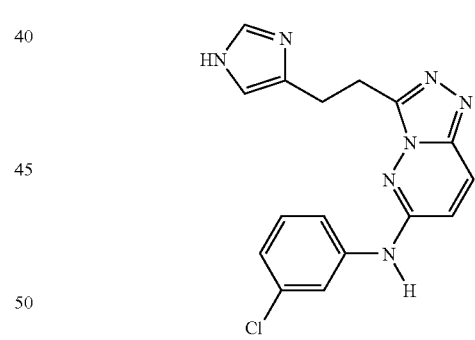
395
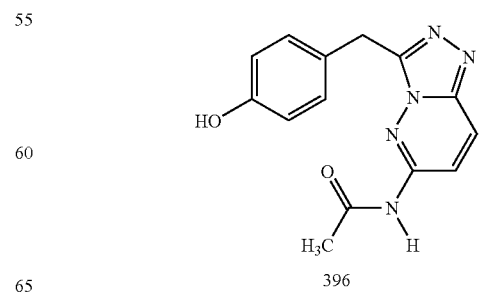
396

TABLE 2-continued
Compounds of formula I-b
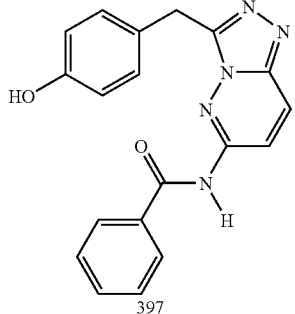
397
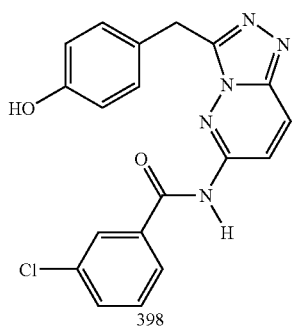
398
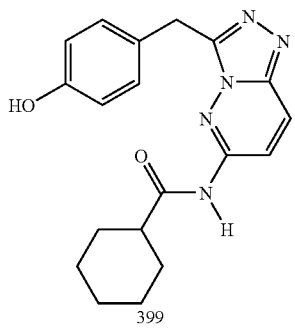
399
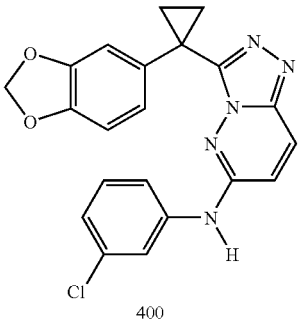
400
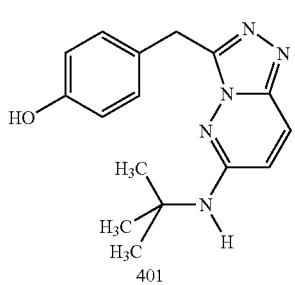
401
TABLE 2-continued
Compounds of formula I-b
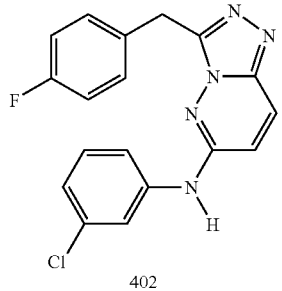
402
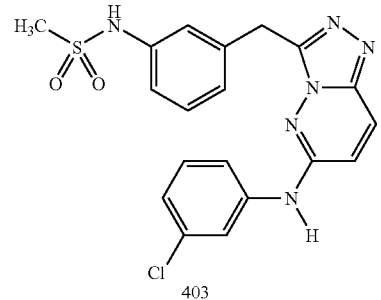
403
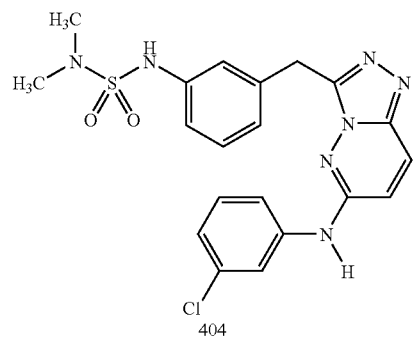
404
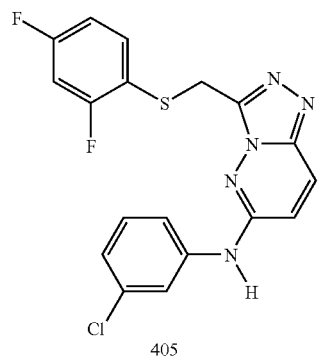
405

TABLE 2-continued
Compounds of formula I-b
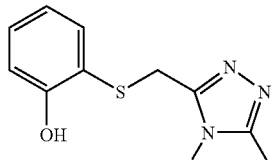
406
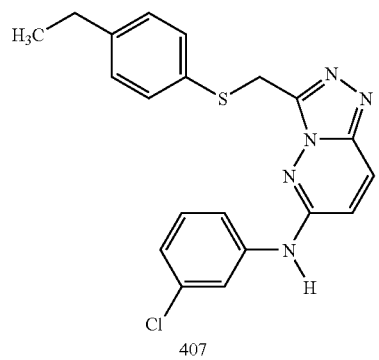
407
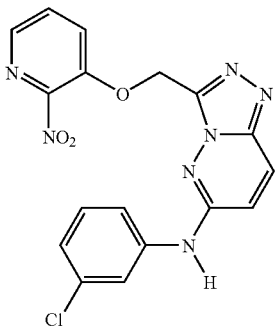
408
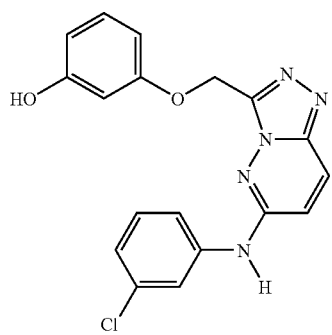
409
TABLE 2-continued
Compounds of formula I-b
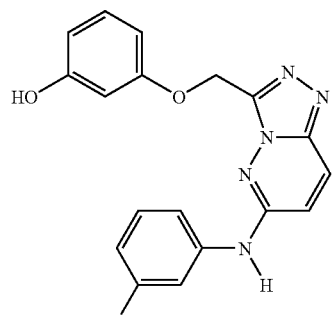
410
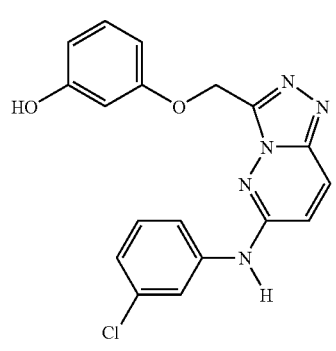
411
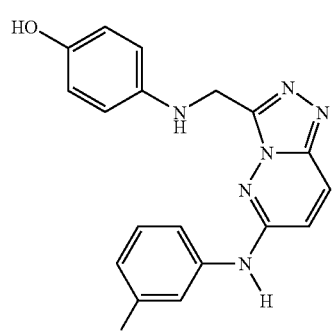
412
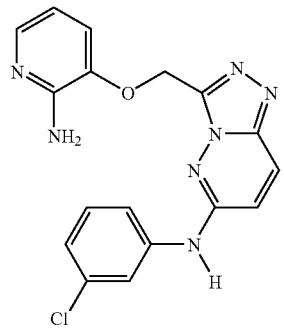
413

TABLE 2-continued
Compounds of formula I-b
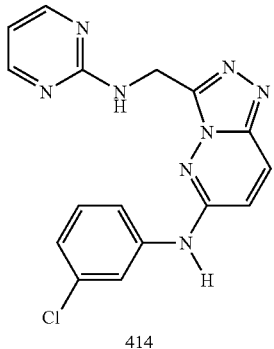
414
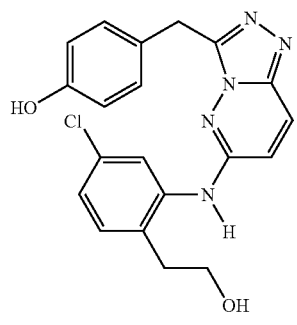
415
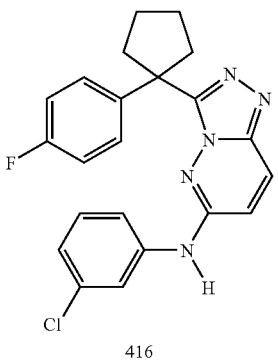
416
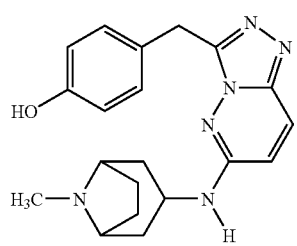
417
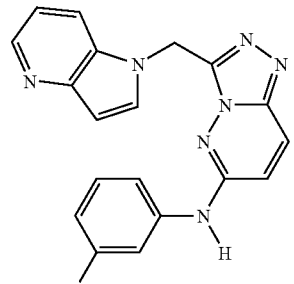
418
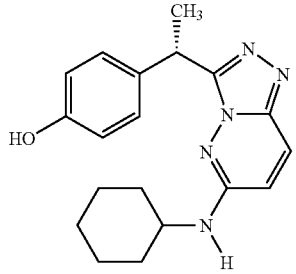
419
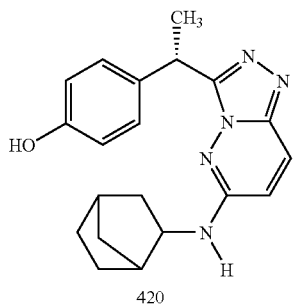
420
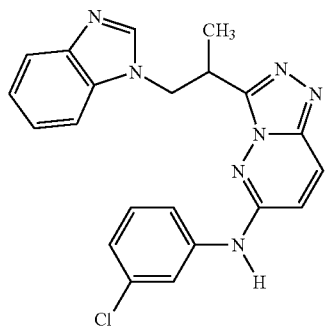
421

TABLE 2-continued

Compounds of formula I-b 422, 423, 424, 425, 426, 427, 428, 429

TABLE 2-continued
Compounds of formula I-b
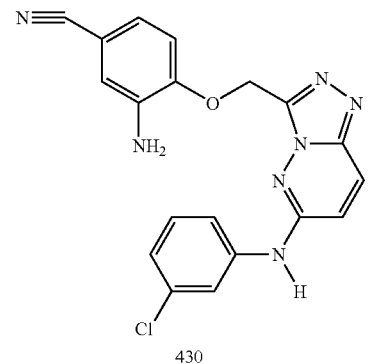
430
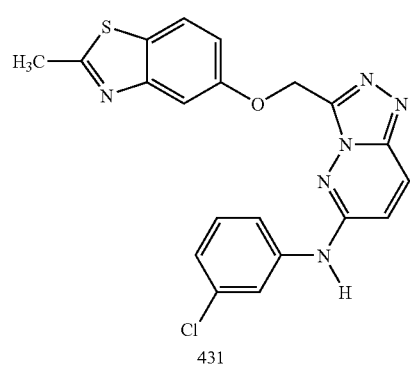
431
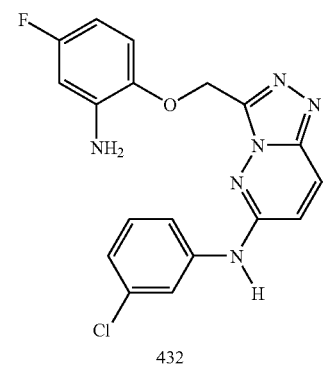
432
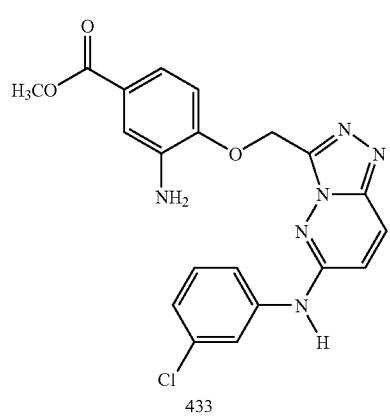
433
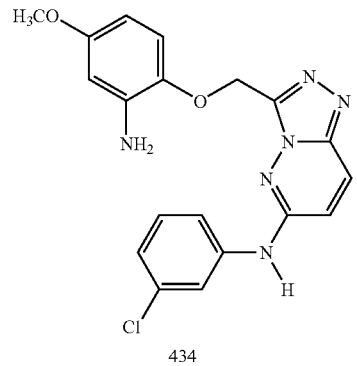
434
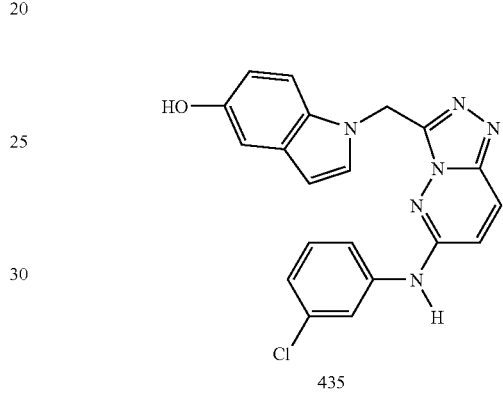
435
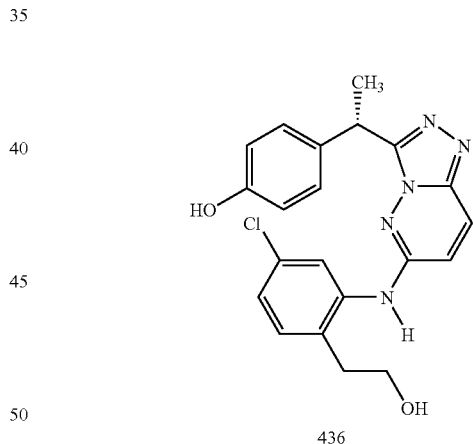
436
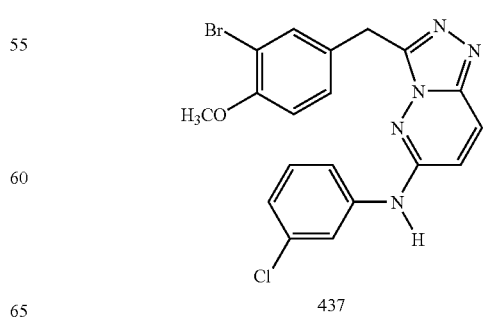
437

TABLE 2-continued
Compounds of formula I-b
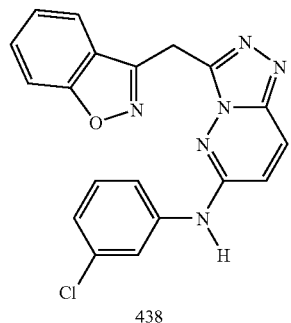
438
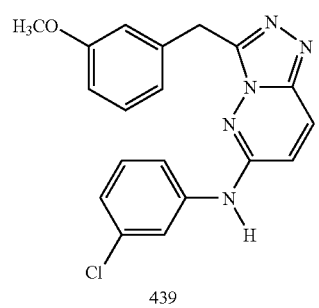
439
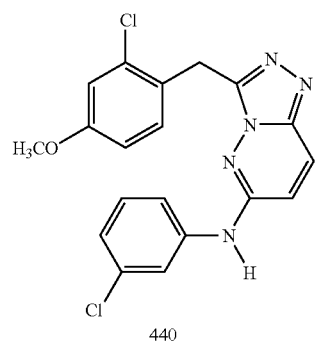
440
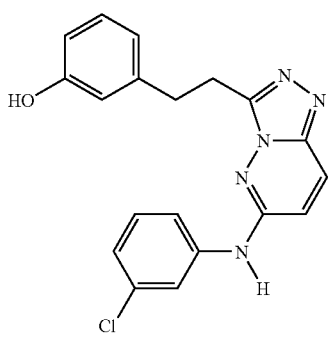
441
TABLE 2-continued
Compounds of formula I-b
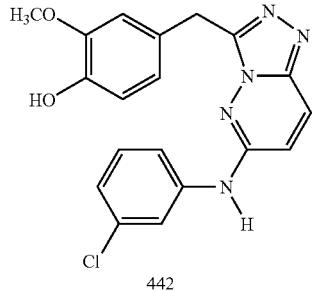
442
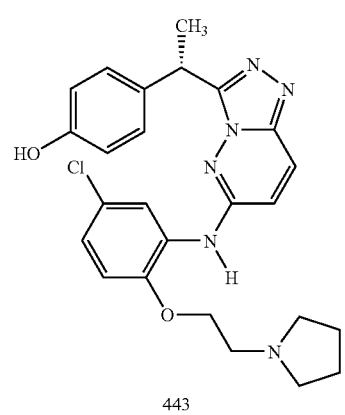
443
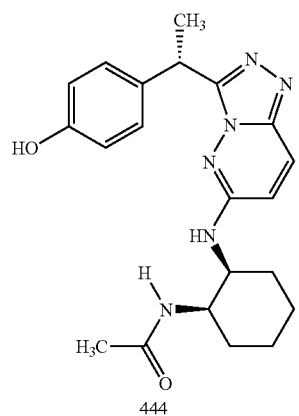
444
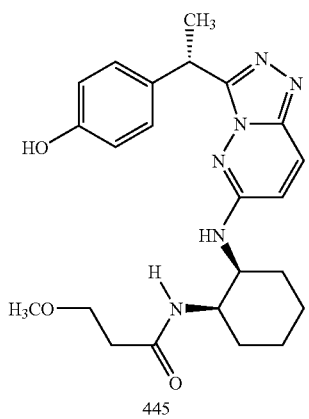
445

TABLE 2-continued
Compounds of formula I-b
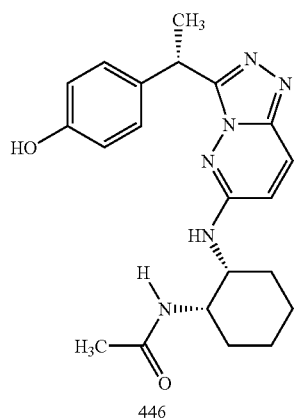
446
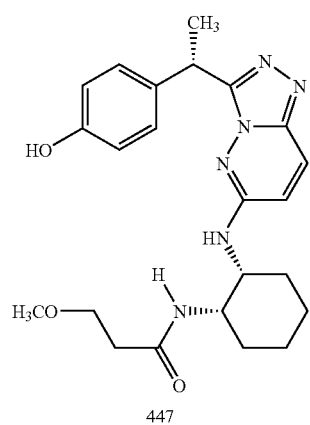
447
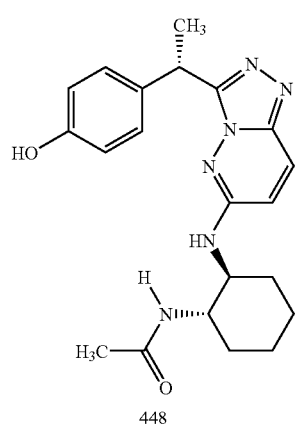
448
TABLE 2-continued
Compounds of formula I-b
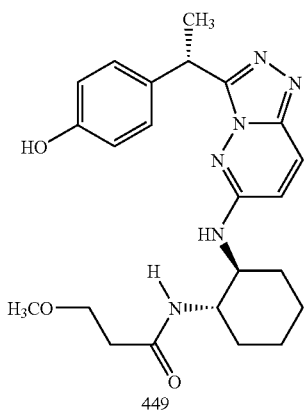
449
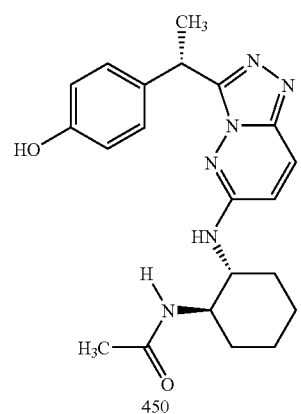
450
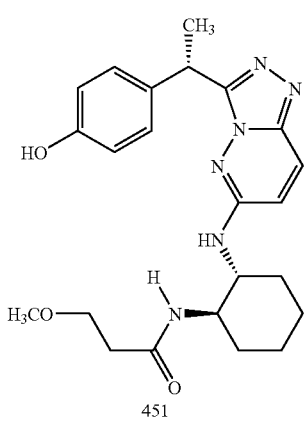
451
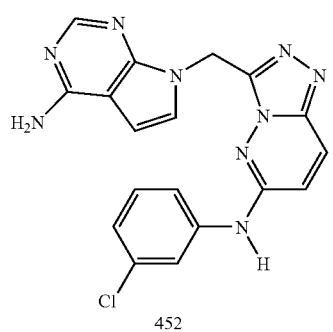
452

TABLE 2-continued
Compounds of formula I-b
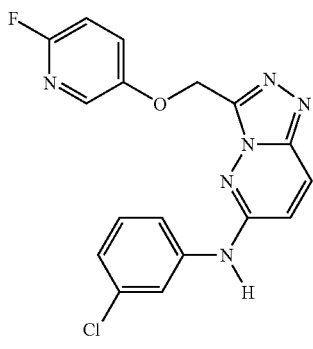
453
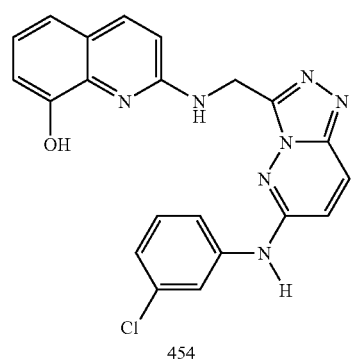
454
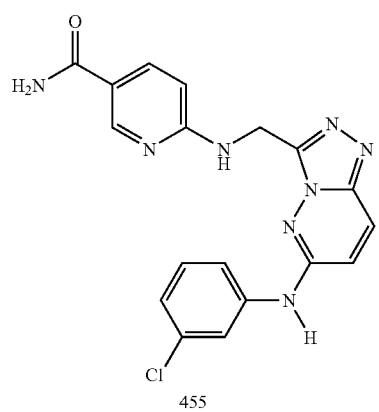
455
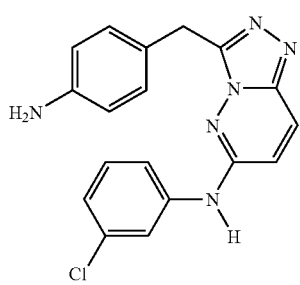
456
TABLE 2-continued
Compounds of formula I-b
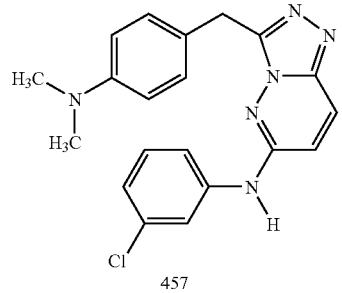
457
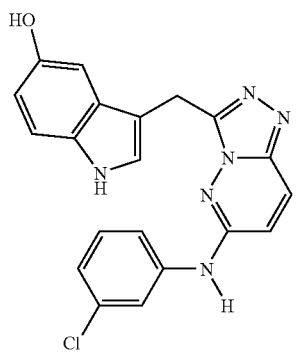
458
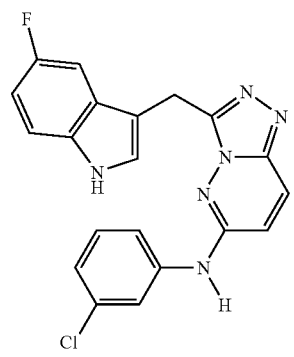
459
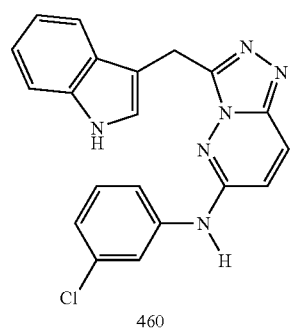
460

TABLE 2-continued
Compounds of formula I-b
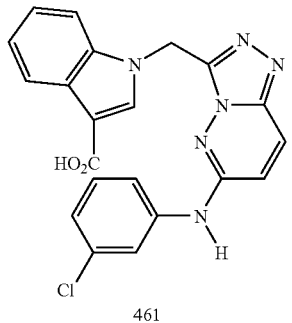
461
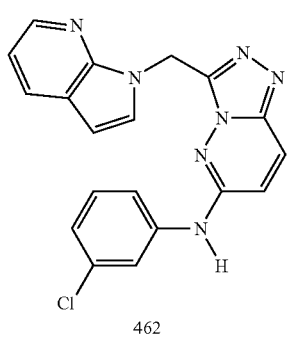
462
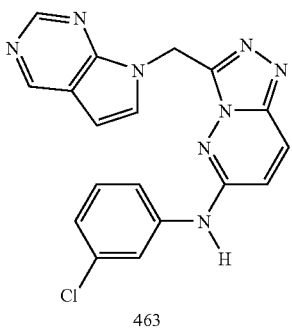
463
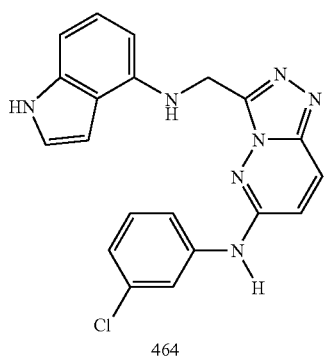
464
TABLE 2-continued
Compounds of formula I-b
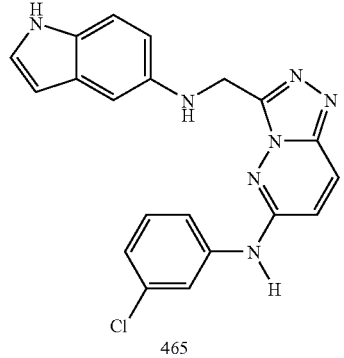
465
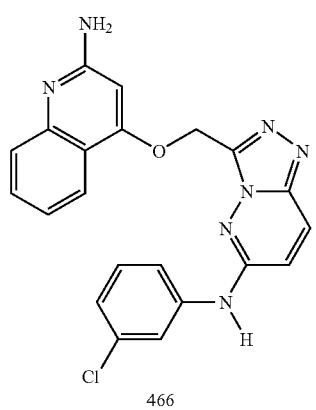
466
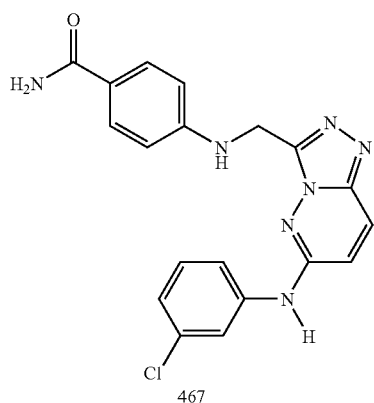
467
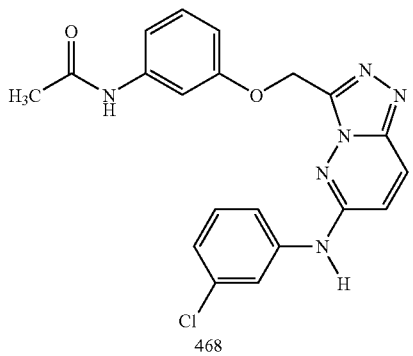
468

TABLE 2-continued
Compounds of formula I-b
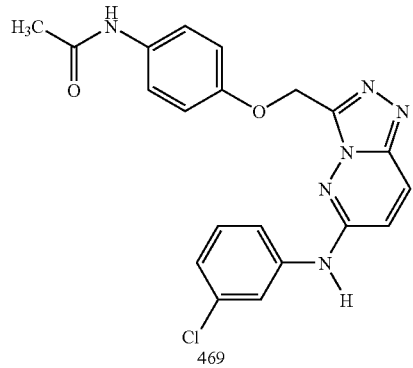
469
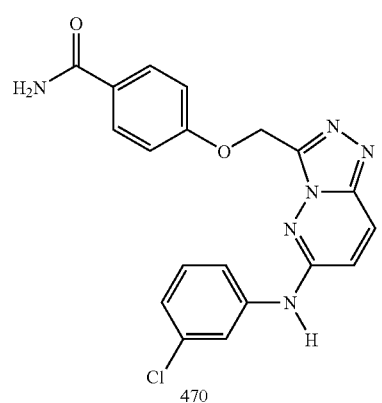
470
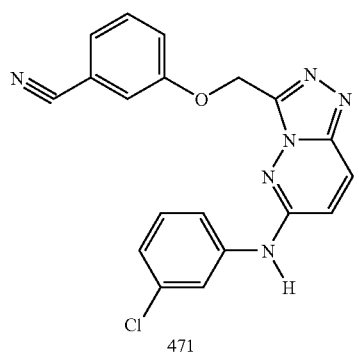
471
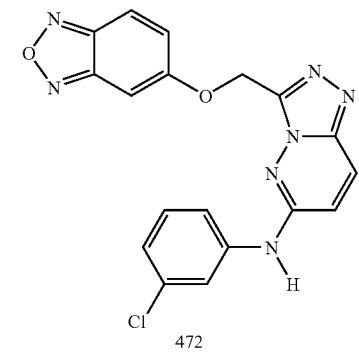
472
TABLE 2-continued
Compounds of formula I-b
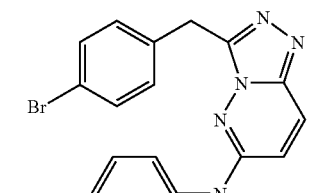
473
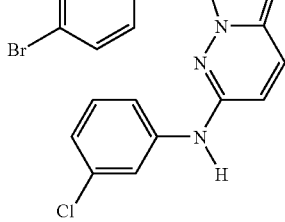
474
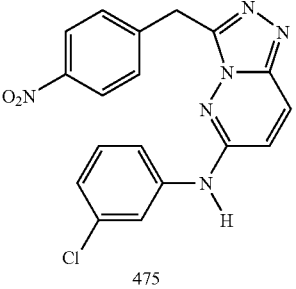
475
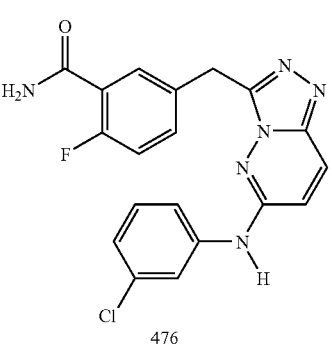
476

TABLE 2-continued
Compounds of formula I-b
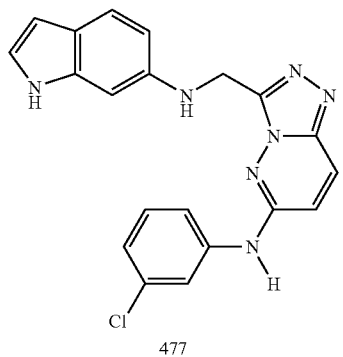
477
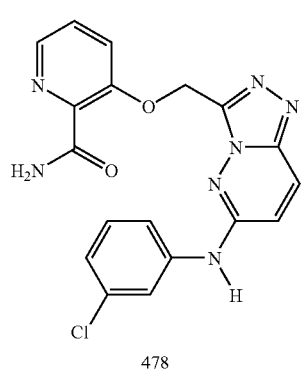
478
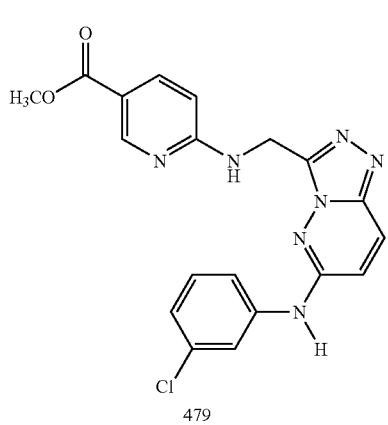
479
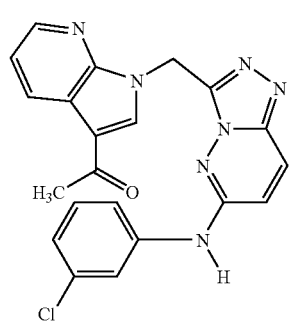
480
TABLE 2-continued
Compounds of formula I-b
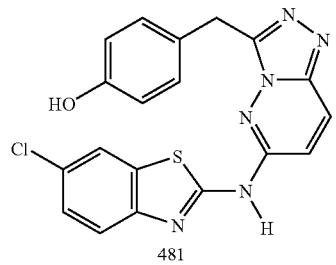
481
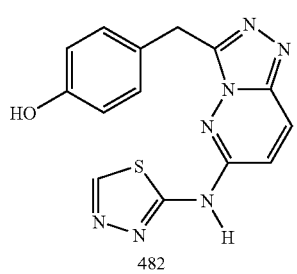
482
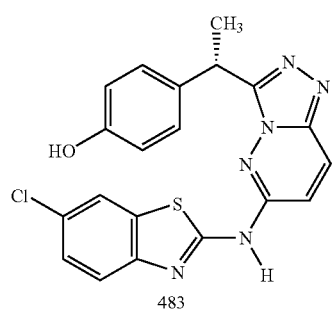
483
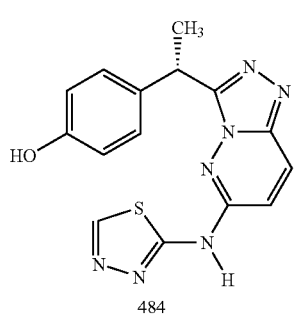
484
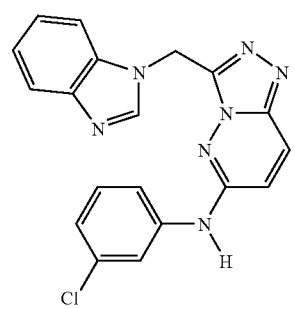
485

TABLE 2-continued
Compounds of formula I-b
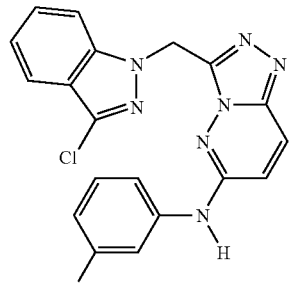
486
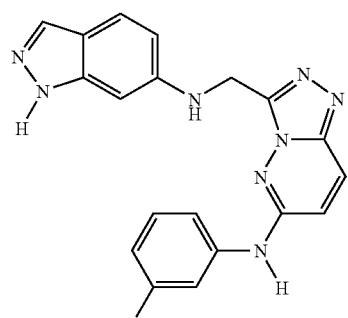
487
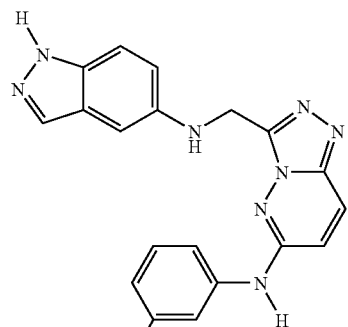
488
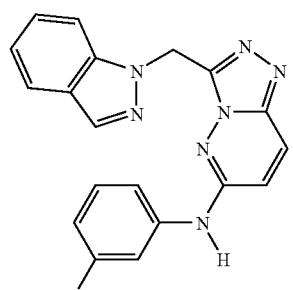
489
TABLE 2-continued
Compounds of formula I-b
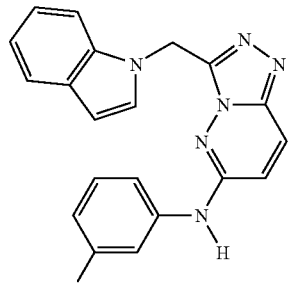
490
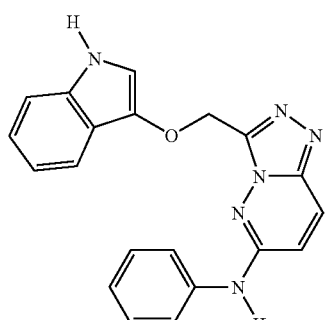
491
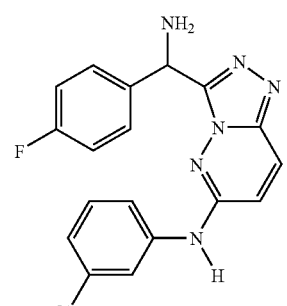
492
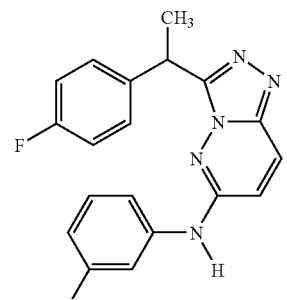
493

TABLE 2-continued
Compounds of formula I-b
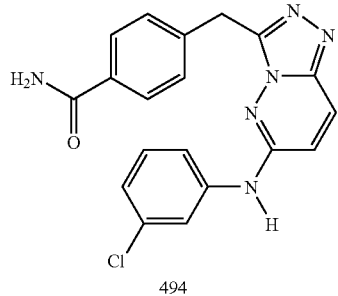
494
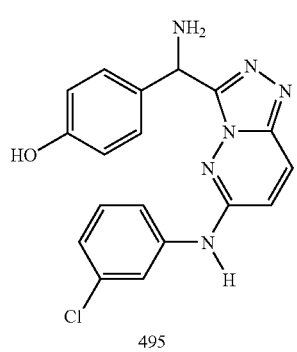
495
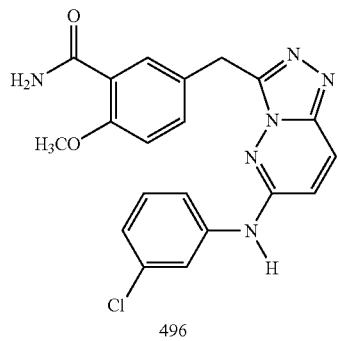
496
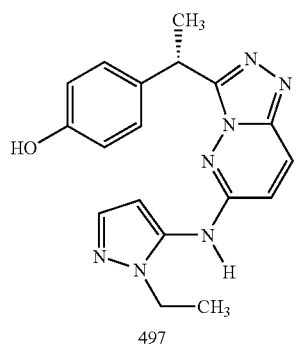
497
TABLE 2-continued
Compounds of formula I-b
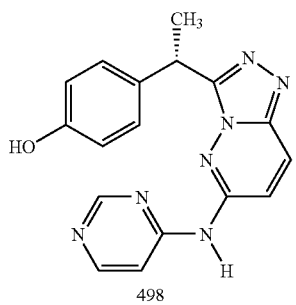
498
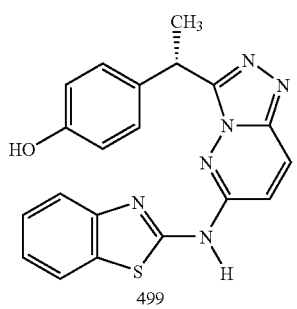
499
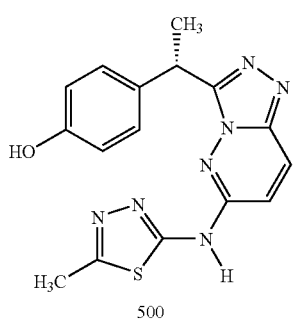
500
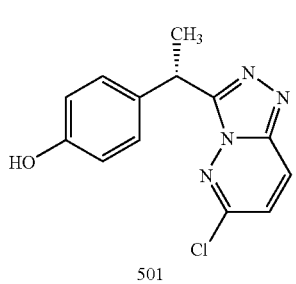
501
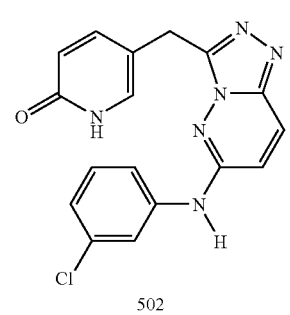
502

TABLE 2-continued
Compounds of formula I-b
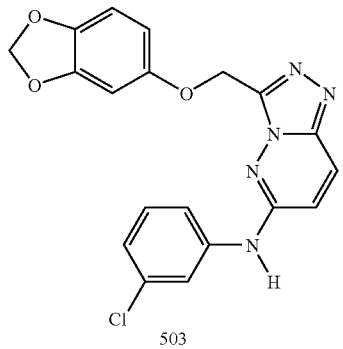
503
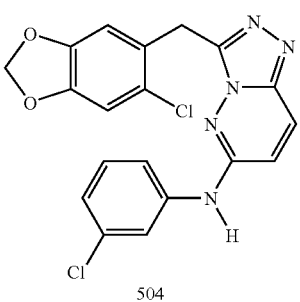
504
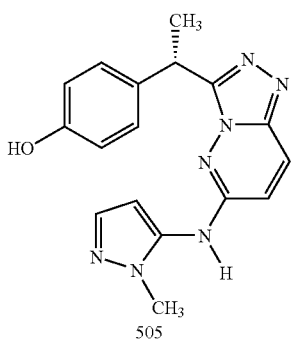
505
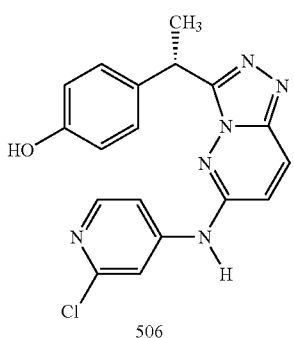
506
TABLE 2-continued
Compounds of formula I-b
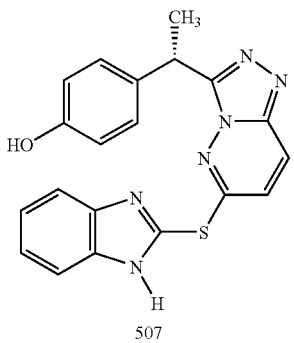
507
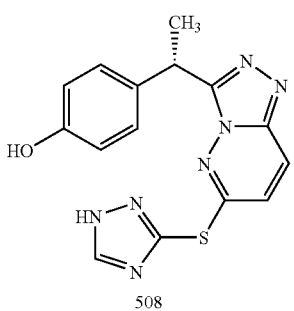
508
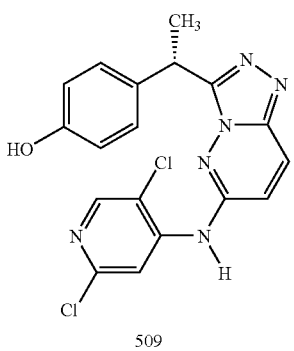
509
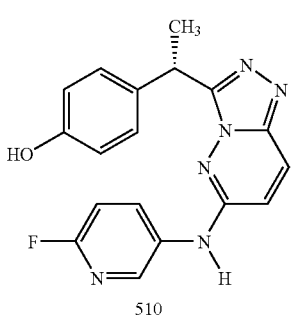
510

TABLE 2-continued
Compounds of formula I-b
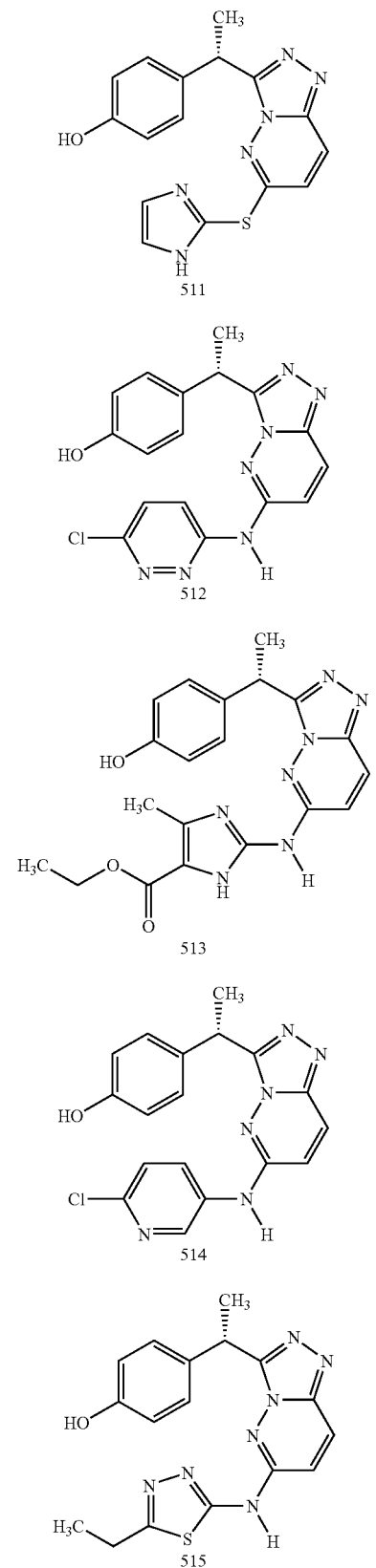
511
512
513
514
515
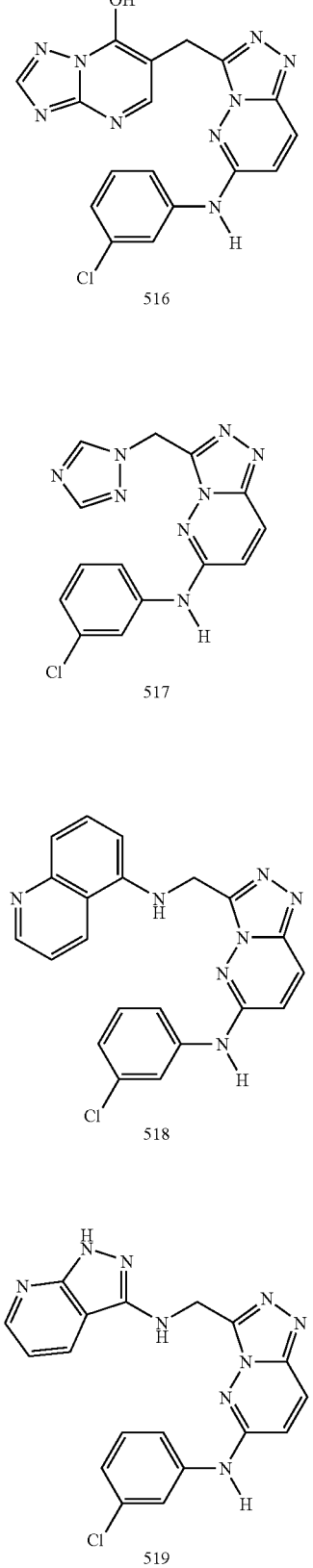
516
517
518
519

TABLE 2-continued
Compounds of formula I-b
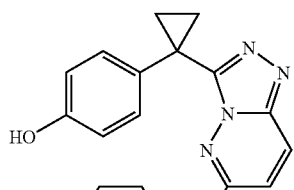
520
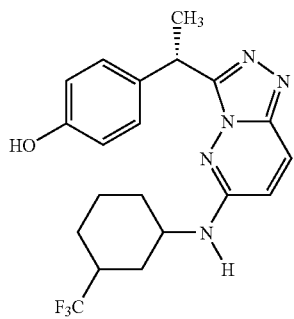
521
TABLE 3
Compounds of formulae I or I-c
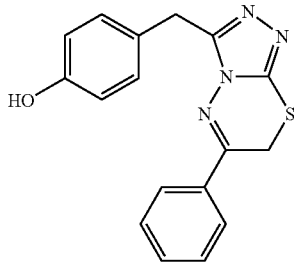
522
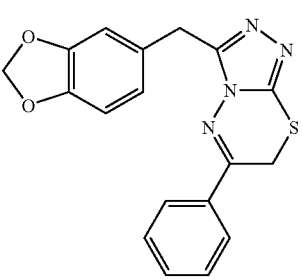
523
TABLE 3-continued
Compounds of formulae I or I-c
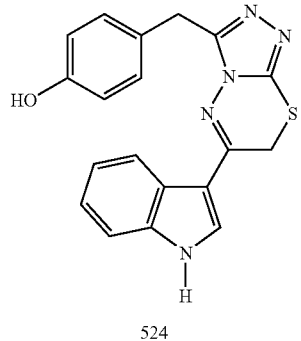
524
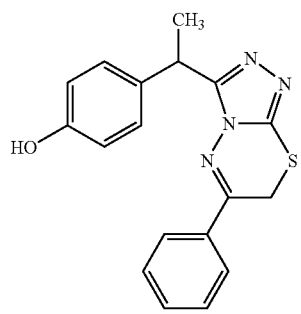
525
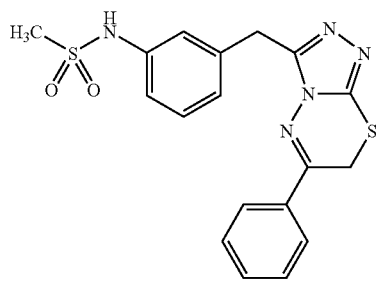
526
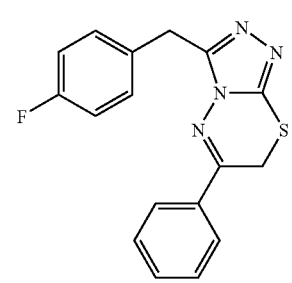
527

TABLE 3-continued
Compounds of formulae I or I-c
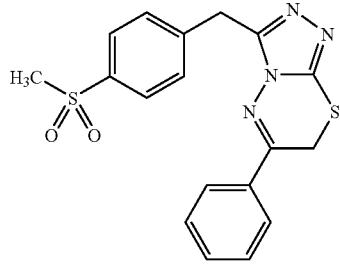
528
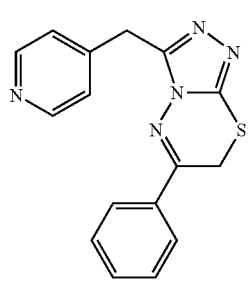
529
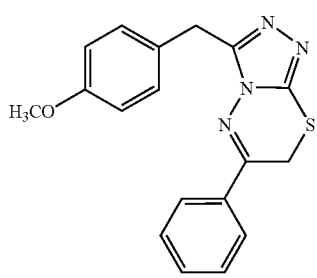
530
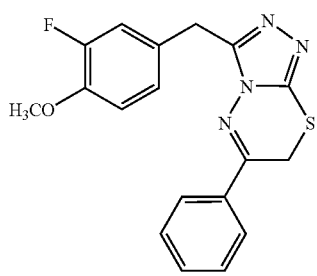
531
TABLE 3-continued
Compounds of formulae I or I-c
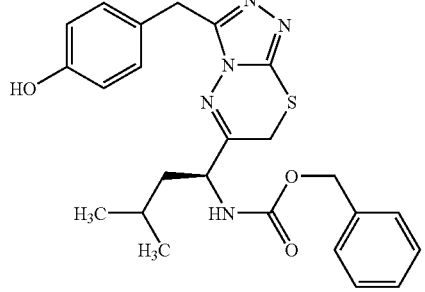
532
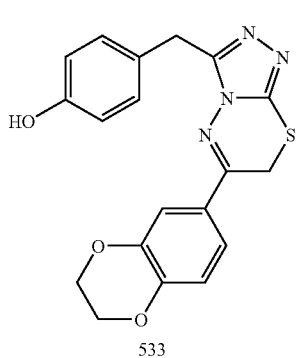
533
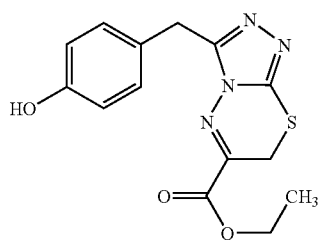
534
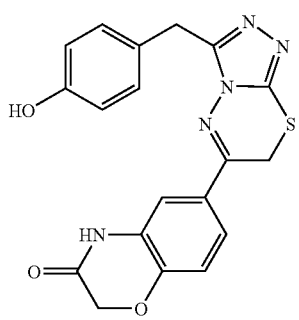
535

TABLE 3-continued
Compounds of formulae I or I-c
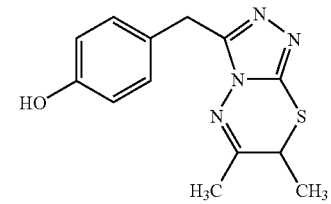
536
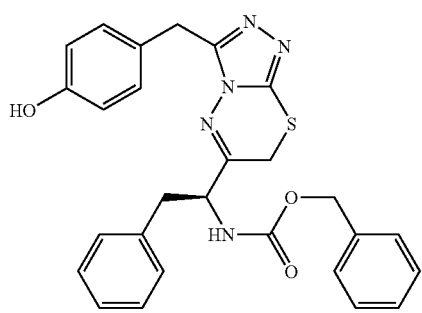
537
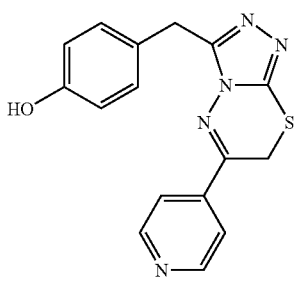
538
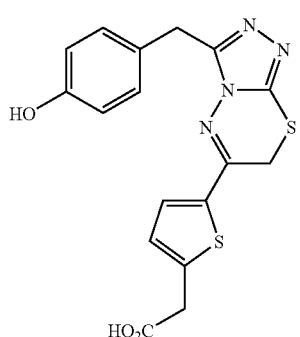
539
TABLE 3-continued
Compounds of formulae I or I-c
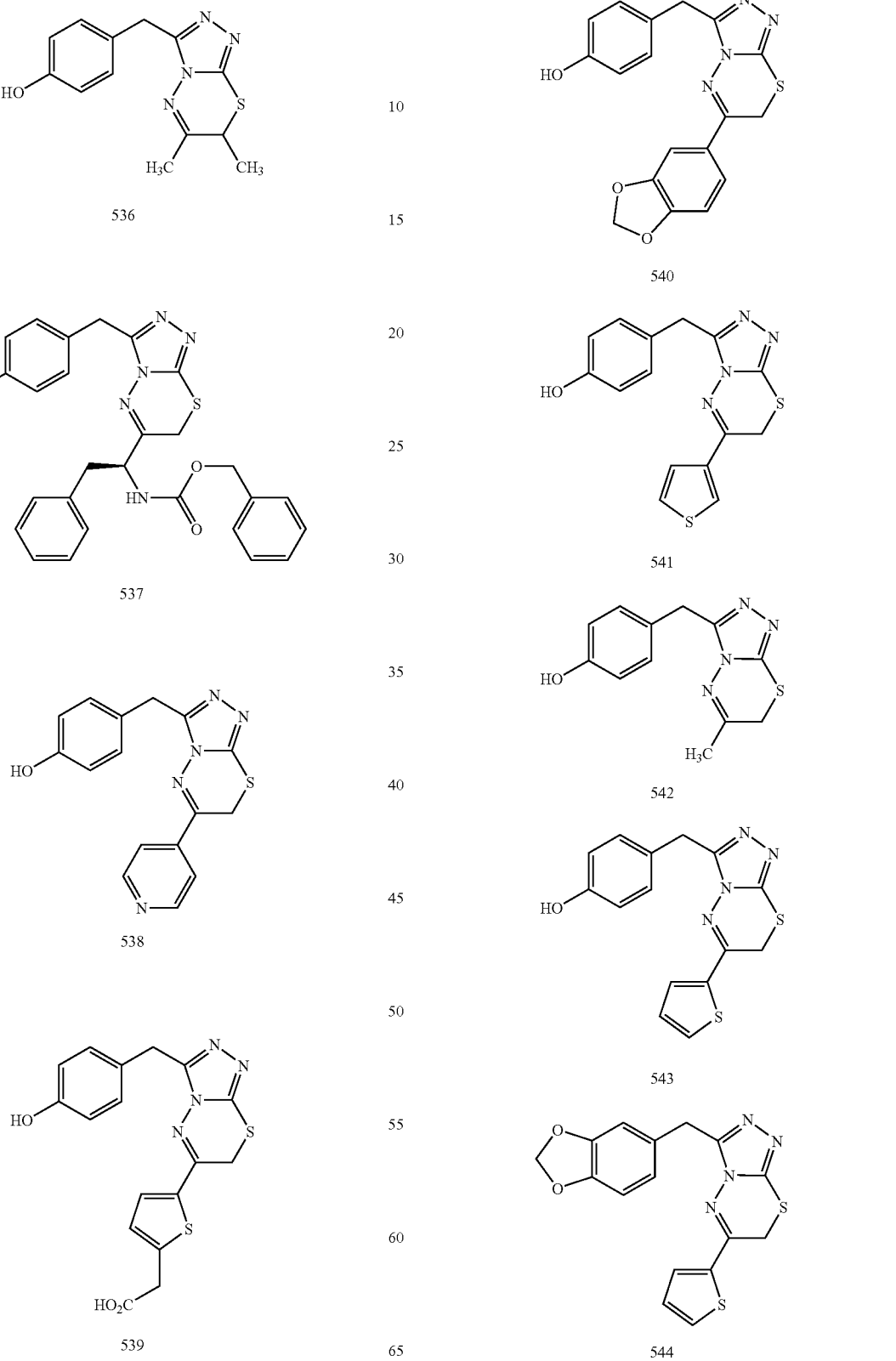
540
541
542
543
544

TABLE 3-continued

Compounds of formulae I or I-c

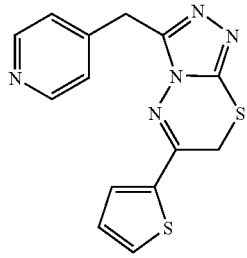

545

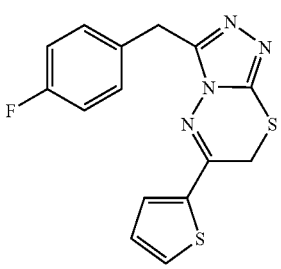

546

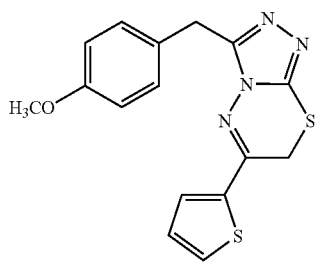

547

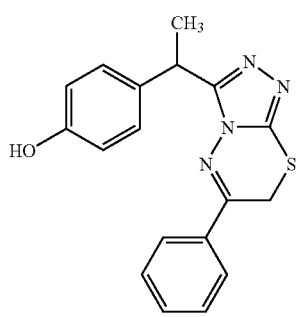

548

Compositions, Formulations, and Administration of Compounds of the Invention

According to another aspect, the invention features pharmaceutical compositions that include a compound of formula I, I-a, I-b, or I-c, or a compound listed in Tables 1-3, and a pharmaceutically acceptable carrier, adjuvant, or vehicle. The amount of compound in the compositions of the invention is such that is effective to detectably inhibit a protein kinase, particularly c-Met in a biological sample or in a patient. The term "c-Met" is synonymous with "cMet", "MET", "Met" or other designations known to one skilled in the art. Preferably a composition of the present invention is formulated for administration to a patient in need of such composition. Most preferably, the composition of this invention is formulated for oral administration to a patient.

The term "patient," as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitory active metabolite or residue thereof. As used herein, the term "inhibitory active metabolite or residue thereof" means that a metabolite or residue thereof is also an inhibitor of c-Met.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: The Science and Practice of Pharmacy, 21 st edition, 2005, ed. D.B. Troy, Lippincott Williams & Wilkins, Philadelphia, and Encyclopedia of Pharmaceiutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar--agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

A compound or composition of the invention can be used as a immunotherapy to treat or lessen the severity of a proliferative disease, condition, or disorder in a patient by administering to the patient a compound or a composition of the invention in an effective amount. Such diseases, conditions, or disorders include cancer, particularly metastatic cancer, atherosclerosis, and lung fibrosis.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include adrenocortical cancer; bladder cancer; bone cancer; brain cancer; breast cancer; cancer of the peritoneum; cervical cancer; colon cancer; colorectal cancer; endometrial or uterine carcinoma; esophogeal cancer; eye cancer; gallbladder cancer; gastrointestinal cancer; glioblastoma; various types of head and neck cancer; hepatic carcinoma; hepatocellular cancer; kidney cancer; laryngeal cancer; liver cancer; lung cancer, such as, for example, adenocarcinoma of the lung, small-cell lung cancer, squamous carcinoma of the lung, non-small cell lung cancer; melanoma and nonmelanoma skin cancer; myeloproliferative disorders, such as, for example, polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML, or juvenile myelomonocytic leukemia; ovarian cancer; pancreatic cancer; prostate cancer, including benign prostatic hyperplasia; rectal cancer; salivary gland carcinoma; squamous cell cancer; testicular cancer; thyroid cancer; and vulval cancer.

The treatment method that includes administering a c-Met inhibitor of the invention can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition of the invention as a single dosage form or separately from the compound or composition as part of a multiple dosage form. The additional therapeutic agent may be administered at the same time as a compound of the invention or at a different time. In the latter case, administration may be staggered by, for example, 6 hours, 12 hours, 1 day, 2 days, 3 days, 1 week, 2 weeks, 3 weeks, 1 month, or 2 months. Non-limiting examples of chemotherapeutic agents or other anti-proliferative agents that may be combined with the compounds of this invention include tamoxifen, raloxifene, anastrozole, exemestane, letrozole, herceptin™ (trastuzumab), Gleevec™ (imatanib), Taxol™ (paclitaxel), cyclophosphamide, lovastatin, minosine, araC, 5-fluorouracil (5-FU), methotrexate (MTX), Taxotere™ (docetaxel), Zoladex™ (goserelin), vincristin, vinblastin, nocodazole, teniposide, etoposide, Gemzar™ (gemcitabine), epothilone, navelbine, camptothecin, daunonibicin, dactinomycin, mitoxantrone, amsacrine, doxorubicin (adriamycin), epirubicin, or idarubicin. In another aspect, the additional chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone).

The invention also features a method of inhibiting the growth of a cell that expresses c-Met or hepatocyte growth factor, or both, that includes contacting the cell with a compound or composition of the invention, thereby causing inhibition of growth of the cell. Examples of a cell whose growth can be inhibited include: a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, or a leukemia cell.

The invention provides a method of inhibiting c-Met kinase activity in a biological sample that includes contacting the biological sample with a compound or composition of the invention. The term "biological sample," as used herein, means a sample outside a living organism and includes, without limitation, cell cultures or extracts thereof; biopsied material obtained from a mammal or extracts thereof, and blood, saliva, urine, feces, semen, tears, or other body fluids or extracts thereof. Inhibition of kinase activity, particularly c-Met kinase activity, in a biological sample is useful for a variety of purposes known to one of skill in the art and is limited to non-therapeutic methods. Examples of such purposes include, but are not limited to, biological specimen storage and biological assays.

The invention also provides a method of inhibiting c-Met kinase activity in a patient, comprising administering to the patient a compound or composition of the invention. In an embodiment, the invention comprises a method of treating or lessening the severity of a c-Met-mediated condition or disease in a patient. The term "c-Met-mediated disease" or "c-MET-mediated condition", as used herein, means any disease state or other deleterious condition in which c-Met is known to play a role. The terms "c-Met-mediated disease" or "c-Met-mediated condition" also mean those diseases or conditions that are alleviated by treatment with a c-Met inhibitor. Such conditions include, without limitation, cancers, such as, for example, gastric adenocarcinoma, gliobastoma, renal cancer, small cell lung carcinoma, colorectal cancer, prostate cancer, brain cancer, liver cancer, pancreatic cancer, and breast cancer, and other proliferative diseases, such as, for example, atherosclerosis and lung fibrosis.

In certain embodiments of the present invention an "effective amount" or "effective dose" of the compound or pharmaceutically acceptable composition is that amount effective for treating or lessening the severity of one or more of the aforementioned disorders. The compounds and compositions, according to the method of the present invention, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

The compounds of this invention or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention.

Suitable coatings and the general preparation of coated implantable devices are described in U.S. Pat. Nos. 6,099,562; 5,886,026; and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics into the composition. Implantable devices coated with a compound of this invention are another embodiment of the present invention. The compounds may also be coated on implantable medical devices, such as beads, or co-formulated with a polymer or other molecule, to provide a "drug depot," thus permitting the drug to be released over a longer time period than administration of an aqueous solution of the drug.

Preparation of Compounds of the Invention
The following definitions describe terms and abbreviations used herein:

| | |
|---|---|
| ATP | adenosine triphosphate |
| Boc | t-butoxycarbonyl |
| DMF | dimethylformamide |
| DTT | dithiothreitol |
| ESMS | electrospray mass spectrometry |
| HEPES | 4-(2-hydroxyethyl)- 1 -piperazineethanesulfonic acid |
| HPLG | high performance liquid chromatography |
| LC-MS | liquid chromatography-mass spectrometry |
| Me | methyl |
| MeOH | methanol |
| NADH | nicotinamide adenine dinucleotide hydride |
| Ph | phenyl |
| r.t. | room temperature |
| tBu | tertiary butyl |
| Tf | trifluorosulfonyl |
| TFA | trifluoacetic acid |
| Ts | toluenesulfonyl |

Purifications by reversed-phase HPLC were conducted on a Waters 20×100 mm YMC-Pack Pro C18 column using a linear water/acetonitrile (0.1% TFA) gradient at a flow rate of 28 mL/minute. Beginning and final composition of the gradient varied for -each compound between 10-40 and 50-90% acetonitrile, respectively.

In general, the compounds of this invention may be prepared by methods described herein or known to those skilled in the art for the preparation of analogous compounds. In order that the invention described herein may be more fully understood, the following examples are set forth. It should be understood that these examples are for illustrative purposes only and are not to be construed as limiting this invention in any manner.

Preparation of Triazolothiadiazoles (Compounds of Formula I-a)

As shown in FIG. 1, a carboxylic acid of formula II is reacted neat with thiocarbonohydrazide with heating (about 170° C.) in a condensation reaction to produce a 4-amino-1, 2,4-triazole-3-thiol of formula III. The compound of formula III is reacted with a carboxylic acid of formula IV in refluxing phosphorus oxychloride to produce a compound of formula I-a, where $R^A$, $L^B$, and $R^B$ are as defined herein for compounds of formula I.

To produce a compound of formula I-d, where $R^A$ and $R^B$ is as defined herein for a compound of formula I, the intermediate of formula III is reacted with an isothiocyante of formula V in DMF with heating. In addition, for the preparation of compounds that include an aryl boronic acid or boronate moiety as part of $R^A$, these groups can be introduced using those methods known to one skilled in the art or by methods described in U.S. Pat. Nos. 6,939,985 and 6,559,310, and in U.S. Patent Application No. 20040133028.

Triazolothiadiazole compounds of the invention prepared by these methods include those compounds listed in Table 1. Analytical characterization data of representative compounds are provided in Table 4.

EXAMPLE 1

Synthesis of Compound 2

Figure 2:
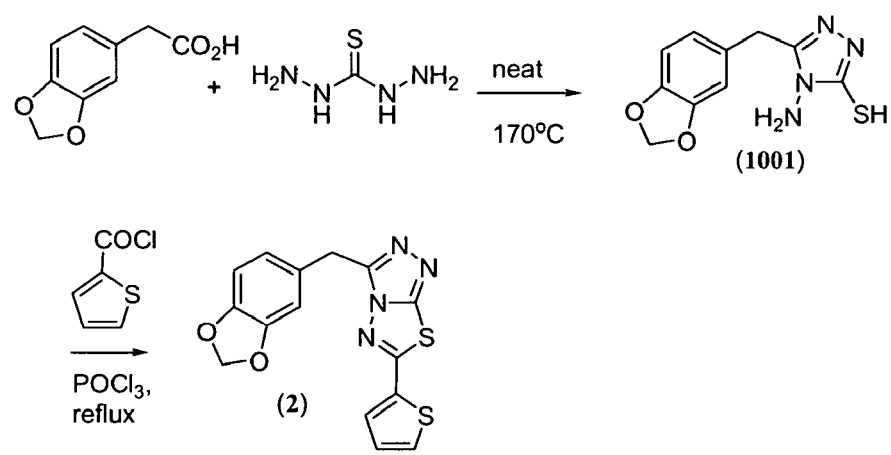
FIG. 2 shows the synthesis of compound 2.

As shown in FIG. 2, 2-(benzo[d][1,3]dioxol-5-yl)acetic acid (1 mmol) and thiocarbonohydrazide (1.5 mmol) were heated at 170° C. for 15 min. The mixture was cooled and taken up in 5% MeOH/CH$_2$Cl$_2$ and saturated NaHCO$_3$. The organics were washed with water, saturated NaCl, dried over Na$_2$SO$_4$, and concentrated in vacuo. The resulting 5-((benzo [d][1,3]dioxol-5-yl)methyl)-4H-4-amino-3-mercapto-1,2,4-triazole (compound 1001) was used as is in the next reaction. Accordingly, a mixture of compound 1001 and thiopene-2-carbonyl chloride (0.176 g, 1.2 mmol) suspended in excess phoshoryl chloride (~10 mL) was refluxed 5 hours. The excess phoshoryl chloride was removed under reduced pressure and the subsequent residue was mixed with crushed ice. The solids were filtered, washed with water, and dried in vaciio. Purification by reversed-phase HPLC produced pure 3-((benzo[d][1,3]dioxol-5-yl)methyl)-6-(thiophen-2-yl)-[1,2,4]triazolo[3,4-b][1,3,4]thiadiazole (compound 2).

EXAMPLE 2

Synthesis of Compound 5

Figure 3:
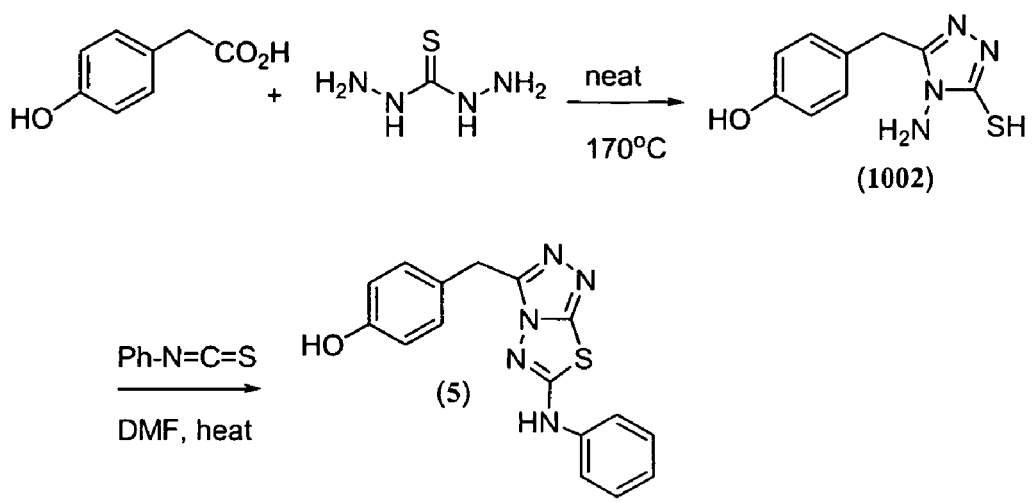
FIG. 3 shows the synthesis of compound 5.

As shown in FIG. 3, 4-hydroxyphenylacetic acid (1 mmol) and thiocarbonohydrazide (1.5 mmol) were heated at 170° C. for 15 minutes. The mixture was cooled to r.t. and taken up in 5% MeOH/CH$_2$Cl$_2$ and saturated NaHCO$_3$. The organics were washed with water, saturated NaCl, dried over Na$_2$SO$_4$, and concentrated in vacuo. The resulting 4-((5-mercapto-4H-1,2,4-triazol-3-yl)methyl)phenol (compound 1002) was used as is in the next reaction. Accordingly, to a solution of compound 1002 (50 mg, 0.224 mmol) in DMF (2.5 mL) was added 1-(isothiocyanatomethyl)benzene (65 µL, 0.50 mmol). The reaction was stirred at 110° C. overnight at ambient pressure, at which point LCMS analysis indicated disappearance of starting material and the presence of the desired thiadiazole. The reaction mixture was concentrated to give a dark oil, which was purified by reversed-phase HPLC to give compound 5 (30 mg, 40% yield) as a white solid.

Preparation of Triazolopyridazines (Compounds of Formulae I-b, I-e, and I-f)

Figure 4:
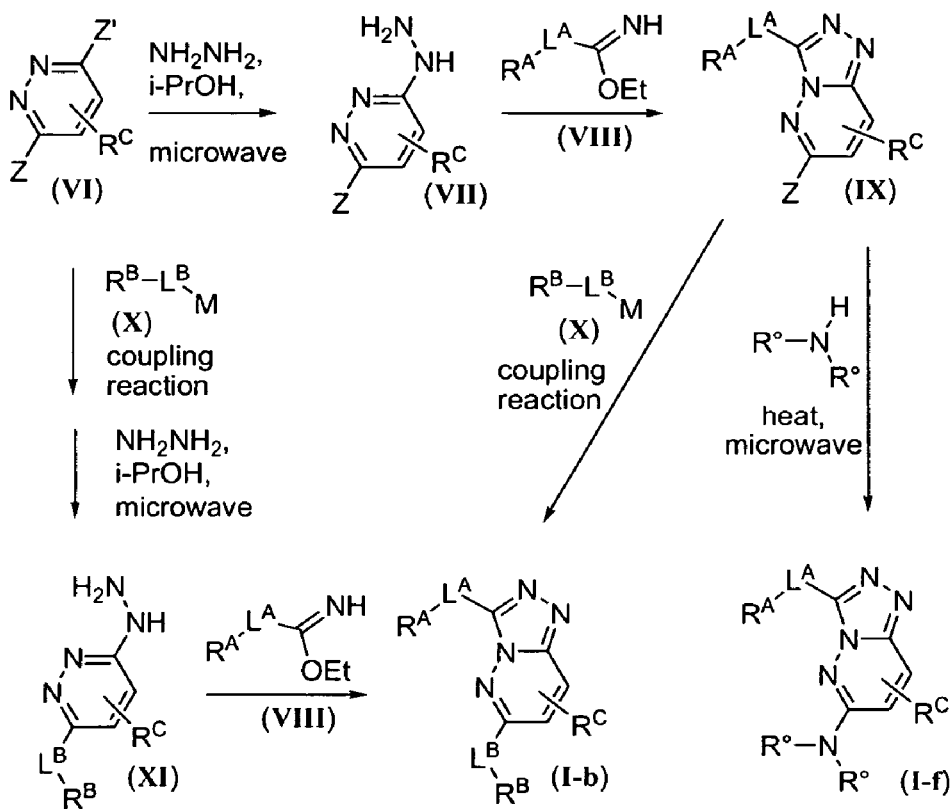
FIG. 4 shows a general scheme for the preparation of triazolopyridazines of the invention (compounds of formula I-b, formula I-f, and formula I-b). Compounds of formula I-e are compounds of formula I-b where $R^C$ is hydrogen.

As shown in FIG. 4, a compound of formula VI, containing leaving groups Z and Z' (e.g., halogen, phosphonate, tosylate, or triflate), which can be the same or different, is reacted with hydrazine in a suitable solvent, such as, for example, isopropanol at an elevated temperature under microwave irradiation to produce a compound of formula VII. Typically, the reaction temperature is above 60° C. If $R^C$ is not hydrogen, the regiochemistry of substitution may be governed by the ease of leaving group displacement and/or the steric bulk of $R^C$. Subsequent reaction of the compound of formula III with an imidate ester of formula VIII produces a compound of formula IX, where each of $R^A$ and $R^C$ is as described for a compound of formula I and $L^A$ is an optionally substituted $C_{1-2}$ alkylene. Typically, this reaction is performed in polar solvent at an elevated temperature, such as, for example, refluxing methanol or ethanol. In one variation, a carboxylic acid or ester can substitute for the imidate ester and the reaction performed neat with heating. The compound of formula IX can then be reacted with a compound of formula X in a catalyst-mediated cross coupling reaction to form a compound of formula I-b. A compound of formula I-e is a compound of formula I-b where $R^C$ is hydrogen. The catalyst used in the cross coupling reaction can be, for example, a palladium catalyst/ligand system (such as, for example, Pd(PPh$_3$)$_4$, Pd(PtBu$_3$)$_4$, Pd[P(Me)(tBu$_3$)]$_4$, PdCl$_2$(PPh$_3$)$_2$, PdCl$_2$(dppf)$_2$, Pd$_2$(dba)$_3$BINAP, or Pd$_2$(dba)$_3$P(o-tol)$_3$ (see Fu and Littke, *Angew. Chem. Int. Ed.* 41:4176-4211, 2002; Nicolaou et al., *Angew. Chem. Int. Ed.* 44:4442-4489, 2005; or Hassen et al., *Chemical Reviews* 102(5): 1359-1469, 2002). The reaction is usually performed in the presence of a base. The M group of the compound of formula X can be, for example, —B(OAlkyl)$_2$ or —B(OH)$_2$(Suzuki reaction), —Mg-Hal (Kumada reaction), —Zn—Hal (Negishi reaction), —Sn(Alkyl)$_3$ (Stille reaction), —Si(Alkyl)$_3$ (Hiyama reaction), —Cu—Hal, —ZrCp$_2$Cl, or —AlMe$_2$. In the preparation of compounds that include an aryl boronic acid or boronate moiety as part of $R^A$ or $R^B$-$L^B$-M, these groups can be introduced using those methods known to one skilled in the art or by methods described in U.S. Pat. Nos. 6,939,985 and 6,559,310, and in U.S. Patent Application No. 20040133028. If so desired, the order of the functionalization of pyrimidine ring may be changed such that the cross-coupling reaction is performed first, followed by reaction with hydrazine.

As an alternative to appending the $L^B R^B$ group to the triazolopyridazine core structure via a catalyst-mediated cross coupling reaction, once a compound of formula IX is obtained, the Z group can be reacted with a nucleophilic moiety, such as, for example, an amine, to form a compound having formula I-f.

Triazolopyridazine compounds of the invention prepared by these methods include those compounds listed in Table 2. Analytical characterization data of representative compounds are provided in Table 4.

EXAMPLE 3

Synthesis of Compound 175

Figure 5:
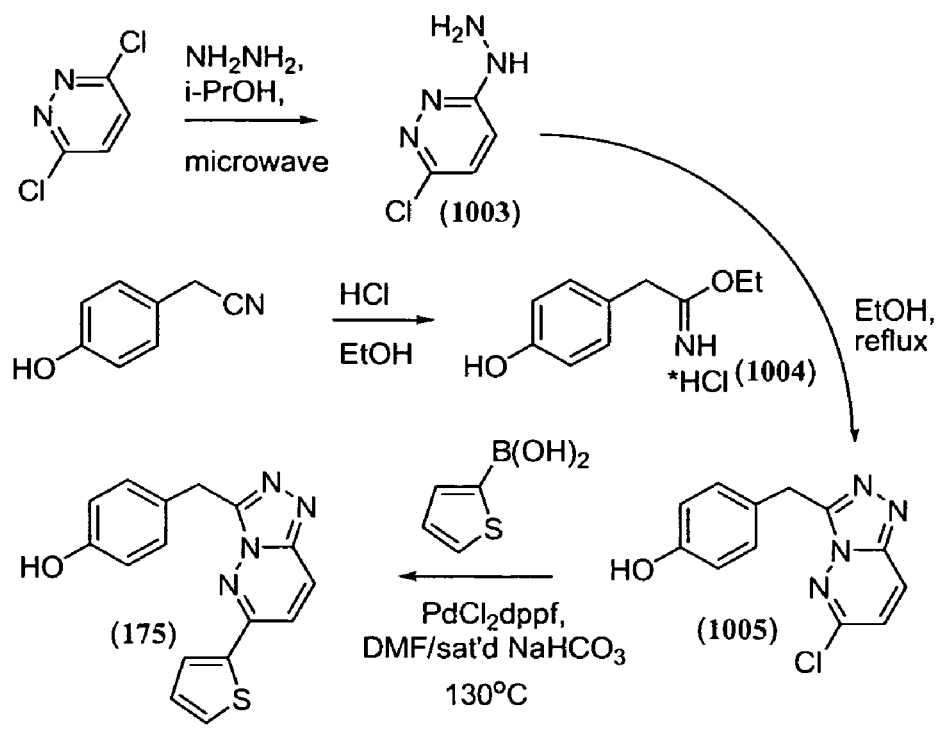
FIG. 5 shows the synthesis of compound 175.

As shown in FIG. 5, a mixture of 40 g (0.27 mole) of 3,6-dichloropyridazine and 40 mL of 80% hydrazine hydrate in 80 mL of ethanol was refluxed for one hour. The reaction mixture was evaporated to dryness and the residue was recrystallized from benzene to give 39 g of 1-(6-chloropyridazin-3-yl)hydrazine (compound 1003) (see Takahayashi, *J. Pharm. Soc. Japan* 75:778-781, 1955).

Separately, HCl gas was bubbled through a solution of 2-(4-hydroxyphenyl)acetonitrile (5.00 g, 37.58 mmol) in ethanol (2.16 mL, 37.58 mmol) at 0° C for approximately 15 minutes. The mixture was stored at 0° C. overnight. After warming the reaction mixture to room temperature and treating with an equal volume of ether, the precipitate was filtered and triturated with ether to yield an imidate ester (compound 1004, 7 g, 32.5 mmol, 87% yield).

A solution of compound 1003 (0.200 g, 1.4 mmol) and compound 1004 (0.636 g, 2.78 mmol) was refluxed in ethanol until the reaction was judged to be complete by HPLC analysis. The reaction mixture was concentrated and diluted with ethyl acetate. The organics were washed with water, brine, and concentrated in vaczio. Purification by preparative HPLC yielded 4-((6-chloro-[1,2,4]triazolo[4,3-b]pyridazin-3-yl)methyl)phenol (compound 1005, 0.147 g, 0.565 mmol, 40.4% yield).

A mixture of compound 1005 (0.050 g, 0.19 mmol), 2-thiophene boronic acid (0.029 g, 0.23 mmol), and $PdCl_2dppf$ (0.005 g) in DMF:saturated $NaHCO_3$ (1:1) was flushed with nitrogen and microwaved at 130° C. for 700 seconds. The reaction mixture was diluted with ethyl acetate and the organic layer washed with water and concentrated in vacuo. Purification by preparative HPLC yielded 4-((6-(thiophen-2-yl)-[1,2,4]triazolo[4,3-b]pyridazin-3-yl)methyl)phenol (compound 175, 0.0109 g, 0.035 mmol, 18.6% yield).

EXAMPLE 4

Synthesis of Compound 190

Figure 6:
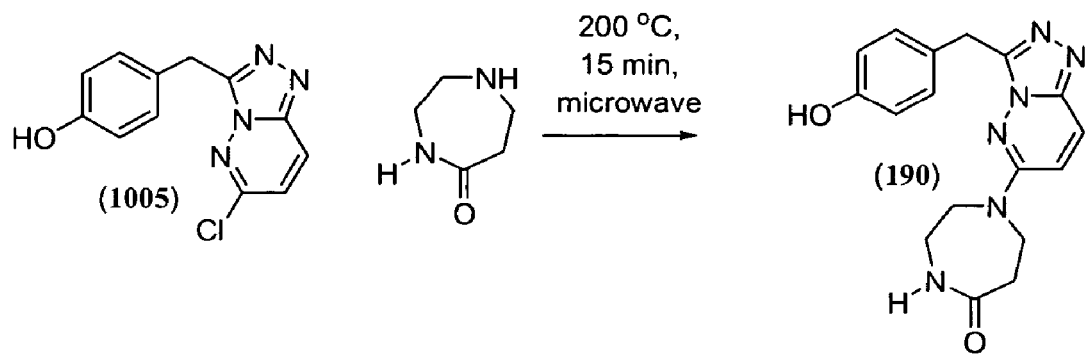
FIG. 6 shows the synthesis of compound 190.

As shown in FIG. 6, compound 1005 (35 mg, 0.13 mmol) was dissolved in NMP (1 mL) with 1,4-diazepan-5-one (100 mg, 0.88 mmol) and the mixture heated at 200 ° C. for 15 minutes in a microwave reactor. The reaction mixture was purified by preparative reversed-phase HPLC to give compound 190 (34 mg, 0.1 mmol, 77% yield).

EXAMPLE 5

Synthesis of Compound 206

Figure 7:
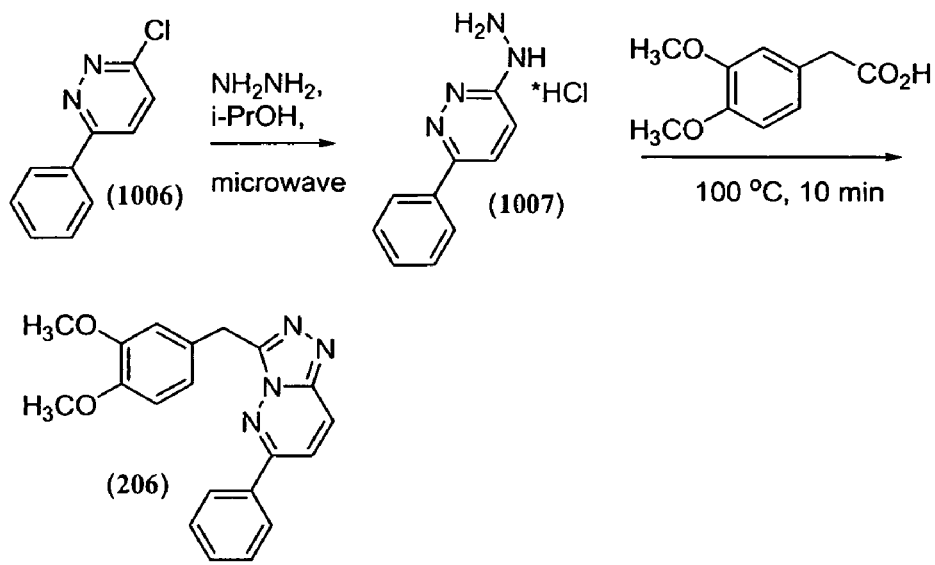
FIG. 7 shows the synthesis of compound 206.

As shown in FIG. 7, a mixture of 3-chloro-6-phenylpyridazine (compound 1006, 1 g, 5.3 mmol) and hydrazine monohydrate (0.51 mL, 10.53 mmol) in isopropanol was microwaved at 180° C. for 30 minutes. The reaction was treated with ether, the resulting precipitate filtered and washed with ether to yield 1-(6-phenylpyridazin-3-yl)hydrazine, which can be treated with 2M HCl in ether to give the corresponding hydrochloride salt (compound 1007) in quantitative yield. Compound 1007 (0.050 g, 0.22 mmol) and 2-(4-methoxyphenyl)acetic acid (0.044 g, 0.22 mmol) were heated neat to 100° C. for 10 minutes. The reaction mixture was diluted with ethyl acetate, and the organic layer was washed with water and brine. Purification by preparative reversed-phase HPLC yielded 3-(3,4-dimethoxybenzyl)-6-phenyl-[1,2,4]triazolo[4,3-b]pyridazine (compound 206, 0.0073 g, 0.021 mmol, 10% yield).

Preparation of Triazolothiadiazines (Compounds of Formulae I-c and I-g)

Figure 8:
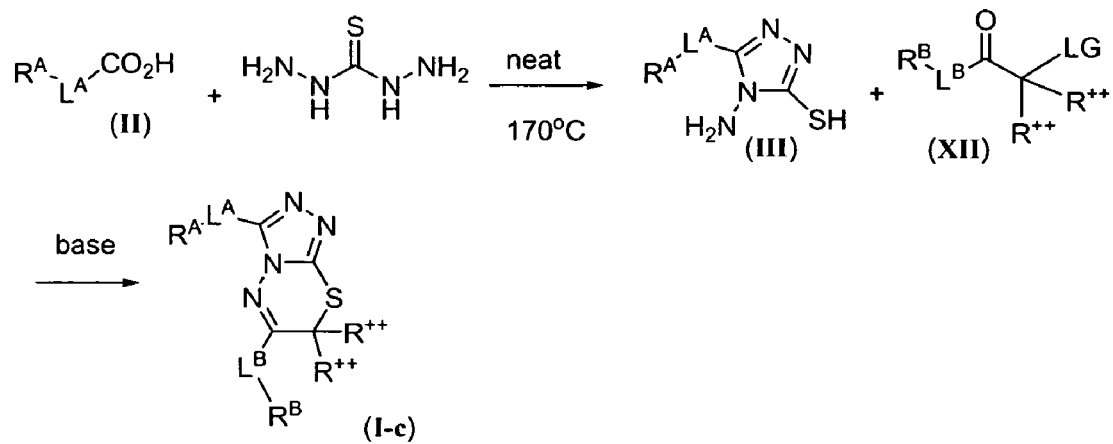
FIG. 8 shows a general scheme for the preparation of triazolothiadiazines of the invention (compounds of formula I-c and formula I-g). Compounds of formula I-g are compounds of formula I-c where $R^{++}$ is hydrogen.

As shown in FIG. 8, a carboxylic acid of formula II is reacted neat with a stoichiometric amount of thiocarbonohydrazide under an inert atmosphere with heating (about 170° C.) in a condensation reaction to produce a 4-amino-1,2,4-triazole-3-thiol of formula III, where $R^A$ and $L^A$ are as defined herein for a compound of formula I. The compound of formula III is reacted with a compound of formula XII under basic conditions, where LG is a leaving group such as, for example, chloro, bromo, iodo, tosyl, or trifyl, to produce a compound of formula I-c, where $R^A$, $L^A$, $R^B$, $L^B$, and $R^{++}$ are as defined herein for a compound of formula I. A compound of formula I-g is a compound of formula I-c where each $R^{++}$ is hydrogen. Suitable bases for this reaction include hindered amine bases such as, for example, triethylamine, N,N-diisopropylethylamine, 2,6-lutidine, 2,6-di-tert-butylpyridine, or 2,6-di-tert-butyl-4-methyl-pyridine. If necessary, the reaction mixture is heated to drive the reaction to completion. If required, any of the functional groups residing on substituents $L^A$, $R^A$, $L^B$, or $R^B$ may be suitably protected with a protecting group by methods known to those skilled in the art.

Triazolothiadiazine compounds of the invention prepared by this method include those compounds listed in Table 3. Analytical characterization data of representative compounds are provided in Table 4.

EXAMPLE 6

Synthesis of Compound 541

Figure 9:
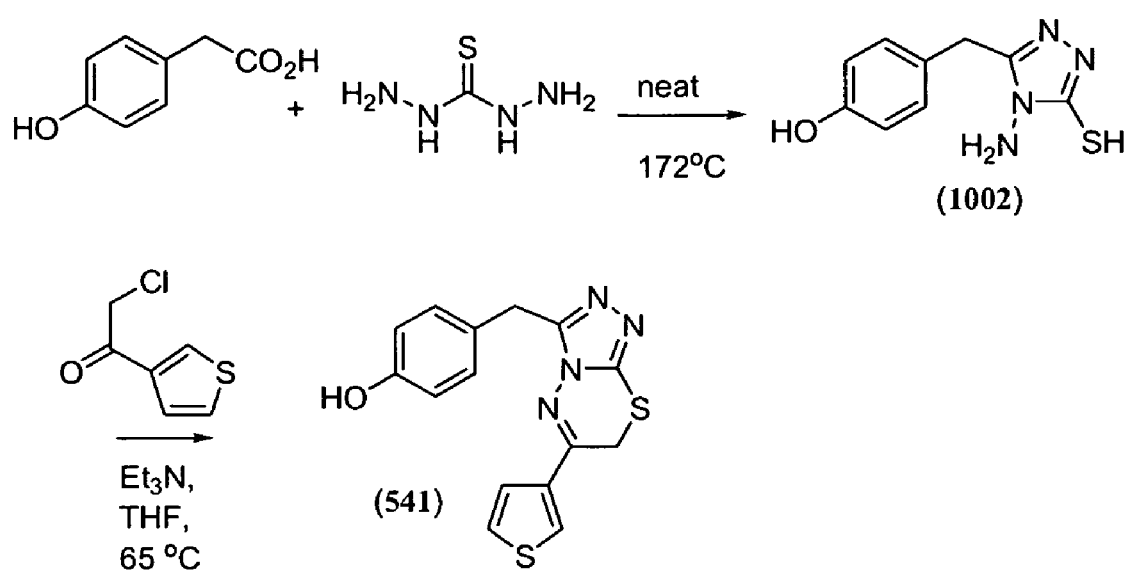
FIG. 9 shows the synthesis of compound 541.

As shown in FIG. 9, compound 1002 can be prepared as described above in Example 2. To compound 1002 (50 mg, 0.224 mmol) in tetrahydrofliran (2.5 mL) was added triethylamine (69 µL, 0.50 mmol), followed by 2-chloro-1-(thiophen-3-yl)ethanone (80 mg, 0.50 mmol). The reaction mixture was stirred at 65° C. overnight, at which point LC-MS analysis indicated the disappearance of starting material and the presence of the desired product. The reaction mixture was concentrated in vacuo to give a dark oil, which was purified by reversed phase HPLC to give compound 541 (40 mg, 75%) as a white solid.

EXAMPLE 7

$K_i$ Determination for the Inhibition of c-Met

Compounds of the invention were screened for their ability to inhibit c-Met kinase activity using a standard coupled enzyme system (Fox et al., *Protein Sci.* 7:2249, 1998). Reactions were carried out in a solution containing 100 mM HEPES (pH 7.5), 10 mM $MgCl_2$, 25 mM NaCl, 300 µM NADH, 1 mM DTT, and 1.5% DMSO. Final substrate concentrations in the assay were 200 µM ATP (Sigma Chemicals, St Louis, Mo.) and 10 µM polyGluTyr (Sigma Chemical Company, St. Louis). Reactions were-carried out at 30° C. and 80 nM c-Met. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and a test compound of the present invention. The assay stock buffer solution (175 µL) was incubated in a 96 well plate with 5 µL of the test compound of the present invention at final concentrations spanning 0.006 µM to 12.5 µM at 30° C. for 10 minutes. Typically, a 12-point titration was conducted by preparing serial dilutions (from 10 mM compound stocks) with DMSO of the test compounds of the present invention in daughter plates. The reaction was initiated by the addition of 20 µL of ATP (final concentration 200 pM). Rates of reaction were obtained using a Molecular Devices Spectramax plate reader (Sunnyvale, Calif.) over 10 minutes at 30° C. The $K_i$ values were determined from the rate data as a function of inhibitor concentration. Selected $K_i$ values are provided in Table 4 as a range, where "A" represents a $K_i$ of less than 0.10 µM, "B" represents a $K_i$ of 0.10 µM to 2.0 µM, and "C" represents a $K_i$ of greater than 2.0 µM.

TABLE 4

Physical and biological data of compounds of formula I.

| No. | c-Met $K_i$ | $^1$H NMR peaks given as δ values (500 MHz - unless indicated otherwise) | ESMS (M + H) |
|---|---|---|---|
| 1 | C | (methanol-$d_4$): 7.40(d, J=7.1 Hz, 2H), 7.36-7.33 (m, 2H), 7.28(t, J=7.3 Hz, 1H), 7.23-7.19(m, 2H), 6.94-6.91(m, 2H), 5.06-5.04(m, 2H), 4.19 (s, 2H), 4.09(s, H) | 338 |
| 2 | B | (DMSO-$d_6$): 8.00(dd, J=1.1, 5.0 Hz, 1H), 7.93 (dd, J=1.1, 3.8 Hz, 1H), 7.30(dd, J=3.8, 5.0 Hz, 1H), 6.90(s, 1H), 6.86-6.80(m, 2H), 5.98(d, J=2.0 Hz, 2H), 4.33(s, 2H) | 343 |
| 3 | C | (DMSO-$d_6$): 7.94(d, 2H), 7.68-7.61(m, 3H), 7.31(d, J=8.6 Hz, 2H), 6.90(dd, J=2.0, 6.7 Hz, 2H), 4.39(s, 2H), 3.71(s, 3H) | 323 |
| 4 | B | | 309 |
| 5 | A | (DMSO-$d_6$): 10.58(s, 1H), 9.28(s, 1H), 7.50(d, J=7.7 Hz, 2H), 7.41-7.38(m, 2H), 7.16(d, J=8.5 Hz, 2H), 7.09(t, J=7.3 Hz, 2H), 6.72(dd, J=2.0, 6.5 Hz, 2H), 4.20(s, 2H) | 324 |
| 6 | C | (methanol-$d_4$)7.15(d, J=8.5 Hz, 2H), 6.73-6.70 (m, 2H), 4.29(s, 2H), 2.71-2.70(s, 3H) | 248 |
| 7 | B | (DMSO-$d_6$): 7.77(s, 2H), 7.05(d, J=8.4 Hz, 2H), 6.68(dd, J=1.9, 6.6 Hz, 2H), 4.08(s, 2H) | 248 |
| 8 | B | (DMSO-$d_6$): 8.64(t, J=5.6 Hz, 1H), 7.37-7.34(m, 2H), 7.31(dd, J=3.2, 5.5 Hz, 2H), 7.07(d, J=8.2 Hz, 2H), 6.66(d, J=8.3 Hz, 2H), 4.47(d, J=5.7 Hz, 2H), 4.08(s, 2H) | 338 |
| 9 | B | (DMSO-$d_6$): 8.73(d, J=12.4 Hz, 2H), 8.00(d, J=7.5 Hz, 1H), 7.59-7.58(m, 1H), 7.05-7.02(m, 2H), 6.67-6.64(m, 2H), 4.57(d, J=5.7 Hz, 2H), 4.07(s, 2H) | 340 |
| 10 | C | (DMSO-$d_6$): 9.26(s, 1H), 8.34(d, J=3.8 Hz, 1H), 7.80(s, 1H), 7.09(d, J=8.6 Hz, 2H), 7.05(s, 1H), 6.69(d, J=8.5 Hz, 2H), 4.19(s, 2H) | 325 |
| 11 | C | (DMSO-$d_6$): 8.25(dd, J=1.2, 8.5 Hz, 2H), 7.79-7.76(m, 1H), 7.61-7.58(m, 2H), 7.33-7.30 (m, 2H), 6.93-6.90(m, 2H), 4.47(s, 2H), 3.62(s, 4H) | 351 |
| 12 | C | (DMSO-$d_6$): 7.24-7.22(m, 2H), 6.91-6.85(m, 2H), 4.14(s,2H), 3.99-3.96(m, 1H), 3.74-3.71(m,4H), 3.50-3.37(m, 3H), 3.32(s, 3H), 2.08-2.00(m, 4H) | 360 |
| 13 | | | 349.20 |
| 14 | B | (DMSO-$d_6$): 13.46(s,H), 9.26(s, 1H), 8.09(d, J=4.5 Hz, 1H), 7.10-7.05(m, 2H), 6.68(d, J=8.4 Hz, 2H), 4.01(s, 2H), 3.89(s, 3H) | 262.20 |
| 15 | C | | 361.30 |
| 16 | A | (DMSO-$d_6$): 10.97(s, 1H), 9.29(s, 1H), 7.99(d, J=8.8 Hz, 2H), 7.61(d, J=8.8 Hz, 2H), 7.18(d, J=8.4 Hz, 2H), 6.73(d, J=8.5 Hz, 2H), 4.22(s, 2H), 3.85(s, 3H) | 382.30 |
| 17 | B | (DMSO-$d_6$): 9.27(s,H), 9.24(s, 1H), 8.27(t, J=5.5 Hz, 1H), 7.09(d, J=8.3 Hz, 2H), 6.68(d, J=8.5 Hz, 2H), 4.09(s, 2H), 3.95(s, 1H), 3.80-3.76(m, 1H), 3.41-3.36(m, 1H), 3.31-3.26(m, 2H), 1.98-1.78(m, 1H), 1.59-1.52(m, 1H) | 332.30 |
| 18 | C | (DMSO-$d_6$): 13.26(s, 1H), 8.56(s, 1H), 7.40-7.34(m, 2H), 7.25(s, 1H), 7.09(d, J=6.8 Hz, 1H), 7.04(d, J=8.3 Hz, 2H), 6.66(d, J=8.3 Hz, 2H), 3.77(s, 2H) | 349.20 |
| 19 | C | (DMSO-$d_6$): 9.25(s, 1H), 8.57(s, 1H), 7.08(d, J=8.4 Hz, 2H), 6.68(d, J=8.4 Hz, 2H), 4.10(s, 2H), 2.51(m, 1H), 0.77(dd, J=1.9, 6.6 Hz, 2H), 0.59-0.57(m, 2H) | 288.20 |
| 20 | B | (DMSO-$d_6$): 9.12(d, J=2.3 Hz, 1H), 8.84-8.83(m, 1H), 8.35-8.32(m, 1H), 7.66(dd, J=4.9, 8.0 Hz, 1H), 7.32(d, J=8.5 Hz, 2H), 6.90(d, J=8.6 Hz, 2H), 4.40(s, 2H), 3.68(s, 3H) | 324.20 |
| 21 | C | (DMSO-$d_6$): 7.38(d, J=4.3 Hz, 4H), 7.34-7.29(m, 1H), 7.23(d, J=8.4 Hz, 2H), 6.93(d, J=8.3 Hz, 2H), 6.88(d, 337.20 J=8.5 Hz, 2H), 4.42(s, 2H), 4.32(d, J=12.6 Hz, 2H), 3.74(d, J=11.9 Hz, 3H) | 337.20 |
| 22 | B | (DMSO-$d_6$): 8.01-8.00(m, 2H), 7.92-7.92(m, 1H), 7.30-7.26(m, 2H), 6.90-6.88(m, 2H), 4.35(s, 2H), 3.72(s, 2H) | 329.20 |
| 23 | C | | 318.20 |
| 24 | C | | 330.20 |
| 25 | C | | 321.20 |
| 26 | B | (DMSO-$d_6$): 10.58(s, 1H), 8.91(s, 1H), 7.51(d, J=8.4 Hz, 2H), 7.40(t, J=7.7 Hz, 2H), 7.09(td, J=7.3, 2.7 Hz, 1H), 6.86(d, J=8.1 Hz, 1H), 6.77(s, 1H), 6.74(dd, J=1.7, 8.1 Hz, 1H), 4.17(s, 2H), 3.73(d, J= 11.1 Hz, 3H). | 354.00 |
| 27 | B | (DMSO-$d_6$): 10.60(s, 1H), 9.72(s, 1H), 7.50(d, J=8.5 Hz, 2H), 7.41-7.38(m, 2H), 7.17(dd, J=1.8, 12.2 Hz, 1H), 7.10(s, 1H), 7.10(dd, J=0.8, 14.7 Hz, 1H), 6.97(d, J=8.2 Hz, 1H), 6.92-6.88(m, 1H), 4.24(s, 2H). | 342.00 |
| 28 | B | (DMSO-$d_6$): 10.08(s, 1H), 8.00(d, J=7.7 Hz, 1H), 7.12-7.09(m, 2H), 7.02-6.99(m, 1H), 6.92(s, 1H), 6.87-6.81(m, 2H), 5.97(d, J=5.4 Hz, 2H), 4.26-4.23(m, 2H), 3.87(s, 3H). | 382.10 |
| 29 | B | (DMSO-$d_6$): 10.05(s, 1H), 9.27(s, 1H), 7.99-7.97(m, 1H), 7.15-7.08(m, 4H), 7.04-6.99(m, 1H), 6.71(dd, J=2.0, 6.5 Hz, 2H), 4.18(s, 2H), 4.14(s, 3H) | 354.10 |
| 30 | B | (DMSO-$d_6$): 10.06(s, 1H), 9.71(s, 1H), 7.97(d, J=7.6 Hz, 1H), 7.15-7.08(m, 3H), 7.01-6.94(m, 2H), 6.91-6.87(m, 1H), 4.21(s, 2H), 3.87(s, 3H). | 372.00 |
| 31 | B | (DMSO-$d_6$): 10.05(d, J=10.1 Hz, 2H), 7.98(d, J=8.0 Hz, 1H), 7.36(d, J=1.5 Hz, 1H), 7.09-7.08(m, 3H), 7.03-7.00(m, 1H), 6.91(d, J=8.3 Hz, 1H), 4.21(s, 2H), 3.87(s, 3H). | 388.00 |
| 32 | B | (DMSO-$d_6$): 10.02(s, 1H), 9.25(s, 1H), 7.89(d, J=8.0 Hz, 1H), 7.15-7.07(m, 4H), 7.01-6.97(m, 1H), 6.71 (d, J=8.4 Hz, 2H), 4.42(q, J=7.1 Hz, 1H), 3.86(s, 3H), 1.68(d, J=7.2 Hz, 3H). | 368.10 |
| 33 | C | (DMSO-$d_6$): 10.06(s, 1H), 8.93(s, 1H), 7.99(d, J=7.6 Hz, 1H), 7.10-7.09(m, 3H), 7.03-7.00(m, 1H), 6.86 (d, J=8.2 Hz, 1H), 6.75(s, 1H), 6.72(dd, J=1.8, 8.2 Hz, 1H), 4.15(s, 2H), 3.95(s, 3H), 3.71(s, 3H). | 384.10 |
| 34 | B | (DMSO-$d_6$): 10.62(s, 1H), 7.29(t, J=8.1 Hz, 1H), 7.20(d, J=1.8 Hz, 1H), 7.02(d, J=8.0 Hz, 1H), 6.91(s, 1H), 6.86(d, J=7.9 Hz, 1H), 6.81(d, J=7.9 Hz, 1H), 6.68 (dd, J=2.3, 8.2 Hz, 1H), 5.97(d, J=0.4 Hz, 2H), 4.25(s, 2H), 3.77(s, 3H). | 382.10 |
| 35 | B | (DMSO-$d_6$): 10.62(s, 1H), 9.71(s, 1H), 7.29(t, J=8.2 Hz, 1H), 7.19(t, J=2.1 Hz, 1H), 7.13-7.11(m, 1H), 7.02(dd, J=1.8, 8.1 Hz, 1H), , 6.95(d, J=8.3 Hz, 1H), 6.91-6.87(m, 1H), 6.68(dd, J=2.3, 8.2 Hz, 1H), 4.23 (s, 2H), 3.76(s, 3H). | 372.10 |
| 36 | B | (DMSO-$d_6$): 14.43(s, 1H), 10.61(s, 1H), 7.34(s, 1H), 7.29(d, J=8.1 Hz, 1H),7.17(d, J=8.3 Hz, 1H), 7.09(d, J=8.3 Hz, 1H), 7.04(d, J=8.1 Hz, 1H), 6.91(d, J=8.4 Hz, 1H), 6.67(d, J=8.4 Hz, 1H), 4.23(s, 2H), 3.77(s, 3H). | 388.00 |
| 37 | A | (DMSO-$d_6$): 10.57(s, 1H), 9.25(s, 1H), 7.28(t, J=8.2 Hz, 1H), 7.21(d, J=2.0 Hz, 1H), 7.14(d, J=8.5 Hz, 2H),6.95-6.94(m, 1H), 6.71-6.65(m, 3H), 4.45(q, J=7.1 Hz, 1H), 3.80-3.76(m, 3H), 1.69(d, J=7.2 Hz, 3H). | 368.10 |
| 38 | B | (DMSO-$d_6$): 10.61(s, 1H), 8.91(s, 1H), 7.29(t, J=8.2 Hz, 1H), 7.21(t, J=2.1 Hz, 1H), 7.02-7.00(m, 1H), 6.86-6.84(m, 1H), 6.73-6.72(m, 2H), 6.67(dd, J=2.4, 8.2 Hz, 1H), 4.17(s, 2H), 3.79-3.76(m, 3H), 3.73-3.69(m, 3H). | 384.10 |
| 39 | B | (DMSO-$d_6$): 10.42(s, 1H), 10.05(s, 1H), 7.43-7.41(m, 2H), 7.37(d, J=2.0 Hz, 1H), 7.10(dd, J=2.1, 8.3 Hz, 1H), 6.99-6.96(m, 2H), 6.92(d, J=8.3 Hz, 1H), 4.21(s, 2H), 3.75(d, J=9.0 Hz, 3H). | 388.00 |
| 40 | A | (DMSO-$d_6$): 10.37(s, 1H), 9.26(s, 1H), 7.37(dd, J=2.1, 6.9 Hz, 2H), 7.14(d, J=8.5 Hz, 2H), 6.96-6.96(m, 2H), 6.72(dd, J=1.8, 6.7 Hz, 2H), 4.41(t, J=7.2 Hz, 1H), 3.76(s, 3H), 1.68(d, J=7.2 Hz, 3H). | 368.10 |
| 41 | C | (DMSO-$d_6$): 9.26(s, 1H), 7.10(d, J=8.4 Hz, 2H), 6.68 (d, J=8.5 Hz, 2H), 4.11(s, 2H), 3.07(s, 6H) | 276.00 |

TABLE 4-continued

Physical and biological data of compounds of formula I.

| No. | c-Met $K_i$ | $^1$H NMR peaks given as δ values (500 MHz - unless indicated otherwise) | ESMS (M + H) |
|---|---|---|---|
| 42 | C | (DMSO-$d_6$): 9.99(s, 1H), 8.33(t, J=5.4 Hz, 1H), 6.88(d, J=1.4 Hz, 1H), 6.85-6.83(m, 1H), 6.75(dd, J=8.0, 17.0 Hz, 1H), 5.97(d, J=3.1 Hz, 2H), 4.15(s, 2H), 4.04-3.99(m, 1H), 3.81-3.76(m, 1H), 3.65(dd, J=7.5, 14.3 Hz, 1H), 3.64(s, 1H), 3.42-3.24(m, 1H), 1.98-1.78(m, 3H), 1.59-1.52(m, 1H) | 360.30 |
| 43 | A | (DMSO-$d_6$): 10.98(s, 1H), 9.29(s, 1H), 7.75(d, J=8.6 Hz, 2H), 7.67(d, J=8.6 Hz, 2H), 7.17(d, J=8.6 Hz, 2H), 6.74(d, J=8.4 Hz, 2H), 4.22(s, 2H) | 392.30 |
| 44 | A | (DMSO-$d_6$): 10.51(s, 1H), 9.27(s, 1H), 7.36(s, 1H), 7.27(d, J=4.9 Hz, 1H), 7.17(d, J=8.4 Hz, 2H), 6.92-6.91(m, 1H), 6.71(d, J=8.3 Hz, 2H), 4.20(s, 2H), 2.34(s, 3H) | 338.30 |
| 45 | A | (methanol-$d_4$): 7.95(t, J=4.9 Hz, 1H), 7.36(d, J=0.9 Hz, 1H), 7.35(s, 1H), 7.16(dd, J=2.0, 6.6 Hz, 2H), 6.76-6.71(m, 2H), 4.24(s, 2H) | 392.20 |
| 46 | A | (DMSO-$d_6$): 10.61(s, 1H), 9.21(s, 1H), 7.51(dd, J=4.7, 9.1 Hz, 2H), 7.24(d, J=8.8 Hz, 2H), 7.15(d, J=8.4 Hz, 2H), 6.72(d, J=8.4 Hz, 2H), 4.19(s, 2H) | 342.10 |
| 47 | C | (DMSO-$d_6$): 7.33-7.30(m, 2H), 7.25-7.22(m, 3H), 6.89(s, 1H), 6.85(d, J=7.9 Hz, 1H), 6.78(d, J=7.9 Hz, 1H), 5.98(s, 2H), 4.27(s, 2H), 2.85-2.81(m, 1H), 2.70-2.66(m, 1H), 1.80-1.74(m, 2H) | 377.40 |
| 48 | C | (DMSO-$d_6$): 8.10(d, J=1.4 Hz, 1H), 7.49(d, J=3.6 Hz, 1H), 6.91(s, 1H), 6.86-6.79(m, 3H), 5.98(s, 2H), 4.34(s, 2H) | 327.30 |
| 49 | C | (DMSO-$d_6$): 7.51(d, J=5.1 Hz, 1H), 7.13(d, J=3.4 Hz, 1H), 7.05-7.03(m, 1H), 6.97(d, J=11.0 Hz, 1H), 6.84(d, J=7.9 Hz, 1H), 6.78(d, J=8.0 Hz, 1H), 5.98(s, 2H), 4.69(s, 2H), 4.30(s, 2H) | 357.30 |
| 50 | A | (DMSO-$d_6$): 10.97(s, 1H), 9.28(s, 1H), 7.55(d, J=1.7 Hz, 1H), 7.32(t, J=1.7 Hz, 1H), 7.17(d, J=8.3 Hz, 2H), 6.73(d, J=8.3 Hz, 2H), 4.20(s, 2H) | 392.20 |
| 51 | C |  | 355.00 |
| 52 | A | (DMSO-$d_6$): 10.73(d, J=12.2 Hz, 1H), 9.29(s, 1H), 7.52-7.49(m, 2H), 7.46-7.41(m, 2H), 7.15(d, J=8.5 Hz, 2H), 6.74-6.71(m, 2H), 4.20(s, 2H), | 358.00; |
| 53 | A | (DMSO-$d_6$): 10.68(s, 1H), 9.27(s, 1H), 7.47(s, 4H),, 7.43(t, J=9.1 Hz, 4H), 7.15(d, J=8.5 Hz, 2H), 6.74-6.72(m, 2H), 4.44(q, J=7.2 Hz, 1H), 1.69(d, J=7.2 Hz, 3H) | 372.00 |
| 54 | A | (DMSO-$d_6$): 10.73(s, 1H), 9.73(s, 1H), 7.52-7.49(m, 2H), 7.44-7.41(m, 2H), 7.16(dd, J=1.9, 12.2 Hz, 1H), 6.97(dd, J=1.7, 8.3 Hz, 1H), 6.93-6.89(m, 1H), 4.24(s, 2H), | 376.00 |
| 55 | B |  | 392.10 |
| 56 | B | (DMSO-$d_6$): 10.74(s, 1H), 7.55-7.52(m, 2H), 7.45-7.43(m, 2H), 6.93-6.84(m, 3H), 5.96(d, J=10.3 Hz, 2H), 4.24(s, 2H). | 386.00 |
| 57 | C | (DMSO-$d_6$): 9.28(s, 1H), 8.10-8.09(m, 2H), 7.69(t, J=7.4 Hz, 1H), 7.58(t, J=7.8 Hz, 2H), 7.09(d, J=8.5 Hz, 2H), 6.71-6.69(m, 2H), 4.25(s, 2H) | 352.00 |
| 58 | B | (DMSO-$d_6$): 10.51(s, 1H), 7.95(d, J=5.5 Hz, 1H), 7.77(d, J=5.4 Hz, 1H), 7.12(d, J=8.5 Hz, 2H), 6.71(d, J=8.5 Hz, 2H), 4.19(s, 2H), 3.83(s, 3H) | 388.00 |
| 59 | A | (DMSO-$d_6$): 10.81(s, 1H), 9.28(s, 1H), 7.49(dt, J=11.5, 3.4 Hz, 1H), 7.42(dd, J=8.2, 15.1 Hz, 1H), 7.21 (dd, J=1.4, 8.2 Hz, 1H), 7.16(d, J=8.4 Hz, 2H), 6.92(td, J=8.4, 3.6 Hz, 1H), 6.71(d, J=8.4 Hz, 2H), 4.21(s, 2H) | 342.00 |
| 60 | A | (DMSO-$d_6$): 10.48(s, 1H), 9.39(s, 1H), 7.39(d, J=8.4 Hz, 2H), 7.20(d, J=8.4 Hz, 2H), 7.15(d, J=8.4 Hz, 2H), 6.72(d, J=8.4 Hz, 2H), 4.18(s, 2H), 2.29(s, 3H) | 338.00 |
| 61 | A | (DMSO-$d_6$): 10.84(s, 1H), 9.25(s, 1H), 8.33(t, J=1.8 Hz, 1H), 7.70(d, J=1.8 Hz, 1H), 7.68(t, J=1.2 Hz, 1H), 7.57-7.54(m, 1H), 7.23(d, J=8.5 Hz, 2H), 6.70(d, J=8.5 Hz, 2H), 4.20(s, 2H), 3.91(s, 3H) | 382.00 |
| 62 | A | (DMSO-$d_6$): 10.80(s, 1H), 9.28(s, 1H), 7.76(t, J=2.0 Hz, 1H), 7.45(s,H), 7.41(t, J=8.1 Hz, 1H), 7.33-7.31(m, 1H), 7.19-7.14(m, 2H), 6.73(dd, J=1.9, 6.6 Hz, 2H), , 4.20(s, 2H), 3.72(s, 1H). | 358.00 |
| 63 | A | (DMSO-$d_6$): 10.78(s,H), 9.27(s, 1H), 7.73(t, J=1.9 Hz, 1H), 7.40(t, J=8.1 Hz, 1H), 7.32-7.26(m, 1H), 7.18-7.14(m, 2H), 6.72(d, J=8.5 Hz, 2H), 4.99(s, 1H), 4.46(q, J=7.2 Hz, 1H), 1.70(d, J=7.2 Hz, 3H). | 372.00 |
| 64 | B | (DMSO-$d_6$): 10.41(s, 1H), 9.72(s, 1H), 7.42(dd, J=3.5, 12.5 Hz, 2H), 7.14(dd, J=1.8, 12.2 Hz, 1H), 6.97-6.95(m, 3H), 6.92-6.89(m, 1H), 4.21(s, 2H), 3.76(s, 3H). | 372.00 |
| 65 | B |  | 382.00 |
| 66 | A | (DMSO-$d_6$): 10.11(s, 1H), 9.25(s, 1H), 7.88(dd, J=1.3, 8.2 Hz, 1H), 7.53(dd, J=1.3, 8.0 Hz, 1H), 7.39(dd, J=1.2, 15.6 Hz, 1H), 7.18(dd, J=1.4, 15.4 Hz, 1H), 7.11(d, J=8.5 Hz, 2H), 6.71(d, J=8.5 Hz, 2H), 4.40(q, J=7.2 Hz, 1H), 1.66(d, J=7.2 Hz, 3H) | 372.00 |
| 67 | B | (DMSO-$d_6$): 10.16(s, 1H), 10.05(s, 1H), 7.98(dd, J=1.4, 8.2 Hz, 1H), 7.55(dd, J=1.4, 8.0 Hz, 1H), 7.43-7.40(m, 1H), 7.33(d, J=2.0 Hz, 1H), 7.22-7.19(m, 1H), 7.07(dd, J=2.1, 8.3 Hz, 1H), 6.91(d, J=8.3 Hz, 1H), 4.18(s, 2H). | 391.90 |
| 68 | B |  | 386.00 |
| 69 | C | (methanol-$d_4$): 7.96(d, J=8.2 Hz, 1H), 7.75-7.72(t, J=8.0, 1H), 7.29(t, J=7.6 Hz, 1H), 7.21(d, J=8.2 Hz, 1H), 6.91(d, J=8.3 Hz, 2H), 6.53(d, J=8.4 Hz, 2H), 3.87(s, 2H), 3.31(s, 3H) | 382.00 |
| 70 | C | (methanol-$d_4$): 8.83(s, 1H), 7.95(d, 1= 9.3 Hz, 1H), 7.69 (d, J=9.1 Hz, 1H), 7.02(d, J=8.4 Hz, 2H), 6.47(d, J=8.4 Hz, 2H), 4.12(s, 2H) | 381.90 |
| 71 | A | (methanol-$d_4$): 8.19(s, 1H), 7.76-7.73(m, 2H), 7.62(d, J=1.4 Hz, 1H), 7.24(d, J=7.3 Hz, 2H), 6.80-6.78(d, J=8.2 Hz, 2H), 6.53(d, J=1.9 Hz, 1H), 4.33(s, 2H) | 390.00 |
| 72 | B | (methanol-$d_4$): 7.30(s, 1H), 7.23(s, 1H), 7.22(d, J=8.2 Hz, 1H), 7.13(d, J=8.1 Hz, 1H), 7.03(d, J=8.5 Hz, 1H), 6.76(d, J=8.4 Hz, 1H), 4.28(s, 2H), 2.29(s, 3H), 2.25(s, 3H) | 352.10 |
| 73 | B | (methanol-$d_4$): 7.76(d, J=2.3 Hz, 1H), 7.29-7.27(m, 1H), 7.24(m, 1H), 7.24(d, J=8.4 Hz, 2H), 6.77(d, J=8.5 Hz, 2H), 4.27(s, 2H), 2.36(s, 3H) | 372.00 |
| 74 | B | (DMSO-$d_6$): 10.27(s, 1H), 9.26(s, 1H), 7.34(d, J=8.7 Hz, 2H), 7.14(d, J=8.4 Hz, 2H), 6.83(d, J=2.7 Hz, 2H), 6.71(d, J=8.5 Hz, 2H), 4.16(s, 2H), 2.91(s, 6H) | 367.10 |
| 75 | A | (DMSO-$d_6$): 9.82(s, 1H), 9.27(s, 1H), 7.76(dd, J=2.6, 11.4 Hz, 1H), 7.28(t, J=7.5 Hz, 1H), 7.13(d, J=8.5 Hz, 2H), 6.92(td, J=8.3, 3.7 Hz, 1H), 6.69(d, J=8.5 Hz, 2H), 4.15(s, 2H), 2.25(s, 3H) | 356.10 |
| 76 | B | (DMSO-$d_6$): 9.78(s, 1H), 9.27(s, 1H), 7.63(dd, J=5.4, 8.9 Hz, 1H), 7.11(d, J=3.0 Hz, 1H), 7.17(dd, J=2.9, 9.5 Hz, 1H), 7.08(d, J=8.5 Hz, 2H), 6.69(d, J=8.5 Hz, 2H), 4.11(s, 2H), 2.26(s, 3H) | 356.10 |
| 77 | A | (DMSO-$d_6$): 9.97(s, 1H), 9.28(s, 1H), 8.10(d, J=2.3 Hz, 1H), 7.54(d, J=8.6 Hz, 1H), 7.17(dd, J=2.6, 8.6 Hz, 1H), 7.05(d, J=8.4 Hz, 2H), 6.69(d, J=8.5 Hz, 2H), 3.83(s, 2H) | 391.90 |
| 78 | A | (DMSO-$d_6$): 10.15(s, 1H), 9.28(s, 1H), 7.97(dd, J=1.2, 8.2 Hz, 1H), 7.55(dd, J=1.3, 8.0 Hz, 1H), 7.44-7.40(m, 1H), 7.22-7.18(m, 1H), 7.11(d, J=8.5 Hz, 2H), 6.71(dd, J=2.8, 11.3 Hz, 2H), 6.71(dd, J=2.8, 11.3 Hz, 2H), 4.16(s, 2H), | 358.00 |

TABLE 4-continued

Physical and biological data of compounds of formula I.

| No. | c-Met $K_i$ | $^1$H NMR peaks given as δ values (500 MHz - unless indicated otherwise) | ESMS (M + H) |
|---|---|---|---|
| 79 | B | (DMSO-d$_6$): 10.16(s, 1H), 9.72(s, 1H), 7.97(dd, J=1.2, 8.2 Hz, 1H), 7.55(dd, J=1.3, 8.0 Hz, 1H), 7.40(m, 1H), 7.22-7.19(m, 1H), 7.11(dd, J=1.6, 12.2 Hz, 1H), 6.93-6.87(m, 2H), 4.19(s, 2H), | 376.00 |
| 80 | A | (DMSO-d$_6$): 10.40(s, 1H), 9.28(s, 1H), 7.42(m, 2H), 7.24(d, J=8.9 Hz, 2H), 7.14(d, J=8.5 Hz, 2H), 6.98-6.97(m, 2H), 4.17(s, 2H), 3.75(d, J=12.5 Hz, 3H), | 354.10 |
| 81 | A | (DMSO-d$_6$): 10.95(s, 1H), 9.29(br s, 1H), 8.74(d, J=2.6 Hz, 1H), 8.35(dd, J=1.1, 4.8 Hz, 1H), 8.05-8.03(m, 1H), 7.53(dd, J=4.8, 8.4 Hz, 1H), 7.16(d, J=8.5 Hz, 2H), 6.72(dd, J=2.9, 11.3 Hz, 2H), 4.22(s, 2H), | 325.00 |
| 82 | A | (DMSO-d$_6$): 10.98(s, 1H), 9.28(s, 1H), 8.72(d, J=2.6 Hz, 1H), 8.36(dd, J=1.1, 4.8 Hz, 1H), 8.00(dt, J=8.4, 2.4 Hz, 1H), 7.56(dd, J=4.9, 8.4 Hz, 1H), 7.37(d, J=8.5 Hz, 2H), 6.72(d, J=8.6 Hz, 2H), 4.48(q, J=7.2 Hz, 1H), 1.70(d, J=7.2 Hz, 3H), | 339.00 |
| 83 | B | (DMSO-d$_6$): 10.99(s, 1H), 9.73(s, 1H), 8.74(d, J=2.4 Hz, 1H), 8.36(d, J=4.7 Hz, 1H), 8.07(dt, J=8.4, 2.4 Hz, 1H), 7.53(dd, J=4.8, 8.4 Hz, 1H), 7.15(dd, J=1.9, 12.2 Hz, 1H), 6.98(dd, J=1.4, 8.3 Hz, 1H), 6.92-6.88(m, 2H), 4.26(s, 2H), | 343.00 |
| 84 | B | (DMSO-d$_6$): 11.01(s, 1H), 8.76(d, J=2.6 Hz, 1H), 8.36(d, J=4.8 Hz, 1H), 8.09(dt, J=8.4, 2.4 Hz, 1H), 7.55(dd, J=4.8, 8.4 Hz, 1H), 6.93-6.84(m, 3H), 5.97(s, 1H), 4.28(s, 1H), | 353.00 |
| 85 | B | (DMSO-d$_6$): 10.37(s, 1H), 7.38(d, J=8.5 Hz, 2H), 6.92(d, J=1.4 Hz, 1H), 6.88(d, J=8.0 Hz, 1H), 6.82(d, J=8.2 Hz, 2H), 5.99(d, J=11.8 Hz, 2H), 4.22(s, 2H), 2.94(s, 6H) | 395.00 |
| 86 | B | (DMSO-d$_6$): 9.26(s, 1H), 8.11(d, J=7.0 Hz, 1H), 7.10(d, J=8.5 Hz, 2H), 6.67(d, J=8.5 Hz, 2H), 4.09(s, H), 3.52(t, J=3.3 Hz, 1H), 1.96-1.93(m, 2H), 1.71-1.69(m, 2H), 1.56(d, J=12.8 Hz, 1H), 1.35-1.20(m, 5H) | 330.10 |
| 87 | C | (DMSO-d$_6$): 9.29(s, 1H), 9.20(d, J=5.6 Hz, 1H), 7.18(d, J=8.5 Hz, 2H), 6.71-6.69(m, 2H),, 4.55(t, J=7.3 Hz, 1H), 2.88(d, J=4.5 Hz, 3H), 1.77(s, 3H). | 304.00 |
| 88 | C | (DMSO-d$_6$): 9.34(s, 1H), 8.62(s, 1H), 8.39(d, J=10.9 Hz, 2H), 7.24-7.19(m, 2H), 6.74-6.65(m, 2H), 4.56(q, J=7.2 Hz, 1H), 1.78-1.69(m, 3H). | 290.00 |
| 89 | C | (DMSO-d$_6$): 9.34(s, 1H), 7.19(d, J=8.4 Hz, 2H), 6.72(s, 2H), 6.67(q, J=8.5 Hz, 2H), 4.58-4.52(m, 1H), 1.98-1.86(m, 8H), 1.80(s, 3H). | 344.00 |
| 90 | C | (DMSO-d$_6$): 9.34(s, 1H), 7.16(m, 2H), 6.74-6.68(m, 2H), 4.61-4.50(m, 1H), 2.90-2.84(m, 1H), 1.72(td, J=20.1, 9.0 Hz, 3H), 0.82(m, 4H). | 330.00 |
| 91 | C | (DMSO-d$_6$): 10.02(s, 2H), 7.71(s, 2H), 7.44-7.31(m, 6H), 7.16(s, 2H), 3.66(s, 2H) | 376.00 |
| 92 | C | (DMSO-d$_6$): 10.71(s, 1H), 9.26(s, 1H), 7.75(s, 1H), 7.48(s, 1H), 7.44-7.38(m, 2H), 7.26(d, J=7.2 Hz, 1H), 7.07(dd, J=3.1, 7.7 Hz, 1H), 7.05(s, 1H), 6.65(t, J=7.6 Hz, 1H), 6.60-6.59(m, 1H), 2.93-2.86(m, 2H), 2.83-2.78(m, 2H) | 372.00 |
| 93 | C | (DMSO-d$_6$): 10.84(s, 1H), 9.13(d, J=2.7 Hz, 1H), 7.52(dt, J=11.5, 3.4 Hz, 1H), 7.44(td, J=8.2, 5.0 Hz, 1H), 7.27(dd, J=1.6, 8.1 Hz, 1H), 7.02(d, J=8.4 Hz, 2H), 6.99-6.91(m, 1H), 6.65(d, J=8.5 Hz, 2H), 3.21-3.18(t, J=7.7 Hz, 2H), 3.02-2.99(t, J=7.7 Hz, 2H) | 356.10 |
| 94 | C | (DMSO-d$_6$): 10.82(s, 1H), 9.14(s, 1H), 7.78(t, J=2.0 Hz, 1H), 7.45-7.39(m, 2H), 7.29(t, J=7.8 Hz, 1H), 7.19-7.15(m, 1H), 7.04(d, J=8.5 Hz, 2H), 6.66(d, J=8.5 Hz, 2H), 3.18(t, J=7.7 Hz, 2H), 3.00(t, J=7.7 Hz, 2H) | 372.00 |
| 95 | C | (DMSO-d$_6$): 10.84(s, 1H), 9.23(s, 1H), 7.51(dt, J=11.4, 3.4 Hz, 1H), 7.44(dd, J=8.2, 15.0 Hz, 1H), 7.28(d, J=1.6, 8.1 Hz, 1H), 7.06(t, J=7.8 Hz, 1H), 6.93(td, J=8.4, 3.5 Hz, 1H), 6.67(d, J=7.6 Hz, 1H), 6.62(d, J=1.9 Hz, 1H), 6.58-6.56(m, 1H), 3.22(t, J=7.7 Hz, 2H), 3.04(t, J=7.7 Hz, 2H) | 356.10 |
| 96 | B | (DMSO-d$_6$): 10.80(s, 1H), 9.33(s, 1H), 7.67(t, J=1.9 Hz, 1H), 7.43-7.37(m, 2H), 7.14(d, J=8.2 Hz, 2H), 6.82(d, J=7.4 Hz, 1H), 6.70(t, J=1.8 Hz, 1H), 6.63(dd, J=1.7, 8.2 Hz, 1H), 4.22(d, J=15.8 Hz, 2H) | 358.00 |
| 97 | A | (DMSO-d$_6$): 10.83(s, 1H), 10.04(s, 1H), 7.47-7.40(m, 1H), 7.36(d, J=2.1 Hz, 1H), 7.24(dd, J=1.8, 8.1 Hz, 1H), 7.12(dd, J=2.1, 8.3 Hz, 1H), 6.92(t, J=8.3 Hz, 2H), 4.25(s, 2H) | 376.00 |
| 98 | A | (DMSO-d$_6$): 10.81(s, 1H), 10.05(s, 1H), 7.67(t, J=2.0 Hz, 1H), 7.43-7.37(m, 2H), 7.34(d, J=2.1 Hz, 1H), 7.16-7.13(m, 1H), 6.93(t, J=4.2 Hz, 1H), 4.24(s, 2H) | 391.90 |
| 99 | B | (DMSO-d$_6$): 10.69(s, 1H), 9.72(s, 1H), 7.89-7.86(m, 1H), 7.26-7.13(m, 3H), 6.95(dd, J=1.8, 8.3 Hz, 1H), 6.91-6.88(m, 1H), 4.23(s, 2H) | 378.00 |
| 100 | A | (DMSO-d$_6$): 10.79(s, 1H), 9.26(s, 1H), 7.45-7.38(m, 2H), 7.17-7.12(m, 3H), 6.91(td, J=8.4, 3.6 Hz, 1H), 6.71(d, J=8.5 Hz, 2H), 4.47(q, J=7.2 Hz, 1H), 1.69(d, J=7.2 Hz, 3H) | 356.10 |
| 101 | A | (methanol-d$_4$): 7.74(td, J=7.0, 2.9 Hz, 1H), 7.22-7.15(m, 3H), 7.01(dt, J=7.2, 2.2 Hz, 1H), 6.76(d, J=8.6 Hz, 2H), 4.49(dd, J=3.8, 7.2 Hz, 1H), 1.78(d, J=7.3 Hz, 3H) | 374.10 |
| 102 | B | (DMSO-d$_6$): 10.66(s, 1H), 9.12(s, 1H), 8.13-8.10(m, 1H), 7.29(d, J=8.4 Hz, 2H), 7.01(d, J=8.4 Hz, 2H), 6.65(d, J=8.4 Hz, 2H), 3.19-3.16(m, 2H), 3.00-2.97(m, 2H) | 390.00 |
| 103 | B | (DMSO-d$_6$): 10.66(s, 1H), 10.06(s, 1H), 8.06-8.02(m, 1H), 7.37(d, J=2.1 Hz, 1H), 7.33-7.26(m, 2H), 7.09(dd, J=2.1, 8.3 Hz, 2H), 6.91(d, J=8.3 Hz, 1H), 4.23(s, 2H) | 410.00 |
| 104 | A | (DMSO-d$_6$): 11.03(s, 1H), 10.04(s, 1H), 7.34(d, J=2.0 Hz, 1H), 7.21(dd, J=2.0, 9.2 Hz, 2H), 7.13(dd, J=2.1, 8.3 Hz, 1H), 6.97-6.93(m, 1H), 6.91(d, J=8.3 Hz, 1H), 4.26(s, 2H) | 394.00 |
| 105 | A | (methanol-d$_4$): 7.44-7.41(m, 1H), 7.38-7.34(m, 1H), 7.22(d, J=8.5 Hz, 2H), 6.87-6.83(m, 1H), 6.78(d, J=8.5 Hz, 2H), 4.55(dd, J=4.8, 7.2 Hz, 1H), 1.81(d, J=7.3 Hz, 3H) | 356.10 |
| 106 | A | (methanol-d$_4$): 7.44-7.41(m, 1H), 7.38-7.34(m, 1H), 7.22(d, J=8.5 Hz, 2H), 6.87-6.83(m, 1H), 6.78(d, J=8.5 Hz, 2H), 4.55(dd, J=4.8, 7.2 Hz, 1H), 1.81(d, J=7.3 Hz, 3H) | 356.10 |
| 107 | A | (methanol-d$_4$): 8.17-8.09(m, 2H), 7.95(d, J=8.6 Hz, 1H), 7.61(d, J=11.5 Hz, 2H), 7.56(s, 2H), 6.67(s, 2H), 4.98(s, 2H) | 370.00 |
| 108 | A | (DMSO-d$_6$): 7.43(dt, J=11.1,3.3Hz, 1H), 7.37(dd, J=8.2, 14.8 Hz, 1H), 7.22(d, J=8.1 Hz, 1H), 7.10(dd, J=1.9, 11.8 Hz, 1H), 7.02(d, J=8.2 Hz, 1H), 6.89(t, J=8.6 Hz, 1H), 6.84(td, J=8.3, 3.5 Hz, 1H), 4.29(s, 2H) | 360.45 |
| 109 | B | (methanol-d$_4$): 8.09-8.05(m, 1H), 7.26-7.20(m, 2H), 7.04(td, J=7.8, 3.9 Hz, 1H), 6.62-6.56(m, 3H), 3.30(t, J=7.4 Hz, 2H), 3.08(t, J=7.4 Hz, 2H) | 390.00 |
| 110 | B | (methanol-d$_4$): 8.04-8.01(m, 1H), 7.25-7.20(m, 2H), 7.14(t, J=7.9 Hz, 2H), 6.82(d, J=7.9 Hz, 2H), 6.69(d, J=7.9 Hz, 1H), 4.30(s, 2H) | 376.00 |
| 111 | B | (methanol-d$_4$): 7.20(d, J=2.0, 9.0 Hz, 2H), 6.98(d, J=8.4 Hz, 2H), 6.73-6.64(m, 3H), 3.30(t, J=7.4 Hz, 2H), 3.08(t, J=7.4 Hz, 2H) | 374.10 |
| 112 | C | (DMSO-d$_6$): 10.41(s, 1H), 7.79(s, 2H), 7.61(s, 1H), 7.41(d, J=0.9 Hz, 1H), 7.36-7.30(m, 3H), 7.18(dd, J=1.9, 6.6 Hz, 2H), 7.11-7.09(m, 1H), 4.25(s, 2H) | 401.00 |

TABLE 4-continued

Physical and biological data of compounds of formula I.

| No. | c-Met $K_i$ | ¹H NMR peaks given as δ values (500 MHz - unless indicated otherwise) | ESMS (M + H) |
|---|---|---|---|
| 113 | C | (DMSO-d₆): 10.18(s, 1H), 7.80(s, 2H), 7.49(d, J=7.8 Hz, 2H), 7.33(d, J=1.8 Hz, 2H), 7.30(d, J=8.5 Hz, 2H), 7.16(d, J=8.5 Hz, 2H), 7.04(t, J=7.4 Hz, 1H), 4.25(s, 2H) | 367.00 |
| 114 | C | (DMSO-d₆): 10.23(s, 1H), 7.80(s, 2H), 7.50(dd, J=4.9, 8.9 Hz, 2H), 7.30(d, J=8.5 Hz, 2H), 7.18-7.14(m, 4H), 4.25(s, 2H) | 385.00 |
| 115 | C | (DMSO-d₆): 9.99(s, 1H), 7.79(s, 2H), 7.39(d, J=8.7 Hz, 1H), 7.29(d, J=8.5 Hz, 2H), 7.14(d, J=8.5 Hz, 2H), 6.89(d, J=8.5 Hz, 2H), 4.24(s, 2H), 3.72(s, 3H) | 397.10 |
| 116 | A | (DMSO-d₆): 10.77(s, 1H), 9.26(s, 1H), 7.73(t, J=1.9 Hz, 1H), 7.40(t, J=8.1 Hz, 1H), 7.27(dd, J=1.5, 8.1 Hz, 1H), 7.17(d, J=8.5 Hz, 2H), 7.14(s, 1H), 6.72(d, J=8.5 Hz, 2H), 4.45(q, J=7.2 Hz, 1H), 1.70(d, J=7.2 Hz, 3H) | 372.00 |
| 117 | A | (DMSO-d₆): 10.68(s, 1H), 9.27(s, 1H), 7.43(t, J=9.7 Hz, 4H), 7.15(d, J=8.5 Hz, 2H), 6.73(d, J=8.5 Hz, 2H), 4.44(q, J=7.2 Hz, 1H), 1.69(d, J= 7.2 Hz, 3H) | 372.00 |
| 118 | B | (DMSO-d₆): 10.68(s, 1H), 9.27(s, 1H), 7.43(t, J=9.7 Hz, 4H), 7.15(d, J=8.5 Hz, 2H), 6.73(d, J=8.5 Hz, 2H), 4.44(q, J==7.2 Hz, 1H), 1.69(d, J=7.2 Hz, 3H) | 372.00 |
| 119 | A | (DMSO-d₆): 11.38(s, 1H), 8.85(d, J=8.4 Hz, 1H), 8.72(d, J=5.7 Hz, 1H), 8.41(d, J=3.3 Hz, 1H), 7.75(dd, J=5.8, 8.3 Hz, 1H), 7.67(t, J=1.9 Hz, 1H), 7.42(t, J=8.1 Hz, 1H), 7.36(d, J=9.3 Hz, 1H), 7.17-7.16(m, 1H), 6.97(d, J=3.3 Hz, 1H), 6.21(s, 2H) | 382.00 |
| 120 | C | (DMSO-d₆): 11.04(s, 1H), 9.22(s, 1H), 7.25(d, J=7.9 Hz, 2H), 7.04(t, J=7.5Hz, 1H), 6.97-6.94(m, 1H), 6.67(d, J=6.9 Hz, 1H), 6.61(s, 1H), 6.57(d, J=7.5 Hz, 1H), 3.22(d, J=6.4 Hz, 2H), 3.03(s, 2H) | 374.40 |
| 121 | C | (DMSO-d₆): 10.70(s, 1H), 9.23(s, 1H), 7.98-7.95(m, 1H), 7.31-7.26(m, 1H), 7.17(t, J=8.7 Hz, 1H), 7.05(t, J=7.7 Hz, 1H), 6.64(d, J=7.6 Hz, 1H), 6.62(s, 1H), 6.57(dd, J=1.9, 8.0 Hz, 1H), 3.20(t, j=7.7, 2H), 3.0(t, J=7.7, 2H) | 374.00 |
| 122 | B | (methanol-d₄): 7.42-7.34(m, 2H), 7.23(dd, J=1.6, 8.2 Hz, 1H), 7.15(t, J=7.9 Hz, 1H), 6.92(s, 1H), 6.87(d, J=7.6 Hz, 1H), 6.83(td, J=8.4, 3.5 Hz, 1H), 6.78(s, 1H), 6.68(dd, J=2.0, 8.1 Hz, 1H), 4.30(s, 2H) | 342.00 |
| 123 | B | (DMSO-d₆): 10.70(s, 1H), 9.34(d, J=9.5 Hz, 1H), 7.90-7.87(m, 1H), 7.28-7.23(m, 1H), 7.19-7.16(m, 1H), 7.12(t, J=7.8 Hz, 1H), 6.75(d, J=7.6 Hz, 1H), 6.73(s, 1H), 6.64(dd, J=1.6, 8.1 Hz, 1H), 4.23(s, 2H) | 360.41 |
| 124 | B | (DMSO-d₆): 11.02(s, 1H), 9.32(s, 1H), 7.20(d, J=1.8 Hz, 1H), 7.18(s, 1H), 7.11(t, J=7.8 Hz, 1H), 6.94(dd, J=7.2, 9.2 Hz, 1H), , 6.80(d, J=7.5 Hz, 1H), 6.68(s, 1H), 6.63(dd, J=1.9, 8.0 Hz, 1H), 4.26(s, 2H) | 360.40 |
| 125 | A | (DMSO-d₆): 10.82(s, 1H), 7.69(s, 1H), 7.43-7.34(m, 2H), 7.15(d, J=7.6 Hz, 1H), 6.94-6.68(m, 3H), 5.95(d, J=7.9 Hz, 2H), 4.26(s, 2H) | 386.40 |
| 126 | B | (DMSO-d₆): 8.09-8.06(m, 1H), 7.33-7.26(m, 2H), 6.92(s, 1H), 6.87(d, J=7.9 Hz, 1H), 6.82(d, J=8.0 Hz, 1H), 5.97(s, 2H), 4.25(s, 2H) | 404.30 |
| 127 | A | | 388.20 |
| 128 | A | (DMSO-d₆): 10.69(s, 1H), 10.06(s, 1H), 7.89-7.86(m, 1H), 7.37(s, 1H), 7.28-7.24(m, 1H), 7.18(dd, J=8.3, 17.3 Hz, 1H), 7.09(d, J=8.2 Hz, 1H), 6.91(d, J=8.2 Hz, 2H), 4.23(s, 2H) | 394.30 |
| 129 | A | (DMSO-d₆): 10.81(s, 1H), 9.71(s, 1H), 7.69(t, J=2.0 Hz, 1H), 7.42-7.35(m, 2H), 7.16-7.11(m, 2H), 6.99(dd, J=1.6, 8.3 Hz, 1H), 6.93-6.87(m, 1H), 4.24(s, 2H) | 376.00 |
| 130 | B | (DMSO-d₆): 10.66(s, 1H), 9.72(s, 1H), 8.03(t, J=7.8 Hz, 1H), 7.33-7.30(m, 1H), 7.26(t, J=8.2 Hz, 1H), 7.14(d, J=12.3 Hz, 1H), 6.95(d, J=8.2 Hz, 1H), 6.89(t, J=8.5 Hz, 1H), 4.23(s, 2H) | 394.30 |
| 131 | A | (methanol-d₄): 7.17(d, J=7.3 Hz, 2H), 7.09-7.02(m, 2H), 6.89(t, J=8.6 Hz, 1H), 6.68(dd, J=7.2, 9.0 Hz, 1H), 4.30(s, 2H) | 378.10 |
| 132 | A | (methanol-d₄): 7.90-7.87(m, 1H), 7.20-7.16(m, 3H), 6.92(s, 1H), 6.76(dd, J=1.9, 6.7 Hz, 2H), 4.48(q, J=7.2 Hz, 1H), 1.82-1.77(m, 3H) | 390.30 |
| 133 | A | (methanol-d₄): 7.19(d, J=8.5 Hz, 2H), 7.14-7.09(m, 2H), 6.76(d, J=8.5 Hz, 2H), 6.69-6.64(m, 1H), 4.50(q, J=7.2 Hz, 1H), 1.79(d, J=7.3 Hz, 3H) | 374.10 |
| 134 | B | (DMSO-d₆): 10.89(s, 1H), 8.68(d, J=7.5 Hz, 1), 8.64(d, j=5.3 Hz, 1H), 8.26(d, J=2.7 Hz, 1H), 7.62-7.59(m, 1H), 7.44-7.39(m, 2H), 7.15(d, J=8.1 Hz, 1H), 6.95(t, J=8.5 Hz, 1H), 6.87(d, J=2.8 Hz, 1H), 6.14(s, 2H) | 365.90 |
| 135 | B | (DMSO-d₆): 10.58(s, 1H), 8.62(d, J=6.0 Hz, 2H), 8.24(d, J=2.9 Hz, 1H), 7.57(t, J=6.8 Hz, 1H), 7.29-7.23(m, 3H), 6.94(d, J=7.1 Hz, 1H), 6.86(d, J=3.1 Hz, 1H), 6.10(d, 2H), 2.35(s, 3H) | 362.00 |
| 136 | A | (DMSO-d₆): 11.03(s, 1H), 8.61(d, J=5.2 Hz, 1H), 8.55(d, J=7.9 Hz, 1H), 8.21(s, 1H), 7.90(s, 1H), 7.68-7.63(m, 2H), 7.55(t, J=6.3 Hz, 1H), 7.48(d, J=6.7 Hz, 1H), 6.82(s, 1H), 6.12(s, 2H) | 416.00 |
| 137 | B | | 392.00 |
| 138 | A | (DMSO-d₆): 10.97(d, J=9.2 Hz, 1H), 9.27(br s, 1H), 8.08(s, 1H), 7.69(d, J=8.7 Hz, 1H), 7.62(t, J=7.9 Hz, 1H), 7.56(d, J=8.3 Hz, 1H), 7.44(d, J=7.5 Hz, 1H), 7.15(d, J=8.3 Hz, 2H), 6.68(d, J=8.2 Hz, 2H), 4.45(q, J=7.2 Hz, 1H), 1.70(d, J=7.2 Hz, 3H). | 406.40 |
| 139 | A | (DMSO-d₆): 10.96(s, 1H), 9.26(br s, 1H), 8.08(s, 1H), 7.62(t, J=7.9 Hz, 1H), 7.56(d, J=8.6 Hz, 1H), 7.44(d, J=7.6 Hz, 1H), 7.15(d, J=8.5 Hz, 2H), 6.68(d, J=8.5 Hz, 2H), 4.45(q, J=7.2 Hz, 1H), 1.70(d, J=7.2 Hz, 3H) | 406.40 |
| 140 | A | (DMSO-d₆): 10.98(s, 1H), 8.01(s, 1H), 7.68(d, J=8.4 Hz, 1H), 7.63(t, J=7.9 Hz, 1H), 7.44(d, J=7.5 Hz, 1H), 6.89(s, 1H), 6.83(s, 1H), 5.96(s, 2H), 4.25(s, 2H). | 420.00 |
| 141 | A | (DMSO-d₆): 10.97(d, J=12.0 Hz, 1H), 9.71(s, 1H), 8.02(s, 1H), 7.67-7.61(m, 2H), 7.45(d, J=7.4 Hz, 1H), 7.12(dd, J=1.8, 12.1 Hz, 1H), 6.97(dd, J=1.4, 8.3 Hz, 1H), 6.88(t, J=8.7 Hz, 1H), 4.23(s, 2H) | 410.40 |
| 142 | B | (DMSO-d₆): 11.00(s, 1H), 10.06(s, 1H), 7.99(s, 1H), 7.70(d, J=8.4 Hz, 1H), 7.64(t, J=7.9 Hz, 1H), 7.45(d, J=7.6 Hz, 1H), 7.33(d, J=1.9 Hz, 1H), 7.13(dd, J=2.0, 8.3 Hz, 1H), 6.91(d, J=8.3 Hz, 1H), 4.23(s, 2H). | 426.00 |
| 143 | B | (DMSO-d₆): 10.99(s, 1H), 9.24(br s, 1H), 8.06(s, 1H), 7.73(d, J=8.3 Hz, 1H), 7.65(t, J=7.9 Hz, 1H), 7.45(d, J=7.6 Hz, 1H), 7.05(t, J=7.8 Hz, 1H), 6.66(d, J=7.6 Hz, 1H), 6.62(s, 1H), 6.58(dd, J=2.1, 8.0 Hz, 1H), 3.23-3.20(m, 2H), 3.06-3.03(m, 2H), | 406.00 |
| 144 | B | (DMSO-d₆): 10.52(s, 1H), 9.34(s, 1H), 7.34(s, 1H), 7.27(dd, J=8.2, 18.4 Hz, 1H), 7.12(t, J=7.8 Hz, 1H), 6.91(d, J=7.0 Hz, 1H), 6.79(d, J=7.6 Hz, 1H), 6.73(d, J=1.8 Hz, 1H), 6.63(dd, J=1.7, 8.1 Hz, 1H), , 4.23(s, 2H), 2.33(s, 3H), | 338.10 |
| 145 | A | | 366.10 |
| 146 | A | (DMSO-d₆): 10.52(s, 1H), 9.71(s, 1H), 7.35(s, 1H), 7.27(dd, J=8.1, 14.5 Hz, 2H), 7.16(dd, J=1.9, 12.2 Hz, 1H), 6.97(dd, J=1.6, 8.3 Hz, 1H), 6.89(t, J=8.7 Hz, 2H), 4.23(s, 2H), 2.33(s, 3H), | 356.20 |
| 147 | C | (DMSO-d₆): 10.53(s, 1H), 10.05(s, 1H), 7.37-7.22(m, 4H), 7.12(dd, J=2.1, 8.3 Hz, 1H), 6.91(d, J=8.3 Hz, 2H), 4.23(s, 2H), 2.34(s, 3H), | 372.10 |

TABLE 4-continued

Physical and biological data of compounds of formula I.

| No. | c-Met $K_i$ | $^1$H NMR NMR peaks given as δ values (500 MHz - unless indicated otherwise) | ESMS (M + H) |
|---|---|---|---|
| 148 | B | (DMSO-d$_6$): 10.54(s, 1H), 9.12(br s,H), 7.37(d, J=9.4 Hz, 2H), 7.29(t, J=7.7 Hz, 1H), 7.03(d, J=8.4 Hz, 2H), 6.93(d, J=7.5 Hz, 1H), 6.64(dd, J=8.3, 14.0 Hz, 2H), 3.19-3.16(m, 2H), 3.02-2.99(m, 2H), 2.34(s, 3H), | 352.20 |
| 149 | A | (DMSO-d$_6$): 10.99(s, 1H), 9.51(hr s, 1H), 9.51(hrs, 1H), 8.10(s, 1H), 7.72-7.63(m, 2H), 7.45(d, J=7.4 Hz, 1H), 7.07-7.01(m, 2H), 6.66-6.62(m, 2H), 3.20-3.17(m, 2H), 3.02-2.98(m, 2H), | 406.40 |
| 150 | B | | 376.40 |
| 151 | A | | 404.40 |
| 152 | A | | 390.60 |
| 153 | A | | 266.20 |
| 154 | A | (DMSO-d$_6$): 10.92(s, 1H), 9.38(s, 1H), 8.70(d, J=2.5 Hz, 1H), 8.34(dd, J=1.2, 4.8 Hz, 1H), 7.97(dt, J=8.4, 2.4 Hz, 1H), 7.51(dd, J=4.8, 8.4 Hz, 1H), 7.19-7.15(m, 2H), 6.71(t, J=8.4 Hz, 2H), 4.48(q, J=7.3 Hz, 1H), 1.70(d, J=7.2 Hz, 3H), | 339.20; |
| 155 | B | (DMSO-d$_6$): 11.23(d, J=4.7 Hz, 1H), 7.72(t, J=1.8 Hz, 1H), 7.55(d, J=8.2 Hz, 1H), 7.43(t, J=8.1 Hz, 1H), 7.15(dd, J=1.2, 7.9 Hz, 1H), 4.77(s, 2H) | 281.90 |
| 156 | A | (methanol-d$_4$): 9.98(s, 1H), 8.31-8.27(m, 4H), 7.86(d, J=8.5 Hz, 2H), 7.42(d, J=8.5 Hz, 2H), 5.12(q, J=7.3 Hz, 1H), 4.14(s, 3H), 2.38(d, J=7.3 Hz, 3H) | 386.10 |
| 157 | B | | 386.00 |
| 158 | B | | 370.10 |
| 159 | A | (DMSO-d$_6$): 10.78(s, 1H), 9.27(s, 1H), 7.81(dd, J=2.7, 6.5 Hz, 1H), 7.43(t, J=9.0 Hz, 1H), 7.30-7.27(m, 1H), 7.16(d, J=8.5 Hz, 2H), 6.73(d, J=8.5 Hz, 2H), 4.45(q, J=7.2 Hz, 1H), 1.69(d, J=7.2 Hz, 3H). | 390.10 |
| 160 | A | (DMSO-d$_6$): 11.19(s, 1H), 8.02(s, 1H), 7.65(s, 1H), 7.64(dd, J=8.4, 19.1 Hz, 1H), 7.46(d, J=7.2 Hz, 1H), 7.37(d, J=3.2 Hz, 1H), 7.01(d, J=8.2 Hz, 1H), 6.91(t, J=7.9 Hz, 1H), 6.52(d, J=2.8 Hz, 1H), 6.38(dd, J=0.4, 7.5 Hz, 1H), 5.75(d, J=5.7 Hz, 2H), 5.75(s, 2H), | 431.00 |
| 161 | A | (DMSO-d$_6$): 11.52(s, 1H), 8.91(d,J= 8.4 Hz, 1H), 8.73(d, J=5.7 Hz, 1H), 8.43(d, J=3.4 Hz, 1H), 7.76(dd, J=5.8, 8.4 Hz, 1H), 7.50(t, J=2.0 Hz, 1H), 7.33(t, J=8.1 Hz, 1H), 7.19(dd, J=1.4, 8.2 Hz, 1H), 7.11(dd, J=1.3, 8.0 Hz, 1H),, 6.99(d, J=3.3 Hz, 1H), 6.76(q, J=7.0 Hz, 1H), 2.13(d, J=7.0 Hz, 3H), | 395.90 |
| 162 | A | | 373.00 |
| 163 | C | Lot 1: in DMSO-d6: 9.24(s, 1H), 9.10(d, 1H), 8.04(t, 1H), 8.78(br, 1H), 7.84(d, 1H), 7.65(d, 1H), 7.41(s, 1H), 7.15(m, 1H), 6.88(m, 2H), 6.48(s, 1H), 2.25(d, 3H) | 423.18 |
| 164 | C | Lot 1: in DMSO-d6: 8.13(sbr, 1H), 8.04(d, 1H), 7.56(d, 1H), 7.15(m, 3H), 6.91(s, 1H), 6.77(t, 1H), 6.54(d, 2H), 6.43(br, 2H), 2.00(d, 3H) | 422.90 |
| 165 | A | | 455.10 |
| 166 | A | | 427.20 |
| 167 | A | | 443.10 |
| 168 | A | | 471.00 |
| 169 | A | (DMSO-d$_6$): 10.80(s, 1H), 7.50(s, 1H), 7.34(m, 2H), 7.23(d, 1H), 7.01(m, 2H), 6.93(t, 1H), 6.55(d, 1H), 6.39(d, 1H), 5.74(s, 2H) | 408.90 |
| 170 | B | | 452.00 |
| 171 | A | (DMSO-d$_6$, 300 mHz): 10.85(s, 1H), 7.70(1H, s), 7.48-7.26(m, 4H), 7.25-7.10(m, 3H), 4.38(s, 2H). | 360.20 |
| 172 | B | (DMSO-d$_6$, 300 mHz): 10.85(s, 1H), 9.24(s, 1H), 7.45(m, 2H), 7.20(m, 2H), 6.92(m, 2H), 6.70(d, 1H), 4.45(q, 1H), 1.68(d, 3H), 1.28(s, 9H) | 412.10 |
| 173 | A | | 396.30 |
| 174 | B | (DMSO-d$_6$): 9.26(s, 1H), 8.41(d, 1H), 7.47(d, 1H), 7.10(d, 2H), 6.69(d, 2H), 4.38(s, 2H) | 261.30 |
| 175 | A | (methanol-d$_4$): 8.15(d, 1H), 7.97(d, 1H), 7.87(d, 1H), 7.72(d, 1H), 7.28(d, 2H), 7.21(t, 1H), 6.72(d, 2H), 4.48(s, 2H) | 309.30 |
| 176 | B | (methanol-d$_4$): 8.24(d, 1H), 8.08(d, 1H), 8.07(d, 1H), 7.92(d, 1H), 7.57(m, 3H), 7.25(d, 2H), 6.73(d, 2H), 4.52(s, 2H) | 303.40 |
| 177 | B | (DMSO-d$_6$): 8.01(d, J=10.2 Hz, 1H), 7.40(d, J=10.2 Hz, 1H), 7.14(d, J=8.4 Hz, 2H), 6.67(d, J=8.4 Hz, 2H), 4.36(s, 2H), 3.58-3.56(m, 4H), 1.64-1.58(m, 6H). | 310.30 |
| 178 | A | (DMSO-d$_6$): 9.61(s, 1H), 9.22(s, 1H), 8.04(d, J=9.8 Hz, 1H), 7.65-7.64(m, 2H), 7.36(s, 1H), 7.35(dd, J=7.5, 8.4 Hz, 1H), 7.13-7.10(m, 2H), 7.05-6.97(m, 2H), 6.70-6.67(m, 2H), 4.30(s, 2H). | 318.40 |
| 179 | C | | 353.50 |
| 180 | B | (DMSO-d$_6$): 9.23(br s, 1H), 9.10(s, 1H), 7.88(d, J=9.8 Hz, 1H), 7.77(t, J=1.6 Hz, 1H), 7.69(t, J=1.5 Hz, 1H), 7.44(s, 1H), 7.08(d, J=8.4 Hz, 2H), 6.73(d, J=9.8 Hz, 1H), 6.64-6.63(m, 2H), 4.27(t, J=7.1 Hz, 2H), 4.17(s, 2H), 3.27(dd, J=6.5, 12.2 Hz, 2H), 2.15(t, J=6.9 Hz, 2H). | 350.30 |
| 181 | A | (DMSO-d$_6$): 9.62(s, 1H), 9.23(br s, 1H), 8.04(d, Hz, 1H), 7.50(t, J=2.1 Hz, 1H), 7.23(t, J=8.1 Hz, 1H), 7.13-7.10(m, 3H), 6.98(d, J=9.9 Hz, 1H), 6.67(dd, J=1.9, 6.6 Hz, 2H), 6.60(dd, J=2.1, 8.0 Hz, 1H), 4.54(t, J=6.0 Hz, 1H), 4.29(s, 2H), 1.27(d, J=6.0 Hz, 6H). | 376.50 |
| 182 | A | (DMSO-d$_6$): 9.61(s,H), 9.22(br s, 1H), 8.04(d, J=9.8 Hz, 1H), 7.76(t, J=1.9 Hz, 1H), 7.52(dd, J=1.7, 7.9 Hz, 1H), 7.29(t, J=7.9 Hz, 1H), 7.08(dd, J=8.5, 11.5 Hz, 3H), 7.00(d, J=9.8 Hz, 1H), 6.66(dcl, J=1.9, 6.6 Hz, 2H), 4.31(s, 2H), 1.28-1.23(m, 9H). | 374.50 |
| 183 | B | (DMSO-d$_6$):.56(s, 1H), 9.23(br s, 1H), 8.02(d, J=9.8 Hz, 1H), 7.57(d, J=8.5 Hz, 2H), 7.18(d, J=8.5 Hz, 2H), 7.12(d, J=8.5 Hz, 2H), 6.99(d, J=9.8 Hz, 1H), 6.68(dd, J=1.8, 6.6 Hz, 2H), 4.29(s, 2H), 2.58(m, 1H), 1.58-1.55(m, 2H), 1.20(d, J=6.9 Hz, 3H), 0.79(t, J=7.4 Hz, 3H). | 374.50 |
| 184 | A | | 348.40 |
| 185 | A | (DMSO-d$_6$): 9.85(s, 1H), 9.22(s, 1H), 8.08(d, J=9.8 Hz, 1H), 7.99(d, J=1.8 Hz, 1H), 7.48(d, J=7.7 Hz, 1H), 7.37(t, J=8.1 Hz, 1H), 7.15(d, J=8.3 Hz, 1H), 7.09(d, J=7.3 Hz, 1H), 6.98(d, J=9.8 Hz, 1H), 6.67(d, J=8.4 Hz, 2H), 4.30(s, 2H). | 352.40 |
| 186 | B | | 352.40 |
| 187 | B | | 326.30 |
| 188 | B | | 342.50 |
| 189 | B | (DMSO-d$_6$): 9.23(br s, 1H), 7.86(d, J=9.9 Hz, 1H), 7.23(d, J=8.0 Hz, 1H), 7.13(d, J=8.4 Hz, 2H), 6.86(d, J=9.9 Hz, 1H), 6.66(dd, J=1.9, 6.6 Hz, 2H), 4.19(s, 2H), 3.77(d, J=7.6 Hz, 1H), 1.71-1.4(m, J=9.4 Hz, 5H), 1.18-1.00(m, 9H). | 352.77 |
| 190 | B | (DMSO-d$_6$): 9.23(br s, 1H), 8.04(d, J=10.2 Hz, 1H), 7.61(s, 1H), 7.34(d, J=10.2 Hz, 1H), 7.14(d, J=8.5 Hz, 2H), 6.66(d J=8.5 Hz, 2H), 4.23(s, 2H), 3.80-3.76(m, 4H), 3.23-3.21(m, 2H), 2.63(t, J=1.8 Hz, 2H). | 339.30 |
| 191 | C | | 376.40 |
| 192 | C | | 358.65 |
| 193 | B | (DMSO-d$_6$): 9.23(br s, 1H), 7.89(d, J=9.9 Hz, 1H), 7.28(d, J=7.9 Hz, 1H), 7.14(d, J=8.5 Hz, 2H), 6.91(d, J=9.9 Hz, 1H), 6.68(m, 2H), 4.20(s, 2H), 3.76(q, J=6.7 Hz, 1H), 1.91-1.84(m, 1H), 1.10(d, J=6.7 Hz, 3H), 0.94(d, J=6.8 Hz, 3H), 0.89(d, J=6.8 Hz, 3H). | 312.30 |
| 194 | B | (DMSO-d$_6$): 9.23(hrs, 1H), 8.07(d, J=10.2 Hz, 1H), 7.45(d, J=10.2 Hz, 1H), 7.15(m, 3H), 6.70(m, 1H), 6.68(dd, J=1.8, 6.6 Hz, 1H), 6.60(dd, J=2.1, 8.2 Hz, 1H), 6.53(t, J=2.2 Hz, 1H), 6.41(dd, J=2.2, 8.1 Hz, 1H), 4.26(s, 2H), 3.75(s, 3H), 3.72(m, 4H), 3.28(m, 4H) | 417.50 |

TABLE 4-continued

Physical and biological data of compounds of formula I.

| No. | c-Met K$_i$ | $^1$H NMR NMR peaks given as δ values (500 MHz - unless indicated otherwise) | ESMS (M + H) |
|---|---|---|---|
| 195 | B | (DMSO-d$_6$): 9.22(br s, 1H), 7.87(d, J=9.9 Hz, 1H), 7.46(t, J=5.5 Hz, 1H), 7.13(d, J=8.4 Hz, 2H), 6.85(d, J=9.9 Hz, 1H), 6.68(s, 1H), 6.66(dd, J=1.9, 6.6 Hz, 1H), 4.20(s, 2H), 3.10(t, J=6.1 Hz, 2H), 1.75-1.59(m, 6H), 1.22-1.15(m, 3H), 0.95(m, 2H). | 338.40 |
| 196 | B | (DMSO-d$_6$): 9.23(br s, 1H), 8.01(d, J=10.2 Hz, 1H), 7.35(d, J=10.2 Hz, 1H), 7.16-7.14(m, 2H), 6.68-6.65(m, 2H), 4.24(s, 2H), 4.09(t, J=11.4 Hz, 1H), 2.93(s, 3H), 1.82(m, 2H), 1.66(m, 3H), 1.59-1.51(m, 2H), 1.42(m,2H), 1.17-1.14(m, 1H). | 338.40 |
| 197 | C | | 353.40 |
| 198 | B | | 314.30 |
| 199 | C | (DMSO-d$_6$): 9.24(br s, 1H), 7.91(d, J=9.8 Hz, 1H), 7.51(d, J=5.1 Hz, 1H), 7.13(d, J=8.4 Hz, 2H), 6.87(d, J=9.9 Hz, 1H), 6.69-6.66(m, 2H), 4.22(s, 2H), 3.32(t, J=7.0 Hz, 2H), 3.27-3.21(m, 4H), 2.20(t, J=8.1 Hz, 2H), 1.90(q, J=7.6 Hz, 2H), 1.77(qn, J=7.0 Hz, 2H). | 367.40 |
| 200 | C | | 379.50 |
| 201 | C | | 372.40 |
| 202 | C | | 390.40 |
| 203 | C | | 353.40 |
| 204 | C | | 355.40 |
| 205 | B | | 400.50 |
| 206 | C | (CDCl$_3$): 8.38(d, J=9.7 Hz, 1H), 8.01-7.98(m, 2H), 7.70(d, J=9.7 Hz, 1H), 7.63-7.58(m, 3H), 7.38(s, 1H), 7.08-7.04(m, 1H), 6.83(d, J=8.2 Hz, 1H), 4.63(s, 2H), 3.85(s, 6H) | 346.90 |
| 207 | B | (CDCl$_3$): 8.44(d, J=9.8 Hz, 1H), 8.00-7.97(m, 2H), 7.74(d, J=9.7 Hz, 1H), 7.64-7.59(m, 3H), 6.97-6.95(m, 2H), 6.78(d, J=7.8 Hz, 1H), 5.94(s, 2H), 3.52(s, 2H) | 330.80 |
| 208 | C | | 303.30 |
| 209 | C | | 359.40. |
| 210 | C | | 359.40 |
| 211 | C | | 303.30 |
| 212 | C | (CDCl$_3$): 8.34(d, J=9.8 Hz, 1H), 7.90-7.87(m, 2H), 7.69(d, J=9.8 Hz, 1H), 7.58-7.51(m, 5H), 7.44(dd, J=1.7, 6.9 Hz, 2H), 4.64(s, 2H), 3.10(s, 6H) | 330.40 |
| 213 | B | (CDCl$_3$): 8.27(d, 1H), 7.96(dd, 2H), 7.63(d, 1H), 7.59(m, 3H), 7.24(d, 1H), 7.16(d, 1H), 6.97(t, 1H), 4.58(s, 2H) | 321.40 |
| 214 | A | | 324.30 |
| 215 | A | | 366.30 |
| 216 | A | | 374.40 |
| 217 | B | | 374.40 |
| 218 | C | | 304.10 |
| 219 | A | | 370.00 |
| 220 | B | | 321.10 |
| 221 | A | | 371.10 |
| 222 | C | | 331.10 |
| 223 | A | | 386.10 |
| 224 | A | | 420.10 |
| 225 | B | | 400.20 |
| 226 | B | | 414.10 |
| 227 | B | | 371.10 |
| 228 | B | | 366.10 |
| 229 | B | | 346.10 |
| 230 | B | | 360.10 |
| 231 | C | | 317.10 |
| 232 | B | | 375.10 |
| 233 | B | | 393.10 |
| 234 | B | | 409.10 |
| 235 | B | | 389.20 |
| 236 | B | | 403.10 |
| 237 | A | | 386.00 |
| 238 | A | | 366.10 |
| 239 | A | | 380.10 |
| 240 | B | | 337.00 |
| 241 | B | | 382.10 |
| 242 | B | | 362.10 |
| 243 | B | | 376.10 |
| 244 | C | | 333.10 |
| 245 | A | | 404.00 |
| 246 | B | | 414.00 |
| 247 | B | | 371.00 |
| 248 | B | | 374.10 |
| 249 | C | | 331.10 |
| 250 | A | | 354.10 |
| 251 | A | | 388.10 |
| 252 | A | | 368.10 |
| 253 | A | | 382.10 |
| 254 | B | | 339.10 |
| 255 | A | | 362.10 |
| 256 | A | | 380.10 |
| 257 | B | | 376.10 |
| 258 | B | | 390.20 |
| 259 | A | | 348.10 |
| 260 | B | | 366.10 |
| 261 | B | | 382.10 |
| 262 | B | | 362.10 |
| 263 | B | | 376.10 |
| 264 | A | | 362.10 |
| 265 | B | | 380.10 |
| 266 | B | | 376.10 |
| 267 | B | (DMSO-d$_6$): 9.24(s, 1H), 7.90(m, 2H), 7.29(d, J=8.4 Hz, 2H), 7.07(d, J=8.3 Hz, 2H), 6.89-6.85(m, 3H), 6.63(d, J=8.3 Hz, 2H), 4.38(s, 2H), 4.20(s, 2H), 3.82(s, 3H). | 362.10 |
| 268 | B | (DMSO-d$_6$): 9.23(s, 1H), 8.03(t, J=5.7 Hz, 1H), 7.93(d, J=9.8 Hz, 1H), 7.41-7.36(m, 1H), 7.23-7.20(m, 2H), 7.14-7.08(m, 1H), 7.02(d, J=8.4 Hz, 2H), 6.92-6.87(m, 1H), 6.62-6.58(m, 2H), 4.51(d, J=5.7 Hz, 2H), 4.18(s, 2H | 350.10 |
| 269 | B | (DMSO-d$_6$): 9.26(s, 1H)7.88(d, J=9.8 Hz, 1H), 7.46(d, J=6.2 Hz, 1H), 7.18-7.14(m, 2H), 6.83(d, J=9.9 Hz, 1H), 6.67(d, J=8.4 Hz, 2H), 4.22(s, 2H), 4.07-4.00(m, 1H), 1.98(m, 2H), 1.72-1.59(m, 4H), 1.52-1.47(m, 2H). | 310.10 |
| 270 | B | | 352.20 |
| 271 | B | | 338.10 |
| 272 | B | | 340.10 |
| 273 | B | | 401.20 |
| 274 | B | | 312.10 |
| 275 | A | (DMSO-d$_6$): 9.23(s, 1H), 7.86(d, J=9.8 Hz, 1H), 7.29(d, J=6.1 Hz, 1H), 7.16(d, J=8.4 Hz, 2H), 6.79(d, J=9.9 Hz, 1H), 6.66(d, J=8.5 Hz, 2H), 4.20(s, 2H), 3.53(m, 1H), 2.28(m, 2H), 1.74(m, 1H), 1.59-1.25(m, 5H), 1.19-1.13(m, 2H). | 336.10 |
| 276 | B | (DMSO-d$_6$): 9.23(s, 1H), 7.89(d, J=9.8 Hz, 1H), 7.35(m, 1H), 7.14(d, J=8.4 Hz, 2H), 6.83(d, J=9.8 Hz, 1H), 6.67(d, J=8.4 Hz, 2H), 4.21(s, 2H), 3.92(q, J=6.5 Hz, 1H), 1.20(d, J=6.4 Hz, 6H | 284.10 |
| 277 | B | (DMSO-d$_6$): 9.23(s, 1H), 7.97(t, J=5.5 Hz, 1H), 7.91(d, J=9.8 Hz, 1H), 7.39-7.26(m, 5H), 7.08-7.04(m, 2H), 6.89(d, J=9.9 Hz, 1H), 6.60(d, J=8.5 Hz, 2H), 4.47(d, J=5.6 Hz, 2H), 4.17(s, 2H). | 332.10 |
| 278 | B | (DMSO-d$_6$): 9.24(s, 1H), 7.88(d, J=9.8 Hz, 1H), 7.30(d, J=7.2 Hz, 1H), 7.14(d, J=8.4 Hz, 2H), 6.85(d, J=9.9 Hz, 1H), 6.66(a, J=8.4 Hz, 2H), 4.21(s, 2H), 3.76(q, J=6.5 Hz, 1H), 1.62-1.47(m, 2H), 1.16(d, J=6.5 Hz, 3H), 0.92-0.86(m, 3H). | 298.10 |
| 279 | B | (DMSO-d$_6$): 9.23(s, 1H), 7.88(d, J=9.8 Hz, 1H), 7.29(d, J=7.5 Hz, 1H), 7.13(d, J=8.2 Hz, 2H), 6.83(d, J=9.8 Hz, 1H), 6.66(d, J=8.3 Hz, 2H), 4.18(s, 2H), 4.00-3.91(m, 1H), 1.70-1.65(m, 1H), 1.55-1.50(m, 1H), 1.30-1.24(m, 1H), 1.16(d, J=6.3 Hz, 3H), 0.91(d, J=6.6 Hz, 3H), 0.87(d, J=6.5 Hz, 3H). | 326.10 |

TABLE 4-continued

Physical and biological data of compounds of formula I.

| No. | c-Met $K_i$ | $^1$H NMR peaks given as δ values (500 MHz - unless indicated otherwise) | ESMS (M + H) |
|---|---|---|---|
| 280 | B | (DMSO-d$_6$): 9.23(s, 1H), 7.89(d, J=9.9 Hz, 1H), 7.31(d, J=7.3 Hz, 1H), 7.18-7.12(m, 2H), 6.85(d, J=9.8 Hz, 1H), 6.66(d, J=8.4 Hz, 2H), 4.21(s, 2H), 3.86(qn, J=6.6 Hz, 1H), 1.60-1.30(m, 4H), 1.17(d, J=6.5 Hz, 3H), 0.89(t, J=7.2 Hz, 3H). | 312.10 |
| 281 | B | (DMSO-d$_6$): 9.24(s, 1H), 7.88(d, J=9.8 Hz, 1H), 7.24(d, J=7.8 Hz, 1H), 7.14(d, J=8.4 Hz, 2H), 6.89(d, J=9.9 Hz, 1H), 6.66(d, J=8.4 Hz, 2H), 4.20(s, 2H), 3.67(dd, J=6.8, 13.0 Hz, 1H), 1.62-1.47(m, 4H), 0.90-0.83(m, 6H). | 312.10 |
| 282 | B | | 328.10 |
| 283 | B | | 339.10 |
| 284 | A | | 338.40 |
| 285 | A | | 350.40 |
| 286 | A | | 364.40 |
| 287 | A | | 357.40 |
| 288 | A | | 346.40 |
| 289 | B | | 364.40 |
| 290 | B | | 380.40 |
| 291 | B | | 360.50 |
| 292 | A | | 404.40 |
| 293 | B | | 366.40 |
| 294 | A | | 386.30 |
| 295 | A | | 346.40 |
| 296 | A | | 380.40 |
| 297 | B | | 360.40 |
| 298 | A | | 372.20 |
| 299 | B | | 396.40 |
| 300 | B | | 396.40 |
| 301 | B | | 390.40 |
| 302 | B | | 354.50 |
| 303 | B | | 300.10 |
| 304 | B | (DMSO-d$_6$): 9.24(s, 1H), 7.90(d, J=9.9 Hz, 1H), 7.39(d, J=7.2 Hz, 1H), 7.12(d, J=8.4 Hz, 2H), 6.88(d, J=9.8 Hz, 1H), 6.67(d, J=8.5 Hz, 2H), 4.21(s, 3H), 4.07-4.01(m, 1H), 3.43(dd, J=5.4, 9.6 Hz, 1H), 3.34(dd, J=5.4, 9.6 Hz, 1H), 3.28(s, 3H), 1.18(d, J=6.6 Hz, 3H). | 314.10 |
| 305 | A | (DMSO-d$_6$): 9.23(s, 1H), 8.20(d, J=9.7 Hz, 1H), 7.69-7.66(m, 2H), 7.59(t, J=7.9 Hz, 1H), 7.24(d, J=9.7 Hz, 1H), 6.82(d, J=8.4 Hz, 2H), 6.61-6.59(m, 2H), 4.09(s, 2H). | 369.10 |
| 306 | B | | 397.20 |
| 307 | C | | 353.20 |
| 308 | B | | 314.10 |
| 309 | B | | 326.20 |
| 310 | B | | 346.10 |
| 311 | C | | 355.20 |
| 312 | B | | 314.10 |
| 313 | B | | 346.10 |
| 314 | B | (methanol-d$_4$): 7.96(d, 1H), 7.78(s, 1H), 7.49(d, 1H), 7.37(m, 3H), 7.06(d, 2H), 7.02(dt, 1H), 4.68(s, 2H); Lot 2: HNIVIR(500 MHz, DMSO-d6)9.88(s, 1H), 8.12(d, J=9.8 Hz, 1H), 7.84(t, J=1.9 Hz, 1H), 7.53-7.48(m, 2H), 7.36-7.33(m, 2H), 7.16(td, J=8.5, 2.7 Hz, 1H), 7.08-7.06(m, 1H), 7.01(d, J=9.8 Hz, 1H), 4.53(s, 2H). | 388.30 |
| 315 | C | (methanol-d$_4$): 7.96(t, 1H), 7.93(d, 1H), 7.42(dd, 1H), 7.40(d, 2H), 7.29(m, 3H), 7.22(d, 1H), 7.07(dd, 1H), 7.03(d, 1H), 4.58(s, 2H) | 336.30 |
| 316 | C | (methanol-d$_4$): 9.0(s, 1H), 8.62(d, 1H), 8.36(d, 1H), 7.93(t, 1H), 7.71(t, 1H), 7.47(dd, 1H), 7.38(d, 1H), 7.32(d, 1H), 7.24(t, 1H), 7.00(d, 1H), 6.68(s, 1H), 4.84(s, 2H), | 365.30 |
| 317 | C | (methanol-d$_4$): 7.98-7.95(m, 2H), 7.55(d, J=7.7 Hz, 1H), 7.49-7.43(m, 2H), 7.31(t, J=8.1 Hz, 1H), 7.21-7.19(m,2H), 7.08-7.05(m, 2H), 4.59(s, 2H) | 351.40 |
| 318 | B | (DMSO-d$_6$): 9.3(br s, 1H), 7.92(d, J=9.8 Hz, 1H), 7.47(d, J=6.7 Hz, 1H), 7.11(d, J=8.5 Hz, 2H), 6.86(d, J=9.9 Hz, 1H), 6.68-6.64(d, J= 8.5 Hz, 2H), 4.22(s, 2H), 3.89(d, J=11.6 Hz, 2H), 3.79(m, 1H), 3.45(m, 2H), 1.91(m, 2H), 1.46-1.38(m, 2H). | 326.10 |
| 319 | A | (DMSO-d$_6$): 9.85(s, 1H), 9.25(hrs, 1H), 8.09(dd, J=1.6, 9.8 Hz, 1H), 7.95(m, 1H), 7.43-7.35(m, 2H), 7.14-7.09(m, 3H), 6.99(d, J=9.8 Hz, 1H), 6.67(m, 2H), 4.58(q, J=7.2 Hz, 1H), 1.74(d, J=7.2 Hz, 3H | 366.20 |
| 320 | A | (DMSO-d$_6$): 9.85(s, 1H), 9.25(br s, 1H), 8.09(dd, J=1.6, 9.8 Hz, 1H), 7.95(m, 1H), 7.43-7.35(m, 2H), 7.14-7.09(m, 3H), 6.99(d, J=9.8 Hz, 1H), 6.67(m, 2H), 4.58(q, J=7.2 Hz, 1H), 1.74(d, J=7.2 Hz, 3H | 366.20 |
| 321 | A | (DMSO-d$_6$): 9.85(s, 1H), 9.25(br s, 1H), 8.09(dd, J=1.6, 9.8 Hz, 1H), 7.95(m, 1H), 7.43-7.35(m, 2H), 7.14-7.09(m, 3H), 6.99(d, J=9.8 Hz, 1H), 6.67(m, 2H), 4.58(q, J=7.2 Hz, 1H), 1.74(d, J=7.2 Hz, 3H | 366.20 |
| 322 | C | | 325.10 |
| 323 | B | (DMSO-d$_6$): 9.23(hrs, 1H), 8.03(d, J=10.2 Hz, 1H), 7.79(d, J=7.7 Hz, 1H), 7.44-7.40(m, 1H), 7.13(m, 2H), 6.67(d, J=8.5 Hz, 2H), 4.23(s, 2H), 4.14(m, 2H), 3.88-3.79(m, 1H), 3.13(t, J=11.3 Hz, 2H), 1.85-1.80(m, 5H), 1.43-1.35(m, 2H). | 367.10 |
| 324 | B | (DMSO-d$_6$): 9.23(br s, 1H), 8.03(d, J=10.2 Hz, 1H), 7.62(d, J=7.6 Hz, 1H), 7.40(d, J=10.2 Hz, 1H), 7.13(d, 8.5 Hz, 2H), 6.67(d, 8.5 Hz, 2H), 4.27(s, 2H), 4.14(m, 2H), 3.87-3.81(m, 1H), 3.13(t, J=11.5 Hz, 2H), 2.32(qn, J=6.8 Hz, 1H), 1.83-1.81(m, 2H), 1.44-1.36(m, 2H), 1.00(dd, J=6.8, 11.3 Hz, H). | 395.10 |
| 325 | B | | 443.20 |
| 326 | C | (DMSO-d$_6$): 9.23(br s, 1H), 8.03(d, J=10.2 Hz, 1H), 7.87(d, J=7.3 Hz, 1H), 7.33(d, J=10.2 Hz, 1H), 7.15(d, J=8.5 Hz, 2W, 6.68-6.66(m, 2H), 4.24(s, 2H), 4.01-3.98(m, 1H), 3.90-3.87(m, 1H), 3.75-3.74(m, 1H), 3.23(t, J=10.1 Hz, 1H), 3.05(dd, J=8.9, 13.0 Hz, 1H), 1.86(s, 3H), 1.82-1.77(m, 2H), 1.53-1.47(m, 2H). | 367.10 |
| 327 | C | (DMSO-d$_6$): 9.23(s, 1H), 8.03(d, J=10.2 Hz, 1H), 7.73(d, J=7.3 Hz, 1H), 7.33(d, J=10.2 Hz, 1H), 7.15(d, J=8.5 Hz, 2H), 6.67-6.65(m, 2H), 4.23(s, 2H), 4.02-3.98(m, 1H), 3.93-3.90(m, 1H), 3.73(m, 1H), 3.22-3.17(m, 1H), 3.04-3.00(m, 1H), 2.42-2.34(m, 1H), 1.86(d, J=8.8 Hz, H), 1.82-1.80(m, 2H), 1.57-1.48(m, 2H), 1.07-1.00(m, 6H). | 395.10 |
| 328 | C | | 443.20 |
| 329 | B | (DMSO-d$_6$): 9.23(s, 1H), 7.89(d, J=9.8 Hz, 1H), 7.66(s, 1H), 7.22-7.18(m, 2H), 6.77(d, J=9.8 Hz, 1H), 6.67(d, J=6.6 Hz, 2H), 4.23(s, 2H), 2.69-2.63(m, 2H), 0.84-0.74(m, 2H), 0.54-0.45(m, 2H). | 282.00 |
| 330 | B | (DMSO-d$_6$): 9.23(br s,H), 7.89(d, J=9.8 Hz, 1H), 7.72(d, J=6.4 Hz, 1H), 7.18-7.13(m, 2H), 6.79(d, J=9.8 Hz, 1H), 6.68-6.66(m, 2H), 4.21(s, 2H), 4.17(q, J=7.6 Hz, 1H), 2.38-2.32(m, 2H), 1.93-1.88(m, 2H), 1.80-1.73(m, 2H) | 296.10 |
| 331 | C | | 453.30 |
| 332 | B | | 425.30 |
| 333 | B | | 457.30 |
| 334 | C | | 443.10 |
| 335 | C | | 397.00 |
| 336 | B | | 381.00 |
| 337 | C | | 411.10 |
| 338 | B | | 367.00 |

TABLE 4-continued

Physical and biological data of compounds of formula I.

| No. | c-Met $K_i$ | $^1$H NMR NMR peaks given as δ values (500 MHz - unless indicated otherwise) | ESMS (M + H) |
|---|---|---|---|
| 339 | C | | 395.00 |
| 340 | C | | 411.00 |
| 341 | C | | 386.90 |
| 342 | C | | 403.00 |
| 343 | C | | 369.00 |
| 344 | C | | 387.00 |
| 345 | C | | 445.30 |
| 346 | C | | 441.30 |
| 347 | B | | 395.30 |
| 348 | C | | 409.40 |
| 349 | C | | 409.00 |
| 350 | C | | 381.40 |
| 351 | B | | 397.10 |
| 352 | C | | 418.30 |
| 353 | C | | 411.40 |
| 354 | B | (CDCl$_3$): 8.58(d, J=2.2 Hz, 1H), 8.20(d, J=9.9 Hz, 1H), 7.81(dd, J=2.5, 8.3 Hz, 1H), 7.71(s, 1H), 7.36(m, 2H), 7.24-7.20(m, 3H), 7.00(d, J=9.9 Hz, 2H), 4.56(s, 2H) | 370.90 |
| 355 | A | (CDCl$_3$): 8.11(d, J=9.5 Hz, 1H), 7.93(s, 1H), 7.61(s, 1H), 7.35-7.31(m, 3H), 7.22(m, 2H), 7.07-7.03(m, 1H), 6.73(d, J=8.1 Hz, 1H), 4.53(t, J=8.7 Hz, 2H), 4.46(s, 2H), 3.16-3.13(m, 2H) | 378.10 |
| 356 | B | CDCl$_3$: 8.73(s, 1H), 8.17(s, 1H)7.83(d, 1H), 7.48(d, 2H)7.27(m, 3H), 7.16(d, 1H), 6.82(d, 2H) 3.74(s, 3H), 1.65(m, 2H), 1.59(m, 2H) | 392.10 |
| 357 | A | CDCl$_3$:: 9.05(s, 1H), 8.15(d, 1H), 7.98(s, 1H), 7.46(d, 1H), 7.32(d, 2H), 7.29(m, 2H), 7.17(m, 1H), 6.83(d, 2H), 4.43(t, 1H), 3.73(s, 3H), 2.48(m, 1H), 2.23(m, 1H), 1.01(t, 3H) | 394.10 |
| 358 | A | (DMSO-d$_6$): 9.24(s, 1H), 8.75(s, 1H), 8.06(d, J=9.9 Hz, 1H), 7.97(d, J=2.1 Hz, 1H), 7.29(d, J=8.2 Hz, 1H), 7.18-7.12(m, 2H), 7.06(d, J=8.5 Hz, 1H), 6.63(d, J=8.5 Hz, 2H), 4.15(s, 2H), 2.24(s, 3H). | 366.10 |
| 359 | A | (DMSO-d$_6$): 9.51(s, 1H), 9.21(s, 1H), 8.46(dd, J=2.6, 7.3 Hz, 1H), 8.12(d, J=9.8 Hz, 1H), 7.37(dd, J=8.8, 11.2 Hz, 1H), 7.30(d, J=9.9 Hz, 1H), 7.19-7.12(m, 2H), 6.65(d, J=8.5 Hz, 2H), 4.27(s, 2H). | 370.00 |
| 360 | A | (DMSO-d$_6$): 9.21(s, 1H), 8.95(s, 1H), 8.45(d, J=1.9 Hz, 1H), 8.06(d, J=9.9 Hz, 1H), 7.40(d, J=9.9 Hz, 1H), 7.16-7.08(m, 3H), 6.66(d, J=8.5 Hz, 2H), 4.26(s, 2H), 3.89(s, 3H). | 382.00 |
| 361 | A | (DMSO-d$_6$): 9.20(s, 1H), 9.09(s, 1H), 8.28(d, J=2.5 Hz, 1H), 8.12(d, J=9.8 Hz, 1H), 7.59(d, J=8.7 Hz, 1H), 7.31(d, J=9.9 Hz, 1H), 7.26(dd, J=2.5, 8.6 Hz, 1H), 7.08(d, J=8.4 Hz, 1H), 6.64(d, J=8.5 Hz, 2H), 4.19(s, 2H). | 386.00 |
| 362 | A | (DMSO-d$_6$): 9.54(s, 1H), 8.43(dd, J=2.6, 7.2 Hz, 1H), 8.14-8.11(m, 1H), 7.38-7.30(m, 2H), 7.18-7.15(m, 1H), 6.85-6.76(m, 3H), 5.96(s, 2H), 4.30(s, 2H). | 398.00 |
| 363 | B | (DMSO-d$_6$): 9.12(s, 1H), 8.26(d, J=2.5 Hz, 1H), 8.13(d, J=9.8 Hz, 1H), 7.58(d, J=8.6 Hz, 1H), 7.33(d, J=9.9 Hz, 1H), 7.24(dd, J=2.5, 8.6 Hz, 1H), 6.80-6.70(m, 3H), 5.99(s, 2H), 4.24(s, 2H). | 414.00 |
| 364 | C | (DMSO-d$_6$): 9.87(s, 1H), 8.11(d, J=9.8 Hz, 1H), 7.88-7.86(m, 3H), 7.60(d, J=8.3 Hz, 2H), 7.46-7.44(m, 1H), 7.36(t, J=8.1 Hz, 1H), 7.10-7.08(m, 1H), 7.00(d, J=9.8 Hz, 1H), 4.59(s, 2H), 3.14(s, 3H) | 414.20 |
| 365 | B | (DMSO-d$_6$): 9.85(s, 1H), 9.31(s, 1H), 8.09(d, J=9.8 Hz, 1H), 7.91(t, J=2.0 Hz, 1H), 7.53(s, H), 7.51(dd, J=1.2, 8.3 Hz, 1H), 7.37(t, J=8.1 Hz, 1H), 7.10-7.07(m, 2H), 6.98(d, J=9.8 Hz, 1H), 6.81(d, J=7.6 Hz, 1H), 6.66(d, J=10.8 Hz, 1H), 6.59(dd, J=1.6, 8.1 Hz, 1H), 4.35(s, 2H) | 352.00 |
| 366 | B | (methanol-d$_4$): 8.02(t, J=2.0 Hz, 1H), 7.92(dd, J=4.1, 9.9 Hz, 1H), 7.53-7.51(m, 1H), 7.33(td, J=8.1, 4.0 Hz, 1H), 7.09-7.01(m, 4H), 6.64-6.61(m, 2H), 3.42-3.35(m, 2H), 3.31(qn, J=1.6 Hz, 2H) | 366.00 |
| 367 | A | (methanol-d$_4$): 8.02(t, J=2.0 Hz, 1H), 7.97(dd, J=4.0, 9.9 Hz, 1H), 7.40-7.33(m, 2H), 7.24-7.22(m, 2H), 7.10(dd, J=4.2, 9.9 Hz, 2H), 6.74-6.71(m, 2H), 4.41(t, J=7.8 Hz, 1H), 2.45-2.40(m, 1H), 2.23-2.17(m, 1H), 1.00(td, J=7.2, 3.7 Hz, 3H) | 380.10 |
| 368 | C | (DMSO-d$_6$): 9.91(s, 1H), 8.74(d, J=9.1 Hz, 1H), 8.63(d, J=5.2 Hz, 1H), 8.31-8.27(m, 1H), 8.22(d, J=7.8 Hz, 1H), 8.10(d, J=9.8 Hz, 1H), 8.00(t, J=2.0 Hz, 1H), 7.73-7.71(m, 1H), 7.59-7.57(m, 1H), 7.43(s,H), 7.40(t, J=8.1 Hz, 1H), 7.13-7.09(m, 1H), 7.02(d, J=9.8 Hz, 1H), 3.45(t, J=7.4 Hz, 2H), 3.33(t, J=7.4 Hz, 2H), | 351.10 |
| 369 | C | (DMSO-d$_6$): 9.86(s, 1H), 9.61(s, 1H), 8.10(d, J=9.8 Hz, 1H), 7.95(t, J=1.9 Hz, 1H), 7.48-7.46(m, 1H), 7.37(d, J= 8.1 Hz, 1H), 7.31(d, J=8.5 Hz, 2H), 7.14(d, J=8.5 Hz, 2H), 7.10-7.08(m, 1H), 6.99(d, J=9.8 Hz, 1H), 4.40(s, 2H), 2.89(s, 3H), | 429.00 |
| 370 | A | | 366.46 |
| 371 | B | | 353.00 |
| 372 | C | | 367.00 |
| 373 | C | | 353.00 |
| 374 | B | | 387.00 |
| 375 | C | | 386.90 |
| 376 | C | | 387.00 |
| 377 | C | | 370.00 |
| 378 | C | | 388.00 |
| 379 | C | | 377.00 |
| 380 | C | | 386.00 |
| 381 | B | | 393.10 |
| 382 | C | | 391.00 |
| 383 | C | | 392.00 |
| 384 | C | | 386.00 |
| 385 | C | | 396.00 |
| 386 | C | | 352.00 |
| 387 | C | | 368.00 |
| 388 | C | | 382.00 |
| 389 | C | | 402.00 |
| 390 | C | | 386.00 |
| 391 | B | | 368.30 |
| 392 | C | | 395.30 |
| 393 | C | | 408.10 |
| 394 | C | | 351.32 |
| 395 | C | | 340.27 |
| 396 | C | (DMSO-d$_6$): 7.98(d, J=9.8 Hz, 1H), 7.36-7.30(m, 2H), 7.10-7.04(m, 2H), 6.92-6.86(m, 2H), 4.39(s, 2H), 2.20(s, 3H). | 284.10 |
| 397 | C | (DMSO-d$_6$): 8.16-8.11(m, 2H), 7.98(t, J=9.9 Hz, 1H), 7.76-7.73(m, 2H), 7.64-7.60(m, 2H), 7.42-7.36(m, 2H), 7.27-7.21(m, 2H), 6.88(br s, 2H), 6.83(m, 1H), 4.34(s, 2H). | 346.10 |
| 398 | C | | 380.00 |
| 399 | C | | 352.20 |
| 400 | A | | 406.10 |
| 401 | B | (DMSO-d$_6$): 9.3(br s, 1H), 7.89(d, J=9.9 Hz, 1H), 7.14(s, 1H), 7.10-7.08(m, 2H), 6.90(d, J=9.9 Hz, 1H), 6.68-6.65(m, 2H), 4.24(s, 2H), 1.34(s, 9H). | 298.10 |
| 402 | A | (DMSO-d$_6$): 9.87(s, 1H), 8.10(d, J=9.8 Hz, 1H), 7.92(t, J=2.0 Hz, 1H), 7.48(dd, J=1.4, 8.2 Hz, 1H), 7.39-7.36(m, 3H), 7.15-7.08(m, 3H), 7.00(d, J=9.8 Hz, 1H), 4.44(s, 2H). | 354.31 |
| 403 | B | (DMSO-d$_6$): 9.86(s, 1H), 9.64(s, 1H), 8.11(d, J=9.8 Hz, 1H), 7.87(t, J=2.0 Hz, 1H), 7.50(dd, J=1.4, 8.2 Hz, 1H), 7.36(t, J=8.1 Hz, 1H), 7.28(t, J=7.8 Hz, 2H), 7.13(d, J=7.7 Hz, 1H), 7.09-7.06(m, 3H), 7.00(d, J=9.9 Hz, 1H), 4.43(s, 2H), 2.88(s, 3H). | 429.27 |
| 404 | C | | 458.34 |
| 405 | C | | 404.00 |
| 406 | C | | 384.10 |

TABLE 4-continued

Physical and biological data of compounds of formula I.

| No. | c-Met $K_i$ | $^1$H NMR NMR peaks given as δ values (500 MHz - unless indicated otherwise) | ESMS (M + H) |
|---|---|---|---|
| 407 | C | | 395.10 |
| 408 | C | | 398.10 |
| 409 | B | | 368.10 |
| 410 | B | | 394.10 |
| 411 | B | | 395.10 |
| 412 | B | | 367.10 |
| 413 | A | | 368.10 |
| 414 | C | | 353.10 |
| 415 | A | (DMSO-d$_6$): 9.22(s, 1H), 8.72(s, 1H), 8.47(d, J=2.4 Hz, 1H), 8.11(d, J=9.9 Hz, 1H), 7.29(d, J=9.9 Hz, 1H), 7.17-7.07(m, 4H), 6.68-6.65(m, 2H), 4.29(s, 2H), 4.09(t, J=4.8 Hz, 2H), 3.78(t, J=4.8 Hz, 2H). | 412.26 |
| 416 | C | | 408.10 |
| 417 | C | | 365.20 |
| 418 | A | Lot 1: 1H NMR(500 Mhz, CD3OD)8.29(d, 1H), 8.1(d, 1H), 7.95(d, 1H), 7.9(s, 1H), 7.78(s, 1H), 7.5(d, 1H), 7.32(t, 1H), 7.1 2(m,2H), 7.03(d, 1H), 6.6(d, 1H), 5.93(s,2H). | 376.00; |
| 419 | A | | 338.10 |
| 420 | A | | 350.10 |
| 421 | C | (DMSO-d$_6$): 10.25(s, 1H), 9.52(s, 1H), 8.07(d, J=9.8 Hz, 1H), 7.86-7.85(m, 2H), 7.77(dd, J=1.9, 6.6 Hz, 1H), 7.57-7.48(m, 3H), 7.37(t, J=8.1 Hz, 1H), 7.15-7.08(m, 2H), 5.06-4.98(m, 2H), 4.15-4.11(m, 1H), 1.57(d, J=7.0 Hz, 3H). | 404.20 |
| 422 | B | (DMSO-d$_6$): 9.23(br s, 1H), 8.07(d, J=10.2 Hz, 1H), 7.46(d, J=10.1 Hz, 1H), 7.28-7.16(m, 6H), 6.67(d, J=8.5 Hz, 2H), 4.74(s, 2H), 4.27(s, 2H), 3.85(t, J=6.0 Hz, 2H), 2.94(t, J=5.9 Hz, 2H). | 358.37 |
| 423 | A | | 403.10 |
| 424 | A | (DMSO-d$_6$): 9.85(s, 1H), 9.22(s, 1H), 8.09-8.07(m, 2H), 7.50-7.47(m, 1H), 7.40(t, J=9.0 Hz, 1H), 7.13(d, J=8.4 Hz, 2H), 6.95(d, J=9.8 Hz, 1H), 6.70-6.67(m, 2H), 4.30(s, 2H) | 370.30 |
| 425 | A | (DMSO-d$_6$): 9.87(s, 1H), 8.10-8.05(m, 2H), 7.52-7.49(m, 1H), 7.41(t, J=9.0 Hz, 1H), 7.25(d, J=8.5 Hz, 2H), 6.96(d, J=9.8 Hz, 1H), 6.87(d, J=8.5 Hz, 2H), 4.36(s, 2H), 3.69(s, 3H). | 384.30 |
| 426 | A | (DMSO-d$_6$): 9.84(s, 1H), 9.23(s, 1H), 8.08(d, J=9.8 Hz, 1H), 8.03(dd, J=2.3, 6.7 Hz, 1H), 7.44-7.38(m, 2H), 7.11(d, J=8.5 Hz, 2H), 6.95(d, J=9.8 Hz, 1H), 6.67(d, J=8.4 Hz, 2H), 4.56(q, J=7.2 Hz, 1H), 1.73(d, J=7.2 Hz, 3H). | 384.30 |
| 427 | B | (DMSO-d$_6$): 9.90(s, 1H), 8.19(dd, J=2.4, 6.7 Hz, 1H), 8.09(d, J=9.8 Hz, 1H), 7.41-7.35(m, 2H), 6.98(d, J=9.8 Hz, 1H), 6.84(d, J=1.6 Hz, 1H); 6.77(d, J=8.1 Hz, 1H), 6.72(dd, J=1.6, 8.1 Hz, 1H), 5.92(s, 2H), 1.53-1.50(m, 2H), 1.47-1.45(m, 2H). | 424.30 |
| 428 | A | (DMSO-d$_6$): 9.92(s, 1H), 8.14(d, J=9.8 Hz, 1H), 7.92(d, J=2.5 Hz, 1H), 7.82(s, 1H), 7.68(d, J=8.2 Hz, 1H), 7.35(t, J=8.1 Hz, 1H), 7.14-7.06(m, 3H), 6.49(d, J=3.3 Hz, 1H), 5.85(s, 2H). | 393.25 |
| 429 | C | | 435.00 |
| 430 | C | | 392.00 |
| 431 | C | | 423.00 |
| 432 | C | | 385.40 |
| 433 | A | | 425.50 |
| 434 | B | | 397.40 |
| 435 | C | | 391.40 |
| 436 | A | (DMSO-d$_6$): 8.70(s, 1H), 8.41(d, J=2.0 Hz, 1H), 8.12(d, J=9.8 Hz, 1H), 7.31(d, J=9.9 Hz, 1H), 7.16(d, J=8.4 Hz, 2H), 7.12-7.07(m, 2H), 6.65(d, J=8.5 Hz, 2H), 4.56(q, J=7.2 Hz, 1H), 4.08(t, J=4.3 Hz, 2H), 3.77(t, J=4.7 Hz, 2H), 1.74(d, J=7.2 Hz, 3H). | 426.28 |
| 437 | B | (methanol-d$_4$): 7.94(s, 1H), 7.92(d, 1H), 7.59(s, 1H), 7.48(d, 1H), 7.28-7.38(m, 2), 7.08(d, 1H), 7.03(d, 1H), 6.95(d, 1H), 4.42(s, 2H), 3.80(s, 3H). | 445.00 |
| 438 | C | (DMSO-d$_6$): 9.86(s, 1H), 8.14(d, J=9.8 Hz, 1H), 7.81-7.72(m, 2H), 7.68-7.56(s, 1H), 7.52-7.48(m, 1H), 7.38-7.33(m, 1H), 7.29(s, 1H), 7.19(t, J=8.1 Hz, 1H), 7.02(t, J=10.1 Hz, 1H), 7.01(s, 1H), 4.92(s, 2H). | 377.00 |
| 439 | B | (DMSO-d$_6$): 9.86(s, 1H), 8.09(d, J=9.8 Hz, 1H), 7.94(t, J=1.9 Hz, 1H), 7.53-7.51(m, 1H), 7.36(t, J=8.1 Hz, 1H), 7.21(t, J=7.9 Hz, 1H), 7.08(dd, J=1.2, 7.9 Hz, 1H), 6.98(d, J=9.9 Hz, 1H), 6.93-6.89(m, 3H), 6.78(dd, J=1.9, 8.3 Hz, 1H), 4.41(s, 2H), 3.66(s, 3H). | 366.00 |
| 440 | A | (DMSO-d$_6$): 9.86(s, 1H), 8.11(d, J=9.8 Hz, 1H), 7.85(s, 1H), 7.54(d, J=8.4 Hz, 1H), 7.35(t, J=8.1 Hz, 1H), 7.20(d, J=8.8 Hz, 1H), 7.08-7.06(m, 2H), 7.00(d, J=9.9 Hz, 1H), 6.85(dd, J=2.6, 8.7 Hz, 1H), 4.47(s, 2H), 3.75(d, J=8.4 Hz, 3H). | 400.00 |
| 441 | C | (DMSO-d$_6$): 9.89(s, 1H), 9.22(d, J=6.9 Hz, 1H), 8.09(d, J=9.8 Hz, 1H), 8.01(d, J=1.4 Hz, 1H), 7.61(d, J=8.4 Hz, 1H), 7.40(t, J=8.2 Hz, 1H), 7.11-7.00(m, 3H), 6.71(d, J=7.8 Hz, 1H), 6.65(s, 1H), 6.58(d, J=8.0 Hz, 1H), 3.32-3.29(m, 2H), 3.07-3.04(m, 2H). | 366.00 |
| 442 | A | (DMSO-d$_6$): 9.87(s, 1H), 8.09(d, J=9.8 Hz, 1H), 7.99(t, J=1.9 Hz, 1H), 7.54-7.52(m, 1H), 7.38(t, J=8.1 Hz, 1H), 7.09(dd, J=1.2, 7.9 Hz, 1H), 6.99(d, J=9.9 Hz, 1H), 6.90(d, J=1.7 Hz, 1H), 6.76-6.74(m, 1H), 6.68(d, J=8.0 Hz, 1H), 4.32(s, 2H), 3.62(s, 3H). | 382.00 |
| 443 | B | | 479.26 |
| 444 | B | | 395.30 |
| 445 | C | | 439.30 |
| 446 | B | | 395.30 |
| 447 | B | | 439.30 |
| 448 | C | | 395.30 |
| 449 | C | | 439.30 |
| 450 | C | | 395.30 |
| 451 | C | | 439.30 |
| 452 | B | | 392.20 |
| 453 | B | | 371.10 |
| 454 | C | | 418.00 |
| 455 | C | | 395.10 |
| 456 | C | | 351.20 |
| 457 | C | | 379.20 |
| 458 | C | | 391.10 |
| 459 | C | | 393.10 |
| 460 | C | | 375.10 |
| 461 | C | | 419.40 |
| 462 | C | | 376.50 |
| 463 | C | | 377.40 |
| 464 | C | | 390.40 |
| 465 | C | | 390.50 |
| 466 | C | | 418.50 |
| 467 | B | | 394.20 |
| 468 | B | | 409.00 |
| 469 | C | | 409.00 |
| 470 | B | | 395.00 |
| 471 | C | | 377.10 |
| 472 | C | | 394.10 |
| 473 | C | | 414.90 |
| 474 | B | | 361.10 |
| 475 | C | | 381.10 |
| 476 | C | | 397.10 |
| 477 | C | | 390.10 |
| 478 | C | | 396.10 |
| 479 | B | | 410.10 |
| 480 | C | | 418.10 |
| 481 | B | | 409.10 |
| 482 | C | | 326.10 |
| 483 | A | | 423.10 |

TABLE 4-continued

Physical and biological data of compounds of formula I.

| No. | c-Met $K_i$ | $^1$H NMR NMR peaks given as δ values (500 MHz - unless indicated otherwise) | ESMS (M + H) |
|---|---|---|---|
| 484 | B | | 340.00 |
| 485 | C | | 376.00 |
| 486 | C | | 410.40 |
| 487 | B | | 391.40 |
| 488 | B | | 391.40 |
| 489 | C | | 376.20 |
| 490 | B | | 393.40 |
| 491 | C | | 391.40 |
| 492 | B | | 369.40 |
| 493 | A | | 368.10 |
| 494 | B | | 379.20 |
| 495 | B | | 366.10 |
| 496 | C | | 409.20 |
| 497 | B | | 350.10 |
| 498 | B | | 334.00 |
| 499 | B | | 389.20 |
| 500 | C | | 354.20 |
| 501 | B | | 275.10 |
| 502 | A | | 353.40 |
| 503 | C | | 396.40 |
| 504 | B | (DMSO-d$_6$): 9.88(s, 1H), 8.11(d, J=9.8 Hz, 1H), 7.87(t, J=2.0 Hz, 1H), 7.59(dd, J=1.4, 8.2 Hz, 1H), 7.36(t, J=8.1 Hz, 1H), 7.12(s, 1H), 7.07(dd, J=1.4, 7.9 Hz, 1H), 7.01(d, J=9.8 Hz, 1H), 6.87(s, 1H), 6.02(s, 2H), 4.45(s, 2H), | 414.40 |
| 505 | B | | 336.30 |
| 506 | A | | 367.50 |
| 507 | A | | 389.50 |
| 508 | B | | 340.30 |
| 509 | A | | 401.40 |
| 510 | B | | 351.50 |
| 511 | C | | 339.10 |
| 512 | B | | 368.50 |
| 513 | B | | 425.50 |
| 514 | B | | 367.20 |
| 515 | B | | 368.50 |
| 516 | C | | 394.10 |
| 517 | B | | 327.00 |
| 518 | A | | 402.20 |
| 519 | A | | 392.20 |
| 520 | A | (DMSO-d$_6$): 9.88(s, 1H), 9.26(br s, 1H), 8.13(s, 1H), 8.09(d, J=9.8 Hz, 1H), 7.38-7.25(m, 2H), 7.13(d, J=8.4 Hz, 2H), 7.08(d, J=7.4 Hz, 1H), 7.01(d, J=9.8 Hz, 1H), 6.63(d, J=8.4 Hz, 2H), 1.52(s, 2H), 1.45(s, 2H). | 378.10 |
| 521 | A | | 406.00 |
| 522 | A | (methanol-d$_4$): 7.99-7.97(m, 2H), 7.59-7.52(m, 3H), 7.16(dd, J=2.0, 6.6 Hz, 2H), 6.71(dd, J=2.1, 6.5 Hz, 2H), 4.25(s,2H), 4.23(s,2H), 0.00(TMS). | 323.00 |
| 523 | B | (DMSO-d$_6$): 8.01-8.00(m, 2H), 7.62-7.56(m, 3H), 6.88-6.78(m,3H), 5.96(s, 2H), 4.40(s, 2H), 4.20(s, 2H),. | |
| 524 | B | (DMSO-d$_6$): 12.51(s, 1H), 9.28(s, 1H), 8.41(d, J=3.0 Hz, 1H), 8.36-8.33(m, 2H), 7.23(dd, J=4.7, 7.9 Hz, 1H), 7.11(d, J=8.4 Hz, 2H), 6.70(d, J=8.5 Hz, 2H), 4.32(s, 2H), 4.23(s, 2H) | 363.00 |
| 525 | A | (DMSO-d$_6$): 9.22(s, 1H), 7.94-7.92(m, 2H), 7.61-7.54(m, 3H), 7.12(dd, J=1.8, 6.7 Hz, 2H), 6.69(s, 2H), 4.45-4.05(m,3H), 3.17(d, J=5.2 Hz, 2H), 1.64(d, J=7.2 Hz, 3H). | 337.00 |
| 526 | C | (methanol-d$_4$): 7.98-7.96(m, 2H), 7.59-7.52(m, 3H), 7.28(t, J=7.9 Hz,H), 7.24(s, 1H), 7.13(d, J=7.6 Hz, 1H), 7.09(dd, J=1.3, 8.1 Hz, 1H), 7.09(s, 1H), 4.35(s, 2H), 4.26(s, 2H), 2.80(s, 3H),. | 400.00 |
| 527 | C | (DMSO-d$_6$): 8.00-7.98(m, 2H), 7.63-7.55(m, 3H), 7.38-7.35(m, 2H), 7.16-7.12(m, 2H), 4.40(s, 2H), 4.29(s, 2H). | 325.00 |
| 528 | C | (DMSO-d$_6$): 7.98-7.96(m, 2H), 7.89-7.87(m, 2H), 7.63-7.55(m, SH), 4.44(s, 2H), 4.4(s, 2H), 3.18(s, 3H). | 385.00 |
| 529 | C | (DMSO-d$_6$): 8.73(s, 1H), 8.60(d, J=5.0 Hz, 1H), 8.05-7.99(m, 3H), 7.63-7.56(m, 4H), 4.44(s, 2H), 4.41(s, 2H). | 308.00 |
| 530 | B | (DMSO-d$_6$): 8.00-7.99(m, 2H), 7.62-7.56(m, 3H), 7.24(d, J=8.6 Hz, 2H), 6.87(dd, J=2.0, 6.7 Hz, 2H), 4.39(s, 2H), 4.21(s, 2H), 3.71(s, 3H),. | 337.00 |
| 531 | C | (DMSO-d$_6$): 8.01-7.99(m, 2H), 7.62-7.56(m, 3H), 7.19-7.16(m, 1H), 7.10-7.09(m, 2H), 4.40(s, 2H), 4.24(s, 2H), 3.79(s, 3H). | 355.00 |
| 532 | C | | 466.40 |
| 533 | A | | 381.30 |
| 534 | B | | 319.20 |
| 535 | B | | 394.30 |
| 536 | C | | 275.30 |
| 537 | C | | 500.40 |
| 538 | B | | 324.30 |
| 539 | B | | 387.30 |
| 540 | A | | 367.30 |
| 541 | A | | 329.20 |
| 542 | B | | 261.20 |
| 543 | A | (DMSO-d$_6$): 9.28(bs,1H), 7.93(d, J=5.1 Hz, 1H), 7.89(dd, J=0.9, 3.8 Hz, 1H), 7.26(dd, J=3.8, 5.0 Hz, 1H), 7.13-7.10(m, 2H), 6.68(dd, J=1.9, 6.6 Hz, 2H), 4.41(s, 2H), 4.08(s, 2H). | 329.00 |
| 544 | A | (DMSO-d$_6$): 7.94(dd, J=1.0, 5.0 Hz, 1H), 7.89(dd, J=1.0, 3.8 Hz, 1H), 7.27(dd, J=3.8, 5.0 Hz, 1H), 6.88(d, J=1.5 Hz, 1H), 6.84(d, J=8.0 Hz, 1H), 6.79(dd, J=1.6, 8.0 Hz, 1H), 5.96(s, 2H), 4.42(s, 2H), 4.13(s, 2H). | 357.00 |
| 545 | C | (DMSO-d$_6$): 8.73(d, J=1.6 Hz, 1H), 8.60(d, J=5.1 Hz, 1H), 8.04(d, J=7.9 Hz, 1H), 7.95(dd, J=1.0, 5.1 Hz, 1H), 7.91(dd, J=1.1, 3.8 Hz, 1H), 7.61(dd, J=5.2, 7.7 Hz, 1H), 7.27(dd, J=3.8, 5.0 Hz, 1H), 4.42(d, J=9.6 Hz, 2H), 4.28(s, 2H). | 314.00 |
| 546 | B | (DMSO-d$_6$): 7.93(dd, J=1.0, 5.1 Hz, 1H), 7.89(dd, J=1.0, 3.8 Hz, 1H), 7.38-7.35(m, 2H), 7.26(dd, J=3.8, 5.0 Hz, 1H), 7.16(s, 2H), 7.13(dd, J=2.2, 9.0 Hz, 2H), 4.42(s, 2H), 4.22(s, 2H). | 331.00 |
| 547 | B | (DMSO-d$_6$): 7.93(d, J=5.0 Hz, 1H), 7.89(d, J=3.6 Hz, 1H), 7.27-7.24(m, 3H), 6.87(dd, J=2.9, 11.5 Hz, 2H), 4.41(s, 2H), 4.14(s, 2H), 3.70(s, 3H). | 343.00 |
| 548 | A | (DMSO-d$_6$): 9.22(d, J=3.4 Hz, 1H), 7.91(dd, J=1.0, 5.1 Hz, 1H), 7.85(dd, J=1.0, 3.8 Hz, 1H), 7.24(dd, J=3.8, 5.0 Hz, 1H), 7.12-7.11(m, 2H), 6.69(s, 1H), 6.67(dd, J=1.8, 6.7 Hz, 1H), 4.43-4.25(m, 4H), 1.63(dd, J=3.9, 7.2 Hz, 3H). | 343.00 |

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

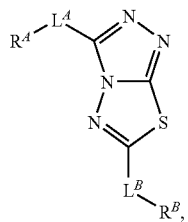

(Ia)

or a pharmaceutically acceptable salt thereof, wherein $L^A$ is selected from

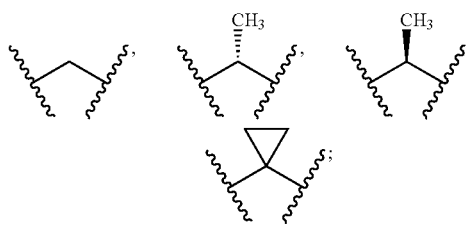

$R^A$ is selected from:

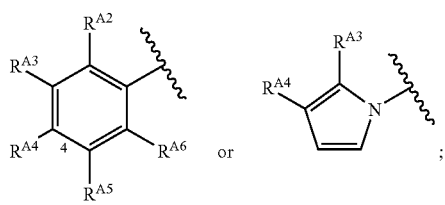

each of $R^{A2}$ and $R^{A6}$ is, independently, selected from hydrogen, halogen, —CN, —C(O)OR$^{++}$, —C(O)R$^{++}$, —C(O)N(R$^{++}$)$_2$, —C(S)N(R$^{++}$)$_2$, —C(NH)N(R$^{++}$)$_2$, —OR$^{++}$, —O(halo(C$_{1-4}$ aliphatic)), —OC(O)N(R$^{++}$)$_2$, —SR$^{++}$, —NO$_2$, —N(R$^{++}$)$_2$, —N(R$^{++}$)C(O)(R$^{++}$), —N(R$^{++}$)C(O)N(R$^{++}$)$_2$, —N(R$^{++}$)C(O)OR$^{++}$, —N(R$^{++}$)N(R$^{++}$)C(O)R$^{++}$, —N(R$^{++}$)N(R$^{++}$)C(O)N(R$^{++}$)$_2$, —N(R$^{++}$)N(R$^{++}$)C(O)OR$^{++}$, —N(R$^{++}$)S(O)$_2$N(R$^{++}$)$_2$, —N(R$^{++}$)S(O)$_2$R$^{++}$, —S(O)$_2$R$^{++}$, —S(O)$_2$N(R$^{++}$)$_2$, —S(O)R$^{++}$, and C$_{1-4}$ aliphatic optionally substituted with substituents independently selected from halogen, —OR$^{++}$, —SR$^{++}$, —NO$_2$, —CN, —N(R$^{++}$)$_2$, or —N(R$^{++}$)C(O)(R$^{++}$);

$R^{A3}$, $R^{A4}$ and the carbons to which they are bonded form a heterocyclyl or heteroaryl ring selected from:

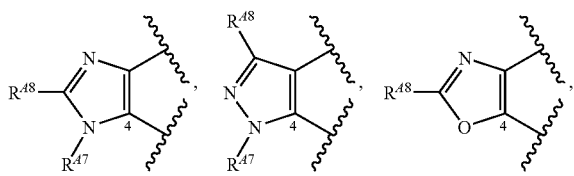

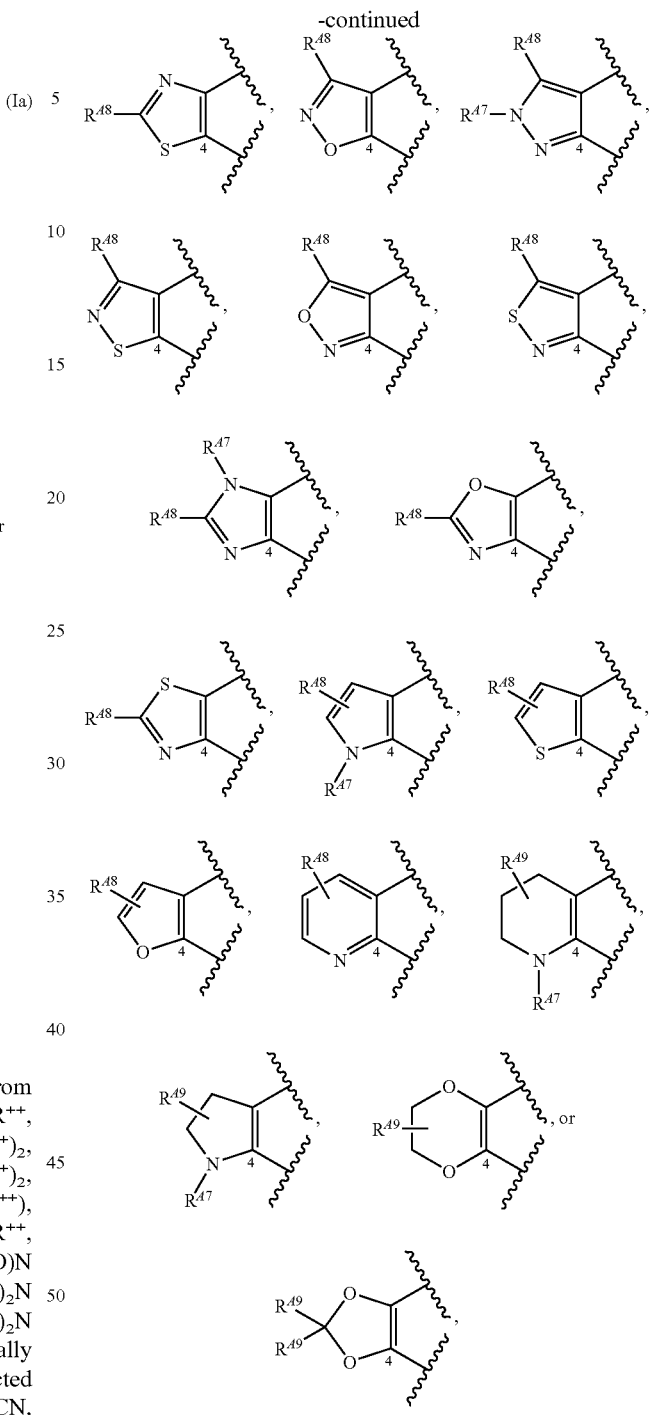

wherein said heterocyclyl or heteroaryl ring is bonded to $R^A$ at the 4-position indicated;

each $R^{A7}$ is, independently, hydrogen, —R$^o$, —N(R$^o$)$_2$, —NR$^o$C(O)R$^o$, —NR$^o$C(O)N(R$^o$)$_2$, —NR$^o$CO$_2$R$^o$, —C(O)CH$_2$C(O)R$^o$, —CO$_2$R$^o$, —C(O)C(O)R$^o$, —C(O)R$^o$, —C(O)N(R$^o$)$_2$, —S(O)$_2$R$^o$, —C(=S)N(R$^o$)$_2$, —C(=NH)—N(R$^o$)$_2$, or —(CH$_2$)$_y$NHC(O)R$^o$;

each $R^{A8}$ is, independently, hydrogen, halogen, —CN, —CO$_2$R$^{++}$, —C(O)R$^{++}$, —C(O)N(R$^{++}$)$_2$, —C(S)N(R$^{++}$)$_2$, —C(NH)N(R$^{++}$)$_2$, —OR$^{++}$, —O(halo(C$_{1-4}$ aliphatic)), —OC(O)N(R$^{++}$)$_2$, —SR$^{++}$, —NO$_2$, —N (R⁺⁺)₂, —N(R⁺⁺)C(O)(R⁺⁺), —N(R⁺⁺)C(O)N(R⁺⁺)₂, —N(R⁺⁺)CO₂R⁺⁺, —N(R⁺⁺)N(R⁺⁺)C(O)R⁺⁺, —N(R⁺⁺)N(R⁺⁺)C(O)N(R⁺⁺)₂, —N(R⁺⁺)N(R⁺⁺)CO₂R⁺⁺, —N(R⁺⁺)SO₂N(R⁺⁺)₂, —N(R⁺⁺)SO₂R⁺⁺, —S(O)₂R⁺⁺, —SO₂N(R⁺⁺)₂, —S(O)R⁺⁺, or a $C_{1-4}$ aliphatic group optionally substituted with substituents independently selected from halogen, —OR⁺⁺, —SR⁺⁺, —NO₂, —CN, —N(R⁺⁺)₂, or —N(R⁺⁺)C(O)(R⁺⁺);

each $R^{A9}$ is, individually, hydrogen, F, Cl, $C_{1-4}$ aliphatic, or halo($C_{1-4}$ aliphatic);

$R^{A5}$ is hydrogen or $R^{Ar}$;

$L^B$ is a covalent bond or —N(R*)—;

$R^B$ is a 6-10 membered aryl ring; a 3-7 membered carbocyclic ring, a 5-10 membered heteroaryl ring having 1-4 heteroatoms independently selected from nitrogen, oxygen, and sulfur; or a 3-10 membered heterocyclyl ring having 1-4 heteroatoms independently selected from nitrogen, oxygen, and sulfur; wherein each of said aryl, heteroaryl, or heterocyclyl rings is optionally substituted with up to five independent occurrences of $R^{Ar}$;

each $R^{Ar}$ is, independently, selected from halogen, —R°, —OR°, —SR°, —OC(O)(C₁₋₈ aliphatic), Ph optionally substituted with up to five independent occurrences of —R°, —CH₂(Ph) optionally substituted with up to five independent occurrences of —R°, —(CH₂)$_y$(Ph) optionally substituted with up to five independent occurrences of —R°, —NO₂, —CN, —N(R°)₂, —NR°C(O)R°, —NR°C(O)N(R°)₂, —NR°C(O)OR°, —NR°NR°C(O)R°, —NR°NR°C(O)N(R°)₂, —NR°NR°C(O)OR°, —C(O)CH₂C(O)R°, —C(O)OR°, —C(O)R°, —C(O)N(R°)₂, —OC(O)N(R°)₂, —S(O)₂R°, —S(O)₂N(R°)₂, —S(O)R°, —NR°S(O)₂N(R°)₂, —NR°S(O)₂R°, —C(S)N(R°)₂, —C(NH)N(R°)₂, and —(CH₂)$_y$NHC(O)R°, wherein y is 1 to 4; or two adjacent $R^{Ar}$ groups taken together are 1,2-methylenedioxy or 1,2-ethylenedioxy;

each $R^{++}$ is, independently, hydrogen or $C_{1-4}$ aliphatic;

each R* is, independently, hydrogen or $C_{1-8}$ aliphatic optionally substituted with up to five independent occurrences of —NH₂, —NH(C₁₋₄ aliphatic), —N(C₁₋₄ aliphatic)₂, halogen, C₁₋₄ aliphatic, —OH, —O(C₁₋₄ aliphatic), —NO₂, —CN, —C(O)OH, —C(O)O(C₁₋₄ aliphatic), —C(O)NH₂, —C(O)NH(C₁₋₄ aliphatic), —C(O)N(C₁₋₄ aliphatic)₂, —O(halo(C₁₋₄ aliphatic)), or halo(C₁₋₄ aliphatic); or two R* on the same nitrogen are taken together with the nitrogen to form a 5-8 membered heterocyclyl or heteroaryl ring having 1-3 heteroatoms independently selected from nitrogen, oxygen, and sulfur; and each R° is, independently, hydrogen, optionally substituted $C_{1-6}$ aliphatic, an unsubstituted 5-6 membered heteroaryl or heterocyclic ring, -Ph, or —O(Ph), wherein each substituent of said optionally substituted aliphatic of R° is, independently, —NH₂, —NH(C₁₋₄ aliphatic), —N(C₁₋₄ aliphatic)₂, halogen, C₁₋₄ aliphatic, —OH, —O(C₁₋₄ aliphatic), —NO₂, —CN, —C(O)OH, —C(O)O(C₁₋₄ aliphatic), —C(O)NH₂, —C(O)NH(C₁₋₄ aliphatic), —C(O)N(C₁₋₄ aliphatic)₂, —O(halo(C₁₋₄ aliphatic)), or halo(C₁₋₄ aliphatic); or two R° on the same nitrogen are taken together with the nitrogen to form a 5-8 membered heterocyclyl or heteroaryl ring having 1-3 heteroatoms independently selected from nitrogen, oxygen, and sulfur.

2. The compound according to claim 1, wherein $R^B$ is selected from the group consisting of:

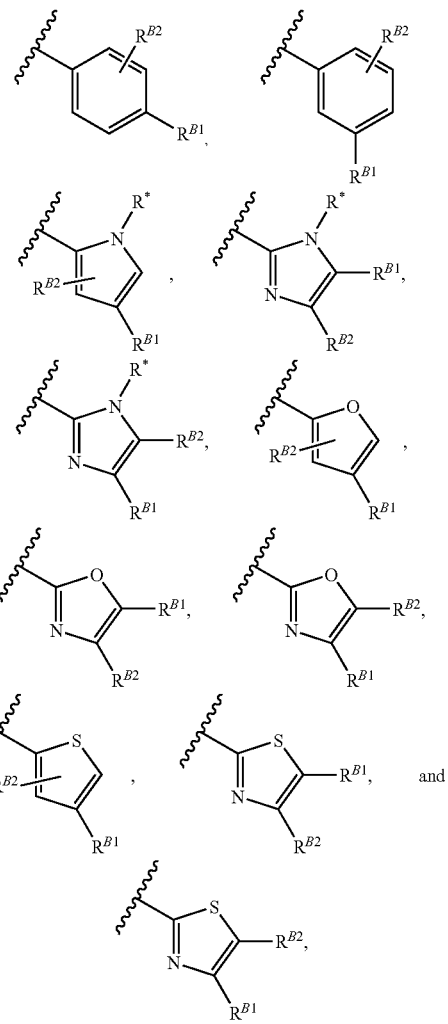

wherein
each of $R^{B1}$ and $R^{B2}$ is, independently, hydrogen or $R^{Ar}$.

3. The compound according to claim 1, wherein $L^B R^B$ is selected from:

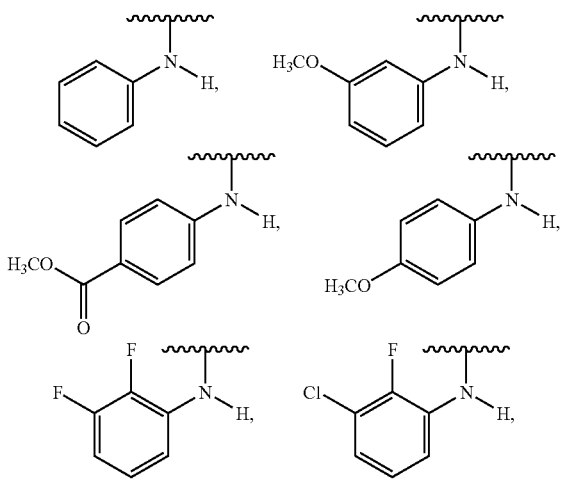

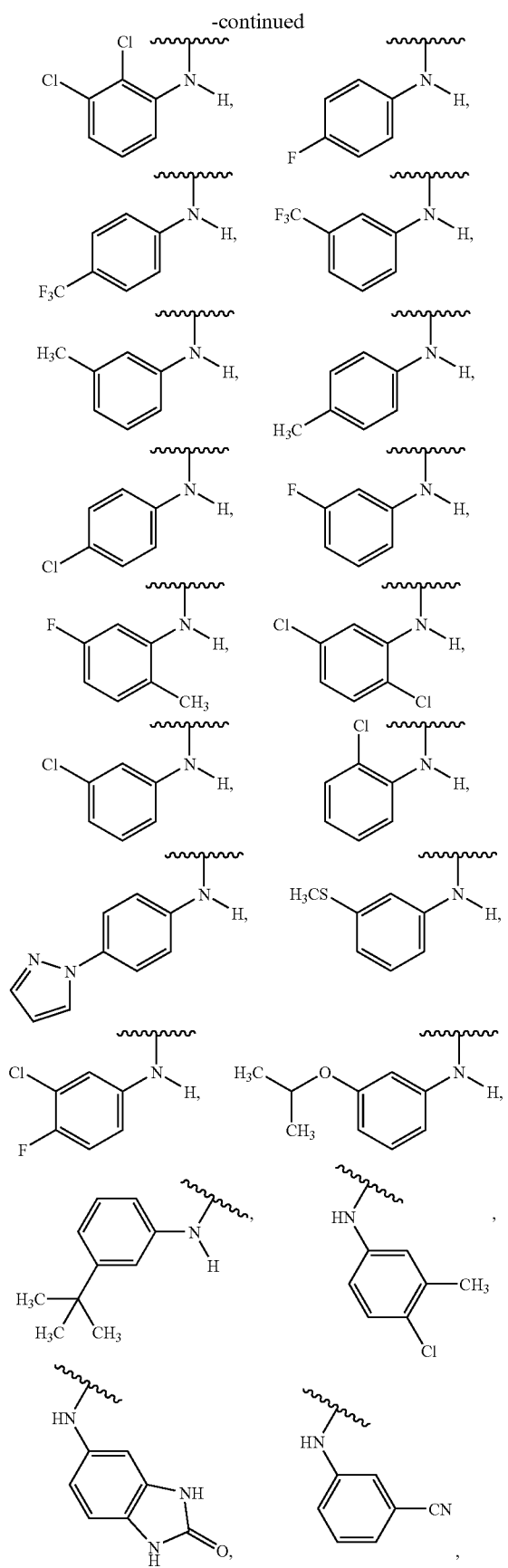
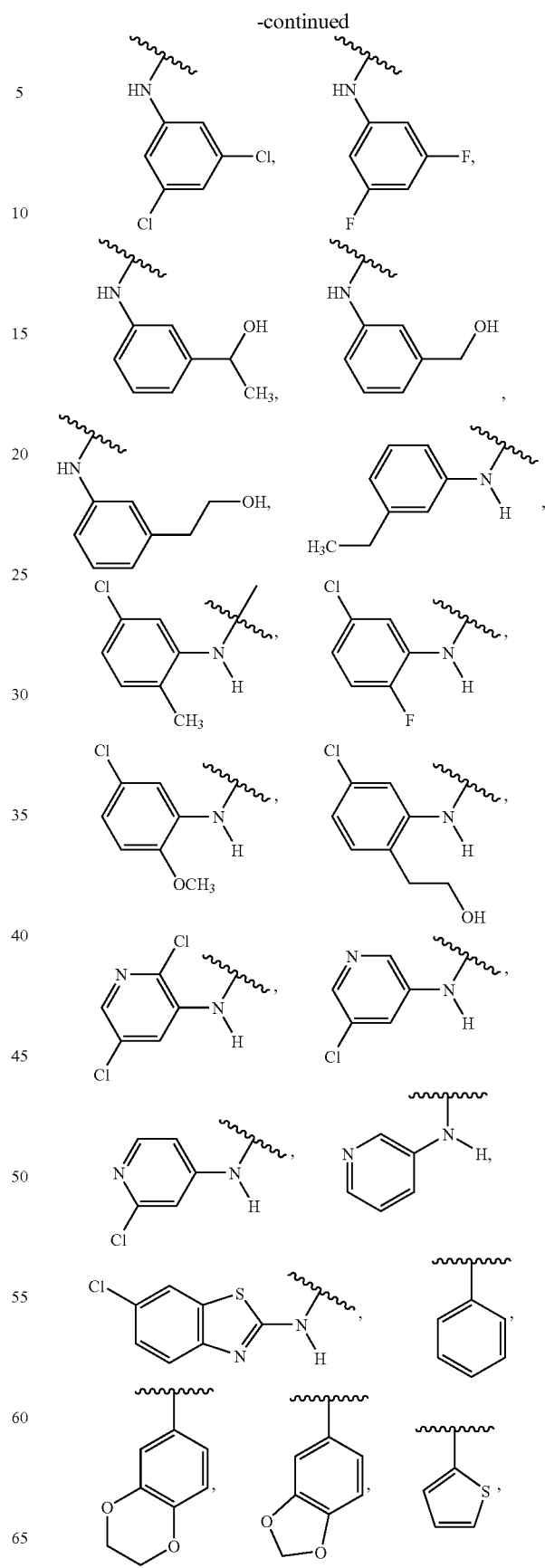

-continued
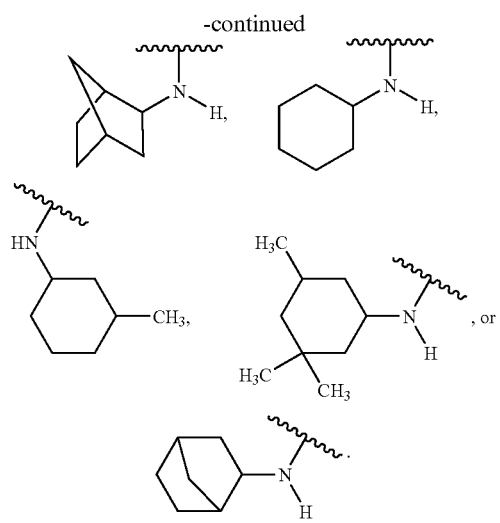
4. A compound according to claim 1 selected from
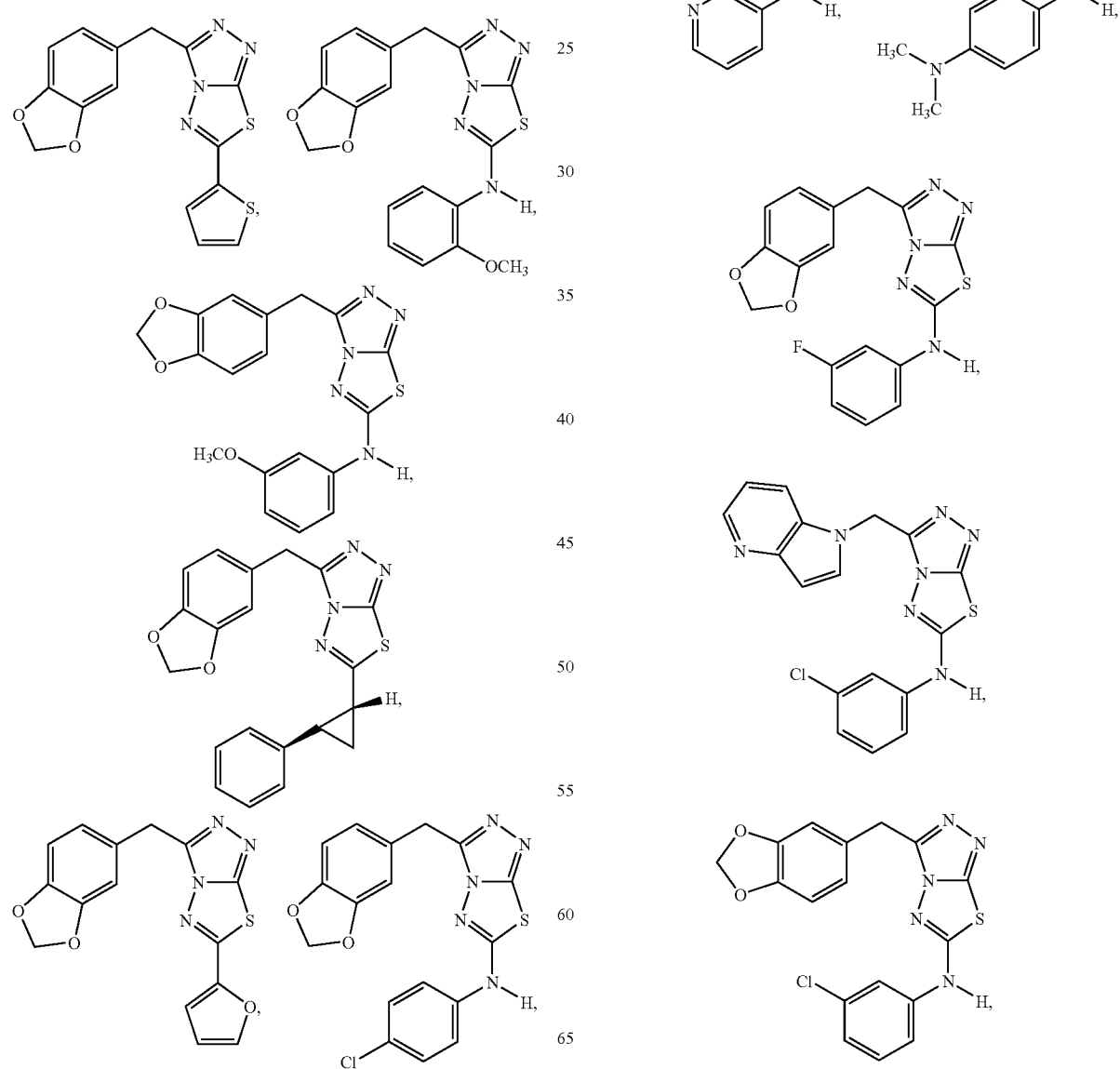
-continued
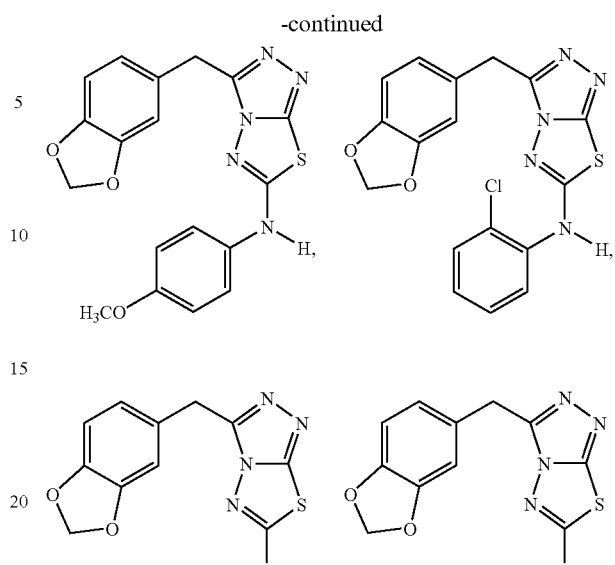

191

-continued

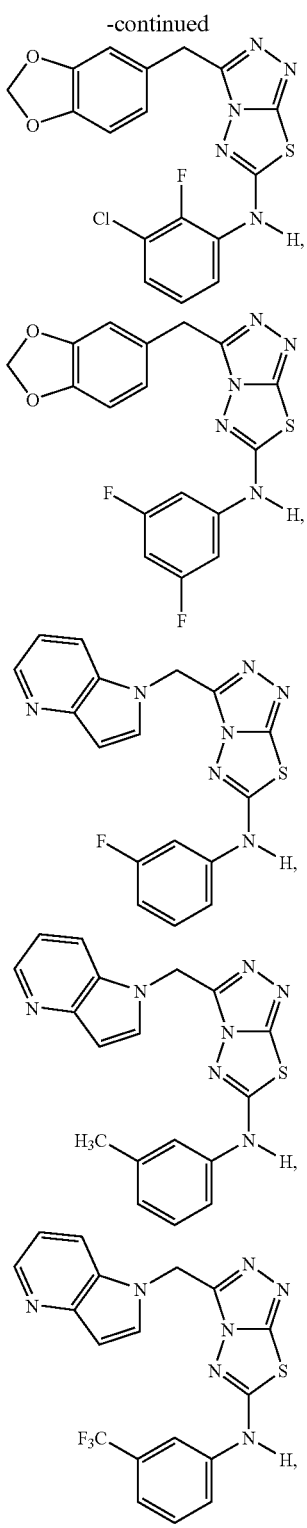

192

-continued

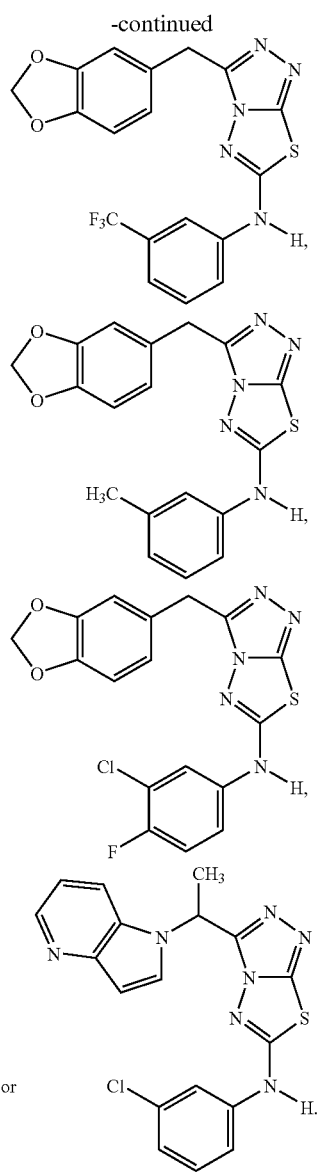

or

5. A pharmaceutical composition comprising a compound according to claim 1 and a pharmaceutically acceptable carrier, adjuvant, or vehicle.

6. A method of treating or lessening the severity of a proliferative disorder in a patient comprising the step of administering to said patient a therapeutically effective dose of a compound according to claim 1 or a composition according to claim 5, wherein said proliferative disorder is gastric adenocarcinoma, gliobastoma, renal cancer, small cell lung carcinoma, colon cancer, colorectal cancer, prostate cancer, brain cancer, liver cancer, pancreatic cancer, or breast cancer.

* * * * *